(12) United States Patent
Smith et al.

(10) Patent No.: US 8,658,167 B2
(45) Date of Patent: Feb. 25, 2014

(54) METHODS AND COMPOSITIONS FOR TREATMENT AND DIAGNOSIS OF FIBROSIS, TUMOR INVASION, ANGIOGENESIS, AND METASTASIS

(71) Applicant: Gilead Biologics, Inc., Foster City, CA (US)

(72) Inventors: Victoria Smith, Burlingame, CA (US); Scott Ogg, San Francisco, CA (US); Peter Van Vlasselaer, Portola Valley, CA (US); Vivian E. Barry, Foster City, CA (US); Derek Marshall, Pacifica, CA (US); Alison Kay Holzer, Redwood City, CA (US); Hector Rodriguez, Brisbane, CA (US); Miho Oyasu, San Mateo, CA (US); Scott Alan McCauley, Brisbane, CA (US); Carlos Aurelio Garcia, San Lorenzo, CA (US); Donna Hiroko Tokuoka Biermann, San Mateo, CA (US)

(73) Assignee: Gilead Biologics, Inc., Foster City, CA (US)

( * ) Notice: Subject to any disclaimer, the term of this patent is extended or adjusted under 35 U.S.C. 154(b) by 0 days.

(21) Appl. No.: 13/707,495

(22) Filed: Dec. 6, 2012

(65) Prior Publication Data

US 2013/0095101 A1    Apr. 18, 2013

Related U.S. Application Data

(63) Continuation of application No. 12/185,054, filed on Aug. 1, 2008.

(60) Provisional application No. 60/963,214, filed on Aug. 2, 2007, provisional application No. 60/963,246, filed on Aug. 2, 2007, provisional application No. 60/963,248, filed on Aug. 2, 2007, provisional application No. 60/963,249, filed on Aug. 2, 2007, provisional application No. 60/963,282, filed on Aug. 2, 2007.

(51) Int. Cl.
*A61K 39/395* (2006.01)

(52) U.S. Cl.
USPC ................. 424/130.1; 424/141.1; 424/152.1

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,485,088 A | 11/1984 | Chvapil |
| 4,545,382 A | 10/1985 | Higgins et al. |
| 4,637,403 A | 1/1987 | Garcia et al. |
| 4,666,828 A | 5/1987 | Gusella |
| 4,683,202 A | 7/1987 | Mullis |
| 4,731,374 A | 3/1988 | Griss et al. |
| 4,748,116 A | 5/1988 | Simonsson et al. |
| 4,801,531 A | 1/1989 | Frossard |
| 4,816,567 A | 3/1989 | Cabilly et al. |
| 4,843,086 A | 6/1989 | Griss et al. |
| 4,879,219 A | 11/1989 | Wands et al. |
| 4,886,812 A | 12/1989 | Griss et al. |
| 4,943,593 A | 7/1990 | Palfreyman et al. |
| 4,946,778 A | 8/1990 | Ladner et al. |
| 4,965,288 A | 10/1990 | Palfreyman et al. |
| 4,997,854 A | 3/1991 | Kagan et al. |
| 5,011,771 A | 4/1991 | Bellet et al. |
| 5,021,404 A | 6/1991 | Folkman et al. |
| 5,021,456 A | 6/1991 | Palfreyman et al. |
| 5,059,714 A | 10/1991 | Palfreyman et al. |

(Continued)

FOREIGN PATENT DOCUMENTS

| EP | 0186087 | 8/1989 |
|---|---|---|
| EP | 0375408 | 6/1990 |

(Continued)

OTHER PUBLICATIONS

U.S. Appl. No. 12/860,632, filed Aug. 2011, Marshall et al.

(Continued)

Primary Examiner — Hong Sang

(57) ABSTRACT

Provided are methodology, compositions and kits to prevent and treat diseases associated with abnormal cell proliferation, angiogenesis and fibrosis, using processed lysyl oxidase or lysyl oxidase-like protein inhibitors, LOX inhibitors and LOXL inhibitors, or synergistic combinations of such inhibitors with therapeutic agents. Provided are methods for selecting tumor invasion, angiogenesis and metastasis inhibiting agents, by contacting cells in EMT states with candidate agents and detecting changes in such states; and methods, compositions, and kits for diagnosing or monitoring diseases associated with abnormal cell proliferation, angiogenesis and fibrosis, using molecules or agents specifically recognizing processed LOX or LOXL. Provided are methods, compositions, medical devices, systems and kits for preventing or treating diseases and conditions associated with fibrosis, including pathological cardiovascular conditions and diseases, e.g., hypertension, hypertensive heart disease, myocardial infarction, atherosclerosis, restenosis, liver fibrosis, kidney fibrosis, lung fibrosis, dermal scaring, keloid formation, and Alzheimer's disease, with LOX or LOXL inhibitors.

30 Claims, 50 Drawing Sheets

(56) References Cited

U.S. PATENT DOCUMENTS

| | | | |
|---|---|---|---|
| 5,120,764 A | 6/1992 | McCarthy et al. |
| 5,182,297 A | 1/1993 | Palfreyman et al. |
| 5,192,659 A | 3/1993 | Simons |
| 5,252,608 A | 10/1993 | Palfreyman et al. |
| 5,262,035 A | 11/1993 | Gregg et al. |
| 5,272,057 A | 12/1993 | Smulson et al. |
| 5,281,521 A | 1/1994 | Trojanowski et al. |
| 5,545,806 A | 8/1996 | Lonberg et al. |
| 5,545,807 A | 8/1996 | Surani et al. |
| 5,625,126 A | 4/1997 | Lonberg et al. |
| 5,633,425 A | 5/1997 | Lonberg et al. |
| 5,641,484 A | 6/1997 | Hung et al. |
| 5,661,016 A | 8/1997 | Lonberg et al. |
| 5,721,138 A | 2/1998 | Lawn |
| 6,015,562 A | 1/2000 | Hinman et al. |
| 6,140,056 A | 10/2000 | Khodadoust |
| 6,225,118 B1 | 5/2001 | Grant et al. |
| 6,277,622 B1 | 8/2001 | Weiss |
| 6,300,092 B1 | 10/2001 | Khodadoust et al. |
| 6,303,318 B1 | 10/2001 | O'Brien |
| 6,316,416 B1 | 11/2001 | Patierno et al. |
| 6,326,174 B1 | 12/2001 | Joyce et al. |
| 6,391,602 B1 | 5/2002 | Khodadoust |
| 6,534,261 B1 | 3/2003 | Cox, III et al. |
| 6,808,707 B2 | 10/2004 | Ensley |
| 7,112,668 B2 | 9/2006 | Rastelli et al. |
| 7,208,300 B2 | 4/2007 | Evans et al. |
| 7,255,856 B2 | 8/2007 | Li et al. |
| 7,255,857 B2 | 8/2007 | Li et al. |
| 7,335,294 B2 | 2/2008 | Heller et al. |
| 7,348,170 B2 | 3/2008 | Yuuki et al. |
| 7,396,920 B2 | 7/2008 | Hemmings et al. |
| 7,445,920 B2 | 11/2008 | Evans et al. |
| 7,585,634 B2 | 9/2009 | Kim et al. |
| 8,163,494 B2 | 4/2012 | Neufeld et al. |
| 8,168,180 B2 | 5/2012 | Neufeld et al. |
| 8,461,303 B2 | 6/2013 | Smith et al. |
| 2001/0005581 A1 | 6/2001 | Grant et al. |
| 2001/0012890 A1 | 8/2001 | Thompson |
| 2002/0072089 A1 | 6/2002 | Holtzman et al. |
| 2002/0123476 A1 | 9/2002 | Emanuele et al. |
| 2002/0128218 A1 | 9/2002 | Emanuele et al. |
| 2002/0151007 A1 | 10/2002 | Khodadoust et al. |
| 2002/0156263 A1 | 10/2002 | Chen |
| 2003/0008023 A1 | 1/2003 | Lu |
| 2003/0017068 A1 | 1/2003 | Larrain et al. |
| 2003/0092037 A1 | 5/2003 | Matsuzaki et al. |
| 2003/0096980 A1 | 5/2003 | Froehler et al. |
| 2003/0099213 A1 | 5/2003 | Lee et al. |
| 2003/0114410 A1 | 6/2003 | Neufeld et al. |
| 2003/0129672 A1* | 7/2003 | Dyer et al. ............ 435/7.9 |
| 2003/0149997 A1 | 8/2003 | Hageman |
| 2003/0152926 A1 | 8/2003 | Murray et al. |
| 2003/0211076 A1 | 11/2003 | Li |
| 2004/0009154 A1 | 1/2004 | Khan et al. |
| 2004/0029114 A1 | 2/2004 | Mack et al. |
| 2004/0156854 A1 | 8/2004 | Mulligan et al. |
| 2004/0171110 A1 | 9/2004 | Evans et al. |
| 2004/0176296 A1 | 9/2004 | Holtzman et al. |
| 2004/0197328 A1 | 10/2004 | Young et al. |
| 2004/0213756 A1 | 10/2004 | Michal et al. |
| 2004/0248871 A1 | 12/2004 | Farjanel et al. |
| 2004/0253220 A1 | 12/2004 | Perrier et al. |
| 2004/0253606 A1 | 12/2004 | Aziz et al. |
| 2004/0258676 A1 | 12/2004 | Perrier et al. |
| 2004/0265230 A1 | 12/2004 | Martinez et al. |
| 2005/0020521 A1 | 1/2005 | Rana et al. |
| 2005/0079538 A1 | 4/2005 | Griffin et al. |
| 2005/0119202 A1 | 6/2005 | Kreutzer et al. |
| 2005/0181375 A1 | 8/2005 | Aziz et al. |
| 2005/0259483 A1 | 11/2005 | Nakamura et al. |
| 2005/0260639 A1 | 11/2005 | Nakamura et al. |
| 2006/0019256 A1 | 1/2006 | Clarke et al. |
| 2006/0083736 A1 | 4/2006 | Law et al. |
| 2006/0088532 A1 | 4/2006 | Alitalo et al. |
| 2006/0088882 A1 | 4/2006 | Jain et al. |
| 2006/0127402 A1 | 6/2006 | Neufeld et al. |
| 2006/0127902 A1 | 6/2006 | Madden et al. |
| 2006/0134172 A1 | 6/2006 | Shepard et al. |
| 2006/0134801 A1 | 6/2006 | Chada et al. |
| 2006/0216722 A1 | 9/2006 | Betholtz et al. |
| 2006/0223760 A1 | 10/2006 | Li et al. |
| 2007/0010469 A1 | 1/2007 | Chan et al. |
| 2007/0021365 A1 | 1/2007 | Erler et al. |
| 2007/0037203 A1 | 2/2007 | Kapeller-Libermann et al. |
| 2007/0054278 A1 | 3/2007 | Cargill |
| 2007/0059745 A1 | 3/2007 | Sharp et al. |
| 2007/0148173 A1 | 6/2007 | Huang et al. |
| 2007/0154481 A1 | 7/2007 | Gelinas et al. |
| 2007/0184439 A1 | 8/2007 | Guilford et al. |
| 2007/0197424 A1 | 8/2007 | Friedman et al. |
| 2007/0225242 A1 | 9/2007 | Erler et al. |
| 2007/0231323 A1 | 10/2007 | Phillips |
| 2007/0243214 A1 | 10/2007 | Schiemann et al. |
| 2008/0031817 A1 | 2/2008 | Mazar et al. |
| 2008/0118928 A1 | 5/2008 | Hageman |
| 2008/0137893 A1 | 6/2008 | Ross et al. |
| 2008/0181896 A1 | 7/2008 | Khan et al. |
| 2008/0187523 A1 | 8/2008 | Zhang et al. |
| 2008/0220424 A1 | 9/2008 | Haber et al. |
| 2008/0248477 A1 | 10/2008 | Holtzman et al. |
| 2008/0261870 A1 | 10/2008 | Trackman et al. |
| 2008/0274453 A1 | 11/2008 | Hageman |
| 2008/0279857 A1 | 11/2008 | Skerry et al. |
| 2008/0286808 A1 | 11/2008 | Schellenberger et al. |
| 2008/0292547 A1 | 11/2008 | Tolleshaug et al. |
| 2008/0305965 A1 | 12/2008 | Moorhouse et al. |
| 2009/0022703 A1 | 1/2009 | Li et al. |
| 2009/0023149 A1 | 1/2009 | Knudsen et al. |
| 2009/0035348 A1 | 2/2009 | Zadini et al. |
| 2009/0053224 A1 | 2/2009 | Smith et al. |
| 2009/0104201 A1 | 4/2009 | Smith et al. |
| 2009/0142301 A1 | 6/2009 | Bevec et al. |
| 2009/0232773 A1 | 9/2009 | Kato et al. |
| 2009/0233270 A9 | 9/2009 | St. Croix et al. |
| 2009/0239947 A1 | 9/2009 | Dai et al. |
| 2009/0275633 A1 | 11/2009 | Esteller |
| 2010/0119515 A1 | 5/2010 | Neufeld et al. |
| 2010/0144603 A1 | 6/2010 | Watnick |
| 2010/0203062 A1 | 8/2010 | Stalmans et al. |
| 2010/0209415 A1 | 8/2010 | Smith et al. |
| 2010/0317721 A1 | 12/2010 | Neufeld |
| 2011/0044907 A1 | 2/2011 | Marshall et al. |
| 2011/0044981 A1 | 2/2011 | Spangler et al. |
| 2011/0076272 A1 | 3/2011 | Smith et al. |
| 2011/0076285 A1 | 3/2011 | Stalmans et al. |
| 2011/0076739 A1 | 3/2011 | McCauley et al. |
| 2011/0200606 A1 | 8/2011 | McCauley et al. |
| 2011/0207144 A1 | 8/2011 | Marshall et al. |
| 2012/0087917 A1 | 4/2012 | Smith et al. |
| 2012/0165398 A1 | 6/2012 | Neufeld et al. |
| 2012/0202206 A1 | 8/2012 | Neufeld et al. |
| 2012/0309020 A1 | 12/2012 | Smith et al. |
| 2013/0017207 A1 | 1/2013 | Smith et al. |

FOREIGN PATENT DOCUMENTS

| | | |
|---|---|---|
| EP | 0799891 | 10/1997 |
| EP | 0960192 | 12/1999 |
| EP | 1149169 | 10/2001 |
| EP | 1616881 | 1/2006 |
| EP | 1690932 | 8/2006 |
| EP | 1693448 | 8/2006 |
| EP | 1715035 | 10/2006 |
| EP | 2078531 | 7/2009 |
| EP | 1315519 | 12/2010 |
| WO | WO-89/12060 | 12/1989 |
| WO | WO-92/20702 | 11/1992 |
| WO | WO-96/00614 | 1/1996 |
| WO | WO-96/40746 | 12/1996 |
| WO | WO-97/00441 | 1/1997 |
| WO | WO-98/06830 | 2/1998 |
| WO | WO-99/65928 | 12/1999 |
| WO | WO-00/44910 | 8/2000 |

(56) References Cited

FOREIGN PATENT DOCUMENTS

| WO | WO-01/83702 | 11/2001 |
|----|----|----|
| WO | WO-01/92495 | 12/2001 |
| WO | WO-02/11667 | 2/2002 |
| WO | WO-02/061092 | 8/2002 |
| WO | WO-02/079492 | 10/2002 |
| WO | WO-02/086443 | 10/2002 |
| WO | WO-03/031939 | 4/2003 |
| WO | WO-03/100016 | 12/2003 |
| WO | WO-2004/023973 | 3/2004 |
| WO | WO-2004/047720 | 6/2004 |
| WO | WO-2004/061423 | 7/2004 |
| WO | WO-2004/091655 | 10/2004 |
| WO | WO-2005/100604 | 10/2005 |
| WO | WO-2006/128740 | 7/2006 |
| WO | WO-2007/045927 | 4/2007 |
| WO | WO-2007/126457 | 11/2007 |
| WO | WO-2008/063479 | 5/2008 |
| WO | WO-2008/070616 | 6/2008 |
| WO | WO-2008/132453 | 11/2008 |
| WO | WO-2008/138578 | 11/2008 |
| WO | WO-2009/010974 | 1/2009 |
| WO | WO-2009/017833 | 2/2009 |
| WO | WO-2009/035791 | 3/2009 |
| WO | WO-2010/080769 | 7/2010 |
| WO | WO-2010/091279 | 8/2010 |
| WO | WO-2011/022667 | 2/2011 |
| WO | WO-2011/022670 | 2/2011 |
| WO | WO-2011/022706 | 2/2011 |
| WO | WO-2011/022709 | 2/2011 |
| WO | WO-2011/022710 | 2/2011 |
| WO | WO-2011/041309 | 4/2011 |
| WO | WO-2011/097513 | 8/2011 |
| WO | WO-2012/139045 | 10/2012 |
| WO | WO-2012/167181 | 12/2012 |

OTHER PUBLICATIONS

U.S. Appl. No. 13/021,555, filed Aug. 2011, McCauley et al.
Office Action mailed Sep. 23, 2010 in U.S. Appl. No. 12/185,054.
Office Action mailed Feb. 15, 2011 in U.S. Appl. No. 12/185,054.
International Preliminary Report on Patentability Chapter I issued Feb. 2, 2010, in PCT/US2008/009354.
Written Opinion of the ISA mailed Apr. 29, 2009, in PCT/US2008/009354.
International Search Report mailed Apr. 29, 2009, in PCT/US2008/009354.
Invitation to Pay Additional Fees mailed Jan. 14, 2009 (including Annex "Communication Relating to the Results of Partial International Search"), in PCT/US2008/009354.
Communication persuant to Article 94(3) EPC dated Jun. 8, 2010, in EP 08795003.6-1222.
Communication persuant to Article 94(3) EPC dated Jul. 19, 2011, in EP 08795003.6-1222.
Communication under Rule 71(3) EPC dated Jul. 23, 2012, in EP 08795003.6-1222.
Partial European Search Report for EP 12172214.4, mailed Nov. 28, 2012.
Patent Examination Report No. 1 for AU 2008282739, issued Nov. 19, 2012.
Office Action mailed Jun. 29, 2007, in U.S. Appl. No. 10/536,440.
Office Action mailed Mar. 28, 2008, in U.S. Appl. No. 10/536,440.
Office Action mailed Nov. 14, 2008, in U.S. Appl. No. 10/536,440.
Office Action mailed Jun. 26, 2009, in U.S. Appl. No. 10/536,440.
Office Action mailed Dec. 30, 2009, in U.S. Appl. No. 10/536,440.
Office Action mailed Jun. 28, 2010, in U.S. Appl. No. 10/536,440.
Office Action mailed Jul. 5, 2011, in U.S. Appl. No. 10/536,440.
Office Action mailed May 14, 2010, in U.S. Appl. No. 12/571,167.
Office Action mailed Nov. 5, 2010, in U.S. Appl. No. 12/571,167.
Office Action mailed Mar. 24, 2011, in U.S. Appl. No. 12/571,167.
Office Action mailed Jul. 28, 2011, in U.S. Appl. No. 12/571,167.
International Preliminary Examination Report mailed Dec. 8, 2003, in PCT/IL01/00728.
Written Opinion mailed Jun. 6, 2003, in PCT/IL01/00728.
International Search Report mailed Dec. 17, 2002, in PCT/IL01/00728.
Invitation to Pay Additional Fees mailed May 23, 2002, in PCT/IL01/00728.
International Search Report mailed Jan. 5, 2006, in PCT/IL03/01008.
Invitation to Pay Additional Fees mailed Jun. 13, 2005, in PCT/IL03/01008.
European Search Report mailed Jul. 29, 2005, in EP 01958338.4-2406.
Communication pursuant to Article 96(2) EPC mailed Nov. 14, 2005, in EP 01958338.4-2406.
Communication pursuant to Article 96(2) EPC mailed Jun. 25, 2007, in EP 01958338.4-2406.
Communication pursuant to Article 94(3) EPC mailed Feb. 10, 2009, in EP 01958338.4-2406.
European Search Report mailed Feb. 29, 2008, in EP 03777136.7-1222.
Communication pursuant to Article 94(3) EPC mailed May 29, 2008, in EP 03777136.7-1222.
European Search Report mailed Dec. 21, 2009, in EP 08020754.1-2402.
European Search Opinion mailed Dec. 21, 2009, in EP 08020754.1-2402.
Communication pursuant to Article 94(3) EPC mailed Oct. 22, 2010, in EP 08020754.1-2402.
Communication pursuant to Article 94(3) EPC mailed Mar. 15, 2011, in EP 08020754.1-2402.
European Search Report mailed Jun. 3, 2009, in EP 08020752.5-1222.
European Search Opinion mailed Jun. 3, 2009, in EP 08020752.5-1222.
Communication pursuant to Article 94(3) EPC mailed Feb. 8, 2010, in EP 08020752.5-1222.
Communication pursuant to Article 94(3) EPC mailed Dec. 27, 2011, in EP 08020752.5-1222.
European Search Report mailed Jun. 3, 2009, in EP 08020753.3-1222.
European Search Opinion mailed Jun. 3, 2009, in EP 08020753.3-1222.
Communication pursuant to Article 94(3) EPC mailed Dec. 27, 2011, in EP 08020753.3-1222.
European Search Report mailed Jul. 13, 2011, in EP 10012458.5-2406.
European Search Opinion mailed Jul. 13, 2011, in EP 10012458.5-2406.
European Search Report mailed Jun. 27, 2011, in EP 10012457.7-2406.
European Search Opinion mailed Jun. 27, 2011, in EP 10012457.7-2406.
Office Action mailed Sep. 23, 2010, in U.S. Appl. No. 12/185,050.
Office Action mailed Feb. 15, 2011, in U.S. Appl. No. 12/185,050.
International Preliminary Report on Patentability Chapter I issued May 11, 2010, in PCT/US2008/072039.
Written Opinion of the ISA mailed Jan. 13, 2009, in PCT/US2008/072039.
International Search Report mailed Jan. 13, 2009, in PCT/US2008/072039.
Communication pursuant to Article 94(3) EPC mailed Jun. 8, 2010, in EP 08830207.0-1222.
Communication pursuant to Article 94(3) EPC mailed Jul. 20, 2011, in EP 08830207.0-1222.
Communication pursuant to Article 94(3) EPC mailed Jul. 4, 2012, in EP 08830207.0-1222.
Communication pursuant to Article 94(3) EPC for EP 08 830 207.0, mailed Nov. 22, 2012.
European Search Report for EP 12172222.7, mailed Nov. 28, 2012.
Notice on the Second Office Action (translation) for CN 200880101321.3, mailed Nov. 23, 2012.
Office Action mailed Jun. 14, 2011, in U.S. Appl. No. 12/652,687.
Office Action mailed Dec. 13, 2011, in U.S. Appl. No. 12/652,687.
Office Action mailed Mar. 30, 2012, in U.S. Appl. No. 12/652,687.
Advisory Action mailed Feb. 23, 2012, in U.S. Appl. No. 12/652,687.

(56) References Cited

OTHER PUBLICATIONS

Notice of Allowance mailed Sep. 18, 2012, in U.S. Appl. No. 12/652,687.
International Preliminary Report on Patentability Chapter I issued Jul. 12, 2011, in PCT/US2010/020159.
Written Opinion of the ISA mailed Sep. 9, 2010, in PCT/US2010/020159.
International Search Report mailed Sep. 9, 2010, in PCT/US2010/020159.
Office Action mailed Jan. 17, 2012, in U.S. Appl. No. 12/701,289.
Office Action mailed Jun. 15, 2012, in U.S. Appl. No. 12/701,289.
Office Action mailed Sep. 24, 2012, in U.S. Appl. No. 12/701,289.
Advisory Action mailed Aug. 30, 2012, in U.S. Appl. No. 12/701,289.
International Preliminary Report on Patentability Chapter I issued Aug. 9, 2011, in PCT/US2010/023359.
Written Opinion of the ISA mailed Apr. 15, 2010, in PCT/US2010/023359.
International Search Report mailed Apr. 15, 2010, in PCT/US2010/023359.
Communication pursuant to Rules 70(2) and 70a(2) EPC for EP 10739181.5, mailed Nov. 5, 2012.
Notice of Allowance for U.S. Appl. No. 12/860,625, mailed Nov. 23, 2012.
International Preliminary Report on Patentability Chapter I issued Feb. 21, 2012, in PCT/US2010/046192.
Written Opinion of the ISA mailed Feb. 17, 2011, in PCT/US2010/046192.
International Search Report mailed Feb. 17, 2011, in PCT/US2010/046192.
Invitation to Pay Additional Fees mailed Nov. 18, 2010, in PCT/US2010/046192.
Examination Report for NZ 598466, mailed Nov. 5, 2012.
Office Action mailed Jul. 13, 2012, in U.S. Appl. No. 12/860,838.
International Preliminary Report on Patentability Chapter I issued Feb. 21, 2012, in PCT/US2010/046248.
Written Opinion of the ISA mailed Jan. 7, 2011, in PCT/US2010/046248.
International Search Report mailed Jan. 7, 2011, in PCT/US2010/046248.
Office Action mailed Jul. 12, 2012, in U.S. Appl. No. 12/860,693.
Final Office Action for U.S. Appl. No. 12/860,693, mailed Nov. 15, 2012.
International Preliminary Report on Patentability Chapter I issued Feb. 21, 2012, in PCT/US2010/046196.
Written Opinion of the ISA mailed Oct. 1, 2010, in PCT/US2010/046196.
International Search Report mailed Oct. 1, 2010, in PCT/US2010/046196.
Office Action mailed May 29, 2012, in U.S. Appl. No. 12/860,632.
Office Action mailed Sep. 11, 2012, in U.S. Appl. No. 12/860,632.
International Preliminary Report on Patentability Chapter I issued Feb. 21, 2012, in PCT/US2010/046247.
Written Opinion of the ISA mailed Sep. 24, 2010, in PCT/US2010/046247.
International Search Report mailed Sep. 24, 2010, in PCT/US2010/046247.
Office Action mailed Dec. 22, 2011, in U.S. Appl. No. 12/892,574.
Office Action mailed Jun. 18, 2012, in U.S. Appl. No. 12/892,574.
Office Action mailed Aug. 31, 2012, in U.S. Appl. No. 12/892,574.
International Preliminary Report on Patentability Chapter I issued Apr. 3, 2012, in PCT/US2010/050542.
Written Opinion of the ISA mailed Nov. 29, 2010, in PCT/US2010/050542.
International Search Report mailed Nov. 29, 2010, in PCT/US2010/050542.
International Preliminary Report on Patentability Chapter I issued Aug. 7, 2012, in PCT/US2011/023791.
Written Opinion of the ISA mailed May 17, 2011, in PCT/US2011/023791.
International Search Report mailed May 17, 2011, in PCT/US2011/023791.
International Preliminary Report on Patentability Chapter I issued Feb. 21, 2012, in PCT/US2010/046244.
Written Opinion of the ISA mailed Feb. 8, 2011, in PCT/US2010/046244.
International Search Report mailed Feb. 8, 2011, in PCT/US2010/046244.
Invitation to Pay Additional Fees mailed Dec. 3, 2010, in PCT/US2010/046244.
Examination Report for NZ 598464, mailed Nov. 5, 2012.
Written Opinion of the ISA mailed Jun. 14, 2012, in PCT/US2012/032600.
International Search Report mailed Jun. 14, 2012, in PCT/US2012/032600.
Written Opinion of the ISA mailed Aug. 10, 2012, in PCT/US2012/037580.
International Search Report mailed Aug. 10, 2012, in PCT/US2012/037580.
Written Opinion of the ISA mailed Sep. 10, 2012, in PCT/US2012/040585.
International Search Report mailed Sep. 10, 2012, in PCT/US2012/040585.
"The role of the Extracellular Matrix in Cancer" Mar. 2001, U.S. Department of Energy: http:www.science.doe.gov/Accomplishments_Awards/Decades_Discovery/85.html.
Adamson, et al. (1974) "The Pathogenesis of Bleomycin-Induced Pulmonary Fibrosis in Mice" Am. J. Pathol. 77(2):185-189.
Akagawa, et al. (2007). "Systematic screening of lysyl oxidase-like (LOXL) family genes demonstrates that LOXL2 is a susceptibility gene to intracranial aneurysms." Hum Genet 121(3-4): 377-87.
Akhtar et al. (2002) "The sponge/Matrigel angiogenesis assay" Angiogenesis 5(1-2):75-80.
Akiri et al. (2003) "Lysyl Oxidase-Related Protein-1 Promotes Tumor Fibrosis and Tumor Progression in Vivo" Cancer Res. 63(7):1657-1666.
Albini et al. (1987) "A Rapid In Vitro Assay for Quantitating the Invasive Potential of Tumor Cells" Cancer Res. 47(12):3239-3245.
Albini et al. (2004) "The chemoinvasion assay: a tool to study tumor and endothelial cell invasion of basement membranes," Int. J. Dev. Biol. 48:563-571.
Aplin et al. (1998) "Signal transduction and signal modulation by cell adhesion receptors: the role of integrins, cadherins, immunoglobulin-cell adhesion molecules, and selectins" Pharmacol Rev. 50(2):197-263.
Arguello et al.(1992) "Incidence and Distribution of Experimental Metastases in Mutant Mice with Defective Organ Microenvironments (Genotypes Sl/Sld and W/Wv)" Cancer Research 52(8):2304-2309.
Armstrong et al. (1999) "Changes in Collagen Turnover in Early Acute Respiratory Distress Syndrome," Am. J. Respir. Crit. Care Med. 160:1910-1915.
Asuncion et al. (2001) "A Novel Human Lysyl Oxidase-Like Gene (LOXL4) on Chromosome 10q24 Has an Altered Scavenger Receptor Cysteine Rich Domain" Matrix Biol. 20(7):487-491.
Atabani, et al. (1997) "Identification of an Immunodominant Neutralizing and Protective Epitope from Measles Virus Fusion Protein by Using Human Sera from Acute Infection" J. Virology 71(10):7240-7245.
Atsawasuwan, et al. (2005). "Expression of lysyl oxidase isoforms in MC3T3-E1 osteoblastic cells." Biochem Biophys Res Commun 327(4): 1042-6.
Atsawasuwan, et al. (2008). "Lysyl oxidase binds transforming growth factor-? and regulates its signaling via amine oxidase activity." J Biol Chem 283(49): 34229-40.
Auerbach et al. (1974) "A simple procedure for the long-term cultivation of chicken embryos" Devel. Biol. 41(2):391-394.
Auerbach et al. (2003) "Angiogenesis Assays: A Critical Overview" Clinical Chemistry 49(1):32-40.
Barker, et al. (2011) "LOXL2-mediated matrix remodeling in metastasis and mammary gland involution" Cancer Res., 71(5):1561-1572.

(56) References Cited

OTHER PUBLICATIONS

Barry-Hamilton et al. (2010) "Allosteric inhibition of lysyl oxidase-like-2 impedes the development of a pathologic microenvironment" Nat.Med. 19(9):1009-1017.
Barzu, et al. "Characterization of B-Cell Epitopes on IpaB, an Invasion-Associated Antigen of Shigella flexneri: Identification of an Immunodominant Domain Recognized during Natural Infection" Infection and Immunity, Sep. 1993, vol. 61, No. 9, pp. 3825-3831.
Bedogni et al. (2004) "Topical treatment with inhibitors of the phosphatidylinositol 3'—kinase/Akt and Raf/mitogen-activated protein kinase kinase/extracellular signal-regulated kinase pathways reduces melanoma development in severe combined immunodeficient mice" Cancer Res. 64(7):2552-2560.
Beilmann et al. (2004) "Human primary co-culture angiogenesis assay reveals additive stimulation and different angiogenic properties of VEGF and HGF" Cytokine 26(4):178-185.
Bendig (1995) "Humanization of Rodent Monoclonal Antibodies by CDR Grafting" METHODS: Companion to Methods in Enzymology 8:83-93.
Berger et al. (2004) "A murine model of ex vivo angiogenesis using aortic disks grown in fibrin clot" Microvascular Res. 68(3):179-187.
Berithaupt, et al. (2008) "Demyelinating Myelin Oligodendrocyte Glycoprotein-Specific Autoantibody Response Is Focused on one Dominant Conformational Epitope Region in Rodents" J. Immunology 181(2):1255-1263.
Betakova, et al. (1998) "Monoclonal Anti-Idiotypic Antibodies Mimicking the Immunodominant Epitope of Influenza Virus Haemagglutinin Elicit Biologically Significant Immune Responses" J. Gen. Virology 79(Pt.3):461-470.
Bhowmick, et al. (2004). "Stromal fibroblasts in cancer initiation and progression." Nature 432(7015): 332-7.
Blacher et al. (2001) "Improved quantification of angiogenesis in the rat aortic ring assay" Angiogenesis 4(2):133-142.
Blast 2 Sequences (LOR-1 and LOR-2) results version BLASTP 2.2.14, Apr. 9, 2006.
Boneberg, et. al. (2009) "Angiogenesis and lymphangiogenesis are downregulated in primary breast cancer" Br. J. Cancer, 101(4):605-614.
Borel et al. (2001) "Lysyl Oxidase-Like Protein from Bovine Aorta. Isolation and Maturation to an Active Form by Bone Morphogenetic Protein-1" J. Biol. Chem. 276(52):48944-48949.
Bouez, et al. (2006) "The Lysyl Oxidase LOX is Absent in Basal and Squamous Cell Carcinomas and its Knockdown Induces an Invading Phenotype in a Skin Equivalent Model" Clinical Cancer Res. 12(5) 1463-1469.
Brody, et al. (1976) "Lung lysyl oxidase and elastin synthesis during compensatory lung growth" Chest 69(2 Suppl):271-272.
Bronson et al. (2005) "LOXL Null Mice Demonstrate Selective Dentate Structural Changes but Maintain Dentate Granule Cell and CA1 Pyramidal Cell Potentiation in the Hippocampus" Neurosci. Lett. 390(2):118-122.
Brown et al. (1996) "A novel in vitro assay for human angiogenesis" Laboratory Investigation 75(4):539-555.
Brown, et al. (2004) "Exploiting Tumour Hypoxia in Cancer Treatment" Nature Reviews 4:437-447.
Brukamp, et al. (2007) "Hypoxia and Podocyte-Specific Vhlh Deletion Confer Risk of Glomerular Disease" Am. J. Physiol. Renal. Physiol. 293(4):F1397-F1407.
Bruns, et al. "Vascular Endothelial Growth Factor Is an In Vivo Survival Factor for Tumor Endothelium in a Murine Model of Colorectal Carcinoma Liver Metastases" Cancer, 2000 vol. 89, No. 3, pp. 488-499.
Burbelo, et al. (1986) "Monoclonal Antibodies to Human Lysyl Oxidase" Coll. Relat. Res. 6(2):153-62.
Butcher, et al. (2009) "A Tense Situation: Forcing Tumour Progression" Nat. Rev. Cancer 9(2):108-122.
Cairns, et al. (2004) "Acute Hypoxia Enhances Spontaneous Lymph Node Metastasis in an Orthotopic Murine Model of Human cervical Carcinoma" Cancer Res. 64:2054-2061.
Cancer Reference Information; Detailed guide: Breast cancer, how is breast cancer diagnosed? www.cancer.org/docroot/CRI_2_4_3X_How_is_breast_cancer_diagnosed, Nov. 16, 2009.
Cardone, et al. (1997). "Prognostic value of desmoplastic reaction and lymphocytic infiltration in the management of breast cancer." Panminerva Med 39(3): 174-7.
Castera (2011) "Invasive and Non-Invasive Methods for the Assessment of Fibrosis and Disease Progression in Chronic Liver Disease," Best Pract. Res. Clin. Gastroent. 25:291-303.
Chan, et al. (2007) "Hypoxia, Gene Expression, and Metastasis" Cancer Metastasis Rev. 26(2):333-339.
Chang & Werb (2001) "The Many Faces of Metalloproteases: Cell Growth, Invasion, Angiogenesis and Metastasis" Trends Cell. Biol. 11(11):537-43.
Chang, et al. (2004) "Gene expression signature of fibroblast serum response predicts human cancer progression: similarities between tumors and wounds" PLoS Biol. 2(2):206-213.
Chanoki, et al. (1995) "Increased Expression of Lysyl Oxidase in Skin with Scleroderma" Br. J. Dermatol. 133(5):710-5.
Chen (2005) "Boyden chamber assay" Methods Mol. Biol. 294:15-22.
Chichester, et al. (1981). "Lung lysyl oxidase and prolyl hydroxylase: increases induced by cadmium chloride inhalation and the effect of β-aminopropionitrile in rats." Am Rev Respir Dis 124(6): 709-13.
Chioza, et al. (2001). "Mutations in the lysyl oxidase gene are not associated with amyotrophic lateral sclerosis." Amyotroph Lateral Scler Other Motor Neuron Disord 2(2): 93-7.
Chow, et al. "Identification and Expression of an Allergen Asp f 13 from Aspergillus Fumigatus and Epitope Mapping Using Human IgE Antibodies and Rabbit Polyclonal Antibodies," Biochem. J, 2000, vol. 346, pp. 423-431.
Christiansen & Rajasekaran (2006) "Reassessing Epithelial to Mesenchymal Transition as a Prerequisite for Carcinoma Invasion and Metastasis" Cancer Res., 66(17):8319-26.
Christiansen, et al. (2004) "Biological Impediments to Monoclonal Antibody-Based Cancer Immunotherapy" Mol. Cancer Ther. 3(11):1493-1501.
Chu & Peters (2008). "Serial analysis of the vascular endothelial transcriptome under static and shear stress conditions." Physiol Genomics 34(2): 185-92.
Chu, et al. (2008). "Glycogen synthase kinase-3? regulates DeltaNp63 gene transcription through the ?-catenin signaling pathway." J Cell Biochem 105(2): 447-53.
Chua et al., (2005) "Pulmonary Fibrosis Searching for Model Answers," Am J. Respir. Cell. Mol. Biol. 33:9-13.
Colman (1994) "Effects of Amino Acid Sequence Changes on Antibody-Antigen Interactions" Res. Immunol. 145(1):33-36.
Conti, et al. (2008). "The desmoplastic reaction surrounding hepatic colorectal adenocarcinoma metastases aids tumor growth and survival via alphav integrin ligation." Clin Cancer Res 14(20): 6405-13.
Csiszar (2001) "Lysyl Oxidases: a Novel Multifunctional Amine Oxidase Family" Prog. Nucl. Acid Res. 70:1-32.
Csiszar (2002) "Somatic Mutation of the Lysyl Oxidase Gene on Chromosome S023.1 in Colorectal Tumors" Int. J. Cancer 97:636-642.
Csiszar, et al. (1996) "Functional analysis of the promoter and first intron of the human lysyl oxidase gene." Mol Biol Rep 23(2): 97-108.
Database Embl [Online] Oct. 28, 2008, "Sequence 15133 from Patent WO2004061423", retrieved from EBI accession No. EMBL:FB530075, Database accession No. FB530075.
Database GENESEQ (Derwent, London, UK), Accession No. A13B07649, Feb. 14, 2002, 99.9% identical to SEQ ID No. 2.
Database Issued Patents (United States Patent & Trademark Office, Alexandria, VA) US Patent No. 6,300,092. Oct. 9, 2001 99.9% identical to SEQ ID No. 2.
De Eguileor et al. (2004) "Hirudo medicinalis: avascular tissues for clear-cut angiogenesis studies?" Current Pharmaceutical Design 10(16)1 979-1998.
Decitre, et al. (1998) "Lysyl oxidase-like protein localizes to sites of de novo fibrinogenesis in fibrosis and in the early stromal reaction of ductal breast carcinomas" Lab. Invest. 78(2):143-151.
Denko, et al. (2003) "Investigating Hypoxic Tumor Physiology through Gene Expression Patterns" Oncogene 22:5907-5914.

(56) References Cited

OTHER PUBLICATIONS

Dermer (1994) "Another Anniversary for the War on Cancer" Biotechnology 12:320.
Dillman, (1989) "Monoclonal antibodies for treating cancer" Ann. Intern. Med. 111(7):592-603.
Entrez Gene data base searching result in National Library of Medicine. 2010.
Erler, et al. (2004) "627 the role of Hypoxia-Induced Lysyl Oxidase in Cancer Progression, Tumor Response to Therapy and Patient Prognosis" Eur. J. Cancer Suppl. 2(8):190.
Erler, et al. (2004) "Lysyl Oxidase is Essential for Hypoxia-Induced Metastasis" Pro. Amer. Assoc. Cancer Res. 47:570.
Erler, et al. (2005) "Hypoxia promotes invasion and metastasis of breast cancer cells by increasing lysyl oxidase expression" Breast Cancer Res. 7 (Suppl 2):P5.05.
Erler, et al. (2006) "12 LOX is Essential for Hypoxia-Induced Metastasis" Radiother. Oncol. 78:S5.
Erler, et al. (2006) "Lysyl Oxidase is Essential for Hypoxia-Induced Metastasis" Nature 440(7088):1222-1226.
Erler, et al. (2006) "Lysyl Oxidase Mediates Hypoxic Control of Metastasis" Cancer Res. 66(21):10238-10241.
Erler, et al. (2009). "Hypoxia-induced lysyl oxidase is a Critical mediator of bone marrow cell recruitment to form the premetastatic niche." Cancer Cell 15(1): 35-44.
Evans et al. (1999) "Vaccine Therapy for Cancer—Fact or Fiction?" QJM. 92(6):299-307.
Example from Wikipedia, the free encyclopedia, "Monoclonal Antibody Therapy," (http://en.wikipedia.org/wiki/Antibody_therapy), accessed on Oct. 4, 2010.
Example of the USPTO's Written Description Training Materials, Revision 1, Mar. 25, 2008, 84 pages in length.
Ferrari, et al. (1991) "Identification of Immunodominant T Cell Epitopes of the Hepatitis B Virus Nucleocapsid Antigen" J. Clin. Invest. 88(1):214-222.
Fidler, et al. (1994) "The implications of angiogenesis for the biology and therapy of cancer metastasis" Cell 79(2):185-188.
Fodstad, et al. (1988) "A New Experimental Metastasis Model in Athymic Nude Mice, the Human Malignant Melanoma Lox" Intl. J. Cancer 41:442-449.A216.
Fogelgren, et al. (2005) "Cellular fibronectin binds to lysyl oxidase with high affinity and is critical f its proteolytic activation" J Biol. Chem. 280(26):24690-24697.
Fong, et al. (2007) "Lysyl oxidase-like 2 expression is increased in colon and esophageal tumors and associated with less differentiated colon tumors" Genes, Chromosomes and Cancer vol. 46(7):644-655.
Freshney (1983) Culture of Animal Cells: A Manual of Basic Technique, Alan R. Liss Inc.: NY:4.
Gacheru, et al. (1997). "Transcriptional and post-transcriptional control of lysyl oxidase expression in vascular smooth muscle cells: effects of TGF-?1 and serum deprivation." J Cell Biochem 65(3): 395-407.
Gelatt, (1977) "Animal models for glaucoma" Invest. Ophthalmol. Visual Sci. 16(7):592-596.
GenBank Public DNA Database Accession No. AAA59541.1 "Lysyl Oxidase [*Homo sapiens*]", Jan. 7, 1995.
GenBank Public DNA Database Accession No. AAB21243.1 "Lysyl Oxidase [*Homo sapiens*]", May 7, 1993.
GenBank Public DNA Database Accession No. AAB23549.1 "Lysyl Oxidase [*Homo sapiens*]", May 8, 1993.
GenBank Public Dna Database Accession No. AAD02130.1 "Lysyl Oxidase [*Homo sapiens*]", May 6, 1999.
GenBank Public Dna Database Accession No. AAH15090.1 "Lysyl Oxidase-Like 1 [*Homo sapiens*]", Jul. 15, 2006.
GenBank Public DNA Database Accession No. AAH74820.1 "Lysyl Oxidase [*Homo sapiens*]", Jul. 15, 2006.
GenBank Public DNA Database Accession No. AAH74872.1 "Lysyl Oxidase [*Homo sapiens*]", Jul. 15, 2006.
GenBank Public DNA Database Accession No. AAK51671.1 "Lysyl Oxidase-Like 3 Protein [*Homo sapiens*]", May 9, 2001.
GenBank Public DNA Database Accession No. AAK71934.1 "Lysyl Oxidase-Related Protein C [*Homo sapiens*]", Jul. 11, 2001.
GenBank Public DNA Database Accession No. AF039291 "*Homo sapiens* Lysyl Oxidase mRNA, Complete cds", May 6, 1999.
GenBank Public DNA Database Accession No. AF282619 "*Homo sapiens* Lysyl Oxidase-like 3 Protein mRNA, Complete cds", May 9, 2001.
GenBank Public DNA Database Accession No. AF338441 "*Homo sapiens* Lysyl Oxidase-Related Protein C (LOXC) mRNA, Complete cds", Jul. 11, 2001.
GenBank Public DNA Database Accession No. BC015090 "*Homo sapiens* Lysyl Oxidase-Like 1, mRNA (cDNA Clone MGC:16541 Image:4040510), Complete cds", Jul. 15, 2006.
GenBank Public DNA Database Accession No. BC018439 "Mus Musculus Lysyl Oxidase, mRNA (cDNA Clone MGC:11525 Image:2655752), Complete cds", Jul. 15, 2006.
GenBank Public DNA Database Accession No. BC074820 "*Homo sapiens* Lysyl Oxidase, mRNA (cDNA Clone MGC:104085 Image:30915536), complete cds", Jul. 15, 2006.
GenBank Public DNA Database Accession No. BC074872 "*Homo sapiens* Lysyl Oxidase, mRNA (cDNA Clone MGC:103851 Image:30915233), Complete cds", Jul. 15, 2006.
GenBank Public DNA Database Accession No. M84150 "Human Lysyl Oxidase Gene, Partial cds", Jan. 7, 1995.
GenBank Public DNA Database Accession No. M94054 "Human Lysyl Oxidase (LOX) mRNA, Complete cds", Jan. 7, 1995.
GenBank Public DNA Database Accession No. NM_002317 "*Homo sapiens* Lysyl Oxidase (LOX), Transcript Variant 1, mRNA", Mar. 13, 2011.
GenBank Public DNA Database Accession No. NM_033325 "Mus Musculus Lysyl Oxidase-Like 2 (Loxl2), mRNA", Mar. 10, 2011.
GenBank Public DNA Database Accession No. NP_002308 "Protein-Lysine 6-Oxidase Isoform 1 Preproprotein [*Homo sapiens*]", Mar. 13, 2011.
GenBank Public DNA Database Accession No. NP_002309 "Lysyl Oxidase 2 Precursor [*Homo sapiens*]", Mar. 27, 2011.
GenBank Public DNA Database Accession No. NP_005567 "Lysyl Oxidase Homolog 1 Preproprotein [*Homo sapiens*]", Mar. 27, 2011.
GenBank Public DNA Database Accession No. NP_034858 "Protein-Lysine 6-Oxidase Precursor [Mus Musculus]", Mar. 11, 2011.
GenBank Public DNA Database Accession No. NP_034859 "Lysyl Oxidase Homolog 1 Precursor [Mus Musculus]", Mar. 12, 2011.
GenBank Public DNA Database Accession No. NP_115587 "Lysyl Oxidase Homolog 4 Precursor [*Homo sapiens*]", Mar. 13, 2011.
GenBank Public DNA Database Accession No. NP_115882 "AP-1 Complex Subunit mu-1 Isoform 2 [*Homo sapiens*]", Mar. 13, 2011.
GenBank Public DNA Database Accession No. NP_201582 "Lysyl Oxidase Homolog 2 Precursor [Mus Musculus]", Mar. 10, 2011.
GenBank Public DNA Database Accession No. S45875 "Lysyl Oxidase [Human, Skin Fibroblasts, mRNA Partial, 1254 nt]", May 8, 1993.
GenBank Public DNA Database Accession No. S78694 "Lysyl Oxidase [Human, mRNA, 1780 nt]", May 7, 1993.
GenBank Public DNA Database Accession No. U89942 "Human Lysyl Oxidase-Related Protein (WS9-14) mRNA, Complete cds", Aug. 18, 2003.
GenBank Public DNA Database, Accession No. AAA59525.1 "Lysyl Oxidase [*Homo sapiens*]", Jan. 7, 1995.
Giampuzzi et al. (2000) "Lysyl Oxidase Activates the Transcription Activity of Human Collagen III Promoter. Possible Involvement of Ku Antigen" J. Biol. Chem. 275(46):36341-36349.
Giampuzzi, et al. (2001) "Down-Regulation Oflysyloxidase-Induced Tumorigenic Transformation in NRK-49F Cells Characterized by Constitutive Activation of Ras Proto-Oncogene" J Biol. Chem. 276(3I):29226-29232.
Go et al. (2003) "The rat aortic ring assay for in vitro study of angiogenesis" Methods Mol. Med. 85:59-64.
González-Iriate et al. (2003) "A modified chorioallantoic membrane assay allows for specific detection of endothelial apoptosis induced by antiangiogenic substances" Angiogenesis 6(3):251-254.
Görögh et al. (2007) "Selective Upregulation and Amplification of the Lysyl Oxidase Like-4 (LOXL4) Gene in Head and Neck Squamous cell Carcinoma" J. Pathol. 212(1):74-82.

(56) References Cited

OTHER PUBLICATIONS

Görögh, et al. (2008). "Functional analysis of the 5' flanking domain of the LOXL4 gene in head and neck squamous cell carcinoma cells." Int J Oncol 33(5): 1091-8.
Grant et al. (2001) "Overview: Rational Integration of Agents Directed at Novel Therapeutic Targets into Combination Chemotherapeutic Regimens" Curr. Opin. Investig Drugs 2(11):1600-1605.
Greenbaum et al. (2003) "Comparing protein abundance and mRNA expression levels on a genomic scale", Genome Biology 40 (9):117. 01-117.08.
Grigorescu (2006) "Noninvasive Biochemical Markers of Liver Fibrosis," J. Gastrointestin. Liver Dis. 15(2):149-159.
Gross, et al. (2001)"Idiopathic Pulmonary Fibrosis" N. Engl. J. Med. 345(7):517-525.
Guedez et al. (2003) "Quantitative assessment of angiogenic responses by the directed in vivo angiogenesis assay" Am. J. Pathol. 162(5):1431-1439.
Gulec et al. (2004) "A new in vitro assay for human tumor angiogenesis: three-dimensional human tumor angiogenesis assay" Ann. Surgical Oncology 11(1):99-104.
Gura (1997) "Systems for Identifying New Drugs Are Often Faulty" Science 278(5347):1041-1042.
Ham, et al. (2008) "144. Inhibition of an Extracellular Matrix Protein Increases Survival in Orthotopic Nude Mouse Models" J. Surg. Res. 144(2):239-240.
Harris et al. (1974) "Connective Tissue Amine Oxidase. II. Purification and Partial Characterization of Lysyl Oxidase from Chick Aorta" Biochim. Biophys. Acta 341(2):332-344.
Harrison & Lazo (1987) "High Dose Continuous Infusion of Bleomycin in Mice: A New Model for Drug-Induced Pulmonary Fibrosis" J. Pharmacol. Exp. Ther. 243(3):1185-1194.
Hartwell (1998) "Angiogenesis in P- and E-selectin-deficient mice" Microcirculation 5(2-3):173-178.
Hayashi, et al. (2004). "Comparative immunocytochemical localization of lysyl oxidase (LOX) and the lysyl oxidase-like (LOXL) proteins: changes in the expression of LOXL during development and growth of mouse tissues." J Mol Histol 35(8-9): 845-55.
Hein, et al. (2001). "Lysyl oxidases: expression in the fetal membranes and placenta." Placenta 22(1): 49-57.
Herrington et al., Principles and basic methodology of DNA/RNA detection by in situ hybridization. Chapter 4, pp. 69-102, Diagnostic Molecular Pathology vol. 1, Phenotyping and genotyping of intact cells, IRL Press, Oxford University Press, 1992.
Higgins, et al. (2007) "Hypoxia promotes a fibrogenesis in vivo via HIF-I stimulation of epithelial-to-mesenchymal transition" Journal Clinical Investigation 117(12):3810-20.
Hockel, et al. (2001) "Tumor Hypoxia: Definitions and Current Clinical, Biologic and Molecular Aspects" Journal of the National Cancer Institute. 93(4):266-276.
Hohenester et al. (1999) "Crystal Structure of a Scavenger Receptor Cysteine-Rich Domain Sheds Light on an Ancient Superfamily" Nat. Struct. Biol. 6(3):228-232.
Hollosi, et al. (2009). "Lysyl oxidase-like 2 promotes migration in noninvasive breast cancer cells but not in normal breast epithelial cells." Int J Cancer 125(2):318-327.
Hornstra et al. (2003) "Lysyl Oxidase is Required for Vascular and Diaphragmatic Development in Mice" J. Biol. Chem. 278(16):14387-14393.
Huang et al. (2001) "Cloning and Characterization of a Human Lysyl Oxidase-Like 3 Gene (hLOXL3)" Matrix Biol. 20(2):153-157.
Ishak et al. (1995) "Histological Grading and Staging of Chronic Hepatitis," J. Hepatol. 22:696-699.
Ito et al. (2001) "Molecular Cloning and Biological Activity of a Novel Lysyl Oxidase-Related Gene Expressed in Cartilage" J. Biol. Chem. 276(26):24023-24029.
Jain (1994) "Barriers to Drug Delivery in Solid Tumors" Scientific American 271(1):58-65.
Jakobsson et al.(1994) "A Morphometric Method to Evaluate Angiogenesis Kinetics in the Rat Mesentry" Intl. J. Exp. Pathol. 75(3):214-219.
Jansen & Csiszar (2007). "Intracellular localization of the matrix enzyme lysyl oxidase in polarized epithelial cells." Matrix Biol 26(2): 136-9.
Jansen, et al. (2006) "Lysyl oxidase regulates kidney epithelial cell phenotype" ASMB Meeting Abstrat/Matrix Biology 25:S92.
Jourdan Le-Saux et al. (1994) "Lysyl Oxidase cDNA of Myofibroblast from Mouse Fibrotic Liver" Biochem. Biophys. Res. Comm. 199(2):587-592.
Jourdan Le-Saux et al. (1999) "The LOXL2 Gene Encodes a New Lysyl Oxidase-Like Protein and Is Expressed at High Levels in Reproductive Tissues" J. Biol. Chem. 274(18):12939-12944.
Jourdan Le-Saux et al. (2001) "Central Nervous System, Uterus, Heart, and Leukocyte Expression of the LOXL3 Gene, Encoding a Novel Lysyl Oxidase-Like Protein" Genomics 74(2):211-218.
Jourdan-Le Saux, et al. (1998). "The human lysyl oxidase-related gene (LOXL2) maps between markers D8S280 and D8S278 on chromosome 8p21.2-p21.3." Genomics 51(2): 305-7.
Jourdan-Le Saux, et al. (2000). "The mouse lysyl oxidase-like 2 gene (mLOXL2) maps to chromosome 14 and is highly expressed in skin, lung and thymus." Matrix Biol 19(2): 179-83.
Julien et al., (2008) "A reproducible and quantifiable model of choroidal neovascularization induced by VEGF a after subretinal adenoviral gene transfer in the rabbit" Molecular Vision 14: 1358-1372.
Jung, et al. (2003). "Purification of enzymatically active human lysyl oxidase and lysyl oxidase-like protein from *Escherichia coli* inclusion bodies." Protein Expr Purif 31(2): 240-6.
Kagan & Li (2003) "Lysyl Oxidase: Properties, Specificity, and Biological Roles Inside and Outside of the Cell" J. Cell. Biochem 88(4):660-672.
Kagan (1994) "Lysyl Oxidase: Mechanism, Regulation and Relationship to Liver Fibrosis" Pathol. Res. Pract. 190(9-10):910-919.
Kagan et al. (1982) "Lysyl Oxidase: Preparation and Role in Elastin Biosynthesis" Meth. Enzymol. 82(a):637-649.
Kagan, et al. (1995) "Expression of Lysyl Oxidase from cDNA Constructs in Mammalian Cells: The Propeptide Region Is Not Essential to the Folding and Secretion of the Functional Enzyme" J. Cell Biochem. 59(3):329-38.
Kagan, et al. (1995). "Catalytic properties and structural components of lysyl oxidase." Novartis Foundation Symp. 192: 100-15; discussion 115-21.
Kagan, H.M. (2000) "Intra-and Extracellular Enzymes of Collagen Biosynthesis as Biological and Chemical Targets in the Control of Fibrosis" Acta Tropica 77(I):147-152.
Kaiser et al. (2006) "Cancer. First pass at cancer genome reveals complex landscape" Science 313(5792):1370.
Kaku, et al. (2007). "Post-translational modifications of collagen upon BMP-induced osteoblast differentiation." Biochem Biophys Res Commun 359(3): 463-8.
Kamath et al. (2001) "Signaling from Protease-Activated Receptor-1 Inhibits Migration and Invasion of Breast Cancer Cells" Cancer Res. 61(15):5933-5940.
Kaneda et al. (2004) "Lysyl Oxidase is a Tumor Suppressor Gene Inactivated by Methylation and Loss of Heterozygosity in Human Gastric Cancers" Cancer Res. 64(18):6410-6415.
Kang, et al. "Prosaposin Inhibits Tumor Metastasis Via Paracrine and Endocrine Stimulation of Stromal p53 and Tsp-1" Proc. Natl. Acad. Sci. U.S.A. 106(29):12115-12120. (2009).
Kenyon, et al. (1991) "Lysyl Oxidase and rrg Messenger RNA" Science 253:802.
Kenyon, et al. (2003) "TGF-[beta]1 Causes Airway Fibrosis and Increased Collagen I and III mRNA in Mice" Thorax 58(9):772-777.
Khakoo, et al. (1997) "Congenital Cutis Laxa and Lysyl Oxidase Deficiency" Clin. Genet. 51(2):109-14.
Kim et al. (1995) "A New Gene with Sequence and Structural Similarity to the Gene Encoding Human Lysyl Oxidase" J. Biol. Chem. 270(13):7176-7182.
Kim et al. (1999) "Coexpression of the Lysyl Oxidase-Like Gene (LOXL) and the Gene Encoding Type III Procollagen in Induced Liver Fibrosis" J. Cell Biochem. 72(2):181-188.
Kim et al. (2003) "Expression and Purification of Enzymatically Active Forms of the Human Lysyl Oxidase-Like Protein 4" J. Biol. Chem. 278(52):52071-52074.

(56) References Cited

OTHER PUBLICATIONS

Kim, et al. (1997). "A highly polymorphic (CA) repeat sequence in the human lysyl oxidase-like gene." Clin Genet 51(2): 131-2.
Kirschmann et al. (2002) "A Molecular Role for Lysyl Oxidase in Breast Cancer Invasion Cancer Res." Cancer Res. 62(15):4478-4483.
Kirschmann, et al. (1999) "Differentially expressed genes associated with the metastatic phenotype in breast cancer" Breast Cancer Res Treat. 55(2):127-136.
Klutke, et al. (2008). "Decreased endopelvic fascia elastin content in uterine prolapse." Acta Obstet Gynecol Scand 87(1): 111-5.
Knodell et al. (1981) "Formulation and Application of a Numerical Scoring System for Assessing Histological Activity in Asymptomatic Chronic Active Hepatitis," Hepatol. 1(5):431-435.
Kragh et al. (2003) "In vivo chamber angiogenesis assay: an optimized Matrigel plug assay for fast assessment of anti-angiogenic activity" Intl. J. Oncology 22(2):305-311.
Kragh et al. (2004) "A versatile in vivo chamber angiogenesis assay for measuring anti-angiogenic activity in mice" Oncology Reports 11(2):303-307.
Krebs & Krawetz (1993) "Lysyl Oxidase Copper-Talon Complex: A Model" Biochim. Biophys. Acta 1202(1):7-12.
Kresse, et al. (2008). "DNA copy number changes in high-grade malignant peripheral nerve sheath tumors by array CGH." Mol Cancer 7: 48.
Laczko, et al. (2007). "Active lysyl oxidase (LOX) correlates with focal adhesion kinase (FAK)/paxillin activation and migration in invasive astrocytes." Neuropathol Appl Neurobiol 33(6): 631-43.
Lazarus et al. (1995) "Induction of Human Monocyte Motility by Lysyl Oxidase" Matrix Biol. 14(9):727-731.
Le et al. (2007) "Expression and Prognostic Significance of a Panel of Tissue Hypoxia Markers in Head-and-Neck Squamous Cell Carcinoma," Int. J. Radiation Oncology Biol. Phys. 69(1):157-175.
Lelievre, et al. (2008). "VE-statin/egfl7 regulates vascular elastogenesis by interacting with lysyl oxidases." EMBO J 27(12): 1658-70.
Levene et al. (1985) "Possibilities for the Therapeutic Control of Fibrosis," Br. J. Dermatol. 112(3):363-371.
Li et al. (1997) "Localization and Activity of Lysyl Oxidase within Nuclei of Fibrogenic Cells" Proc. Natl. Acad. Sci. USA 94(24):12817-12822.
Li et al. (1999) "Liver Fibrogenesis and the Role of Hepatic Stellate Cells: New Insights and Prospects for Therapy," J. of Gastroentero. and Hepatol. 14:618-633.
Li, et al. (2007) "Tumor microenvironment: the role of the tumor stroma in cancer." J Cell Biochem 101(4): 805-15.
Lichtenberg et al. (1999) "The rat Subcutaneous Air Sac model: a quantitative assay of antiangiogenesis in induced vessels" Am. J. Pharmacol. Toxicology 84(1):34-40.
Lucero & Kagan (2006). "Lysyl oxidase: an oxidative enzyme and effector of cell function." Cell Mol Life Sci 63(19-20): 2304-16.
Lugassy, et al. (2012) "The Enzymatic Activity of Lysyl Oxidas-like-2 (LOXL2) Is Not Required for LOXL2-induced Inhibition of Keratinocyte Differentiation", Journal of Biological Chemistry 287(5):3541-3549.
Luo, et al. (1998) "Differential Inhibition of Fluid Accumulation and Tumor Growth in Two Mouse Ascites Tumors by an Antivascular Endothelial Growth Factor/Permeability Factor Neutralizing Antibody" Cancer Res. 58(12):2594-2600.
Luo, et al. (1998) "Significant expression of vascular endothelial growth factor/vascular permeability factor in mouse ascites tumors" Cancer Res., 58(12):2652-2660.
Macartney-Coxson, et al. (2008). "Metastatic susceptibility locus, an 8p hot-spot for tumour progression disrupted in colorectal liver metastases: 13 candidate genes examined at the DNA, mRNA and protein level." BMC Cancer 8: 187.
Madakamutil, et al. "Immunodominance in the TCR Repertoire of ? TCR Peptide-Specific CD4+ Treg Population that Controls Experimental Autoimmune Encephalomyelitis" J. Immunology 2008, vol. 180, pp. 4577-4585.

Maier et al. (2009) "Correlation of mRNA and protein in complex biological samples", FEBS Letters 583 (24):3966-3973.
Mäki & Kivirikko (2001) "Cloning and Characterization of a Fourth Human Lysyl Oxidase Isoenzyme" Biochem. J. 355(Pt 2):381-387.
Mäki, et al. (2001). "Cloning and characterization of a fifth human lysyl oxidase isoenzyme: the third member of the lysyl oxidase-related subfamily with four scavenger receptor cysteine-rich domains." Matrix Biol 20(7): 493-6.
Manns et al. (2011) "A Phase-2B Trial to Evaluate the Safety, Tolerability and Efficacy of a Caspase Inhibitor, GS-9450, in Adults Failing PEG/RBV Therapy for Chronic HCV Infection," J Hepatology. (2011) 54 Supplement 1: S55-S56.
Masson et al. (2002) "Mouse Aortic Ring Assay: A New Approach of the Molecular Genetics of Angiogenesis" Biol. Proc. Online 4:24-31.
Mattioli, et al. (1995) "Mimicry of the Immunodominant Conformation-Dependent Antigenic Site of Hepatitis a Virus by Motifs Selected from Synthetic Peptide Libraries," Journal of Virology 69(9):5294-5299.
Mbeunkui, et al. (2007) "Identification of differentially secreted biomarkers using LC-MS/MS in isogenic cell lines representing a progression of breast cancer" Journal Proteome Res. 6:2993-3002.
Mckechnie et al. (2003) "Hr44 Secreted wtih exosomes: Loss from Ciliary epithelium in response to inflammation" IOVS 44(6): 2650-2656.
Mehal et al. (2011) "Expressway to the Core of Fibrosis," Nat. Med. 17(5):552-553.
Miller et al. (2004) "A novel technique for quantifying changes in vascular density, endothelial cell proliferation and protein expression in response to modulators of angiogenesis using the chick chorioallantoic membrane (CAM) assay" J. Translational Med. 2(1):4.
Molnar et al. (2003) "Structural and functional diversity of lysyl oxidase and the LOX-like proteins" Biochim Biophys Acta. 1647(1-2):220-224.
Molnar, et al. (2005). "Drosophila lysyl oxidases Dmloxl-1 and Dmloxl-2 are differentially expressed and the active DmLOXL-1 influences gene expression and development." J Biol Chem 280(24): 22977-85.
Monticone, et al. (2004). "Gene expression profile of human bone marrow stromal cells determined by restriction fragment differential display analysis." J Cell Biochem 92(4): 733-44.
Morbidelli et al. (2004) "The rabbit corneal pocket assay for the study of angiogenesis" Cancer Treatment Res. 117:147-151.
Müller, et al. (2006). "Lung fibroblasts from patients with emphysema show markers of senescence in vitro." Respir Res 7: 32.
Murawaki et al. (1991) "Serum Lysyl Oxidase Activity in Chronic Liver Disease in Comparison with Serum Levels of Prolyl Hydroxylase and Laminin" Hepatology 14(6):1167-1173.
Nagaoka, et al. (2008). "1,25(OH)2D3 regulates collagen quality in an osteoblastic cell culture system." Biochem Biophys Res Commun 377(2): 674-8.
Nakken, et al. (2007). "Multiple inflammatory-, tissue remodelling- and fibrosis genes are differentially transcribed in the livers of Abcb4 (-/-) mice harbouring chronic cholangitis." Scand J Gastroenterol 42(10): 1245-55.
National Cancer Institute; Staging: Questions and answers, www.cancer.gov/cancertopics/factsheet/detection/staging, Nov. 6, 2009.
NCBI dbSNP record for LOXL2, available at http://www.ncbi.nlm.nih.gov/projects/SNP/snp_ref.cqi?locusld=4017, retrieved Apr. 19, 2012.
Nehls et al. (1995) "A novel, microcarrier-based in vitro assay for rapid and reliable quantification of three-dimensional cell migration and angiogenesis" Microvascular Res. 50(3):311-322.
Nelson et al. (1988) "Effect of beta-Aminopropionitrile and Ascorbate on Fibroblast Migration" Proc. Soc. Exp. Biol. Med. 188(3):346-352.
Nguyen et al. (1994) "Quantitation of angiogenesis and antiangiogenesis in the chick embryo chorioallantoic membrane" Microvascular Res. 47(1):31-40.
Nicosia et al. (1990) "Growth of microvessels in serum-free matrix culture of rat aorta. A quantitative assay of angiogenesis in vitro" Laboratory Investig. 63(1):115-122.

(56) References Cited

OTHER PUBLICATIONS

Nissanov et al. (1995) "Automatic vessel segmentation and quantification of the rat aortic ring assay of angiogenesis" Laboratory Investig. 73(5):734-739.
Noblesse, et al. (2004) "Lsyl oxidase-like and lysysl oxidase are present in the dermis and epidermis of a skin equivalent and in himan skin and are associate to elastic fibers" J. Investig. Dermatol., 122:621-630.
Norrby (1992) "On the quantitative rat mesenteric-window angiogenesis assay" EXS 61:282-286.
Norrby (2006) "In vivo models of angiogenesis" J. Cell. Mol. Med. 10(3):588-612.
Ogata et al. (1996) "Changes in alveolar capilary formation in growing rat lung by repeated injections of a lathyrogen" Growth, Development and Aging 60:153-160.
Okada et al. (1995) "A quantative in vivo method of analyzing human tumor-induced angiogenesis in mice using agarose microencapsulation and hemoglobin enzyme-linked immunosorbent assay" Japan. J. Cancer Res. 86(12):1182-1188.
Ooshima & Midorikawa (1977) "Increased lysyl Oxidase Activity in Blood Vessels of Hypertensive Rats and Effect of beta-Aminopropionitrile on Arteriosclerosis" Jpn. Circ. J. 41(12):1337-40.
Orimo & Weinberg (2006). "Stromal fibroblasts in cancer: a novel tumor-promoting cell type." Cell Cycle 5(15): 1597-601.
Orimo, et al. (2001). "Cancer-associated myofibroblasts possess various factors to promote endometrial tumor progression." Clin Cancer Res 7(10): 3097-105.
Palamakumbura et al. (2002) "A Fluorometric Assay for Detection of Lysyl Oxidase Enzyme Activity in Biological Samples" Anal. Biochem. 300(2):245-251.
Palamakumbura, et al. (2004) "The Propeptide Domain of Lysyl Oxidase Induces Phenotypic Reversion of Ras-Transformed cells" J. Biol. Chem. 279(39):40593-40600.
Panchenko, et al. (1996) "Metalloproteinase activity secreted by fibrogenic cells in the processing of prolysyl oxidase Potential Role of Procollagen C-Proteinase" J Biol Chem. 271(12):7113-7119.
Parsons-Wingerter et al. (2000) "Fibroblast growth factor-2 selectively stimulates angiogenesis of small vessels in arterial tree" Arteriosclerosis Thrombosis Vasc. Biol. 20(5):1250-1256.
Pascal, et al. (2005). "Comparison of replicative senescence and stress-induced premature senescence combining differential display and low-density DNA arrays." FEBS Lett 579(17): 3651-9.
Paul (1993) Fundamental Immunology, 3rd Ed., Raven Press: NY:292-295.
Payne, et al. (2005) "Lysyl oxidase regulates breast cancer cell migration and adhesion through a hydrogen peroxide-mediated mechanism" Cancer Res. 65(24):11429-11436.
Payne, et al. (2007). "Paradoxical roles for lysyl oxidases in cancer—a prospect." J Cell Biochem 101(6): 1338-54.
Peinado, et al. (2005) "A Molecular Role for Lysyl Oxidase-Like 2 Enzyme in Snail Regulation and Tumor Progression" EMBO J. 24(19):3446-3458.
Peinado, et al. (2005). "Switching on-off Snail: LOXL2 versus GSK3?." Cell Cycle 4(12): 1749-52.
Peinado, et al. (2008) "Lysyl Oxidase-like 2 as a New Poor Prognosis Marker of Squamous Cell Carcinomas" Cancer Research 68(12):4541-4550.
Peroutka, et al. (2008) "Enhanced Protein Expression in Mammalian Cells Using Engineered SUMO Fusions: Secreted phospholipase A2" Protein Sci. 17(9):1586-1595.
Peyrol, et al. (1997) "Lysyl oxidase gene expression in the stromal reaction to in situ and invasive ductal breast carcinoma" Am J. Pathol. 150(2):497-507.
Pinnell (1982) "Molecular Defects in the Ehlers-Danlos Syndrome" J. Invest. Dermatol. 79(Supp 1):90S-92S.
Pires Martins, et al. (2001). "Whole-body gene expression by data mining." Genomics 72(1): 34-42.
Polgar, et al. (2007). "Lysyl oxidase interacts with hormone placental lactogen and synergistically promotes breast epithelial cell proliferation and migration." J Biol Chem 282(5): 3262-72.
Postlethwaite, et al. (1987) "Stimulation of the chemotactic migration of human fibroblasts by transforming growth factor?" J. Exp. Med. 165(1):251-256.
Postovit, et al. (2008). "Hypoxia/reoxygenation: a dynamic regulator of lysyl oxidase-facilitated breast cancer migration." J Cell Biochem 103(5): 1369-78.
Pouysségur, et al. (2006) "Hypoxia Signalling in Cancer and Approaches to Enforce Tumour Regression" Nature 441(7092):437-443.
Presta et al. (1999) "Purine analogue 6-methylmercaptopurine riboside inhibits early and late phases of the angiogenesis process" Cancer Res. 59(10):2417-2424.
R&D Systems. Ordering Information: Catalog No. MAB2639. Anti-human lysyl oxidase homolog 2 monoclonal antibody. Apr. 18, 2005.
Radisky, et al. (2001) "Tumors Are Unique Organs Defined by Abnormal Signaling and Context" Semin. Cancer Bio. 11(2):87-95.
Rakic et al. (2003) "Placental Growth Factor, a Member of the VEGF Family, Contributes to the Development of Choroidal Neovascularization" Invest. Ophthalmol. Vis. Sci. 44(7):3186-3193.
Rayton et al. (1979) "Induction of Lysyl Oxidase with Copper. Properties of an In Vitro System" J. Biol. Chem. 254(3):621-626.
Reed et al.(2007) "Culture of murine aortic explants in 3-dimensional extracellular matrix: a novel, miniaturized assay of angiogenesis in vitro" Microvascular Res. 73(3):248-252.
Reichmann, et al. (1988) "Reshaping Human Antibodies for Therapy" Nature 332(6162):323-327.
Ren, et al. (1998) "Reduced lysyl oxidase messenger RNA levels in experimental and human prostate cancer" Cancer Res. 58:1285-1290.
Resnick, et al. (1994) "The SRCR Superfamily: A Family Reminiscent of the Ig Superfamily" Trends Biochem. Sci. 19(1):5-8.
Ribatti (2004) "The first evidence of the tumor-induced angiogenesis in vivo by using the chorioallantoic membrane assay dated 1913" Leukemia 18(8):1350-1351.
Ribatti et al. (1996) "The chick embryo chorioallantoic membrane as a model for in vivo research on angiogenesis" Intl. J. Devel. Biol. 40(6):1189-1197.
Ribatti et al. (1997) "New model for the study of angiogenesis and antiangiogenesis in the chick embryo chorioallantoic membrane: the gelatin sponge/chorioallantoic membrane assay" J. Vascular Res. 34(6):455-463.
Ribatti et al. (2000) "The Chick Embryo Chorioallantoic Membrane as a Model for In Vivo Research on Anti-Angiogenesis" Curr. Pharmacol. Biotechnol. 1(1):73-82.
Richardson et al. (2003) "Observations on the use of the avian chorioallantoic membrane (CAM) model in investigations into angiogenesis" Curr. Drug Targets Cardiovasc. Hematol. Disorders 3(2):155-185.
Rodriguez et al. (2010) "Modulation of lysyl oxidase-like 2 enzymatic activity by an allosteric antibody inhibitor" J. Biol. Chem. 285:20964-20974.
Rodriguez, et al. (2008) Regulation of lysyl oxidase in vascular cells: lysyl oxidase as a new player in cardiovascular diseases. Cardiovasc Res. 79(I):7-13.
Roskoski (2007) "Vascular endothelial growth factor (VEGF) signaling in tumor progression" Critical Reviews in Oncology/Hematology 62:179-213.
Rost, et al. (2003) "Reduction of LOX- and LOXL2-mRNA expression in head and neck squamous cell carcinomas" Anticancer Res. 23(2B):1565-1573.
Royce, et al. (1980) "Reduced Lysyl Oxidase Activity in Skin Fibroblasts from Patients with Menkes' Syndrome," Biochem. J. 192(2):579-86.
Rozalski, et al. (1989) "Epitope Specificities of Murine Monoclonal and Rabbit Polyclonal Antibodies against Enterobacterial Lipopolysaccharides of the Re Chemotype" Infection and Immunity, 57(9):2645-2652.
Rucker et al. (1998) "Copper, Lysyl Oxidase, and Extracellular Matrix Protein Cross-Linking" Am. J. Clin. Nutr. 67(5 Suppl):996S-1002S.

(56) References Cited

OTHER PUBLICATIONS

Ruckert, et al. (2009) "Functional analysis of LOXL2 in pancreatic carcinoma" International Journal of Colorectal Disease; Clinical and Molecular Gastroenterology and Surgery, Springer, Berlin, DE, 25(3):303-311.
Rudikoff, et al. (1982) "Single Amino Acid Substitution Altering Antigen-Binding Specificity" PNAS USA 79(6):1979-1983.
Saito, et al. (1997) "Regulation of a novel gene encoding a lysyl o5cidase-related protein in cellular adhesion and senescence" J. Biol Chem. 272(13):8157-8160.
Salnikow, et al. (2008). "Regulation of hypoxia-inducible genes by ETS1 transcription factor." Carcinogenesis 29(8): 1493-9.
Sappino, et al. (1988) "Smooth-Muscle Differentiation in Stromal Cells of Malignant and Non-Malignant Breast Tissues" Int. J. Cancer 41(5):707-712. Abstract Only.
Sasaki et al. (1998) "Mac-2 Binding Protein is a Cell-Adhesive Protein of the Extracellular Matrix Which Self-Assembles into Ring-Like Structures and Binds ?1 Integrins, Collagens and Fibronectin" EMBO J. 17(6):1606-1613.
Satoh, et al. (2003) "Inhibition of local adhesion kinase by antisense oligonucleotides enhances the sensitivity of breast cancer cells to camptothecins" Biocell 27(1):47-55.
Schena et al. (2005) "Pathogenic Mechanisms of Diabetic Nephropathy," J. Am. Soc. Nephrol. 16:S30-S33.
Scheuer (1991) "Classification of Chronic Viral Hepatitis: A Need for Reassessment," J. Hepatol. 13:372-374.
Schlotzer-Schrehardt, et al. (2008). "Genotype-correlated expression of lysyl oxidase-like 1 in ocular tissues of patients with pseudoexfoliation syndrome/glaucoma and normal patients." Am J Pathol 173(6): 1724-35.
Schmidt, et al. (2007). "[Mapping of a deletion interval on 8p21-22 in prostate cancer by gene dosage PCR]." Verh Dtsch Ges Pathol 91: 302-7.
Sebban, et al. (2009). "Lysyl oxidase-like 4 is alternatively spliced in an anatomic site-specific manner in tumors involving the serosal cavities." Virchows Arch 454(1): 71-9.
Selman, et al. (2006) "Gene Expression Profiles Distinguish Idiopathic Pulmonary Fibrosis from Hypersensitivity Pneumonitis" Am. J. Respir. Crit.Care Med. 173(2):188-198.
Sequence search result (Neufeld) 2010.
Sevil, et al. (1996) "Pharmacokinetic Analysis of Beta-Aminopropionitrile in Rabbits" Vet Res. 27(2):117-123 (Abstract only).
Sheppard (2006) "Transforming Growth Factor?: A Central Modulator of Pulmonary and Airway Inflammation and Fibrosis" Proc. Am. Thorac. Soc. 3(5):413-417.
Sheridan, et al. (1979) "Increased Lysyl Oxidase Activity in Aortas of Hypertensive Rats and Effect of Beta-Aminopropionitrile" Exp Mol Pathol. 30(2):315-324.
Shieh, et al. (2007) "Association of expression aberrances and genetic polymorphisms of lysyl oxidase with areca-associated oral tumorigenesis" Clinical Cancer Res. 13(15):4378-4385.
Siegel et al. (1978) "Biochemical and Immunochemical Study of Lysyl Oxidase in Experimental Hepatic Fibrosis in the Rat" Proc. Natl. Acad. Sci. USA 75(6):2945-2949.
Siegers, et al. (1986) "Hepatoprotection by Malotilate against Carbon Tetrachloride-Alcohol Induced Liver Fibrosis" Inflammation Res. 18(5-6):600-603. Abstract Only.
Siemann et al. "Tumor Vasculature: a Target for Anticancer Therapies" in: "Vascular-Targeted Therapies in Oncology", Mar. 10, 2006, John Wiley & Sons. Ltd. Chichester, UK.
Sion, et al. (2006) "Lysyl oxidase (lox) and hypoxia-induced metastases" Cancer Biology & Therapy, 5(8):909-911.
Sivakumar, et al. (2008) "Upregulation of Lysyl Oxidase and MMPs During Cardiac Remodeling in Human Dilated Cardiomyopathy" Mol Cell Biochem 307(1-2):159-167.
Smith-Mungo & Kagan (1998) "Lysyl Oxidase: Properties, Regulation and Multiple Functions in Biology" Matrix Biol. 16: 387-98.

Sommer, et al. (1993) "Transient expression of lysyl oxidase by liver myofibroblasts in murine schistosomiasis" Laboratory Investigation 69(4):460-470.
Sørensen, et al. (2007) "Hypoxia-induced Expression of Endogenous Markers in Vitro is Highly Influenced by pH" Radiotherapy and Oncology 83:362-366.
Stapleton, et al. (1987) "Neutralization Escape Mutants Define a Dominant Immunogenic Neutralization Site on Hepatitis a Virus," Journal of Virology 61(2):491-498.
Stassar, et al. (2001) "Identification of Human renal cell carcinoma associated genes by suppression subtractive hybridization" Br. J. Cancer 85(9):1372-1382.
Stassen (1976) "Properties of Highly Purified Lysyl Oxidase from Embryonic Chick Cartilage" Biophys. Acta 438(1):49-60.
Stiffey-Wilusz et al. (2001) "An ex vivo angiogenesis assay utilizing commercial porcine carotid artery: modification of the rat aortic ring assay" Angiogenesis 4(1):3-9.
Szabo, et al. (1997). "The human lysyl oxidase-like gene maps between STS markers D15S215 and GHLC.GCT7C09 on chromosome 15." Hum Genet 101(2): 198-200.
Szauter, et al. (2005). "Lysyl oxidase in development, aging and pathologies of the skin." Pathol Biol (Paris) 53(7): 448-56.
Tamura, et al. (1998) "Inhibition of Cell Migration, Spreading, and Focal Adhesions by Tumor Suppressor PTEN" Science 280:1614-1618.
Tang, et al. (1983). "Reaction of aortic lysyl oxidase with ?-aminopropionitrile." J Biol Chem 258(7): 4331-8.
Tang, et al. (1984). "?-substituted ethylamine derivatives as suicide inhibitors of lysyl oxidase." J Biol Chem 259(2): 975-9.
Tarp, et al. (2007) "Identification of a Novel Cancer-Specific Immunodominant Glycopeptide Epitope in the MUC1 Tandem Repeat," Glycobiology 17(2):197-209.
Thiery, et al. (2003) "Epithelial-Mesenchymal Transitions in Development and Pathologies" Curr. Opin. Cell. Biol. 15(6):740-6.
Thomassin, et al. (2005) "The Pro-Regions of Lysyl Oxidase and Lysyl Oxidase-Like 1 Are Required for Deposition onto Elastic Fibers" J Biol. Chem. Dec. 30, 2005; 280(52):42848-55.
Tockman et al. (1992) "Consideration in Bringing a Cancer Biomarker to Clinical Application" Cancer Res. 52:2711s-2718s.
Topp, et al. (1998) "Antibody Transport in Cultured Tumor Cell Layers" J. Control. Release 53(1-3):15-23.
Trackman & Kagan (1979). "Nonpeptidyl amine inhibitors are substrates of lysyl oxidase." J Biol Chem 254(16): 7831-6.
Trackman et al. (1981) "Development of a Peroxidase-Coupled Fluorometric Assay for Lysyl Oxidase" Anal. Biochem. 113(2):336-342.
Trackman, et al. (1991) "Cloning of rat aorta lysyl oxidase cDNA: Complete codons and predicted amino acid sequence" Biochem. 29(20)4863-4870 (1990 and Corrected Page: Biochem. 30(33):8282.
Trentham, et al. (1977) "Autoimmunity to Type II Collagen: An Experimental Model of Arthritis" J. Experimental Medicine 146:857-868.
Trivedy, et al. (1999) "The Upregulation of Lysyl Oxidase in Oral Submucous Fibrosis and Squamous Cell Carcinoma" J. Oral Pathol. Med. 28(6):246-251.
Tzortzaki et al. (2006) "Active Remodeling in Idiopathic Interstitial Pneumonias: Evaluation of Collagen Types XII and XIV," J. Histochem. & Cytochem. 54(6):693-700.
Vadasz, et al. (2005). "Abnormal deposition of collagen around hepatocytes in Wilson's disease is associated with hepatocyte specific expression of lysyl oxidase and lysyl oxidase like protein-2." J Hepatol 43(3): 499-507.
Van Bergen et al. "The role of LOXa nd LOXL2 in wound healing after glaucoma filtration surgery", European association for vision and eye research, Oct. 8, 2010, Retrieved from the Internet: URL:http://www.everbe/view_abstract.php?abs_id=5411.
Van Lancker, et al. (1995) "Patterns of axillary lymph node metastasis in breast cancer" Am. J. Clin. Oncol. 18(3):267-272.
Van Roy, et al. (1986) "Invasiveness and Metastatic Capability of Rat Fibroblast-like Cells before and after Transfection with Immortalizing and Transforming Genes" Cancer Res. 46:4787-4795.

(56) References Cited

OTHER PUBLICATIONS

Vautherot, et al. "Bovine Coronavirus Spike Glycoprotein: Localization of an Immunodominant Region at the Amino-Terminal End of S2" Journal of General Virology, 1992, vol. 73, pp. 3289-3294.
Waldmann (2003) "Immunotherapy: Past, Present and Future" Nat. Med. 9(3):269-277.
Walling, et al. (2004) "Agiessive basal cell carcinoma: Presentation, pathogenesis, and management" Cancer and Metastasis Reviews 23:389-402.
Walters & Kleeberger (2008) "Mouse Models of Bleomycin-Induced Pulmonary Fibrosis" Current Protocols Pharmacol. 40:5.46.1-5.46.17.
Wang et al. (2007) "Lysyl Oxidase Inhibition Reduces Rat Liver Fibrosis after Bile Duct Ligation" Gastroenterology & Digestive Disease Week Meeting—108th Annual Meeting of the American-Gastroenterological-Association. Washington, DC. May 19-24, 2007; 132(4):A827.
Watanabe et al. (2010) "Nucleolin as cell surface receptor for tumor necrosis factor-alpha inducing protein: a carcinogenic factor of Helicobacter pylori", Journal of Cancer Research and Clinical Oncology 136(6):911-921.
Watters et al. (1987) "Idiopathic Pulmonary Fibrosis. Pretreatment Bronchoalveolar Lavage Cellular Constituents and Their Relationships with Lung Histopathology and Clinical Response to Therapy" Am. Rev. Respir. Dis. 135(3):696-704. Abstract Only.
Weiner (1999) "An Overview of Monoclonal Antibody Therapy of Cancer" Seminars Oncology 26(4):41-50.
Weise, et al. (2008). "LOXL4 is a selectively expressed candidate diagnostic antigen in head and neck cancer." Eur J Cancer 44(9): 1323-31.
Whaley-Connell et al. (2006) "Chronic Kidney Disease and the Cardiometabolic Syndrome," J. Clin. Hypert. 8(8):546-548.
Wu et al. (2007) "LOXL1 and LOXL4 are Epigenetically Silenced and Can Inhibit Ras/Extracellular Signal-Regulated Kinase Signaling Pathway in Human Bladder Cancer" Cancer Res. 67(9):4123-4129.
Zhang et al. (2007) "Hypoxia Enhances Metastatic Efficiency in HT-1060 Fibrosarcoma Cells by Increasing Cell Survival in Lungs Not Cell Adhesion and Invasion" Cancer Res. 67(18):7789-7797.
Zhu et al. (2002) "The thin prep rat aortic ring assay: a modified method for the characterization of angiogenesis in whole mounts" Angiogenesis 5(1-2):81-86.
Examination Report for NZ 598456, mailed Nov. 6, 2012.
Supplementary European Search Report for EP 10810673.3, mailed Nov. 26, 2012.
Supplementary European Search Report for EP 10810675.8, mailed Dec. 4, 2012.
Patent Examination Report No. 1 for AU 2008299784, mailed Dec. 12, 2012.
Non-Final Office Action for U.S. Appl. No. 12/860,834, mailed Jan. 10, 2013.
Office Action mailed Nov. 26, 2012, in U.S. Appl. No. 13/204,336.
Office Action mailed Jan. 7, 2013, in U.S. Appl. No. 13/204,336.
Office Action mailed Jan. 28, 2013, in U.S. Appl. No. 12/185,054.
Final Office Action mailed May 10, 2013, in U.S. Appl. No. 12/185,054.
Notice of Allowance mailed Feb. 6, 2013, in U.S. Appl. No. 12/185,050.
Notice of Reasons for Rejection (translation) mailed Feb. 1, 2013, for JP 2010-519263.
Office Action mailed Feb. 28, 2013, in U.S. Appl. No. 12/652,687.
Office Action mailed Feb. 15, 2013, in U.S. Appl. No. 13/021,555.
Extended Search Report mailed Mar. 5, 2013, for EP 10810702.0.
Communication Pursuant to Rules 70(2) and 70a(2) EPC mailed Mar. 22, 2013, for EP 10810702.0.
Extended Search Report mailed Mar. 21, 2013, for EP 12172214.4.
Campbell, Monoclonal Antibody Technology, "General Properties and Applications of Monoclonal Antibodies," Chapter 1, 1-32 (Elsevier Science Publishers B.V.) (1984).

Fujimoto et al. (2009) "Reciprocal Regulation of LOX and LOXL2 Expression During Cell Adhesion and Terminal Differentiation in Epidermal Keratinocytes," Journal of Dermatological Science 55(2):91-98.
Maki et al. (2002) "Inactivation of the Lysyl Oxidase Gene Lox Leads to Aortic Aneurysms, Cardiovascular Dysfunction, and Perinatal Death in Mice," Circulation 106(19):2503-2509.
Mollenhauer, et al. (1987) "Distribution of Extracellular Matrix Proteins in Pancreatic Ductal Adenocarcinoma and Its Influence on Tumor Cell Proliferation in Vitro," 2(1):14-24.
Portolano, et al. (1993). "Lack of Promiscuity in Autoantigen-Specific H and L Chain Combinations as Revealed by Human H and L Chain Roulette," J Immunol 150(3):880-887.
Tannock. "Experimental Chemotherapy," Ch. 19, p. 338 and 352-359, in The Basic Science of Oncology, Tannock and Hill, eds., New York 1992.
Terui, et al. (2006) "Blockade of Bulky Lymphoma-Associated CD55 Expression by RNA Interference Overcomes Resistance to Complement-Dependent Cytotoxicity with Rituximab," Cancer Sci. 97:72-79.
Advisory Action for U.S. Appl. No. 12/185,054, mailed Aug. 20, 2013.
Office Action (translation) for Japanese Application No. 2010-519951, mailed Jul. 12, 2013.
Decision on Rejection (translation) for CN 200880101321.3, mailed Jul. 3, 2013.
First Office Action (translation) for CN 201080047979.8, mailed Jun. 28, 2013.
Non-Final Office Action for U.S. Appl. No. 13/487,109, mailed Aug. 8, 2013.
Final Office Action for U.S. Appl. No. 13/021,555 mailed Jul. 19, 2013.
Final Office Action for U.S. Appl. No. 12/860,834, mailed Jul. 26, 2013.
Final Office Action for U.S. Appl. No. 12/652,687, mailed Aug. 1, 2013.
Notice of Allowance (translation) for JP 2010-519263, mailed Jun. 21, 2013.
American Thoracic Society International Consensus Statement (2000) "Idiopathic Pulmonary Fibrosis: Diagnosis and Treatment" Am J Respir Grit Care Med 161:646-664.
Peng et al. (2009) "Secreted LOXL2 is a Novel Therapeutic Target that Promotes Gastric Cancer Metastasis via the Src/FAK Pathway," Carcinogenesis 30(10):1660-1669.
Schietke et al. (2010) "The Lysyl Oxidases LOX and LOXL2 are Necessary and Sufficient to Repress E-cadherin in Hypoxia: Insights into Cellular Transformation Processes Mediated by HIF-1," Journal of Biological Chemistry 285(9):6658-6669 (Published, JBC Papers in Press, Dec. 21, 2009).
Caldas et al. (2003) "Humanization of the Anti-CD 18 Antibody 6.7: An Unexpected Effect of a Framework Residue in Binding to Antigen," Mol. Immunol. 39(15):941-952.
Casset et al. (2003) "A Peptide Mimetic of an Anti-CD4 Monoclonal Antibody by Rational Design," Biochem. Biophys. Res. Commun. 307(1): 198-205.
Chien et al. (1989) "Significant Structural and Functional Change of an Antigen-binding Site by a Distant Amino Acid Substitution: Proposal of a Structural Mechanism," Proc. Natl. Acad. Sci. USA 86(14): 5532-5536.
Giusti et al. (1987) "Somatic Diversification of S107 from an Antiphosphocholine to an Anti-DNA Autoantibody is Due to a Single Base Change in its Heavy Chain Variable Region," Proc. Natl. Acad. Sci. USA 84(9):2926-2930.
Gussow et al. (1991) "Humanization of Monoclonal Antibodies," Methods in Enzymology 203:99-121.
Harmsen and Haard (2007) "Properties, Production, and Applications of Camelid Single-domain Antibody Fragments," Appl. Microbiol. Biotechnol. 77:13-22.
Holm et al. (2007) "Functional Mapping and Single Chain Construction of the Anti-Cytokeratin 8 Monoclonal Antibody TS1," Mol. Immunol. 44(6):1075-1084.

(56) References Cited

OTHER PUBLICATIONS

Jiang et al., (2005) "A Novel Peptide Isolated from a Phage Display Peptide Library with Trastuzumab can Mimic Antigen Epitope of HER-2" J. Biol. Chem. 280(6):4656-4662.

Maccallum et al. (1996) "Antibody-antigen Interactions: Contact Analysis and Binding Site Topography," J. Mol. Biol. 262(5):732-745.

Mariuzza et al. (1987) "The Structural Basis of Antigen-antibody Recognition," Annu. Rev. Biophys. Chem. 16:139-159.

Pascalis, et al. (2002) "Grafting of "Abbreviated" Complementarity-Determining Regions Containing Specificity-Determining Residues Essential for Ligand Contact to Engineer a Less Immunogenic Humanized Monoclonal Antibody," J. Immunol. 169(6):3076-3084.

Stancoviski et al. (1991) "Mechanistic Aspects of the Opposing Effects of Monoclonal Antibodies to the ERBB2 Receptor on Tumor Growth," Proc. Natl. Acad. Sci USA 88:8691-8695.

Vajdos et al. (2002) "Comprehensive Functional Maps of the Antigen-binding Site of an Anti-ErbB2 Antibody Obtained with Shotgun Scanning Mutagenesis," J. Mol. Biol. 320(2):415-428.

Wu et al. (1999) "Humanization of a Murine Monoclonal Antibody by Simultaneous Optimization of Framework and CDR Residues," J. Mol. Biol. 294(1):151-162.

First Examination Report for New Zealand Patent Application No. 601615 mailed Apr. 4, 2013.

Notice of the Second Office Action for CN 200880110519.8, mailed Dec. 31, 2012.

Office Action mailed Jun. 3, 2013, in U.S. Appl. No. 13/619,139.

Understanding Cancer Series: Cancer Slide 8: Invasion and Metastasis, www.cancer.gov/cancertopics/understandingcancer/cancer/slide8, posted Jan. 28, 2005, reviewed Sep. 30, 2009.

Decision to Grant for EP 10012458.5 dated Sep. 12, 2013.

Search Report and Written Opinion for SN 201201215-9 mailed Jul. 19, 2013.

First Office Action (translation) for CN 201080047970.7 mailed Jul. 16, 2013.

\* cited by examiner

LOX Multigene Family:
Genomic and Protein Organization

S. Payne, et al. (2007). J. Cellular Biochemistry

Epithelial-Mesenchymal Transition (EMT): Role in Invasion and Metastasis

EMT and MET Markers

LOX / LOXL and EMT: Alter Drug Sensitivity Profile in Tumor Cells

FIG. 7
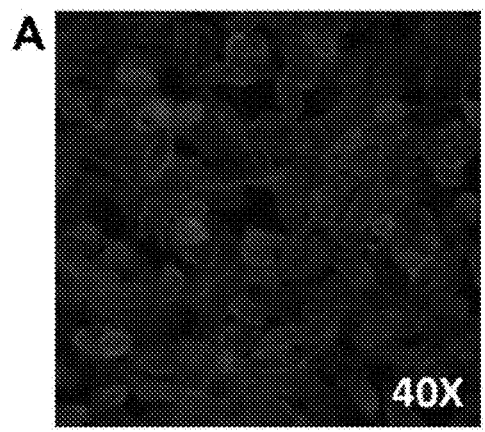
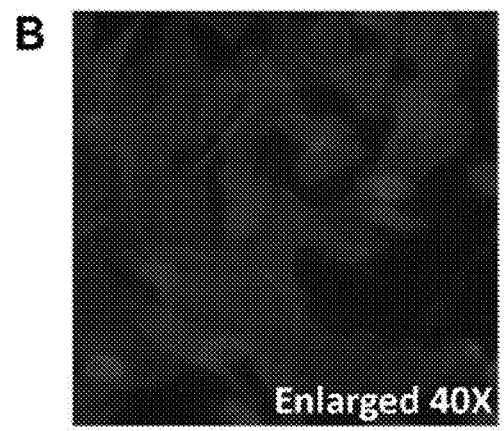
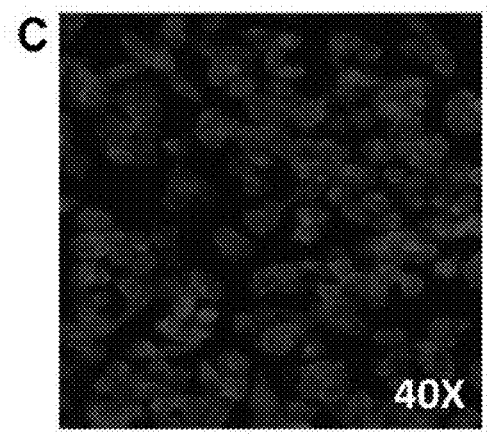
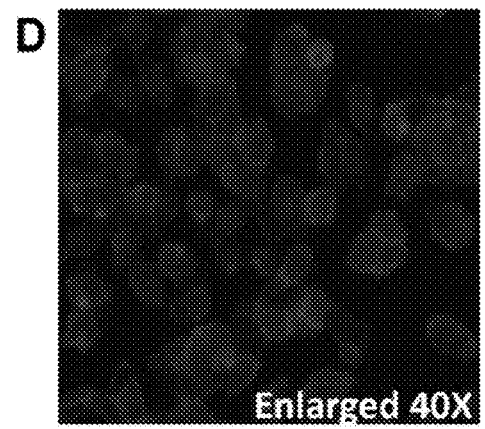
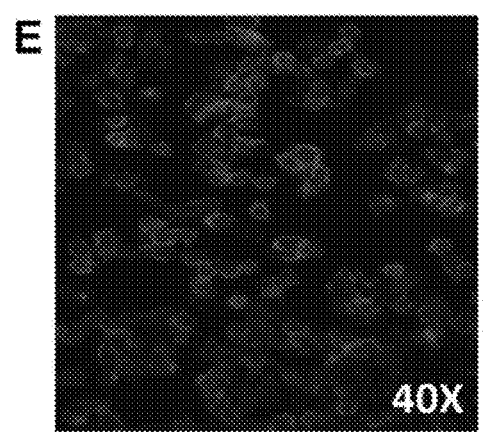
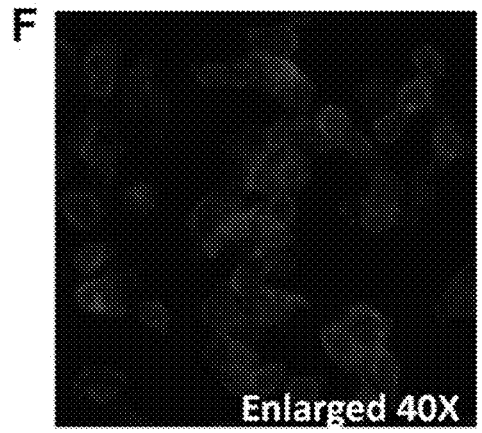

FIG. 12
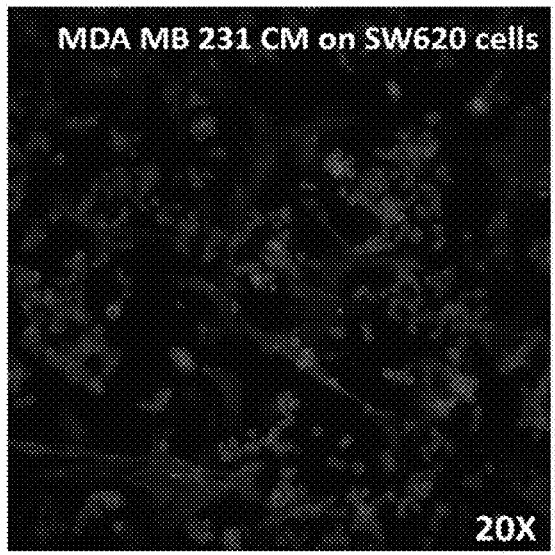
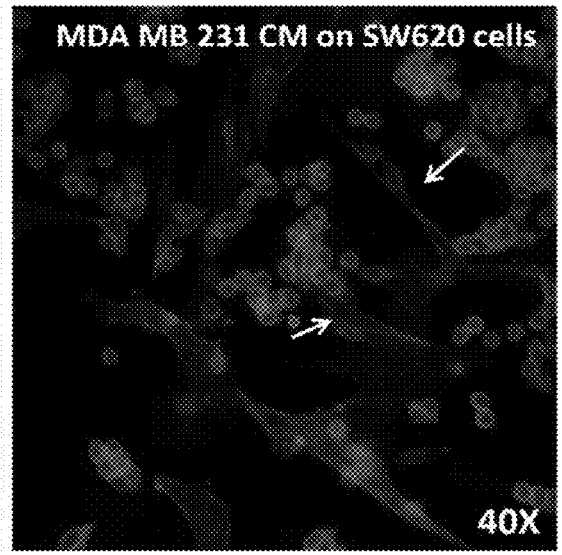
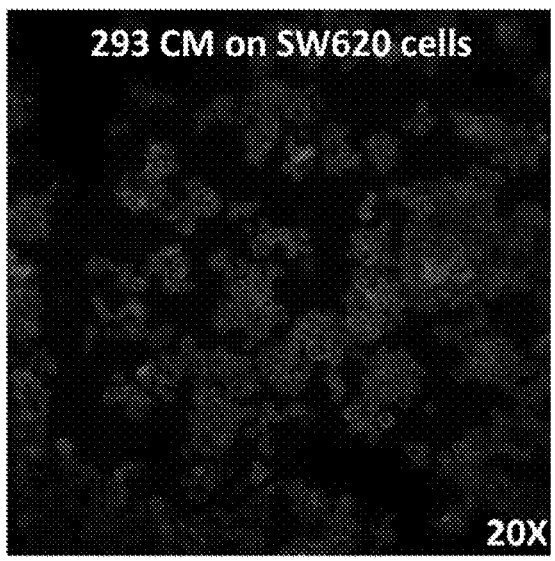
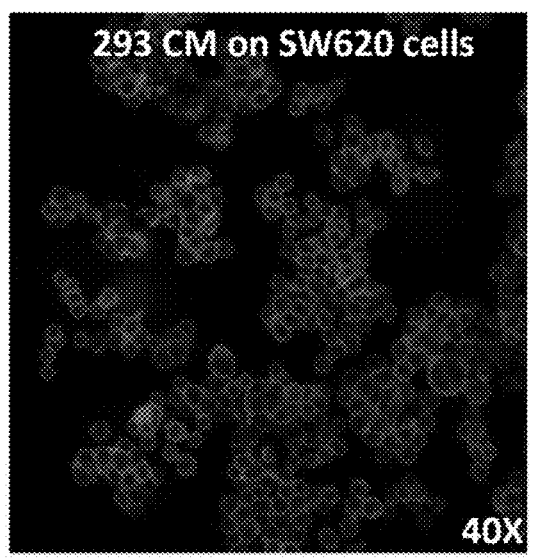

FIG. 14
A Distribution of Un-cleaved vs Cleaved LOX in Normal and Tumor Tissues
  
*Un-cleaved*  *Cleaved*
*Intracellular*  *Extracellular*
  *(Intracellular)*
B LOX / LOXL and EMT: Block Uptake of Enzyme and Role in EMT
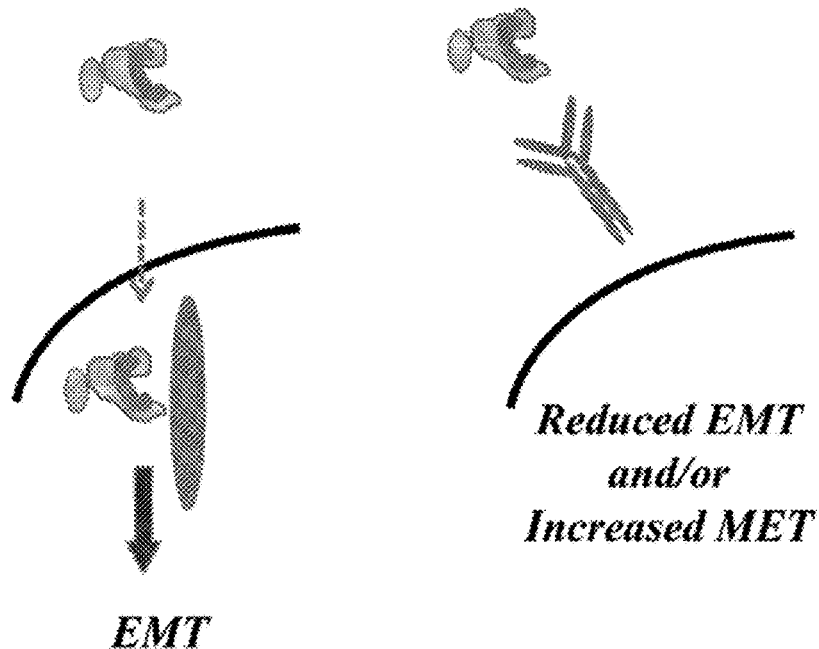
*EMT*  *Reduced EMT and/or Increased MET*

FIG. 16
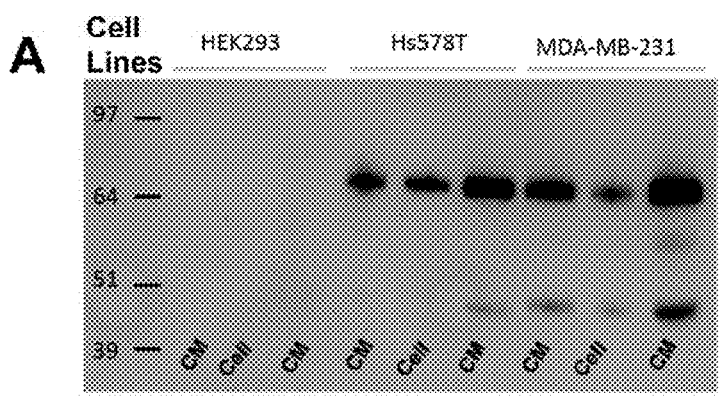
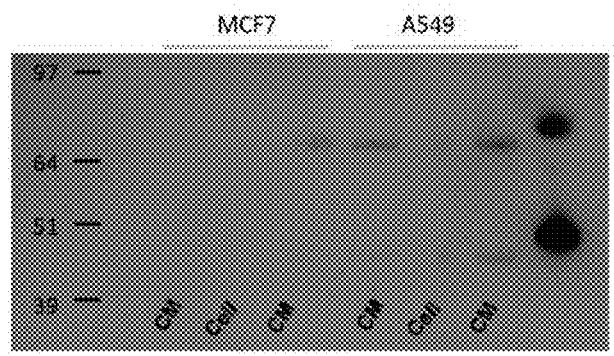
CM: conditioned media
Cell: cell lysate
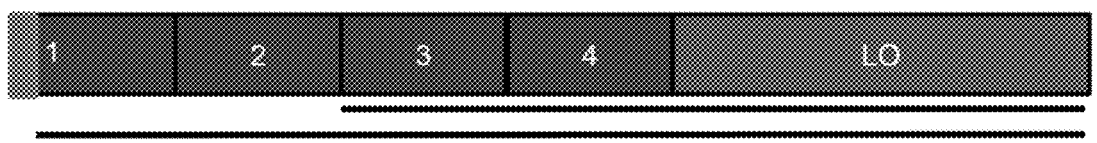

CM= conditioned media
FT: flow through after purification
W: wash
Eluate: eluted, purified LOXL2

Column fractions
(purification)

Pro LOXL2 = full length LOXL2 (minus signal sequence)
Mature LOXL2 = cleaved LOXL2

Substrates:
Kagan: = GGGGEKGGGGG peptide (mimics collagen telopeptide)
DAP = diaminopentane FIG. 21
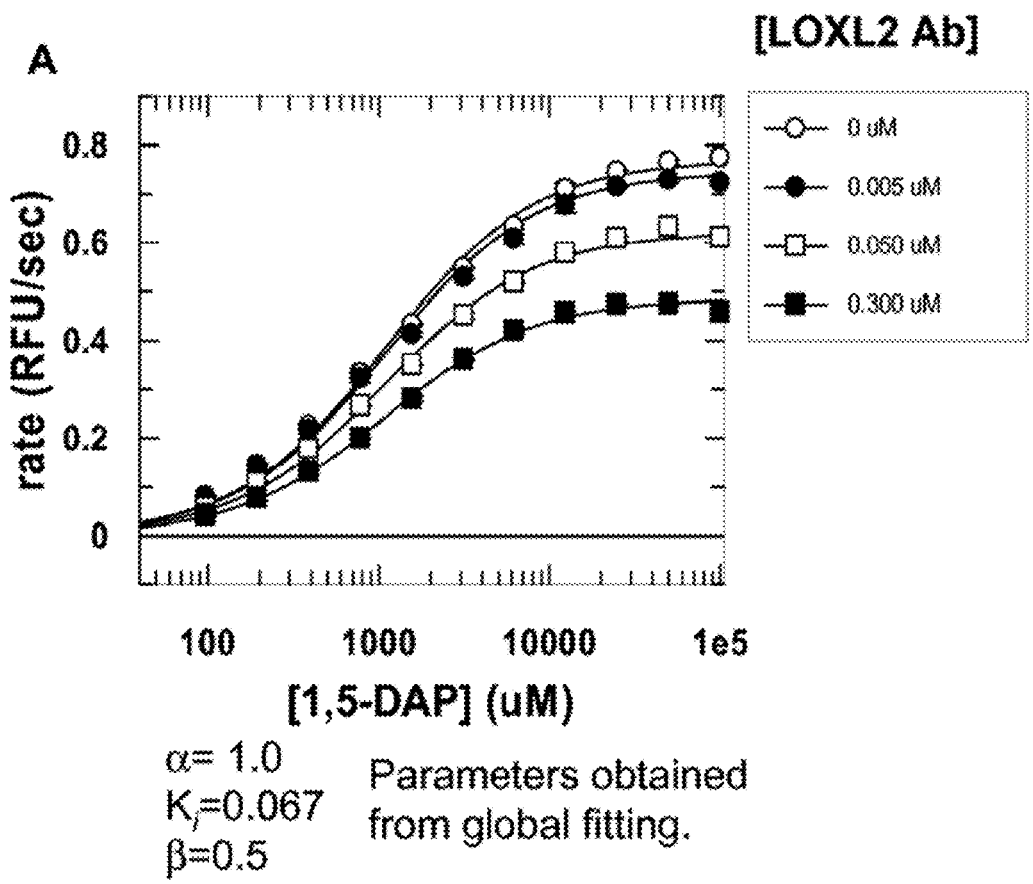
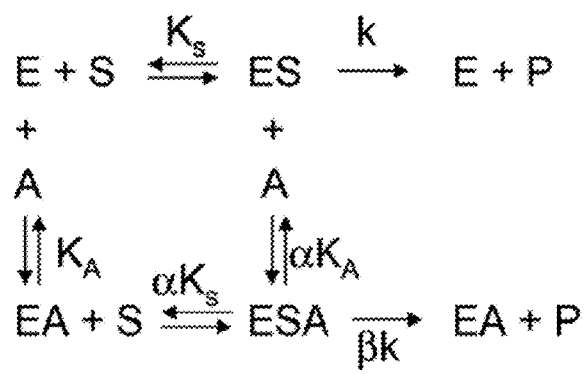

FIG. 21
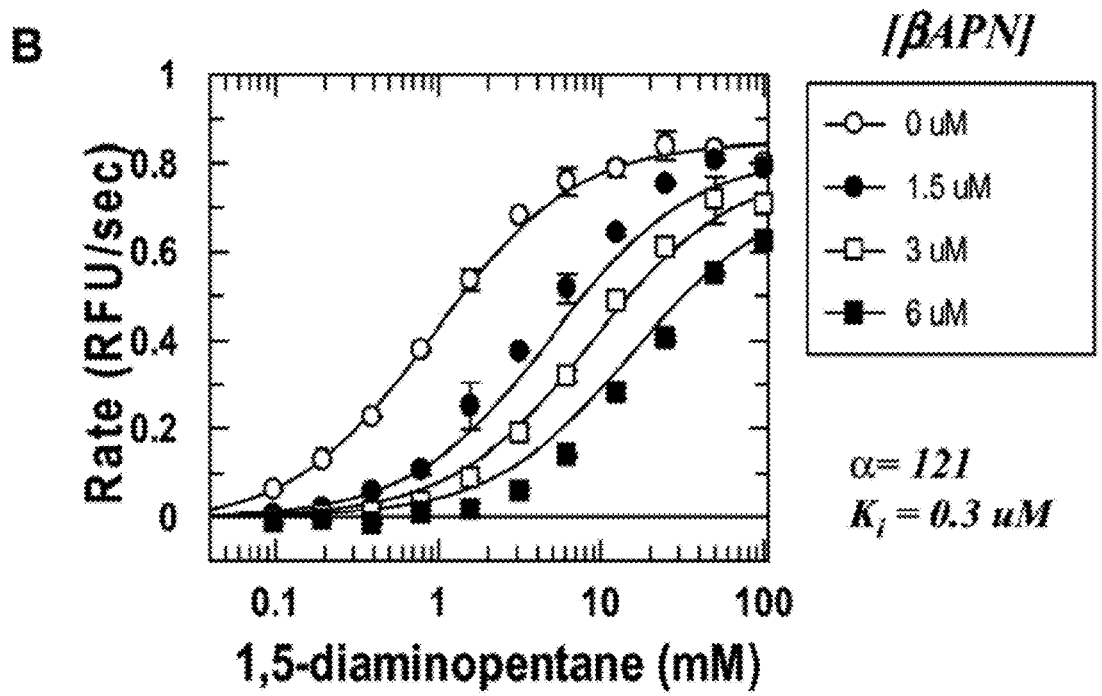
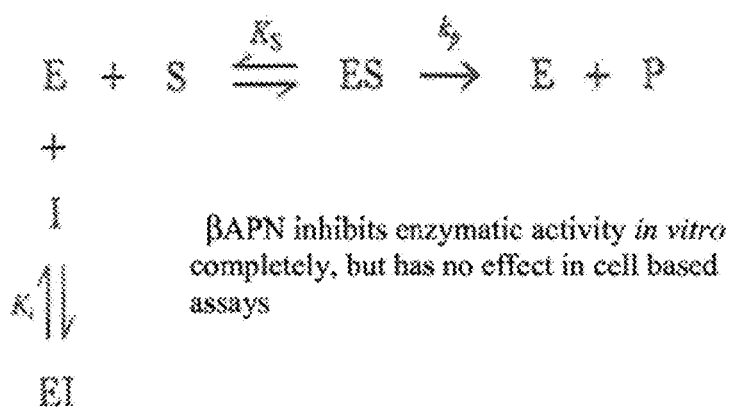
βAPN inhibits enzymatic activity *in vitro* completely, but has no effect in cell based assays

FIG. 24
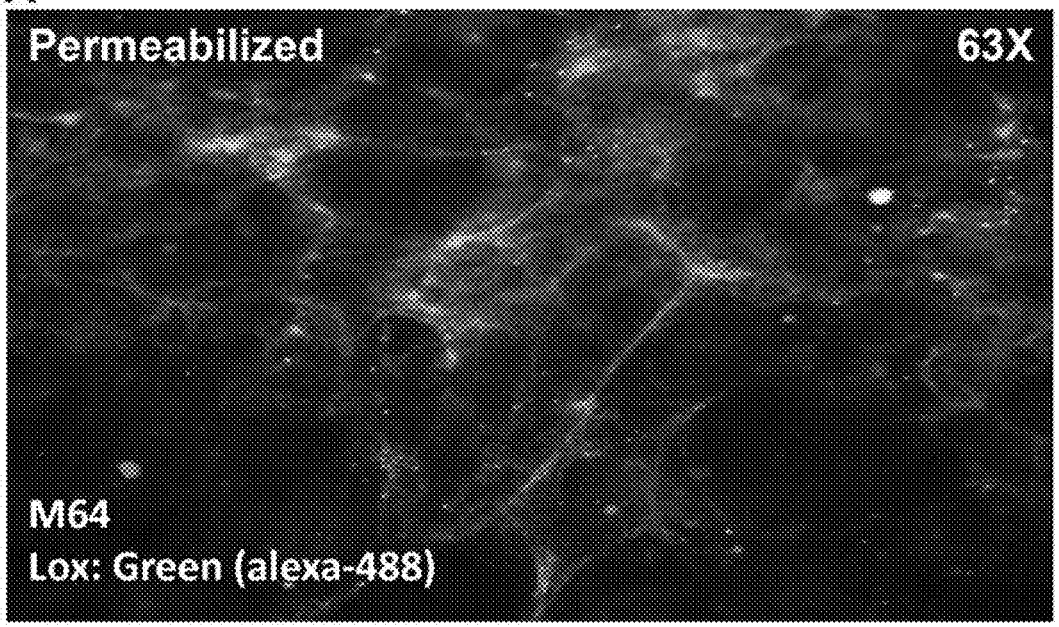
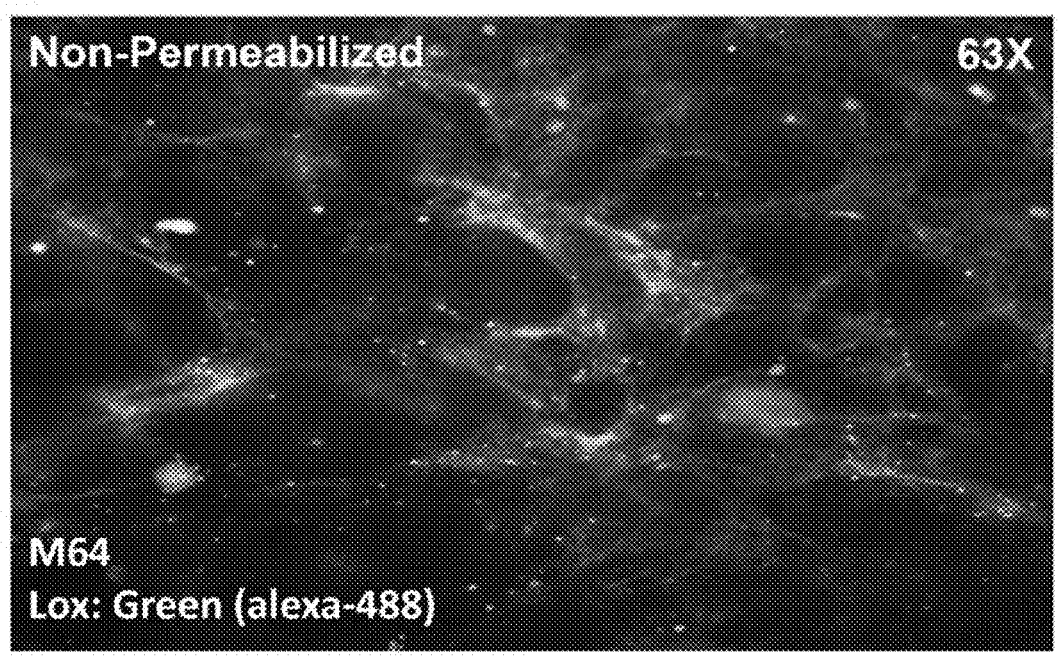

FIG. 26
A  Collagen I
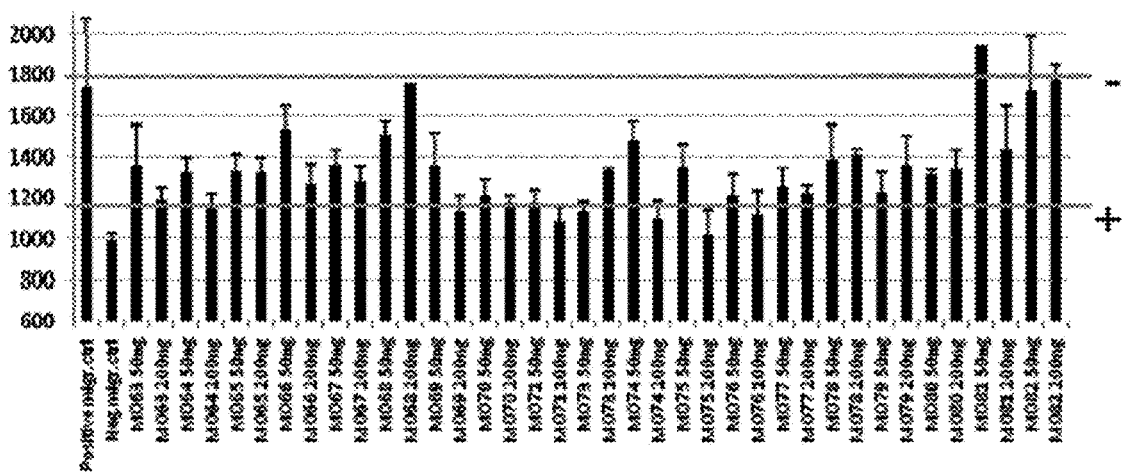
B  Collagen IV
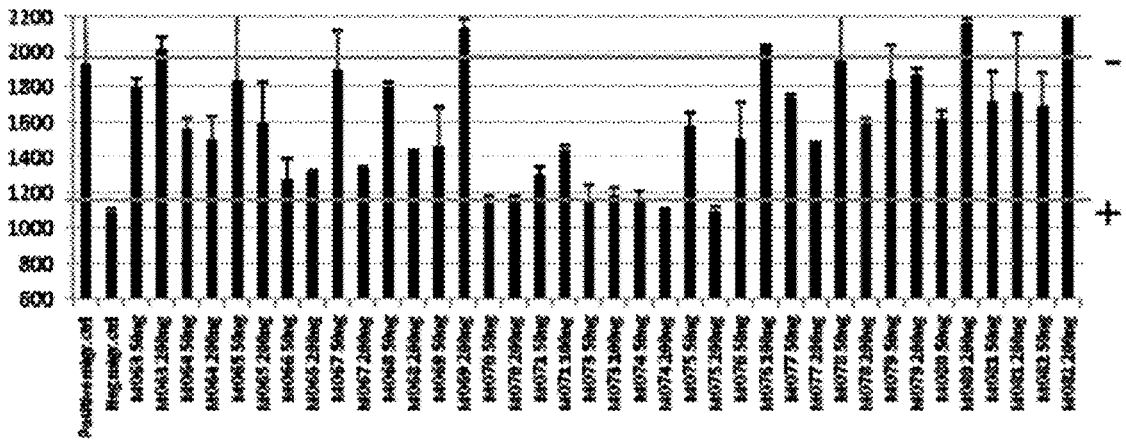

FIG. 31
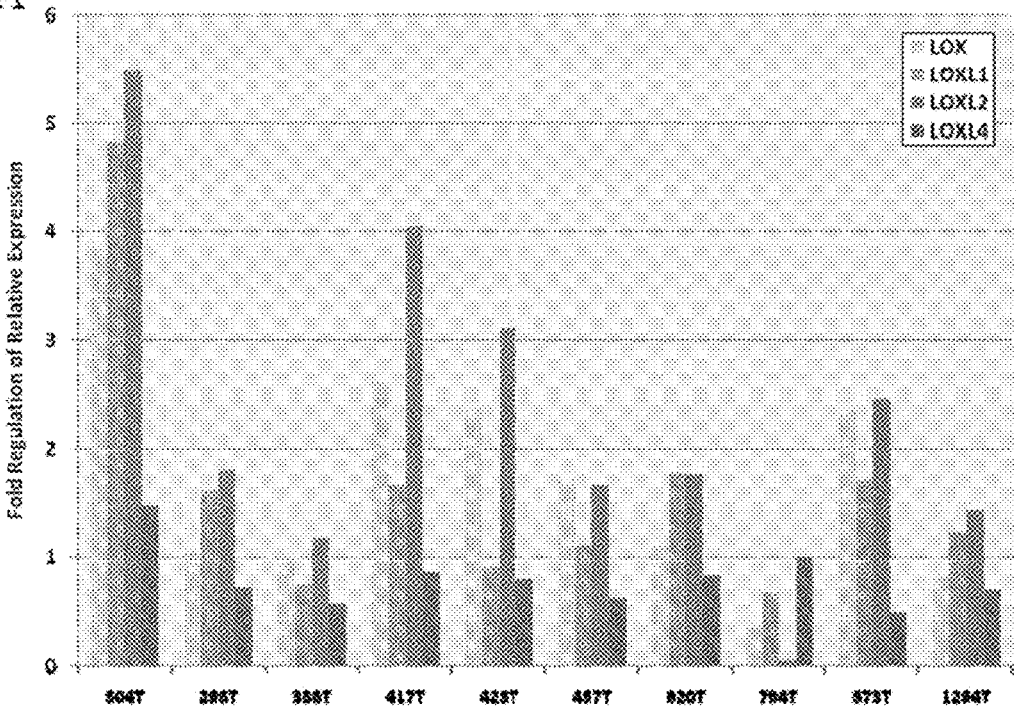
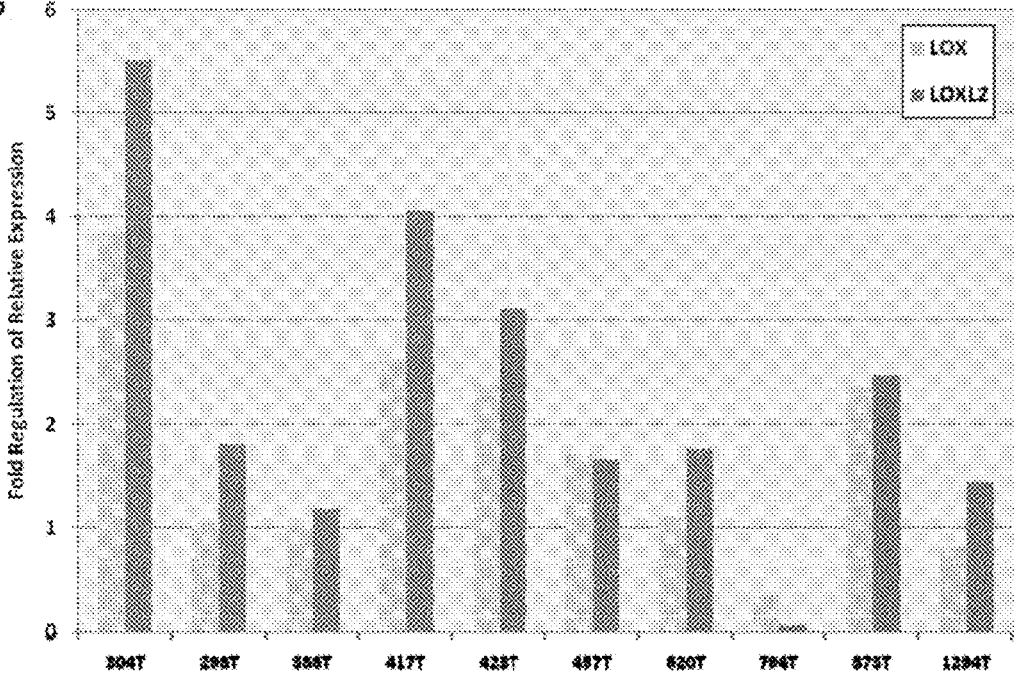

FIG. 35
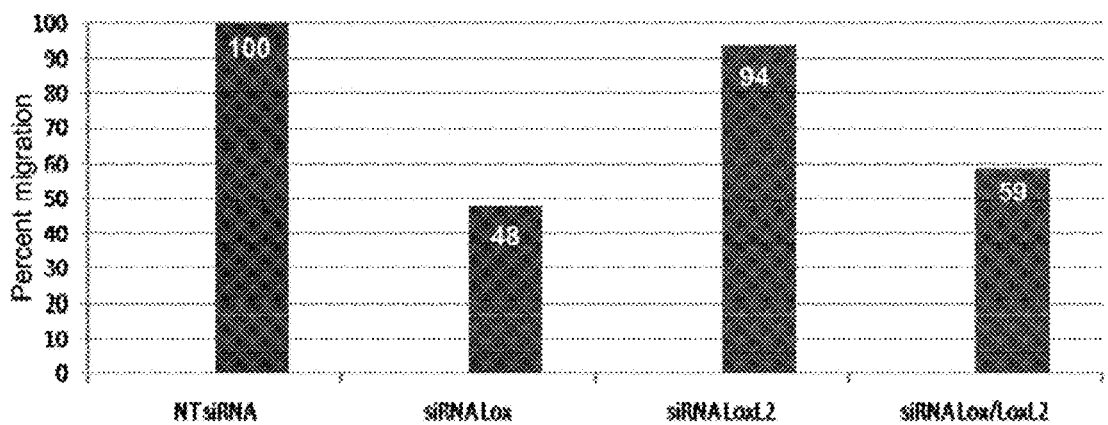
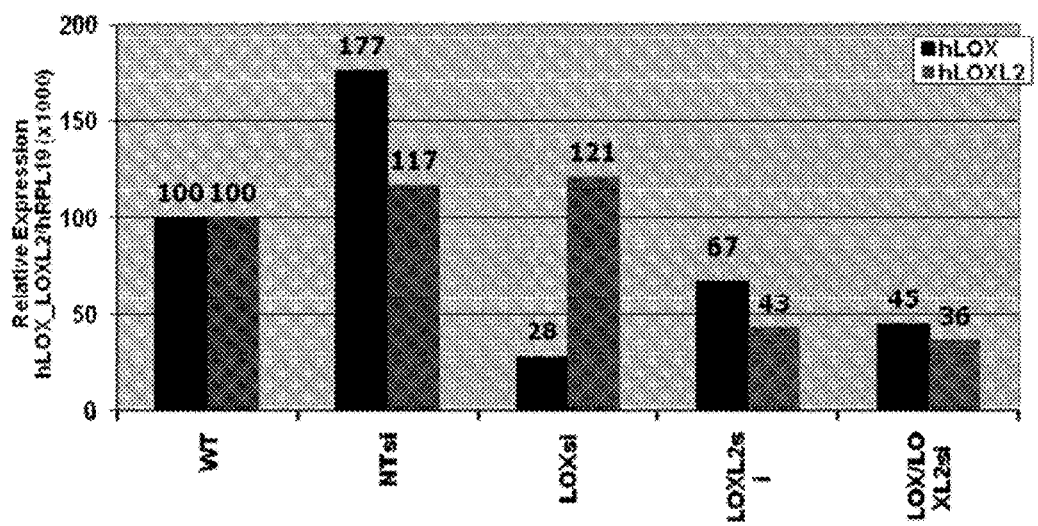

FIG. 43

Competitive inhibition
• Inhibitor typically bears structural similarity to substrate
• Inhibition noticeable at low substrate concentrations but can be overcome at high substrate concentrations Uncompetitive inhibition
• Inhibitor binds at site that becomes available after substrate is bound at the active site
• Inhibition most noticeable at high substrate concentration Non-competitive inhibition
• Inhibitor binds at site away from substrate binding site
• Relative inhibition is the same at all substrate concentrations

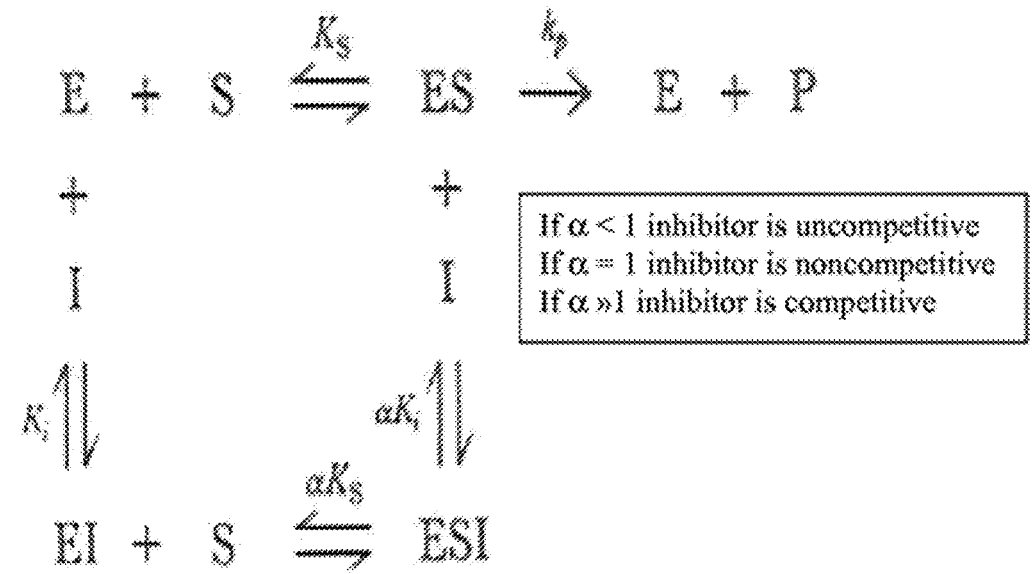

If α < 1 inhibitor is uncompetitive
If α = 1 inhibitor is noncompetitive
If α » 1 inhibitor is competitive

SEQUENCE LISTING

```
<160> NUMBER OF SEQ ID NOS: 59

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Arg Val Asp Gly Met Val Gly Asp Asp Pro Tyr Asn Pro Tyr Lys
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Thr Tyr Glu Arg Pro Arg Pro Gly Gly Arg Tyr Arg Pro Gly
1               5                   10                  15

<210> SEQ ID NO 3
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Arg Leu Leu Arg Phe Ser Ser Gln Ile His Asn Asn Gly Gln Ser
1               5                   10                  15

Asp Phe Arg Pro Lys Asn Gly Arg
            20
```

```
<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Asp Thr Ser Cys Asp Tyr Gly Tyr His Arg Arg Phe Ala
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Asp Thr Glu Cys Glu Gly Asp Ile Gln Lys Asn Tyr Glu
1               5                   10

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Pro Tyr Tyr Ile Gln Ala Ser Thr Tyr Val Gln Lys Met Ser Met
1               5                   10                  15

Tyr Asn Leu Arg Cys
            20

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asn Ala Glu Met Val Gln Gln Thr Thr Tyr Leu Glu Asp Arg Pro Met
1               5                   10                  15

Phe Met Leu Gln Cys
            20

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ser Gln Tyr Gly Pro Gly Arg Arg Arg Asp Pro Gly Ala
1               5                   10

<210> SEQ ID NO 9
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Trp Glu Trp His Ser Cys His Gln His Tyr His
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Trp Glu Trp His Ser Cys His Gln His Tyr His
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Trp Ile Trp His Asp Cys His Arg His Tyr His
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Trp Val Trp His Glu Cys His Gly His Tyr His
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Trp Val Trp His Gln Cys His Arg His Tyr His
1               5                   10

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Ile Asp Cys Gln Trp Ile Asp Ile Thr Asp Val Lys Pro Gly Asn
1               5                   10                  15
```

Tyr

<210> SEQ ID NO 15
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Ile Asp Cys Gln Trp Ile Asp Ile Thr Asp Val Gln Pro Gly Asn
1               5                   10                  15

Tyr

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Ile Asp Cys Gln Trp Val Asp Ile Thr Asp Val Pro Pro Gly Asp
1               5                   10                  15

Tyr

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Ile Asp Cys Gln Trp Ile Asp Ile Thr Asp Val Lys Pro Gly Asn
1               5                   10                  15

Tyr

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Ile Asp Cys Gln Trp Val Asp Ile Thr Asp Val Gly Pro Gly Asn
1               5                   10                  15

Tyr

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Ala Pro Asp Leu Val Leu Asn Ala Glu
1               5                   10

```
<210> SEQ ID NO 20
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
auaacagcca ggacucaauc ccugu                                          25

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cttgactggg gaagggtctg                                                20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aaaacggggc tcaaatcacg                                                20

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
atcccaccct tggcattgct tggt                                           24

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agcagacttc ctccccaacc                                                20

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cagtaggtcg tagtggctga ac                                             22
```

```
<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
cacggcacac ctgggagtgg cac                                              23

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggggtttgtc cacagagctg                                                  20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acgtgtcact ggagaagagc                                                  20

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
tggagcagca ccaagagcca gtct                                             24

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gtgtgcgaca aaggctggag                                                  20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccgcgttgac cctcttttcg                                                  20

<210> SEQ ID NO 32
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
aagcccagca tcccgcagac cac                                              23

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cttaccacac acatgggtgt ttc                                              23

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tcaagcactc cgtaactgtt gg                                               22

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
ccttggaagc acagacctcg ggca                                             24

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccggctgctc agaagatac                                                   19

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ttcaggtaca ggctgtgata cat                                              23

<210> SEQ ID NO 38
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 38
tggcgatcga tcttcttaga ttcacg                                             26

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
caagagggaa gcagagcctt c                                                  21

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gcaccttctg aatgtaagag tctc                                               24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
accaaggagc acgcaccaca acga                                               24

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggccttcgcc accacctatc                                                    20

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gtagtacacg tagccctgtt cg                                                 22

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 44
ccagccatcc tcctacccgc agca                                        24

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gctatgtaga ggccaagtcc tg                                          22

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cagtgacacc ccagccattg                                             20

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
tcctcctacg gtccaggcga aggc                                        24

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcaaggagag aatagacaga gaag                                        24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
agcatggtgt cctcattcat aaag                                        24

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 50
acatccaccc atcccatccc accc                                          24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
caagacaggt ccagtagagt tagg                                          24

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aggtcttata ccacctgagc aag                                           23

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
acagagcaca gccgcctcac tgga                                          24

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
agaaggtgac ctggatgaga a                                             21

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tgatacatat ggcggtcaat ct                                            22

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
```

```
cttctcagga gataccggga atccaag                                           27
```

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

```
Gly Gly Gly Gly Glu Lys Gly Gly Gly Gly Gly
1               5                   10
```

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

```
Thr Ala Pro Asp Leu
1               5
```

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 59

```
His His His His His His
1               5
```

METHODS AND COMPOSITIONS FOR TREATMENT AND DIAGNOSIS OF FIBROSIS, TUMOR INVASION, ANGIOGENESIS, AND METASTASIS

CROSS-REFERENCE

This application is a divisional of pending U.S. patent application Ser. No. 12/185,054 filed Aug. 1, 2008, which claims the benefit of U.S. Provisional Application No. 60/963,282, entitled "Methods for Selecting Inhibitors of Tumor Invasion, Angiogenesis, and Metastasis," filed Aug. 2, 2007; U.S. Provisional Application No. 60/963,249, entitled "Treatment of Diseases With Inhibitors of Active Lysyl Oxidase," filed Aug. 2, 2007; U.S. Provisional Application No. 60/963,214, entitled "Treatment of Diseases Through Inhibition of Both Lysyl Oxidase and Lysyl Oxidase-Like Proteins," filed Aug. 2, 2007; U.S. Provisional Application No. 60/963,248, entitled "Diagnosis or Monitoring of Diseases by Assessing Active Lysyl Oxidase Levels or Activity," filed Aug. 2, 2007; and U.S. Provisional Application No. 60/963,246, entitled "Combination Therapy Including Lysyl Oxidase Modulators," filed Aug. 2, 2007; and is related to co-pending U.S. patent application entitled "LOX and LOXL2 Inhibitors and Uses Thereof", filed Aug. 1, 2008, Ser. No. 12/185,054, and PCT Patent Application entitled "LOX and LOXL2 Inhibitors and Uses Thereof", filed Aug. 1, 2008, Serial No. PCT/US2008/072039. The entire contents of these applications are incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 246102006801SeqList.txt, date recorded: Dec. 3, 2012, size: 15,172 bytes).

BACKGROUND

1. Cancer

Cancer is a serious public health problem in the United States and other developed countries. Currently, one in four deaths in the United States is due to cancer. Cancer therapy involves treating patients with chemotherapeutic drugs to kill tumor cells. However, subsets of tumor cells are frequently resistant to drug therapy and survive to re-populate at sites of origin and at distant metastatic sites, leading to detectable disease recurrence and morbidity. Many carcinoma tumor cells that have the properties of increased invasive and metastatic capacity, and altered drug resistance, are thought to have undergone a morphological transformation encompassing or similar to EMT (epithelial-mesenchymal transition). Cells undergoing EMT lose the normal adhesive properties of epithelial cells and undergo a spectrum of changes including loss of E-cadherin expression and expression of mesenchymal markers, increased motility, increased invasiveness, and increased resistance to cell death.

The leading therapies for cancer are currently surgery, radiation and chemotherapy. Chemotherapeutic approaches such as antitumor antibiotics, alkylating agents, nitrosourea compounds, vinca alkaloids, steroid hormones, and anti-metabolites form the bulk of therapies available to oncologists. Despite advances in the field of cancer treatment, cancer remains a major health problem.

2. Angiogenesis

Angiogenesis, the formation of new blood vessels out of pre-existing capillaries, is a sequence of events that is of key importance in a broad array of physiologic and pathologic processes. Normal tissue growth, such as in embryonic development, wound healing, and the menstrual cycle, is characterized by dependence on new vessel formation for the supply of oxygen and nutrients as well as removal of waste products. A large number of different and unrelated diseases are also associated with formation of new vasculature. Among certain pathologies are conditions in which angiogenesis is low, and should be enhanced to improve disease conditions. More frequently, however, excessive angiogenesis is an important characteristic of various pathologies, including pathologies characterized or associated with an abnormal or uncontrolled proliferation of cells. Pathologies which involve excessive angiogenesis include, for example, cancer (both solid and hematologic tumors), cardiovascular diseases (such as atherosclerosis and restenosis), chronic inflammation (rheumatoid arthritis, Crohn's disease), diabetes (diabetic retinopathy), psoriasis, endometriosis, neovascular glaucoma and adiposity. These conditions may benefit from chemotherapeutic inhibition of angiogenesis.

Generally speaking, the angiogenic process entails the proliferation and migration of a normally quiescent endothelium, the controlled proteolysis of the pericellular matrix, and the synthesis of new extracellular matrix components by developing capillaries. The establishment of new intra- and intercellular contacts and the morphological differentiation of endothelial cells to capillary-like tubular networks provide support for their subsequent maturation, branching, remodeling and selective regression to form a highly organized, functional microvascular network. The autocrine, paracrine and amphicrine interactions of the vascular endothelium with its surrounding stromal components, as well as with the pro-angiogenic and angiostatic cytokines and growth factors orchestrating physiologic angiogenesis, are normally tightly regulated both spatially and temporally.

Angiogenesis is crucial to the growth of neoplastic tissues. For more than 100 years, tumors have been observed to be more vascular than normal tissues. Several experimental studies have suggested that both primary tumor growth and metastasis require neovascularization. In contrast to the well orchestrated process described above for normal tissue growth, the pathologic angiogenesis necessary for active tumor growth is generally sustained and persistent, with the initial acquisition of the angiogenic phenotype being a common mechanism for the development of a variety of solid and hematopoietic tumor types. Tumors that are unable to recruit and sustain a vascular network typically remain dormant as asymptomatic lesions in situ. Metastasis is also angiogenesis-dependent: for a tumor cell to metastasize successfully, it generally gains access to the vasculature in the primary tumor, survive the circulation, arrest in the microvasculature of the target organ, exit from this vasculature, grow in the target organ, and induce angiogenesis at the target site. Thus, angiogenesis appears to be necessary at the beginning as well as the completion of the metastatic cascade.

The criticality of angiogenesis to the growth and metastasis of neoplasms thus provides an optimal potential target for chemotherapeutic efforts. Appropriate anti-angiogenic agents may act directly or indirectly to influence tumor-associated angiogenesis either by delaying its onset (i.e., blocking an "angiogenic switch") or by blocking the sustained and focal neovascularization that is characteristic of many tumor types. Anti-angiogenesis therapies directed against the tumor-associated endothelium and the multiple molecular and cellular processes and targets implicated in sustained pathologic angiogenesis are being actively evaluated for their safety and efficacy in multiple clinical trials. However, there has been limited success to date with the discovery and/or identification of safe and/or effective anti-angiogenic agents.

3. Fibrosis

Fibrosis is the abnormal accumulation of fibrous tissue that can occur as a part of the wound-healing process in damaged tissue. Such tissue damage may result from physical injury, inflammation, infection, exposure to toxins, and other causes. Examples of fibrosis include dermal scar formation, keloids, liver fibrosis, lung fibrosis (e.g., silicosis, asbestosis), kidney fibrosis (including diabetic nephropathy), scleroderma, and glomerulosclerosis.

Liver (hepatic) fibrosis, for example, occurs as a part of the wound-healing response to chronic liver injury. Fibrosis occurs as a complication of haemochromatosis, Wilson's disease, alcoholism, schistosomiasis, viral hepatitis, bile duct obstruction, exposure to toxins, and matabolic disorders. This formation of scar tissue is believed to represent an attempt by the body to encapsulate the injured tissue. Liver fibrosis is characterized by the accumulation of extracellular matrix that can be distinguished qualitatively from that in normal liver. Left unchecked, hepatic fibrosis progresses to cirrhosis (defined by the presence of encapsulated nodules), liver failure, and death.

As summarized by Li and Friedman (*Gastroenterol. Hepatol.* 14:618-633, 1999), actual and proposed therapeutic strategies for liver fibrosis include removal of the underlying cause (e.g., toxin or infectious agent), suppression of inflammation (using, e.g., corticosteroids, IL-1 receptor antagonists, or other agents), down-regulation of stellate cell activation using, e.g., gamma interferon or antioxidants), promotion of matrix degradation, or promotion of stellate cell apoptosis. Despite recent progress, many of these strategies are still in the experimental stage, and existing therapies are aimed at suppressing inflammation rather than addressing the underlying biochemical processes. Thus, there remains a need in the art for materials and methods for treating fibrosis, including liver and lung fibrosis.

There is a need in the art for improved methods for treating cancer, diseases associated with abnormal or undesirable angiogenesis and fibrosis. The present disclosure addresses this need and provides related advantages.

SUMMARY

I. Treatment by Inhibiting Processed LOX or LOXL

The present disclosure provides innovative methodology and related compositions and kits for preventing and treating various diseases associated with abnormal cell proliferation, angiogenesis and fibrosis, by using an inhibitor of lysyl oxidase (LOX) or lysyl oxidase-like protein(s) (LOXL). The LOX or LOXL may be a full-length or processed form. The full-length LOX or LOXL is a proenzyme or propeptide form (ie without the signal sequence) whereas the processed form, or cleavage form is a mature form. Both full-length and processed forms of LOX or LOXL can be active. The LOX or LOXL can be a secreted form, which can also be active. The inhibition of LOX or LOXL is effective in preventing and treating tumor invasion and metastasis, and for treating diseases associated with abnormal angiogenesis and fibrotic diseases.

In one embodiment, methods are provided for treating or preventing tumor invasion or metastasis in a subject in vivo, comprising: administering to the subject an effective amount of an inhibitor of active LOX or LOXL.

In another embodiment, methods are provided for reducing tumor growth in a subject in vivo, comprising: administering to the subject an effective amount of an inhibitor of processed LOX or LOXL such that the tumor growth is reduced by at least 25%, 50%, 75%, 90%, or 95%. In some embodiments, the tumor is a metastatic tumor.

In yet another embodiment, methods are provided for increasing or enhancing the chances of survival of a subject with metastatic tumor, comprising: administering to a subject in need thereof an effective amount of an inhibitor of processed LOX or LOXL protein, thereby increasing or enhancing the chances of survival of the subject treated by a certain period of time. For example, the survival of the subject may be increased by at least 10 days, 1 month, 3 months, 6 months, 1 year, 1.5 years, 2 years, 3 years, 4 years, 5 years, 8 years, or even 10 years.

The LOX or LOXL may be a mature form of the LOX or LOXL after proteolytic processing or cleavage. Examples of LOXL include but are not limited to LOXL1, LOXL2, LOXL3, and LOXL4. In some embodiments, the inhibitor of LOX or LOXL may be an inhibitor of active LOX, LOXL2 or LOXL4. In some of these embodiments, the inhibitor of LOX or LOXL inhibits both active LOX and LOXL2.

The LOX or LOXL inhibitor may be, for example, an antibody against LOX or LOXL, a small molecule inhibitor, siRNA, shRNA or an antisense polynucleotide against LOX or LOXL. The inhibitors may be noncompetitive inhibitors.

II. Treatment by Inhibition of Both LOX and LOXL

The present disclosure also provides innovative methodology and related compositions and kits for preventing and treating various diseases associated with abnormal cell proliferation, angiogenesis and fibrosis, through inhibition of both lysyl oxidase (LOX) and one or more lysyl oxidase-like proteins (LOXL). Simultaneous inhibition of both LOX and LOXL is effective in preventing or treating invasion and metastasis of a wide variety of tumors, and for treating diseases associated with abnormal angiogenesis and fibrotic diseases.

In one embodiment, methods are provided for treating or preventing tumor invasion or metastasis in a subject in vivo, comprising: administering to the subject an effective amount of an inhibitor of LOX and an inhibitor of LOXL.

In another embodiment, methods are provided for reducing tumor growth in a subject in vivo, comprising: administering to the subject an effective amount of an inhibitor of LOX and an inhibitor of a LOXL such that the tumor growth is reduced by at least 25%, 50%, 75%, 90%, or even 95%. According to some embodiments, the tumor is a metastatic tumor.

In yet another embodiment, methods are provided for increasing or enhancing the chances of survival of a subject with a metastatic tumor, comprising: administering to a subject in need thereof an effective amount of an inhibitor of LOX and an inhibitor of a LOXL, thereby increasing or enhancing the chances of survival of the subject treated by a certain period of time. For example, the survival of the subject is increased by at least 10 days, 1 month, 3 months, 6 months, 1 year, 1.5 years, 2 years, 3 years, 4 years, 5 years, 8 years, or even 10 years.

The inhibitor of LOX and the inhibitor of the LOXL can be different, each specifically inhibiting LOX and LOXL, respectively. Alternatively, the inhibitor of LOX and the inhibitor of LOXL can be the same molecule which inhibits both LOX and LOXL. The LOXL may be, for example, LOXL1, 2, 3, or 4. In some embodiments, the LOXL is LOXL2 or 4. In certain embodiments, the LOXL is LOXL2.

The LOX or LOXL may be a full-length or processed form. The LOX or LOXL may be a proenzyme form or a mature form, and both forms can be active. The LOX or LOXL can be a secreted form, which can also be active. The processed form of the LOX or LOXL is a form after proteolytic processing or cleavage.

Examples of LOXL include but are not limited to LOXL1, LOXL2, LOXL3, and LOXL4. In some embodiments, the inhibitor of LOX or LOXL may be an inhibitor of active LOX, LOXL2 or LOXL4. In some of these embodiments, the inhibitor of LOX or LOXL inhibits both active LOX and LOXL2.

The LOX or LOXL inhibitor may be, for example, an antibody against LOX or LOXL, a small molecule inhibitor, siRNA, shRNA or an antisense polynucleotide against LOX or LOXL. The inhibitors may be noncompetitive inhibitors.

III. Combination Therapy

The present disclosure further provides compositions, kits, methods for preventing and treating diseases associated with abnormal cell proliferation, angiogenesis and fibrosis, such as cancer, tumors, diabetic retinopathy, macular degeneration, liver fibrosis, kidney fibrosis, lung fibrosis, scleroderma, atherosclerosis, and Alzheimer's disease by using modulators (e.g., activators/agonists or inhibitors/antagonists) of lysyl oxidase (LOX) or lysyl oxidase-like proteins (LOXL).

Inhibitors of LOX or LOXL may be combined with other therapeutic agents, such as chemotherapeutic agents, anti-neoplastic biologics, anti-angiogenetic agents, and anti-fibrotic agents, to prevent or treat these diseases or conditions. It is believed that inhibition of LOX or LOXL could slow or halt the progression of the epithelial-mesenchymal transition (EMT) in tumor cells, or induce a mesenchymal-epithelial transition (MET) to a less tumorigenic state, thereby rendering the tumor or diseased cells more susceptible to chemotherapeutic drugs, anti-neoplastic biologics, anti-angiogenetic agents, and anti-fibrotic agents. A synergistic combination of an inhibitor of LOX or LOXL with another therapeutic agent is useful for preventing or inhibiting tumor invasion and metastasis, inhibiting growth of primary tumors by sensitizing the tumor cells to the cytotoxic effects of the therapeutic agent, and also for efficaciously prevention or treatment of cancer.

IV. Selection of Agents

In another aspect, the present disclosure provides innovative methods for selecting agents that prevent or inhibit tumor invasion, angiogenesis and metastasis. According to the present disclosure, inhibition of lysyl oxidase (LOX) or lysyl oxidase-like protein (LOXL) may slow or halt the progression of the epithelial-mesenchymal transition (EMT) in tumor cells, or induce a mesenchymal-epithelial transition (MET) to a less tumorigenic state, thereby preventing or inhibiting the invasion, angiogenesis and metastasis of the tumor, and rendering the primary tumor cells more susceptible to other therapeutic intervention, such as irradiation, chemotherapeutic drugs, anti-neoplastic biologics, anti-angiogenetic agents, and anti-fibrotic agents.

In one embodiment, methods are provided for selecting an inhibitor of tumor invasion, angiogenesis or metastasis, comprising: contacting cells that are in an EMT state with an inhibitor of LOX or a LOXL; detecting a change in the EMT state of the cells, wherein reduction of the EMT state or a shift from the EMT to a MET state indicates that the LOX or LOXL inhibitor is an inhibitor of tumor invasion, angiogenesis or metastasis.

V. Diagnosis

In yet another aspect, the present disclosure provides innovative methodology and related compositions and kits for diagnosing or monitoring various diseases associated with abnormal cell proliferation, angiogenesis and fibrosis, by using molecules or agents that specifically recognize active or mature forms of lysyl oxidase or lysyl oxidase-like proteins. The inventors believe the processed LOX or LOXL are important biomarkers for tumor invasion and metastasis, and for diseases associated with abnormal angiogenesis and fibrotic diseases. The processed forms of LOX or LOXL can be active. The LOX or LOXL may be a proenzyme form or a mature form. The LOX or LOXL can also be a secreted form, which can also be active.

In one embodiment, methods are provided for diagnosing or monitoring cancer metastasis in a subject, comprising: assessing processed LOX or LOXL levels or activity in the blood or in a tumor, whereby a change in processed LOX or LOXL levels or activity in the blood or in the tumor in comparison with a reference sample indicates the presence of metastatic tumor growth. The change may be an increase or a decrease in processed LOX or LOXL levels or activity. Generally, an increase in processed LOX or LOXL levels or activity in the blood or tumor sample, as compared to a reference sample, indicates the presence of metastatic tumor growth.

In another embodiment, methods are provided for monitoring a subject's response to a therapy including a modulator of LOX/LOXL such as the treatment of cancer, tumors, angiogenesis, and fibrotic diseases. In another embodiment, the method comprises: detecting a change in the level of collagen telopeptides or hydroxyproline content in the subject after administration of a modulator of LOX or LOXL to the subject, wherein the change indicates that the LOX or LOXL modulator has a therapeutic effect on the subject. The change can be an increase or decrease. For example, a decrease in collagen telopeptides or hydroxyproline content can be indicative of a therapeutic effect.

The method comprises detecting a change in the level C-reactive protein, or other acute-phase reactants, in the subject after administration of a modulator of LOX or LOXL to the subject, wherein the change indicates that the LOX or LOXL modulator has a therapeutic effect on the subject. The change may be an increase or a decrease in C-reactive protein levels. Generally, a decrease in C-reactive protein levels indicates a decrease in LOX activity.

VI. Treatment of Fibrosis

In another aspect, methods are provided for preventing, treating, or ameliorating fibrosis in a subject in vivo, comprising administering to the subject an effective amount of an inhibitor of a lysyl oxidase (LOX) or lysyl oxidase-like protein (LOXL). The inhibitor of LOX or LOXL may be an inhibitor of an active form of LOX or LOXL.

Exemplary forms of fibrosis include, but are not limited to, cardiac fibrosis, liver fibrosis, kidney fibrosis, lung fibrosis, dermal scarring and keloids, and Alzheimer's disease. In still further embodiments, cardiac fibrosis is associated with hypertension, hypertensive heart disease (HHD), myocardial infarction (MI), atherosclerosis, and restenosis.

The kidney fibrosis may include, but not be limited to, diabetic nephropathy, vesicoureteral reflux, tubulointerstitial renal fibrosis, glomerulonephritis or glomerular nephritis (GN), focal segmental glomerulosclerosis, membranous glomerulonephritis, or mesangiocapillary GN. The liver fibrosis may include, but not be limited to, cirrhosis, and associated conditions such as chronic viral hepatitis, non-alcoholic fatty liver disease (NAFLD), alcoholic steatohepatitis (ASH), non-alcoholic steatohepatitis (NASH), primary biliary cirrhosis (PBC), biliary cirrhosis, autoimmune hepatitis). Lung fibrosis may include idiopathic pulmonary fibrosis (IPF) or cryptogenic fibrosing alveolitis, chronic fibrosing interstitial pneumonia, interstitial lung disease (ILD), and diffuse parenchymal lung disease (DPLD)). Cardiac fibrosis, congestive heart failure, cardiomyopathy, post-myocardial infarction defects in heart function; atherosclerosis; rheumatoid arthritis; glaucoma; age-related macular degeneration (wet AMD and dry AMD); emphysema, chronic obstructive pulmonary disease (COPD); multiple sclerosis; and chronic asthma may also be prevented, treated, or ameliorated with compositions of described herein.

Also provided herein are compositions, devices, systems, and kits for delivering inhibitors of LOX/LOXL locally to the site of fibrosis. Medical devices such as catheters and stents may be used to deliver locally, thus substantially reducing the risk of toxicity or other side effects associated with systemic delivery of such inhibitors of LOX/LOXL.

The inhibitors of LOX/LOXL may be delivered to a subject prior to, concurrently, or post a pathological cardiac condition or disease, such as hypertension, hypertensive heart disease (HHD), myocardial infarction (MI), atherosclerosis, and restenosis, to prevent the onset of, to reduce the risk of, or to retreat pathological fibrosis associated with such a pathological cardiac condition or disease. For example, an inhibitor of LOX/LOXL may be administered at least 1 hr, 2 hrs, 3 hrs, 5 hrs, or 10 hrs, or 1, 2, 3, 4, 5, 6, 7, 8, 9, 10, 11, 12, 13, 14 or more days after the onset of such a pathological cardiac condition or disease.

The LOX or LOXL may be a full-length or processed form. The LOX or LOXL may be a proenzyme form or a mature form, and both forms can be active. The LOX or LOXL can be a secreted form, which can also be active. The processed form of the LOX or LOXL is a form after proteolytic processing or cleavage.

Examples of LOXL include but are not limited to LOXL1, LOXL2, LOXL3, and LOXL4. In some embodiments, the inhibitor of LOX or LOXL may be an inhibitor of active LOX, LOXL2 or LOXL4. In some of these embodiments, the inhibitor of LOX or LOXL inhibits both active LOX and LOXL2.

The LOX or LOXL inhibitor may be, for example, an antibody against LOX or LOXL, a small molecule inhibitor, siRNA, shRNA or an antisense polynucleotide against LOX or LOXL. The inhibitors may be noncompetitive inhibitors.

BRIEF DESCRIPTION OF THE DRAWINGS

FIG. 7 shows induction of MET-like change by depleting LOXL2 in MDA-MB-231. (A-B) MDA-MB-231 WT cells and (C-F) MDA-MB-231 shLoxl2 (C, D): pool 1; (E, F): pool 2) stable knockdown cells were stained with rhodamine phalloidin (actin cytoskeleton stain). Cells are elongated and spindly-shaped in WT cells (A-B) while MDA-MB-231 shLoxl2 stable knockdown cells are rounded and smaller in shape (C-F). F-actin staining (rhodamin phalloidin) moves from fibrillar to circular/cell rim upon LOXL2 depletion by shRNA knockdown.

FIG. 12 shows SW620 cells incubated with Conditioned Media (CM) from MDA MB 231 cells undergo EMT phenotype changes. (A-B) SW620 cells are incubated with Conditioned Media (CM) from MDA MB 231 cells, at 20× and 40×. Arrows indicate morphology of SW620 cells undergoing EMT-like phenotype. Cells undergo EMT phenotype (as indicated by rhodamine phalloidin staining) changes 72 hours later. (C-D) SW620 cells incubated with Conditioned Media (CM) from 293 wildtype cells maintain typical "normal" round shape −72 hours later, at 20× and 40×. Conditioned media (CM) from MDA MB 231 or 293 cells is 3 day CM.

FIG. 14 is a schematic of (A) uncleaved and intracellular LOX/LOXL and cleaved, active LOX/LOXL and (B) active LOX/LOXL cellular uptake and activity promotes EMT, while uptake of active LOX/LOXL is blocked when bound to an inhibitor such as an antibody, reducing EMT and/or increasing MET.

FIG. 16 shows 2 forms of LOXL2 predominate in cell lines. (A) LOXL2 protein expression and secretion in cell lines. Breast tumor cell lines: Hs578t, MDA-MB-231, MCF7; Lung tumor cell line: A549. (B) Schematic of LOXL2 forms commonly detected.

FIG. 21 is a graph demonstrating a mode of inhibition of LOXL2. (A) AB0023 is a non-competitive inhibitor of LOXL2, whereas (B) βAPN is a competitive inhibitor of LOXL2. E=enzyme, P=product, S=substrate, I/A=inhibitor/antibody.

FIG. 24 shows confluent Hs578t and anti-LOX antibody internalization and uptake of (A) permeabilized or (B) non-permeabilized cells. Cells were 2 days post-confluent, 4 days after plating at 50,000 cells/well in 8 chamber slides. Cells were incubated for 3 hours with anti-Lox M64 and detected with Alexa 488-green. Similar results of internalization and uptake of Loxl2 mAbs was obtained.

FIG. 31 depicts the expression of LOX/LOXL in lung adenocarcinoma samples relative to expression in adjacent normal tissue from the same patient. A) LOX, LOXL1, LOXL2, LOXL4, and B) is the same data as A) with only LOX and LOXL2 plotted. T: tumor; N: normal.

FIG. 43 illustrates common modes of enzymatic inhibition.

DETAILED DESCRIPTION

Figure 1:
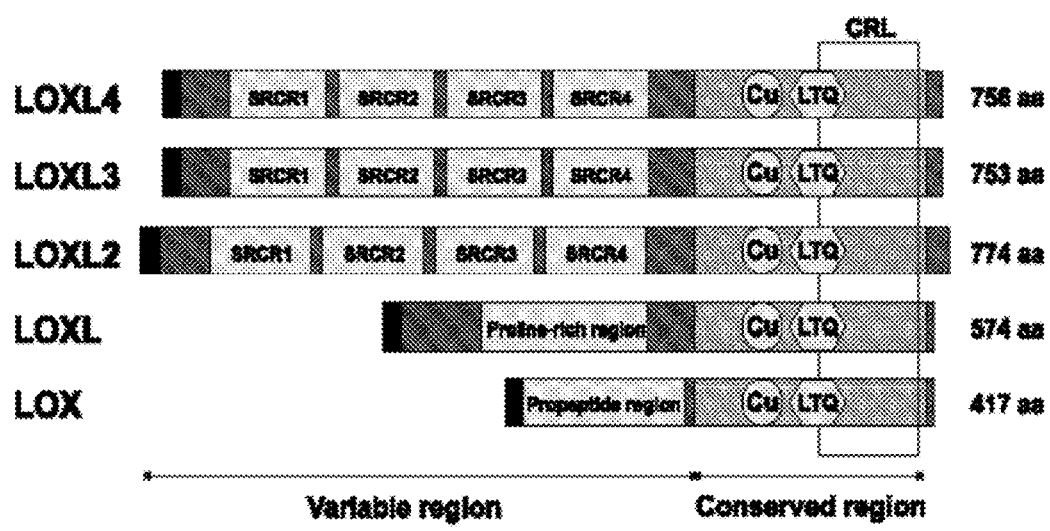
FIG. 1 is a schematic of the LOX/LOXL genomic and protein organization.
Figure 2:
FIG. 2 is a sequence alignment of LOX/LOXL with predicted and determined N- and O-glycosylation sites, bipartite nuclear localization signals, and procollagen C-proteinase sites.
Figure 3:
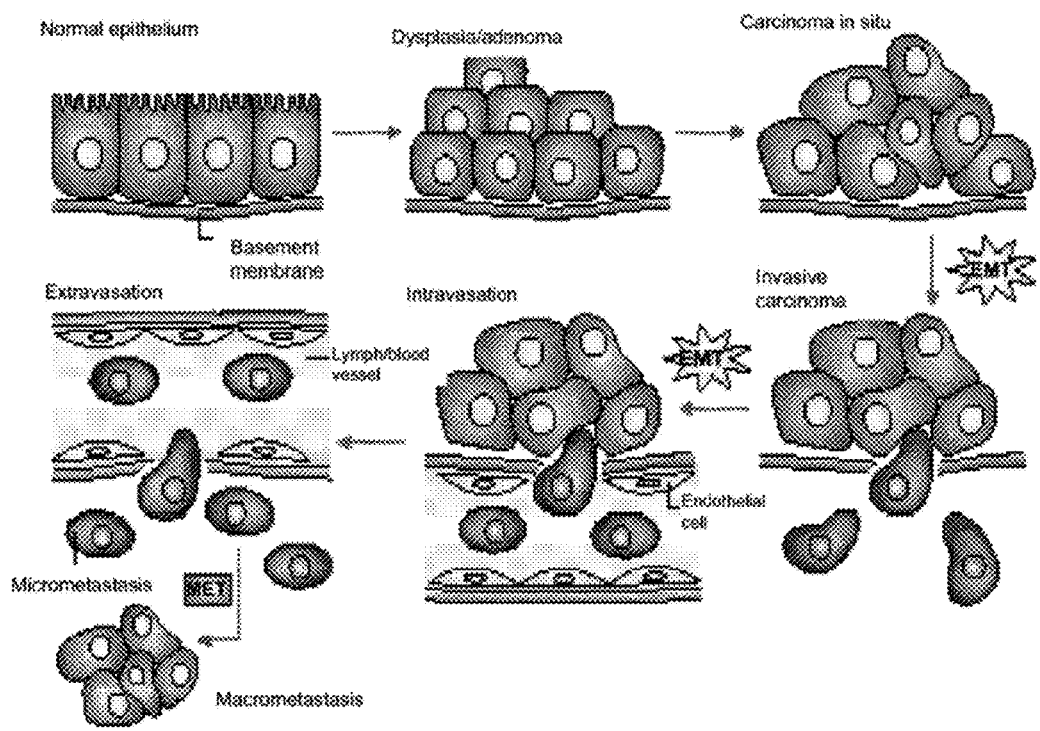
FIG. 3 illustrates the epithelial-mesenchymal transition and its role in invasion and metastasis.

I. Treatment by Inhibition of LOX or LOXL

The present disclosure provides innovative methodology and related compositions and kits for preventing and treating various diseases associated with abnormal cell proliferation, angiogenesis and fibrosis, by using an inhibitor of processed form of lysyl oxidase (LOX) or lysyl oxidase-like proteins (LOXL).

While not wishing to be bound by theory, inhibition of the processed forms of LOX or LOXL is effective in preventing or treating tumor invasion and metastasis, and for treating diseases associated with abnormal angiogenesis and fibrotic diseases.

In one embodiment, methods are provided for treating or preventing tumor invasion or metastasis in a subject in vivo, comprising: administering to the subject an effective amount of an inhibitor of a LOX or LOXL.

In another embodiment, methods are provided for reducing tumor growth in a subject in vivo, comprising: administering to the subject an effective amount of an inhibitor of a processed LOX or LOXL such that the tumor growth is reduced by at least 25%, 50%, 75%, 90%, or 95%. According to some embodiments, the tumor may be a metastatic tumor.

In yet another embodiment, methods are provided for increasing or enhancing the chances of survival of a subject with metastatic tumor, comprising: administering to a subject in need thereof an effective amount of an inhibitor of processed LOX or LOXL, thereby increasing or enhancing the chances of survival of the subject treated by a certain period of time. In some embodiments, the survival of the subject is increased by at least 10 days, 1 month, 3 months, 6 months, 1 year, 1.5 years, 2 years, 3 years, 4 years, 5 years, 8 years, or 10 years.

The processed forms of LOX or LOXL can be active. The LOX or LOXL can also be a secreted form, which can also be active. The active LOX or LOXL may be a mature form of the LOX or LOXL after proteolytic processing or cleavage. Examples of LOXL include but are not limited to LOXL1, LOXL2, LOXL3, and LOXL4. In some embodiments, the inhibitor LOX or LOXL is an inhibitor of active LOX, LOXL2 or LOXL4. For example, the inhibitor of LOX or LOXL inhibits both active LOX and active LOXL2.

The LOX or LOXL inhibitor may be an antibody against LOX or LOXL, a small molecule inhibitor, siRNA, shRNA or an antisense polynucleotide against LOX or LOXL.

In some embodiments, the LOX or LOXL inhibitor is an antibody specifically binding to a region of LOX or LOXL having an amino acid sequence selected from SEQ ID NOs: 1-18 as shown in Tables 1 and 2 below.

As described in more detail below and in the EXAMPLE section, various inhibitors of active LOX or LOXL (such as small molecules or antibodies) may be used to inhibit tumor invasion, angiogenesis or metastasis, and for treating cancer, tumors, and diseases associated with abnormal angiogenesis and fibrotic diseases.

II. Treatment by Inhibition of Both LOX and LOXL

The present disclosure also provides innovative methodology and related compositions and kits for preventing and treating various diseases associated with abnormal cell proliferation, angiogenesis and fibrosis, by using an inhibitor of a processed form of lysyl oxidase (LOX) or lysyl oxidase-like proteins (LOXL).

Simultaneous inhibition of both LOX and LOXL is effective in preventing or treating invasion and metastasis of a wide variety of tumors, and for treating diseases associated with abnormal angiogenesis and fibrotic diseases.

In one embodiment, methods are provided for treating or preventing tumor invasion or metastasis in a subject in vivo, comprising administering to the subject an effective amount of an inhibitor of LOX and an inhibitor of a LOXL.

In another embodiment, methods are provided for reducing tumor growth in a subject in vivo, comprising administering to the subject an effective amount of an inhibitor of LOX and an inhibitor of a LOXL such that the tumor growth is reduced by at least 25%, 50%, 75%, 90%, or 95%. According to some embodiments, the tumor may be metastatic tumor.

In yet another embodiment, methods are provided for increasing or enhancing the chances of survival of a subject with metastatic tumor, comprising administering to a subject in need thereof an effective amount of an inhibitor of LOX and an inhibitor of a LOXL, thereby increasing or enhancing the chances of survival of the subject treated by a certain period of time. In some embodiments, the survival of the subject is increased by at least 10 days, 1 month, 3 months, 6 months, 1 year, 1.5 years, 2 years, 3 years, 4 years, 5 years, 8 years, or 10 years.

The inhibitor of LOX and the inhibitor of the LOXL can be different, each specifically inhibiting LOX and the LOXL, respectively. Alternatively, the inhibitor of LOX and the inhibitor of LOXL can be the same molecule which inhibits both LOX and the LOXL. In some embodiments, the LOXL is LOXL1, 2, 3 or 4. In some of these embodiments, the LOXL is LOXL2 or 4, for example, the LOXL is LOXL2.

Optionally, the inhibitor of LOX or LOXL inhibits a form of the LOX or LOXL after proteolytic processing or cleavage. The LOX or LOXL may be a proenzyme form or a mature form. The LOX or LOXL may be an active form. The full length or processed forms of LOX or LOXL can be active.

Optionally, the inhibitor of LOX or LOXL inhibits a secreted form of the LOX or LOXL.

The LOX or LOXL inhibitor may be an antibody against LOX or LOXL, a small molecule inhibitor, siRNA, shRNA or an antisense polynucleotide against LOX or LOXL.

In some embodiments, the LOX or LOXL inhibitor is an antibody specifically binding to a region of LOX or LOXL having an amino acid sequence selected from SEQ ID NOs: 1-18 as shown in Tables 1 and 2 below.

As described in more detail below and in the EXAMPLE section, various inhibitors of LOX or LOXL (such as small molecules or antibodies) may be used to inhibit tumor invasion, angiogenesis or metastasis, and for treating cancer, tumors, and diseases associated with abnormal angiogenesis and fibrotic diseases.

III. Combination Therapy

The present disclosure also provides innovative methodology and related compositions and kits for preventing and treating various diseases associated with abnormal cell proliferation, angiogenesis and fibrosis, by using a combination therapy including a modulator of lysyl oxidase (LOX) or lysyl oxidase-like proteins (LOXL).

As described in detail below, inhibition of LOX or LOXL could slow or halt the progression of epithelial-mesenchymal transition (EMT) in tumor cells, or induce a mesenchymal-epithelial transition (MET) to a less tumorigenic state, thereby rendering the tumor or diseased cells more susceptible to irradiation, chemotherapeutic drugs, anti-neoplastic biologics, anti-angiogenetic agents, and anti-fibrotic agents.

IV. Selection of Agents

The present disclosure provides innovative methods for selecting agents that prevent or inhibit tumor invasion, angiogenesis and metastasis. These agents can be used alone or in combination with other therapeutic agents to prevent or treat diseases associated with abnormal cell proliferation, angiogenesis and fibrosis, such as cancer, tumors, diabetic retinopathy, macular degeneration, scleroderma, liver fibrosis, kidney fibrosis, lung fibrosis, scleroderma, atherosclerosis, and Alzheimer's disease.

According to the present disclosure, methods are provided for selecting an inhibitor of tumor invasion, angiogenesis or metastasis, comprising contacting cells that are in an epithelial-mesenchymal transition (EMT) state with an inhibitor of lysyl oxidase (LOX) or a lysyl oxidase-like protein (LOXL); detecting a change in the EMT state of the cells, wherein reduction of the EMT state or a shift from the EMT to a MET state indicates that the LOX or LOXL inhibitor is an inhibitor of fibrosis, tumor invasion, angiogenesis or metastasis. Thus, also provided herein are methods for using the EMT-MET assays to screen for LOX/LOXL inhibitors that facilitate the transition from EMT to MET in tumor cells.

While not wishing to be bound by the theory, the role of LOX and LOXL in EMT is associated with uptake of active LOX or LOXL by tumor cells, allowing LOX or LOXL to interact with relevant intracellular cofactors; and inhibition of LOX or LOXL could slow or halt the progression of EMT in tumor cells, or induce a MET to a less tumorigenic state, thereby preventing or inhibiting the invasion, angiogenesis and metastasis of the tumor, and rendering the primary tumor cells more susceptible to other therapeutic intervention, such as irradiation, chemotherapeutic drugs, anti-neoplastic biologics, anti-angiogenetic agents, and anti-fibrotic agents.

An EMT state of cells has the characteristics of positive vimentin or fibronectin staining with low levels of E-cadherin staining and an elongated and remodeled actin cytoskeleton as revealed by phalloidin staining of F-actin. Thus, the reduction of the EMT state or a shift from the EMT to a MET state can be monitored by measuring or detecting a decrease in vimentin or fibronectin staining an increase in E-cadherin staining, and/or remodeling of the actin cytoskeleton by phalloidin staining of F-actin.

Optionally, in vitro or in vivo tumor invasion or migration may be used to assess EMT or MET phenotypes of the cells, as increased invasiveness and migratory capacity are associated with EMT. For example, an in vitro wound-healing or scratch assay may be used to monitor the transition from EMT to MET state, as cells in a state of EMT that are more invasive and migratory should fill the scratch more rapidly than less invasive or migratory cells.

As described in more detail below and in the EXAMPLE section, various LOX or LOXL inhibitors (such as small molecules or antibodies) may be tested for their ability to inhibit tumor invasion, angiogenesis or metastasis by using the EMT-MET transition assay. Inhibition of the full length or processed forms of LOX or LOXL are effective in preventing or treating tumor invasion and metastasis. Thus, also provided therein are methods for screening, selecting and designing candidate compounds for inhibition of active forms of LOX or LOXL, and methods for generating antibodies against active forms of LOX or LOXL.

V. Diagnosis

The present disclosure provides innovative methodology and related compositions and kits for diagnosing or monitoring various diseases associated with abnormal cell proliferation, angiogenesis and fibrosis, by using molecules or agents that specifically recognize a processed form of lysyl oxidase (LOX) or lysyl oxidase-like proteins (LOXL). Without being bound by theory, the processed forms of LOX or LOXL are important biomarkers for tumor invasion and metastasis, and for diseases associated with abnormal angiogenesis and fibrotic diseases.

In one embodiment, methods are provided for diagnosing or monitoring cancer metastasis in a subject, comprising assessing processed LOX or LOXL levels or activity in the blood or in a tumor, whereby a change in processed LOX or LOXL levels or activity in the blood or in the tumor in comparison with a reference sample, indicates the presence of metastatic tumor growth. The change may be an increase or a decrease in processed LOX or LOXL levels or activity. Generally, an increase in processed LOX or LOXL levels or activity in the blood or tumor sample, as compared to a reference sample, indicates the presence of metastatic tumor growth.

As described in more detail below, levels of processed LOX or LOXL can be assessed by various methods including but are not limited to immunohistochemistry by using antibodies that specifically bind to the processed form of LOX or LOXL. Enzymatic activity of active LOX or LOXL can be measured by using various methods including but not limited to chromogenic and fluorometric assays.

VI. Treatment of Fibrosis

Also provided herein are compositions, methods, and kits for preventing and treating various diseases associated with fibrosis, by using an inhibitor of an active form of lysyl oxidase (LOX) or lysyl oxidase-like proteins (LOXL).

In one aspect, a method is provided for treating a pathological cardiac condition or disease in a subject, comprising: administering to the subject an effective amount of an inhibitor of LOX or LOXL. For example, the pathological cardiac condition or disease may be hypertension, hypertensive heart disease (HHD), myocardial infarction (MI), atherosclerosis, or restenosis.

In another aspect, a method is provided for preventing a pathological cardiac condition or disease in a subject, comprising: administering to the subject an effective amount of an inhibitor of LOX or LOXL prior to, concurrently, or post an adverse cardiac event. The adverse cardiac event may be myocardial infarction, such as acute myocardial infarction.

The inhibitor of LOX or LOXL may be administered prior to, concurrently, or post the adverse cardiac event. For example, the inhibitor may be administered at least 1 hr, 2 hrs, 3 hrs, 5 hrs, or 10 hrs, or 1, 2, 3, 4, 5, 6, 7, 8, 9, 10, 11, 12, 13, 14 or more days after myocardial infarction.

The inhibitor of LOX or LOXL may be delivered to the subject locally to the site of fibrosis caused by the adverse cardiac event.

In yet another aspect, a device is provided for preventing or treating a pathological cardiac condition or disease in a subject, comprising: a component comprising an inhibitor of LOX or LOXL. The component may be a stent incorporating an inhibitor of LOX or LOXL, which may be a small molecule with a molecular weight below 500 Dalton, such as β-aminoproprionitrile (BAPN). The inhibitor may be coated on the stent.

Alternatively, the device may comprise a catheter for delivering the inhibitor of LOX or LOXL locally to the site of cardiac fibrosis caused by the adverse cardiac event.

In still another aspect, a kit is provided comprising: a pharmaceutical composition comprising an inhibitor of LOX or LOXL in a pharmaceutically acceptable excipient; and instructions for how to treat or prevent a pathological cardiac condition or disease using the pharmaceutical composition.

Also provided are methods, compositions, and kits for treating or preventing a disease associated with fibrosis in a subject, comprising: administering to the subject an effective amount of an inhibitor of LOX or LOXL. The disease associated with fibrosis can be selected from liver fibrosis, kidney fibrosis, lung fibrosis, dermal scaring and keloid formation, and Alzheimer's disease.

The inhibitor of LOX or LOXL may be an inhibitor of an active LOX or LOXL. The active LOX or LOXL may be a mature form of the LOX or LOXL after proteolytic processing or cleavage. Examples of LOXL include but are not limited to LOXL1, LOXL2, LOXL3, and LOXL4. The inhibitor LOX or LOXL can be an inhibitor of active LOX, LOXL2 or LOXL4. In some embodiments, the inhibitor LOX or LOXL inhibits both active LOX and active LOXL2.

The LOX or LOXL inhibitor may be an antibody against LOX or LOXL, a small molecule inhibitor, siRNA, shRNA or an antisense polynucleotide against LOX or LOXL.

In certain embodiments, the LOX or LOXL inhibitor is an antibody specifically binding to a region of LOX or LOXL having an amino acid sequence selected from the group consisting of SEQ ID NOs:1-18, as shown in Tables 1 and 2 below.

As described in more detail below and in the examples, various inhibitors of LOX or LOXL (such as small molecules or antibodies) may be used.

1. Lysyl Oxidase and Lysyl Oxidase-Like Proteins

As used herein, the term "lysyl oxidase" refers to an enzyme that catalyzes the following reaction: peptidyl-L-lysyl-peptide+$O_2$+$H_2O$→peptidyl-allysyl-peptide+$NH_3$+$H_2O_2$. Other synonyms for lysyl oxidase (EC 1.4.3.13) include protein-lysine 6-oxidase and protein-L-lysine:oxygen 6-oxidoreductase (deaminating). See, e.g., Harris et al., *Biochim. Biophys. Acta* 341:332-44 (1974); Rayton et al., *J. Biol. Chem.* 254:621-26 (1979); Stassen, *Biophys. Acta* 438: 49-60 (1976). A copper-containing quinoprotein with a lysyl adduct of tyrosyl quinone at its active center, lysyl oxidase catalyzes the oxidation of peptidyl lysine to result in the formation of peptidyl alpha-aminoadipic-delta-semialdehyde. Once formed, this semialdehyde can spontaneously condense with neighboring aldehydes or with other lysyl groups to from intra- and interchain cross-links. See, e.g., Rucker et al., *Am. J. Clin. Nutr.* 67:9965-10025 (1998). An example of lysyl oxidase or lysyl oxidase-like protein include the enzyme having an amino acid sequence substantially identical to a polypeptide expressed or translated from one of the following sequences: EMBL/GenBank accessions: M94054; AAA59525.1—mRNA; S45875; AAB23549.1—mRNA; S78694; AAB21243.1—mRNA; AF039291; AAD02130.1—mRNA; BC074820; AAH74820.1—mRNA; BC074872; AAH74872.1—mRNA; M84150; AAA59541.1—Genomic DNA. One embodiment of LOX is human lysyl oxidase (hLOX) preproprotein.

Examples of a lysyl oxidase like enzyme or protein are described in Molnar et al., *Biochim Biophys Acta.* 1647:220-24 (2003); Csiszar, *Prog. Nucl. Acid Res.* 70:1-32 (2001); and in WO 01/83702 published on Nov. 8, 2001, all of which are herein incorporated by reference. (It is noted that in these 3 publications, "LOXL1" was referred to as "LOXL" whereas in the present disclosure "LOXL" is referred to a lysyl oxidase-like protein in general, not just LOXL1.) These enzymes include LOXL1, encoded by mRNA deposited at GenBank/EMBL BC015090; AAH15090.1; LOXL2, encoded by mRNA deposited at GenBank/EMBL U89942; LOXL3, encoded by mRNA deposited at GenBank/EMBL AF282619; AAK51671.1; and LOXL4, encoded by mRNA deposited at GenBank/EMBL AF338441; AAK71934.1.

"Lysyl oxidase" or LOX also encompasses a functional fragment or a derivative that still substantially retains its enzymatic activity catalyzing the deamination of lysyl residues. Typically, a functional fragment or derivative retains at least 50% of its lysyl oxidation activity. In some embodiments, a functional fragment or derivative retains at least 60%, 70%, 80%, 90%, 95%, 99% or 100% of its lysyl oxidation activity. It is also intended that a lysyl oxidase can include conservative amino acid substitutions that do not substantially alter its activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity. See, e.g., Watson, et al., *Molecular Biology of the Gene,* 4th Edition, 1987, The Benjamin/Cummings Pub. Co., p. 224.

Details of some examples lysyl oxidase or lysyl oxidase-like proteins are provided below.

Lysyl oxidase is a copper containing amine oxidase that oxidizes primary amine substrates to reactive aldehydes. Lysyl oxidase catalyzes oxidative deamination of peptidyl lysine and hydroxylysine residues in collagens, and peptidyl lysine residues in elastin, and is essential for the formation of the extracellular matrix. The resulting peptidyl aldehydes spontaneously condense and undergo oxidation reactions to form the lysine-derived covalent cross-links required for the normal structural integrity of the extracellular matrix. Hydrogen peroxide ($H_2O_2$) and ammonium are released in quantities stoichiometric with the peptidyl aldehyde product. See, e.g., Kagan et al., *J. Cell. Biochem* 88:660-672 (2003).

The main activity of LOX is the oxidation of specific lysine residues in collagen and elastin outside of the cell, however, it may also act intracellularly, where it may regulate gene expression (Li et al., *Proc. Natl. Acad. Sci. USA* 94:12817-12822 (1997), Giampuzzi et al., *J. Biol. Chem.* 275:36341-36349 (2000)) In addition, LOX induces chemotaxis of monocytes, fibroblasts and smooth muscle cells (Lazarus et al., *Matrix Biol.* 14:727-731 (1995) Nelson et al., *Proc. Soc. Exp. Biol. Med.* 188:346-352 (1988)). LOX itself is induced by a number of growth factors and steroids such as TGF-β, TNF-α, and interferon (Csiszar, *Prog. Nucl. Acid Res.* 70:1-32 (2001)). Recent studies have attributed other roles to LOX in diverse biological functions such as developmental regulation, tumor suppression, cell motility, and cellular senescence. The diverse role of LOX, and its recently discovered amino oxidase family, LOX-like (LOXL), may play important roles with their intracellular and extracellular localization.

Five different lysyl oxidases are known to exist in both humans and mice, LOX and four LOX related, or LOX-like proteins (LOXL, LOXL2, LOXL3, LOXL4), referred to collectively as "LOX/LOXL" for the purposes of this disclosure. The five forms of lysyl oxidases reside on five different chromosomes. These family members show some overlap in structure and function, but appear to have distinct functions as well. For example, targeted LOX deletion by mutagenesis appears to be lethal at parturition in mice (Hornstra et al., *J. Biol. Chem.* 278:14387-14393 (2003)), whereas LOXL deficiency causes no severe developmental phenotype (Bronson et al., *Neurosci. Lett.* 390:118-122 (2005)).

LOX has highly conserved protein domains, conserved in several species including human, mouse, rat, chicken, fish and Drosophila. The human LOX family has a highly conserved C-terminal region containing the 205 amino acid LOX catalytic domain. The conserved region contains the copper binding (Cu), conserved cytokine receptor like domain (CRL), and the lysyl-tyrosylquinone cofactor site (LTQ). The predicted extracellular signal sequences are represented by the hatched boxes. Twelve cysteine residues are also similarly conserved, wherein two of them reside within the prepropeptide region and ten are in the catalytically active processed form of LOX (Csiszar, *Prog. Nucl. Acid Res.* 70:1-32 (2001)). The conserved region also includes a fibronectin binding domain.

The prepropeptide region of LOX contains the signal peptide, and is cleaved, the cleavage site predicted to be between Cys21-Ala22, to generate a signal sequence peptide and a 48 kDa amino acid propeptide form of LOX, also referred herein as full-length form. The propeptide is N-glycosylated during passage through the Golgi that is secreted into the extracellular environment where the proenzyme, or propeptide, is cleaved between Gly168-Asp169 by a metalloendoprotease, a procollagen C-proteinase, which are products of the Bmp1, Tll1 and Tll2 genes, to produce a processed or mature form of the enzyme. BMP I (bone morphogenetic protein I) is a procollagen C-proteinase that processes the propeptide to yield a functional 30 kDa enzyme and an 18 kDa propeptide. The sequence coding for the propeptide is moderately (60-70%) conserved, whereas the sequence coding for the C-terminal 30 kDa region of the proenzyme in which the active site is located is highly conserved (approximately 95%). (Kagan and Li, *J. Cell. Biochem.* 88:660-672 (2003); Kagan et al., *J. Cell Biochem.* 59:329-38 (1995)). The N-glycosyl units are also subsequently removed.

Similar potential signal peptides have been predicted at the amino terminus of LOXL, LOXL2, LOXL3, and LOXL4. The predicted signal cleavage sites are between Gly25-Gln26 for LOXL, between Ala25-Gln26, for LOXL2, and between Gly25-Ser26 for LOXL3. The consensus for BMP-1 cleavage in procollagens and pro-LOX is between Ala/Gly-Asp, and often followed by an acidic or charged residue. A potential cleavage site to generate processed LOXL is Gly303-Asp304, however, it is then followed by an atypical Pro. LOXL3 also has a potential cleavage site at Gly447-Asp448, which is followed by an Asp, processing at this site may yield a mature peptide of similar size to mature LOX. A potential cleavage site of BMP-1 was also identified within LOXL4, at residues Ala569-Asp570 (Kim et al., *J. Biol. Chem.* 278:52071-52074 (2003)). LOXL2 may also be proteolytically cleaved analogously to the other members of the LOXL family and secreted into media (Akiri et al., *Cancer Res.* 63:1657-1666 (2003)).

A feature not known to be common amongst LOX and LOXL is the scavenger receptor cysteine rich (SRCR) domains. LOX and LOXL lack SRCR domains, whereas LOXL2, LOXL3, and LOXL4 each have four SRCR domains at the N-terminus. SRCR domains are found in secreted, transmembrane, or extracellular matrix proteins. SRCR domains are also known to mediate ligand binding in a number of secreted and receptor proteins (Hoheneste et al., *Nat. Struct. Biol.* 6:228-232 (1999); Sasaki et al., *EMBO J.* 17:1606-1613 (1998)). Another domain unique to LOXL is the presence of a proline rich domain (Molnar et al., *Biochimica Biophsyica Acta* 1647:220-224 (2003)).

Tissue distribution may also differ amongst LOX and the various LOXL. LOX is highly expressed in the heart, placenta, testis, lung, kidney and uterus, but marginally in the brain and liver. LOXL1 is expressed in the placenta, kidney, muscle, heart, lung, and pancreas, and as with LOX, has much lower expressing in the brain and liver (Kim et al., *J. Biol. Chem.* 270:7176-7182 (1995)). LOXL2 is highly expressed in the uterus, placenta, and other organs, but similar to LOX and LOXL, lowly expressed in the brain and liver (Jourdan Le-Saux et al., *J. Biol. Chem.* 274:12939:12944 (1999)). LOXL3 is highly expressed in the testis, spleen, and prostate, moderately in placenta, and not in the liver, whereas LOXL4 is highly expressed in the liver (Huang et al., *Matrix Biol.* 20:153-157 (2001); Maki and Kivirikko, *Biochem. J.* 355: 381-387 (2001); Jourdan Le-Saux et al., *Genomics* 74:211-218 (2001); Asuncion et al., *Matrix Biol.* 20:487-491 (2001)).

The expression, or implication of LOX and the different LOXL proteins, in diseases may also vary. This may be due to a number of reasons, such as the difference in tissue distribution, processing, domains, regulation of activity, as well as other differences between the proteins. For example, LOX and LOXL are implicated in fibrotic diseases as both LOX and LOXL are highly expressed in myo-fibroblasts around fibrotic areas (Kagen, *Pathol. Res. Pract.* 190:910-919 (1994); Murawaki et al., *Hepatology* 14:1167-1173 (1991); Siegel et al., *Proc. Natl. Acad. Sci. USA* 75:2945-2949 (1978); Jourdan Le-Saux et al., *Biochem. Biophys. Res. Comm.* 199:587-592 (1994); Kim et al., *J. Cell Biochem.* 72:181-188 (1999)). LOX and the various LOXL are also implicated in a number of cancers. For example, LOXL1 and LOXL4 have been shown to be epigenetically silenced and can inhibit ras/extracellular signal-regulated kinase signaling pathway in human bladder cancer (Wu et al., *Cancer Res.* 67:4123-4129 (2007)). Others have shown selective upregulation and amplification of the LOXL4 gene in head and neck squamous cell carcinoma (Gorough et al., *J. Pathol.* 212:74-82 (2007)). LOX and LOXL2 have also been implicated in a number of tumors, such as colon and esophageal cancers (Csiszar, *Prog. Nucl. Acid Res.* 70:1-32 (2001)). In breast cancer, LOX and the LOXL family members have been linked to the cancer (Kirschmann et al., *Cancer Res.* 62:448-4483 (2002)).

2. Screening for Modulators of Active LOX/LOXL

Modulators of active LOX/LOXL can also be selected by using a wide variety of screening assays. The active LOX/LOXL, after secretion and proteolytic cleavage of the preproprotein, can be selected by using a wide variety of screening assays. In one embodiment, methods are provided for selecting a compound that binds to an active LOX/LOXL, comprising incubating a candidate binding compound with a polypeptide of an active LOX or LOXL; and determining if binding has occurred.

In another embodiment, methods are provided for identifying a modulator, e.g., activators/agonists or inhibitors/antagonists of an active LOX/LOXL, comprising incubating a candidate compound with active LOX/LOXL; assaying a biological activity of the active LOX/LOXL; and determining if the biological activity of the active LOX/LOXL has been altered.

In another embodiment, methods are provided for identifying activators or inhibitors of active LOX/LOXL, comprising incubating a candidate compound in a cell culture containing active LOX/LOXL; and detecting the change of biological activity of the cells in the culture, wherein the change of the biological activity of the cells in the culture is indicative for an activator or inhibitors of active LOX/LOXL. The change in biological activity may be a LOX/LOXL specific function, LOX/LOXL enzymatic activity, or levels of LOX/LOXL. In some embodiments, the biological activity is a cellular function, such as migration, EMT/MET, or others and the change is compared to control or reference sample(s). For example, controls may be negative control samples may include a culture with decrease levels of active LOX/LOXL to which the candidate compound is added or a culture with the same amount of active LOX/LOXL but no candidate compound added. In some embodiments, separate cultures containing different amounts of active LOX/LOXL are contacted with a candidate compound. For example, if a change in biological activity is observed, and if the change is greater in the culture having higher amounts of active LOX/LOXL, the compound is identified as an activator of active LOX/LOXL.

In another example, expressing significant amount of LOX and/or LOXL can be used as a source for active LOX/LOXL for the screening assays described herein, whereas whole cell lysate would contain not only active LOX and/or LOXL but also inactive LOX and/or LOXL.

The compound or plurality of compounds may be chemically synthesized or microbiologically produced and/or comprised in, for example, samples, e.g., cell extracts from, e.g., plants, animals or microorganisms. Furthermore, the compound(s) may be known in the art but hitherto not known to be capable of suppressing or activating active LOX/LOXL. The reaction mixture may be a cell free extract or may comprise a cell or tissue culture: Suitable set ups for the method of the disclosure are known to the person skilled in the art and are, for example, generally described in Alberts et al., *Molecular Biology of the Cell, third edition* (1994) and in the appended examples. A plurality of compounds may be, e.g., added to the reaction mixture, culture medium, injected into a cell or otherwise applied to a transgenic animal. The cell or tissue that may be employed in the method of the disclosure is a host cell, mammalian cell or non-human transgenic animal of the disclosure.

If a sample containing a compound or a plurality of compounds is identified in the method of the disclosure, then it is either possible to isolate the compound from the original sample identified as containing the compound capable of suppressing or activating active LOX/LOXL, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, for example, until the sample identified according to the method of the disclosure only comprises a limited number of or only one substance(s). In some embodiments the sample comprises substances of similar chemical and/or physical properties, and in some embodiments, the substances are identical.

Several methods are known to the person skilled in the art for producing and screening large libraries to identify compounds having specific affinity for a target, such as active LOX/LOXL. These methods include the phage-display method in which randomized peptides are displayed from phage and screened by affinity chromatography to an immobilized receptor; see, e.g., WO 91/17271, WO 92/01047, U.S. Pat. No. 5,223,409.

In another approach, combinatorial libraries of polymers immobilized on a chip are synthesized using photolithography; see, e.g., U.S. Pat. No. 5,143,854, WO 90/15070 and WO 92/10092. The immobilized polymers are contacted with a labeled receptor and scanned for label to identify polymers binding to the receptor. The synthesis and screening of peptide libraries on continuous cellulose membrane supports that can be used for identifying binding ligands of the polypeptide of the disclosure and thus possible inhibitors and activators is described, for example, in Kramer, *Methods Mol. Biol.* 87 (1998), 25-39. This method can also be used, for example, for determining the binding sites and the recognition motifs in the active LOX/LOXL. In like manner, the substrate specificity of the DnaK chaperon was determined and the contact sites between human interleukin-6 and its receptor; see Rudiger, *EMBO J.* 16 (1997), 1501-1507 and Weiergraber, *FEBS Lett.* 379 (1996), 122-126, respectively.

Furthermore, the above-mentioned methods can be used for the construction of binding epitopes derived from the active LOX/LOXL. A similar approach was successfully described for peptide antigens of the anti-p24 (HIV-1) monoclonal antibody; see Kramer, *Cell* 91 (1997), 799-809. A general route to fingerprint analyses of peptide-antibody interactions using the clustered amino acid peptide library was described in Kramer, *Mol. Immunol.* 32 (1995), 459-465. In addition, antagonists of the active LOX/LOXL can be derived and identified from monoclonal antibodies that specifically react with the polypeptide of the disclosure in accordance with the methods as described in Doring, *Mol. Immunol.* 31 (1994), 1059-1067.

More recently, WO 98/25146 described further methods for screening libraries of complexes for compounds having a desired property, e.g., the capacity to agonize, bind to, or antagonize a polypeptide or its cellular receptor. The complexes in such libraries comprise a compound under test, a tag recording at least one step in synthesis of the compound, and a tether susceptible to modification by a reporter molecule. Modification of the tether is used to signify that a complex contains a compound having a desired property. The tag can be decoded to reveal at least one step in the synthesis of such a compound. Other methods for identifying compounds which interact with the polypeptides according to the disclosure or nucleic acid molecules encoding such molecules are, for example, the in vitro screening with the phage display system as well as filter binding assays or "real time" measuring of interaction using, for example, the BIAcore apparatus (Pharmacia).

All these methods can be used in accordance with the present disclosure to identify activators/agonists and inhibitors/antagonists of the active LOX/LOXL or related polypeptide.

Various sources for the basic structure of such an activator or inhibitor can be employed and comprise, for example, mimetic analogs of the polypeptides of the disclosure. Mimetic analogs of the polypeptide of the disclosure or biologically active fragments thereof can be generated by, for example, substituting the amino acids that are expected to be essential for the biological activity with, e.g., stereoisomers, i.e. D-amino acids; see e.g., Tsukida, *J. Med. Chem.* 40 (1997), 3534-3541. Furthermore, in case fragments are used for the design of biologically active analogs pro-mimetic components can be incorporated into a peptide to reestablish at least some of the conformational properties that may have been lost upon removal of part of the original polypeptide; see, e.g., Nachman, *Regul. Pept.* 57 (1995), 359-370. Furthermore, the active LOX/LOXL can be used to identify synthetic chemical peptide mimetics that bind to or can function as a ligand, substrate, binding partner or the receptor of the polypeptide of the disclosure as effectively as does the natural polypeptide; see, e.g., Engleman, *J. Clin. Invest.* 99 (1997), 2284-2292. For example, folding simulations and computer redesign of structural motifs of the active LOX/LOXL can be performed using appropriate computer programs (Olszewski, *Proteins* 25 (1996), 286-299; Hoffman, *Comput. Appl. Biosci.* 11 (1995), 675-679). Computer modeling of protein folding can be used for the conformational and energetic analysis of detailed peptide and protein models (Monge, *J. Mol. Biol.* 247 (1995), 995-1012; Renouf, *Adv. Exp. Med. Biol.* 376 (1995), 37-45). The appropriate programs can be used for the identification of interactive sites of the Lysyl Oxidase polypeptide and its interacting proteins by computer assisted searches for complementary peptide sequences (Fassina,

*Immunomethods* 5 (1994), 114-120). Further appropriate computer systems for the design of protein and peptides are described in the prior art, for example in Berry, *Biochem. Soc. Trans.* 22 (1994), 1033-1036; Wodak, *Ann. N.Y. Acad. Sci.* 501 (1987), 1-13; Pabo, *Biochemistry* 25 (1986), 5987-5991. The results obtained from the above-described computer analysis can be used for, e.g., the preparation of peptide mimetics of the protein of the disclosure or fragments thereof. Such pseudopeptide analogues of the natural amino acid sequence of the protein may very efficiently mimic the parent protein (Benkirane, *J. Biol. Chem.* 271 (1996), 33218-33224). For example, incorporation of easily available achiral O-amino acid residues into a protein of the disclosure or a fragment thereof results in the substitution of amide bonds by polymethylene units of an aliphatic chain, thereby providing a convenient strategy for constructing a peptide mimetic (Banerjee, *Biopolymers* 39 (1996), 769-777). Superactive peptidomimetic analogues of small peptide hormones in other systems are described in the prior art (Zhang, *Biochem. Biophys. Res. Commun.* 224 (1996), 327-331). Appropriate peptide mimetics of a modulator of an active LOX/LOXL can also be identified by the synthesis of peptide mimetic combinatorial libraries through successive amide alkylation and testing the resulting compounds, e.g., for their binding and immunological properties. Methods for the generation and use of peptidomimetic combinatorial libraries are described in the prior art, for example in Ostresh, *Methods in Enzymology* 267 (1996), 220-234 and Dorner, *Bioorg. Med. Chem.* 4 (1996), 709-715. Furthermore, a three-dimensional and/or crystallographic structure of the polypeptide of the disclosure can be used for the design of peptide mimetic inhibitors of the biological activity of the polypeptide of the disclosure (Rose, Biochemistry 35 (1996), 12933-12944; Rutenber, *Bioorg. Med. Chem.* 4 (1996), 1545-1558).

The structure-based design and synthesis of low-molecular-weight synthetic molecules that mimic the activity of the native biological polypeptide is further described in, e.g., Dowd, *Nature Biotechnol.* 16 (1998), 190-195; Kieber-Emmons, *Current Opinion Biotechnol.* 8 (1997), 435-441; Moore, *Proc. West Pharmacol. Soc.* 40 (1997), 115-119; Mathews, *Proc. West Pharmacol. Soc.* 40 (1997), 121-125; Mukhija, *European J. Biochem.* 254 (1998), 433-438.

It is also well known to the person skilled in the art, that it is possible to design, synthesize and evaluate mimetics of small organic compounds that, for example, can act as a substrate or ligand to the active LOX/LOXL or the related polypeptide. For example, it has been described that D-glucose mimetics of hapalosin exhibited similar efficiency as hapalosin in antagonizing multidrug resistance assistance-associated protein in cytotoxicity; see Dinh, *J. Med. Chem.* 41 (1998), 981-987.

The inhibitors disclosed herein, such as antibodies, can bind to LOX/LOXL and can be competitive inhibitors, uncompetitive inhibitors or non-competitive inhibitors. With respect to competitive inhibition, an inhibitor usually bears structural similarity to substrate. Inhibition will be noticeable at low substrate concentrations, but can be overcome at high substrate concentrations. With respect to uncompetitive inhibition, an inhibitor binds at site that becomes available after substrate is bound at the active site. Inhibition will be most noticeable at high substrate concentration. With respect to non-competitive inhibition, an inhibitor binds at site away from substrate binding site and relative inhibition will generally be the same at all substrate concentrations. In one embodiment, an antibody or antigen binding fragment thereof, described herein specifically binds both full-length and processed LOX or LOXL2. In one aspect, both full-length and processed LOX or LOXL2 are active forms of the enzyme.

3. Antibodies Against LOX/LOXL

As used herein, the term "antibody" means an isolated or recombinant binding agent that comprises the necessary variable region sequences to specifically bind an antigenic epitope. Therefore, an antibody is any form of antibody or fragment thereof that exhibits the desired biological activity, e.g., binding the specific target antigen. Thus, it is used in the broadest sense and specifically covers monoclonal antibodies (including full-length monoclonal antibodies), polyclonal antibodies, human antibodies, humanized antibodies, chimeric antibodies, nanobodies, diabodies, multispecific antibodies (e.g., bispecific antibodies), and antibody fragments including but not limited to scFv, Fab, and $Fab_2$, so long as they exhibit the desired biological activity. The term "human antibody" therefore refers to antibodies containing sequences of human origin, except for possible non-human CDR regions, and does not imply that the full structure of an Ig molecule be present, only that the antibody has minimal immunogenic effect in a human.

"Antibody fragments" comprise a portion of an intact antibody, for example, the antigen binding or variable region of the intact antibody. Examples of antibody fragments include Fab, Fab', $F(ab')_2$, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$ fragment that has two antigencombining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain ($CH_1$) of the heavy chain. Fab fragments differ from Fab' fragments by the addition of a few residues at the carboxy terminus of the heavy chain $CH_1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

In some embodiments the anti-LOX/LOXL antibody is a humanized antibody or a human antibody. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immununoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence.

The humanized antibody optimally also will comprise at least a portion of an immunoglobulin constant region (Fc), typically that of a human immunoglobulin (Jones et al., *Nature*, 321:522-525 (1986); Riechmann et al., *Nature*, 332: 323-329 (1988); and Presta, *Curr. Op. Struct. Biol.* 2:593-596 (1992)).

Methods for humanizing non-human antibodies are well known in the art. Generally, a humanized antibody has one or more amino acid residues introduced into it from a source that is non-human. These non-human amino acid residues are often referred to as "import" or "donor" residues, which are typically taken from an "import" or "donor" variable domain. Humanization can be essentially performed following the method of Winter and co-workers (Jones et al., *Nature*, 321: 522 525 (1986); Riechmann et al., *Nature*, 332:323 327 (1988)); Verhoeyen et al. *Science*, 239:1534 1536 (1988)), by substituting rodent CDRs or CDR sequences for the corresponding sequences of a human antibody. Accordingly, such "humanized" antibodies include chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, *J. Mol. Biol.*, 227:381 (1991); Marks et al., *J. Mol. Biol.*, 222:581 (1991)). The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86-95 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., *Bio/Technology* 10, 779-783 (1992); Lonberg et al., *Nature* 368 856-859 (1994); Morrison, *Nature* 368, 812 13 (1994); Fishwald et al., *Nature Biotechnology* 14, 845-51 (1996); Neuberger, *Nature Biotechnology* 14, 826 (1996); Lonberg and Huszar, *Intern. Rev. Immunol.* 13: 65-93 (1995).

The antibodies may also be affinity matured using known selection and/or mutagenesis methods as described above. In some embodiments, affinity matured antibodies have an affinity which is five times, more than ten times, more than twenty times, or even more than thirty times greater than the starting antibody (generally murine, rabbit, chicken, humanized or human) from which the matured antibody is prepared.

The anti-LOX/LOXL antibody may also be a bispecific antibody. Bispecific antibodies are monoclonal, any may be human or humanized antibodies that have binding specificities for at least two different antigens. In the present case, one of the binding specificities is for LOX, the other one is for any other antigen, for example, for a cell-surface protein or receptor or receptor subunit. In additional embodiments, one of the binding specificities is for LOX, and the other is for a LOXL protein; e.g., LOXL2 or LOXL4.

The anti-LOX/LOXL antibody may also be an immunoconjugate. Such immunoconjugates comprise an anti-LOX antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope. In some embodiments, the antibody of the present disclosure specifically binds to a human LOX/LOXL (such as hLOX and hLOXL1-4) with dissociation constant $K_d$ equal to or lower than 100 nM, optionally lower than 10 nM, optionally lower than 1 nM, optionally lower than 0.5 nM, optionally lower than 0.1 nM, optionally lower than 0.01 nM, or optionally lower than 0.005 nM, in the form of monoclonal antibody, scFv, Fab, or other form of antibody measured at a temperature of about 4° C., 25° C., 37° C. or 42° C.

Optionally, the antibody of the present disclosure binds to one or more proteolytic cleavage sites of LOX or LOXL, such as the cleavage site for processing a mature form of LOX/LOXL, thereby effectively blocking processing of the LOX or LOXL to reduce the level of active LOX or LOXL.

Optionally, the antibody of the present disclosure specifically and selectively binds to the full-length form of LOX, with a greater binding affinity, for example, at least 10 times, at least 100 times, or even at least 1000 times greater, than the binding affinity to the preproprotein of human LOX, the mature or processed human LOX, or other lysyl oxidase-like or lysyl oxidase-related proteins (e.g., LOXL1, LOXL2, LOXL3, and LOXL4; see Molnar et al. (2003) *Biochim Biophys. Acta.* 1647:220-224; Csiszar, *Prog. Nucl. Acid Res.* 70:1-32 (2001); and WO 01/83702 published on Nov. 8, 2001).

Optionally, the antibody of the present disclosure specifically and selectively binds to the mature or processed form of LOX, with a greater binding affinity, for example, at least 10 times, at least 100 times, or even at least 1000 times greater, than the binding affinity to the preproprotein of human LOX, the full-length form of human LOX, or other lysyl oxidase-like or lysyl oxidase-related proteins (e.g., LOXL1, LOXL2, LOXL3, and LOXL4; see Molnar et al. (2003) *Biochim Biophys. Acta.* 1647:220-224).

In some embodiments, the antibody specifically binds to an epitope in a region of hLOX selected from SEQ ID NOs:1-18.

Optionally, the antibody of the present disclosure binds to both human LOX and human LOXL2, with a greater binding affinity, for example, 10 times, at least 100 times, or even at least 1000 times greater, than the binding affinity to other lysyl oxidase-like or lysyl oxidase-related proteins (e.g., LOXL1, LOXL3, and LOXL4; see Molnar et al. (2003) *Biochim Biophys. Acta.* 1647:220-224).

Optionally, the antibody of the present disclosure not only binds to LOX or LOXL but also reduces or inhibits uptake or internalization of LOX or LOXL (e.g., via integrin beta 1 or other cellular receptors or proteins. It is believed that such an antibody could reduce EMT and thus is useful for the applications disclosed herein.

Optionally, the antibody of the present disclosure not only binds to LOX or LOXL but also reduces or inhibits the lysyl oxidase enzymatic activity of LOX or LOXL. It is believed that such an antibody could reduce EMT and thus is useful for the applications disclosed herein.

Binding of LOX/LOXL with other proteins, such as cellular receptors (e.g. uptake receptor integrin beta1), BTK (burton agammagloublinemia tyrosine kinase), or other integrins is also performed using the aforementioned assay, wherein instead of ECM proteins are used, cellular receptors (e.g. uptake receptor integrin beta1), BTK (burton agammagloublinemia tyrosine kinase) or other integrins are used.

Those LOX/LOXL antibodies that inhibit LOX/LOXL binding to ECM proteins, cellular receptors, and integrins, are selected as candidates for further development.

Figure 41:
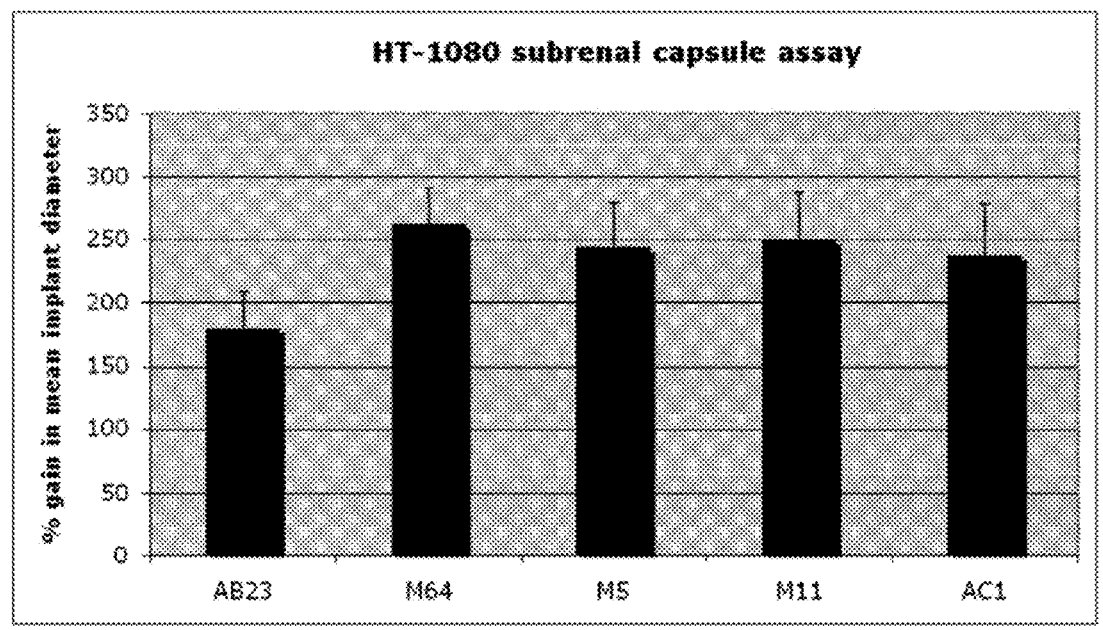
FIG. 41 is a graph showing mean gain of implant size from HT1080 tumor cell implantation into the subrenal capsule of nude mice. Implants were allowed to form tumors for 10 days. Mice were treated twice per week with various antibodies (30 mg/kg, intraperitoneal injection). Each group of five mice were treated with: AC1: negative control antibody; M64, M5, or M11: "non-LOXL2" antibodies (anti-LOX antibodies); or AB23: LOXL2 antibody. Trend with AB23: ~25% smaller average tumor size in this aggressive primary tumor model.
Figure 42:
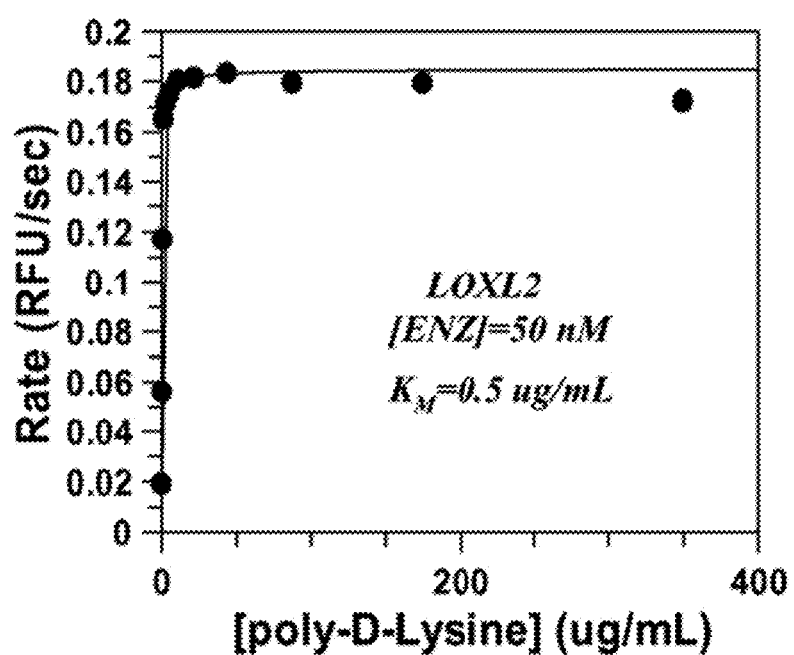
FIG. 42 illustrates Lysyl Oxidase Enzymology. LOX/LOXL enzymes act via a ping-pong mechanism which can be described by Michaelis-Menten kinetics.
Figure 44:
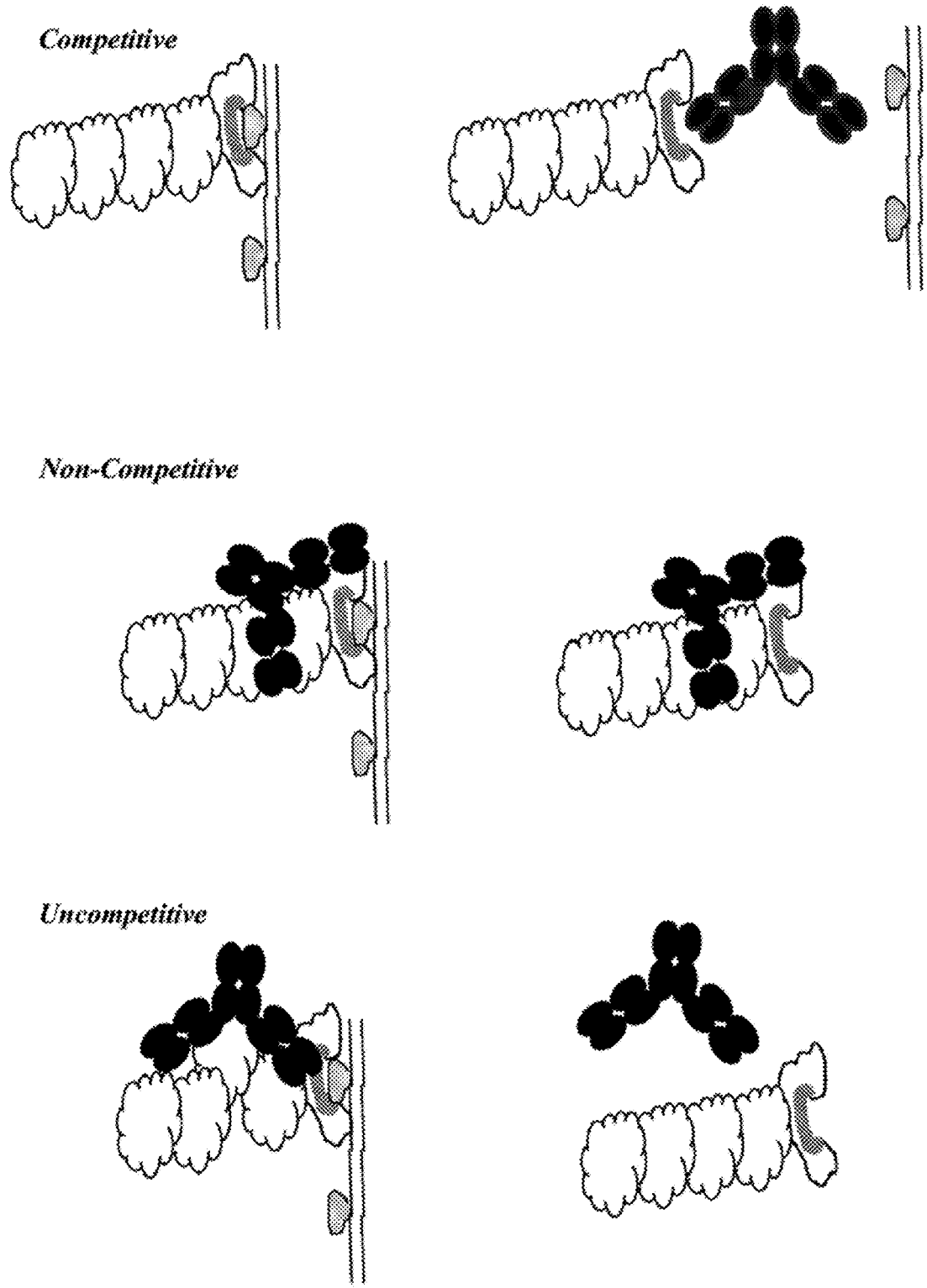
FIG. 44 illustrates modes of enzymatic inhibition, such as inhibition of LOXL2.

LOX/LOXL enzymes act via a ping-pong mechanism which can be described by Michaelis-Menten kinetics (FIG. 41). The LOX/LOXL antibodies of the present disclosure can be competitive inhibitors, uncompetitive inhibitors or non-competitive inhibitors of LOX/LOXL. The mechanism of action antibodies that act as competitive inhibitors, uncompetitive inhibitors and non-competitive inhibitors is illustrated in FIG. 42. With respect to competitive inhibition, an inhibitor usually bears structural similarity to substrate. Inhibition will be noticeable at low substrate concentrations, but can be overcome at high substrate concentrations. With respect to uncompetitive inhibition, an inhibitor binds at site that becomes available after substrate is bound at the active site. Inhibition will be most noticeable at high substrate concentration. With respect to non-competitive inhibition, an inhibitor binds at site away from substrate binding site. Relative inhibition will generally be the same at all substrate concentrations. Thus, inhibitors can be LOX/LOXL antibodies, such as LOXL2, which are competitive inhibitors, uncompetitive inhibitors or non-competitive inhibitors (FIG. 43).

4. Polynucleotides Targeting LOX/LOXL

Inhibitors of LOX or LOXL levels or activity can be effected using an antisense polynucleotide capable of specifically hybridizing with an mRNA transcript encoding LOX or LOXL.

Optionally, the polynucleotide inhibitors of the present disclosure can reduce or inhibits uptake or internalization of LOX or LOXL. It is believed that such a polynucleotide inhibitor could reduce EMT and thus is useful for the applications disclosed herein.

Optionally, the polynucleotide inhibitors of the present disclosure can reduce or inhibit the lysyl oxidase enzymatic activity of LOX or LOXL. It is believed that such a polynucleotide inhibitor could reduce EMT and thus is useful for the applications disclosed herein.

Design of antisense molecules which can be used to efficiently downregulate LOX or LOXL2 is typically effected while considering two aspects factors used in the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

Several considerations are typically taken into account when designing antisense oligonucleotides. For efficient in vivo inhibition of gene expression using antisense oligonucleotides or analogs, the oligonucleotides or analogs typically fulfill the following requirements (i) sufficient specificity in binding to the target sequence; (ii) solubility in water; (iii) stability against intra- and extracellular nucleases; (iv) capability of penetration through the cell membrane; and (v) when used to treat an organism, low toxicity. Algorithms for identifying those sequences with the highest predicted binding affinity for their target mRNA based on a thermodynamic cycle that accounts for the energy of structural alterations in both the target mRNA and the oligonucleotide are available, for example, as described in Walton et al. *Biotechnol Bioeng* 65:1-9 (1999).

Such algorithms have been successfully used to implement an antisense approach in cells. For example, the algorithm developed by Walton et al. enabled scientists to successfully design antisense oligonucleotides for rabbit β-globin (RBG) and mouse tumor necrosis factor-α (TNF α) transcripts. The same research group has also reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system are also published (Matveeva et al., *Nature Biotechnology* 16: 1374-1375 (1998)).

An antisense molecule which can be used with the present disclosure includes a polynucleotide or a polynucleotide analog of at least 10 bases, for example, between 10 and 15, between 15 and 20 bases, at least 17, at least 18, at least 19, at least 20, at least 22, at least 25, at least 30, or even at least 40 bases which is hybridizable in vivo, under physiological conditions, with a portion of a polynucleotide strand encoding a polypeptide at least 50% homologous to SEQ ID NO:1, 4, 5 or 7 or at least 75% homologous to an N-terminal portion thereof as determined using the BestFit software of the Wisconsin sequence analysis package, utilizing the Smith and Waterman algorithm, where gap creation penalty equals 8 and gap extension penalty equals 2.

The antisense oligonucleotides used by the present disclosure can be expressed from a nucleic acid construct administered into the tissue, in which case inducible promoters can be used such that antisense expression can be switched on and off, or alternatively such oligonucleotides can be chemically synthesized and administered directly into the tissue, as part of, for example, a pharmaceutical composition.

The ability of chemically synthesizing oligonucleotides and analogs thereof having a selected predetermined sequence offers means for downmodulating gene expression. Four types of gene expression modulation strategies may be considered.

At the transcription level, antisense or sense oligonucleotides or analogs that bind to the genomic DNA by strand displacement or the formation of a triple helix, may prevent transcription. At the transcript level, antisense oligonucleotides or analogs that bind target mRNA molecules lead to the enzymatic cleavage of the hybrid by intracellular RNase H. In this case, by hybridizing to the targeted mRNA, the oligonucleotides or oligonucleotide analogs provide a duplex hybrid recognized and destroyed by the RNase H enzyme. Alternatively, such hybrid formation may lead to interference with correct splicing. As a result, in both cases, the number of the target mRNA intact transcripts ready for translation is reduced or eliminated.

At the translation level, antisense oligonucleotides or analogs that bind target mRNA molecules prevent, by steric hindrance, binding of essential translation factors (ribosomes), to the target mRNA, a phenomenon known in the art as hybridization arrest, disabling the translation of such mRNAs.

Unmodified oligonucleotides are typically impractical for use as antisense sequences since they have short in vivo half-lives, during which they are degraded rapidly by nucleases. Furthermore, they are often difficult to prepare in more than milligram quantities. In addition, such oligonucleotides are usually poor cell membrane penetrants. Thus, oligonucleotide analogs are usually devised in a suitable manner.

For example, problems arising in connection with double-stranded DNA (dsDNA) recognition through triple helix formation have been diminished by a clever "switch back" chemical linking, whereby a sequence of polypurine on one strand is recognized, and by "switching back," a homopurine sequence on the other strand can be recognized. Also, good helix formation has been obtained by using artificial bases, thereby improving binding conditions with regard to ionic strength and pH.

RNA oligonucleotides may also be used for antisense inhibition as they form a stable RNA-RNA duplex with the target, suggesting efficient inhibition. However, due to their low stability, RNA oligonucleotides are typically expressed inside the cells using vectors designed for this purpose. This approach may be used when attempting to target an mRNA that encodes an abundant and long-lived protein.

Antisense therapeutics can be used to treat many life-threatening diseases with a number of advantages over traditional drugs. Traditional drugs typically intervene after a disease-causing protein is formed. Antisense therapeutics, however, can block mRNA transcription/translation and intervene before a protein is formed, and since antisense therapeutics target only one specific mRNA, they can be more effective with fewer side effects than current protein-inhibiting therapy.

Several clinical trials have demonstrated safety, feasibility and activity of antisense oligonucleotides. For example, antisense oligonucleotides suitable for the treatment of cancer have been successfully used (Holmund et al., *Curr. Opin. Mol. Ther.* 1:372-385 (1999)), while treatment of hematological malignancies via antisense oligonucleotides targeting c-myb gene, p53 and Bcl-2 had entered clinical trials and had been shown to be tolerated by patients (Gerwitz, *Curr. Opin. Mol. Ther.* 1: 297-306 (1999)).

More recently, antisense-mediated suppression of human heparanase gene expression has been reported to inhibit pleural dissemination of human cancer cells in a mouse model (Uno et al., *Cancer Res* 61:7855-60 (2001)).

The first antisense drug was recently approved by the FDA. The drug, Fomivirsen, was developed by Isis, and is indicated for local treatment of cytomegalovirus in patients with AIDS who are intolerant of or have a contraindication to other treatments for CMV retinitis or who were insufficiently responsive to previous treatments for CMV retinitis (Pharmacotherapy News Network).

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Another mechanism for inhibiting LOX or LOXL is RNA interference (RNAi), an approach which utilizes small interfering dsRNA (siRNA or small hairpin RNA, shRNA) molecules that are homologous to the target mRNA and lead to its degradation (Carthew, *Curr. Opin. Cell. Biol.* 13: 244-248 (2001)). For example, infection of diverse types of cancer cells with expression of a LOXL2 specific shRNA is effective in altering both their morphology and invasiveness.

RNA interference is typically a two-step process. In the first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 bp duplexes (siRNA), each with 2-nucleotide 3' overhangs (Hutvagner and Zamore, *Curr. Opin. Genet. Dev.* 12: 225-232 (2002); Bernstein, *Nature* 409:363-366 (2001)).

In the effector step, the siRNA duplexes bind to a nuclease complex to form the RNA-induced silencing complex (RISC). An ATP-dependent unwinding of the siRNA duplex is required for activation of the RISC. The active RISC then targets the homologous transcript by base pairing interactions and typically cleaves the mRNA into approximately 12 nucleotide fragments from the 3' terminus of the siRNA (Hutvagner and Zamore, *Curr. Opin. Genet. Dev.* 12: 225-232 (2002); Hammond et al., *Nat. Rev. Gen.* 2:110-119 (2001); Sharp, *Genes. Dev.* 15:485-490 (2001)). Although the mechanism of cleavage is still to be elucidated, research indicates that each RISC contains a single siRNA and an RNase (Hutvagner and Zamore, *Curr. Opin. Genet. Dev.* 12: 225-232 (2002)).

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC (Hutvagner and Zamore, *Curr. Opin. Genet. Dev.* 12: 225-232 (2002); Hammond et al., *Nat. Rev. Gen.* 2:110-119 (2001); Sharp, *Genes. Dev.* 15:485-490 (2001)). RNAi is also described in Tuschl, *Chem. Biochem.* 2: 239-245 (2001); Cullen, *Nat. Immunol.* 3:597-599 (2002); and Brantl, *Biochem. Biophys. Act.* 1575:15-25 (2002).

Synthesis of RNAi molecules suitable for use with the present disclosure can be effected as follows. First, the LOX or LOXL mRNA sequence is scanned downstream of the AUG start codon for AA dinucleotide sequences. Occurrence of each AA and the 3' adjacent 19 nucleotides is recorded as potential siRNA target sites. The siRNA target sites are selected from the open reading frame, as untranslated regions (UTRs) are richer in regulatory protein binding sites. UTR-binding proteins and/or translation initiation complexes may interfere with binding of the siRNA endonuclease complex (Tuschl, *Chem. Biochem.* 2: 239-245 (2001)). It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (ambion.com/techlib/tn91/912.html). Second, potential target sites are compared to an appropriate genomic database (e.g., human, mouse, rat etc.) using any sequence alignment software, such as the BLAST software available from the NCBI server (ncbi.nlm.nih.gov/BLAST/). Putative target sites which exhibit significant homology to other coding sequences are filtered out.

Qualifying target sequences are selected as template for siRNA synthesis. Selected sequences can include those with low G/C content as these have been shown to be more effective in mediating gene silencing as compared to those with G/C content higher than 55%. Several target sites can be selected along the length of the target gene for evaluation. For better evaluation of the selected siRNAs, a negative control is used in conjunction. Negative control siRNA can include the same nucleotide composition as the siRNAs but lack significant homology to the genome. Thus, a scrambled nucleotide sequence of the siRNA may be used, provided it does not display any significant homology to any other gene.

The siRNA molecules of the present disclosure can be transcribed from expression vectors which can facilitate stable expression of the siRNA transcripts once introduced into a host cell. These vectors are engineered to express shRNAs, which are processed in vivo into siRNA molecules capable of carrying out gene-specific silencing (Brummelkamp et al., *Science* 296:550-553 (2002); Paddison et al., *Genes Dev.* 16:948-958 (2002); Paul et al., *Nature Biotech.* 20: 505-508 (2002); Yu et al., *Proc. Natl. Acad. Sci. USA* 99:6047-6052 (2002)).

ShRNAs are single-stranded polynucleotides with a hairpin loop structure. The single-stranded polynucleotide has a loop segment linking the 3' end of one strand in the double-stranded region and the 5' end of the other strand in the double-stranded region. The double-stranded region is formed from a first sequence that is hybridizable to a target sequence, such as a polynucleotide encoding LOX or LOXL, or a LOX or LOXL mRNA, and a second sequence that is complementary to the first sequence, thus the first and second sequence form a double stranded region to which the linking sequence connects the ends of to form the hairpin loop structure. The first sequence can be hybridizable to any portion of a polynucleotide encoding LOX/LOXL. The double-stranded stem domain of the shRNA comprises a restriction endonuclease site.

The stem-loop structure of shRNAs can have optional nucleotide overhands, such as 2-bp overhands, for example, 3' UU-overhangs. While there may be variation, stems typically range from approximately 15 to 49, approximately 15 to 35, approximately 19 to 35, approximately 21 to 31 bp, or approximately 21 to 29 bp, and the loops can range from approximately 4 to 30 bp, for example, about 4 to 23 bp.

For expression of shRNAs within cells, plasmid vectors containing either the polymerase III H1-RNA or U6 promoter, a cloning site for the stem-looped RNA insert, and a 4 5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

An example of a suitable expression vector is the pSUPER™, which includes the polymerase-III H1-RNA gene promoter with a well defined start of transcription and a termination signal consisting of five thymidines in a row (T5) (Brummelkamp et al., *Science* 296:550-553 (2002)). The cleavage of the transcript at the termination site is at a site following the second uridine, thus yielding a transcript which resembles the ends of synthetic siRNAs, which also contain nucleotide overhangs. siRNA is cloned such that it includes the sequence of interest, i.e., LOX or LOXL separated by a short spacer from the reverse complement of the same sequence. The resulting transcript folds back on itself to form a stem-loop structure, which mediates LOX or LOXL RNAi.

Another suitable siRNA expression vector encodes the sense and antisense siRNA under the regulation of separate polIII promoters (Miyagishi and Taira, *Nature Biotech.* 20:497-500 (2002)). The siRNA, generated by this vector also includes a five thymidine (T5) termination signal.

Since approaches for introducing synthetic siRNA into cells by lipofection can result in low transfection efficiencies in some cell types and/or short-term persistence of silencing effects, vector mediated methods have been developed.

Thus, siRNA molecules utilized by the present disclosure can be delivered into cell using retroviruses. Delivery of siRNA using retroviruses provides several advantages over methods, such as lipofection, since retroviral delivery typically is more efficient, uniform and immediately selects for stable "knock-down" cells (Devroe and Silver, *BMC Biotechnol.* 2:15 (2002)).

Recent scientific publications have validated the efficacy of such short double stranded RNA molecules in inhibiting target mRNA expression and thus have clearly demonstrated the therapeutic potential of such molecules. For example, RNAi has been utilized to inhibit expression of hepatitis C (McCaffrey et al., *Nature* 418:38-39 (2002)), HIV-1 (Jacque et al., *Nature* 418:435-438 (2002)), cervical cancer cells (Jiang and Milner, *Oncogene* 21:6041-6048 (2002)) and leukemic cells (Wilda et al., *Oncogene* 21, 5716-5724 (2002)).

5. Anti-Neoplastic or Anti-Fibrotic Agents

According to the present disclosure, an inhibitor of LOX or LOXL can be combined with a chemotherapeutic agent to sensitize the tumor cells (e.g., transition from the EMT state to the MET state) to the chemotherapeutic agent, thus not only preventing or inhibiting tumor invasion and metastasis but also inhibiting primary tumor growth.

As used herein the term "chemotherapeutic agent" or "chemotherapeutic" (or "chemotherapy", in the case of treatment with a chemotherapeutic agent) is meant to encompass any non-proteinaceous (i.e., non-peptidic) chemical compound useful in the treatment of cancer. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; acetogenins (e.g., bullatacin and bullatacinone); a camptothecin (including synthetic analogue topotecan); bryostatin; callystatin; CC-1065 (including its adozelesin, carzelesin and bizelesin synthetic analogues); cryptophycins (articularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, foremustine, lomustine, nimustine, ranimustine; antibiotics such as the enediyne antibiotics (e.g. calicheamicin, especially calicheamicin gamma1I and calicheamicin phiI1, see, e.g., Agnew, Chem. Intl. Ed. Engl., 33: 183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubincin (Adramycin™) (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as demopterin, methotrexate, pteropterin, trimetrexate; purine analogs such as fludarabine, 6-mercaptopurine, thiamiprine, thioguanine; pyrimidine analogues such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replinisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK™; razoxane; rhizoxin; sizofuran; spirogermanium; tenuazonic acid; triaziquone; 2,2',2''-trichlorotriethylamine; trichothecenes (e.g., T-2 toxin, verracurin A, roridin A and anguidine); urethane; vindesine; dacarbazine; mannomustine; mitobronitol; mitolactol; pipobroman; gacytosine; cytosine arabinoside ("Ara-C"); cyclophosphamide; thiopeta; taxoids, e.g. paclitaxel (TAXOL™, Bristol Meyers Squibb Oncology, Princeton, N.J.) and docetaxel (TAXOTERE™, Rhone-Poulenc Rorer, Antony, France); chlorambucil; gemcitabine (Gemzar™); 6-thioguanine; mercaptopurine; methotrexate; platinum analogs such as cisplatin and carboplatin; vinblastine; platinum; etoposide (VP-16); ifosfamide; mitroxantrone; vancristine; vinorelbine (Navelbine™); novantrone; teniposide; edatrexate; daunomycin; aminopterin; xeoloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above. Also included in the definition of "chemotherapeutic agent" are anti-hormonal agents that act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston™); inhibitors of the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids or derivatives of any of the above.

In some embodiments, the anti-neoplastic agent in combination with the LOX/LOXL modulator is a tyrosine kinase inhibitor. For example, ZD1839 (Iressa™ of AstraZeneca K.K.) shows a competitive effect for ATP in ATP binding site of EGFR (epidermal growth factor receptor) tyrosine kinase, and inhibits tyrosine kinase activity by inhibiting autophosphorylation of tyrosine kinase.

As a result, the anticancer effect is expressed by blocking an EGFR-equipping signal transduction (ligands such as epidermal growth factor (EGF) are bound to the extracellular domain of EGFR, followed by activation of EGFR tyrosine kinase in the intracellular domain, causing not only autophosphorylation of EGFR but also phosphorylation of various intracellular target proteins, then transducing the proliferation signals from the cancer cell surface to nucleus, resulting in proliferation, infiltration, metastasis, and angiogenesis of cancer cells.

IMC-C225 or cetuximab (Erbitux™) which is an EGFR-targeting monoclonal antibody) recognizes the receptor part of EGFR on a cell membrane surface and inhibits the autophosphorylation of EGFR thereby inhibiting the tyrosine kinase activity. Herceptin, a monoclonal antibody against Her2/Neu which is homologous to EGFR, and imatinib mesylate (GLEEVEC™, formerly STI-571) can inhibit both tyrosine kinase activities of BCR-Abl and c-kit (non-patent document No. 2). Sorafenib (Nexavar™) is a small molecular inhibitor of Raf kinase, PDGF (platelet-derived growth factor), VEGF receptor 2 & 3 kinases and c-Kit.

As used herein, monoclonal antibodies against tumor antigens are antibodies elicited against antigens expressed by tumors and leukemic cells, for example, tumor-specific antigens. The monoclonal antibody also includes fully human and humanized antibody.

Other examples of therapeutic antibodies for cancer therapy include Trastuzumab (HERCEPTIN™; Overexpression of HER2 protein is associated with more aggressive disease and poorer prognosis in the clinic); Rituximab (RITUXAN™) that is raised against CD20 on lymphoma cells and selectively deplete normal and malignant CD20+ pre-B and mature B cells; Alemtuzumab (CAMPATH™), a monoclonal antibody that specifically targets CD52 antigen that is found on B and T lymphocytes and used for the treatment of chronic lymphocytic leukemia (CLL) and lymphoma; and Gemtuzumab zogamicin (MYLOTARG™), an antibody conjugate that combines a specific antibody against CD33 with a chemotherapeutic drug (zogamicin) and is indicated for the treatment of relapsed adult acute myelocytic leukemia.

In another embodiment, anti-angiogenic agent is combined with a LOX/LOXL inhibitor to treat cancer and other diseases associated with abnormal or undesirable angiogenesis. Examples of anti-angiogenic agents include, but are not limited to, retinoid acid and derivatives thereof, 2-methoxyestradiol, ANGIOSTATIN™, ENDOSTATIN™, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((I-azetidine-2-carboxylic acid (LACA), cishydroxyproline, d,I-3, 4-dehydroproline, thiaproline, $\alpha$-dipyridyl, $\beta$-aminopropionitrile fumarate, 4-propyl-5-(4-pyridinyl)-2(3h)-oxazolone; methotrexate, mitoxantrone, heparin, interferons, 2 macroglobulin-serum, chimp-3, chymostatin, $\beta$-cyclodextrin tetradecasulfate, eponemycin; fumagillin, gold sodium thiomalate, d-penicillamine (CDPT), beta.-1-anticollagenase-serum, alpha.2-antiplasmin, bisantrene, lobenzarit disodium, n-2-carboxyphenyl-4-chloroanthronilic acid disodium or "CCA", thalidomide; angiostatic steroid, cargboxynaminoimidazole; metalloproteinase inhibitors such as BB94. Other anti-angiogenesis agents include antibodies, for example, monoclonal antibodies against these angiogenic growth factors: bFGF, aFGF, FGF-5, VEGF isoforms, VEGF-C, HGF/SF and Ang-1/Ang-2. Ferrara N. and Alitalo, K "*Clinical application of angiogenic growth factors and their inhibitors*" (1999) *Nature Medicine* 5:1359-1364. Other anti-angiogenesis agents may include inhibitors of VEGF transcription.

Exemplary anti-fibrotic agents include, but are not limited to the compounds such as $\beta$-aminoproprionitrile (BAPN), as well as the compounds disclosed in U.S. Pat. No. 4,965,288 to Palfreyman, et al., issued Oct. 23, 1990, entitled "Inhibitors of lysyl oxidase, relating to inhibitors of lysyl oxidase and their use in the treatment of diseases and conditions associated with the abnormal deposition of collagen"; U.S. Pat. No. 4,997,854 to Kagan, et al., issued Mar. 5, 1991, entitled "Anti-fibrotic agents and methods for inhibiting the activity of lysyl oxidase in situ using adjacently positioned diamine analogue substrate," relating to compounds which inhibit LOX for the treatment of various pathological fibrotic states, which are herein incorporated by reference. Further exemplary inhibitors are described in U.S. Pat. No. 4,943,593 to Palfreyman, et al., issued Jul. 24, 1990, entitled "Inhibitors of lysyl oxidase," relating to compounds such as 2-isobutyl-3-fluoro-, chloro-, or bromo-allylamine; as well as, e.g., U.S. Pat. No. 5,021,456; U.S. Pat. No. 5,5059,714; U.S. Pat. No. 5,120,764; U.S. Pat. No. 5,182,297; U.S. Pat. No. 5,252,608 (relating to 2-(1-naphthyloxymethyl)-3-fluoroallylamine); and U.S. Patent Application No. 2004/0248871, which are herein incorporated by reference. Exemplary anti-fibrotic agents also include the primary amines reacting with the carbonyl group of the active site of the lysyl oxidases, including those which produce, after binding with the carbonyl, a product stabilized by resonance, such as the following primary amines: ethylenediamine, hydrazine, phenylhydrazine, and their derivatives, semicarbazide, and urea derivatives, aminonitriles, such as $\beta$-aminopropionitrile (BAPN), or 2-nitroethylamine, unsaturated or saturated haloamines, such as 2-bromo-ethylamine, 2-chloroethylamine, 2-trifluoroethylamine, 3-bromopropylamine, p-halobenzylamines, selenohomocysteine lactone. In another embodiment, the anti-fibrotic agents are copper chelating agents, penetrating or not penetrating the cells. Additional exemplary compounds include indirect inhibitors such compounds blocking the aldehyde derivatives originating from the oxidative deamination of the lysyl and hydroxylysyl residues by the lysyl oxidases, such as the thiolamines, for example, D-penicillamine, or its analogues such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio) butane sulphinate, 2-acetamidoethyl-2-acetamidoethanethiol sulphanate, sodium-4-mercaptobutanesulphinate trihydrate.

6. Formulations, Kits and Routes of Administration

Therapeutic compositions comprising compounds identified as LOX/LOXL modulators using the disclosed methods are also contemplated. In one embodiment, provided herein is a therapeutic composition for prophylaxis and treatment of metastatic tumor growth, the composition comprising a therapeutically effective amount of a LOX/LOXL inhibitor in a pharmaceutically acceptable carrier substance; wherein the inhibitor inhibits lysyl oxidase or lysyl oxidase-like protein, such as LOXL-2, wherein the amount of the inhibitor is effective in preventing and treating metastatic tumor growth. In another embodiment, provided herein is a therapeutic composition for prophylaxis and treatment of metastatic tumor growth comprising a therapeutically effective amount of a LOX/LOXL inhibitor in a pharmaceutically acceptable carrier in combination with radiation, surgery, chemotherapy, or an anticancer biologic which is not the LOX/LOXL inhibitor.

As used herein, the term "therapeutically effective amount" or "effective amount" refers to an amount of a therapeutic agent that when administered alone or in combination with another therapeutic agent to a cell, tissue, or subject is effective to prevent or ameliorate the disease condition or the progression of the disease. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. For example, when in vivo administration of a LOX/LOXL antibody is employed, normal dosage amounts may vary from about 10 ng/kg to up to 100 mg/kg of mammal body weight or more per day, for example, about 1 µg/kg/day to 50 mg/kg/day, optionally about 100 µg/kg/day to 20 mg/kg/day, 500 µg/kg/day to 10 mg/kg/day, or 1 mg/kg/day to 10 mg/kg/day, depending upon the route of administration.

Various pharmaceutical compositions and techniques for their preparation and use will be known to those of skill in the art in light of the present disclosure. For a detailed listing of suitable pharmacological compositions and associated administrative techniques one may refer to the detailed teachings herein, which may be further supplemented by texts such as *Remington: The Science and Practice of Pharmacy* 20th Ed. (Lippincott, Williams & Wilkins 2003).

The compositions further include pharmaceutically acceptable materials, composition or vehicle, such as a liquid or solid filler, diluent, excipient, solvent or encapsulating material, i.e., carriers. These carriers are involved in transporting the subject chemical from one organ, or portion of the body, to another organ, or portion of the body. Each carrier should be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Another aspect of the present disclosure relates to kits for carrying out the combined administration of the LOX/LOXL modulator with the other therapeutic agent. In one embodiment, the kit comprises a LOX/LOXL inhibitor formulated in a pharmaceutical carrier, and at least one therapeutic agent that is not the LOX/LOXL inhibitor, formulated as appropriate, in one or more separate pharmaceutical preparations.

The formulation and delivery methods will generally be adapted according to the site and the disease to be treated. Exemplary formulations include, but are not limited to, those suitable for parenteral administration, e.g., intravenous, intra-arterial, intramuscular, or subcutaneous administration, including formulations encapsulated in micelles, liposomes or drug-release capsules (active agents incorporated within a biocompatible coating designed for slow-release); ingestible formulations; formulations for topical use, such as creams, ointments and gels; and other formulations such as inhalants, aerosols and sprays. The dosage of the compounds of the disclosure will vary according to the extent and severity of the need for treatment, the activity of the administered composition, the general health of the subject, and other considerations well known to the skilled artisan.

Agents as described herein can be incorporated into pharmaceutical compositions suitable for administration. Such compositions typically comprise the agent and a pharmaceutically acceptable carrier. Supplementary active compounds can also be incorporated into the compositions.

In yet other embodiments, the agents described herein are delivered locally. Localized delivery allows for the delivery of the agent non-systemically, for example, to the site of fibrosis, to reduce the entire body of the subject as compared to systemic delivery. Such local delivery may be achieved through the use of various medically implanted devices including, but not limited to, stents and catheters. Methods for coating, implanting, embedding, and otherwise attaching desired agents to medical devices such as stents and catheters are established in the art and contemplated herein.

Implanted stents have been used to carry medicinal agents, such as thrombolytic agents. U.S. Pat. No. 5,163,952 discloses a thermal memoried expanding plastic stent device formulated to carry a medicinal agent in the material of the stent itself. U.S. Pat. No. 5,092,877 discloses a stent of a polymeric material which may have a coating associated with the delivery of compounds. Other patents which are directed to devices of the class utilizing bio-degradable and bio-sorbable polymers include U.S. Pat. No. 4,916,193, U.S. Pat. No. 4,994,071. By way of example, U.S. Pat. No. 5,304,121, discloses a coating applied to a stent consisting of a hydrogel polymer and a preselected compounds such as cell growth inhibitors or heparin. Methods of making a coated intravascular stent carrying a therapeutic material are described in U.S. Pat. No. 5,464,650 wherein a polymer coating material is dissolved in a solvent and the therapeutic material dispersed in the solvent. The solvent is then evaporated after application.

U.S. Pat. No. 6,120,536 describes additional types of coatings for use with a wide variety of prosthetic devices, including stents. Examples of additional medical or prosthetic devices that may be useful with the agents described herein include, but are not limited to, blood exchanging devices, vascular access ports, central venous catheters, cardiovascular catheters, extracorpeal circuits, vascular grafts, pumps, heart valves, and cardiovascular sutures. Regardless of detailed embodiments as described herein, applicability of the disclosure should not be considered limited with respect to implant design, implant location or materials of construction. The use of devices coated with the agents described herein, including stents and catheters, allows for the agents to be delivered to specific or localized sites. Such site-specific delivery can provide a means for use of dosages and drugs such as beta-aminopropionitrile (BAPN) and related compounds or other amine oxidase inhibitors (such as those small molecule inhibitors of LOX/LOXL described above) that are not otherwise amenable to systemic delivery due to solubility, systemic toxicity concerns, or other issues. By way of example, BAPN is known to be useful for LOX inhibition, but this compound is highly toxic, presenting problems for its effective use when administered systemically. The use of a stent, catheter, or other medical device for delivery of an active agent or compound such as BAPN permits use of the compound at effective dosages in a targeted or localized manner, thus decreasing the systemic toxic effects associated with such compounds and current routes of administration.

7. Composition Indications

The pharmaceutical formulations according to the present disclosure may be used to treat a wide variety of diseases.

As used herein, "prevention" includes to prophylaxis, prevention of onset of symptoms, prevention of progression of a disease or disorder associated with fibrosis or correlated with LOX/LOXL activity. As used herein, "inhibition," "treatment," "treating," and "ameliorating" are used interchangeably and refer to, for example, stasis of symptoms, prolongation of survival, partial or full amelioration of symptoms, and partial or full eradication of a condition, disease or disorder associated with fibrosis or correlated with LOX/LOXL activity.

Compositions may be administered to a patient (e.g., a mammal such as a human or a non-human animal such as a primate, rodent, cow, horse, pig, sheep, etc.) in therapeutically effective amounts which are effective for producing a desired therapeutic effect by inhibiting a disease or disorder such as those described herein which are associated with fibrosis or LOX/LOXL activity, at a reasonable benefit/risk ratio applicable to any medical treatment. For human administration of the present compositions, the compositions may be formulated using methodology known by one of ordinary skill in the art. A therapeutically effective amount is an amount that achieves at least partially a desired therapeutic or prophylactic effect in an organ or tissue. In one example, the amount of an inhibitor of LOX/LOXL necessary to bring about prevention and/or therapeutic treatment of a disease or disorder is not fixed per se. The amount of an inhibitor of LOX/LOXL administered will vary with the type of disease or disorder, extensiveness of the disease or disorder, and size of the mammal suffering from the disease or disorder.

A response is achieved when the patient experiences partial or total alleviation, or reduction of signs or symptoms of illness, and specifically includes, without limitation, prolongation of survival. The expected progression-free survival times may be measured in months to years, depending on prognostic factors including the number of relapses, stage of disease, and other factors. Prolonging survival includes without limitation times of at least 1 month, about at least 2 months, about at least 3 months, about at least 4 months, about at least 6 months, about at least 1 year, about at least 2 years, about at least 3 years, or more. Overall survival may also be measured in months to years. The patient's symptoms may remain static or may decrease.

Nonlimiting indications that may be treated using the pharmaceutical formulations of the present disclosure include those involving undesirable or uncontrolled cell proliferation. Such indications include benign tumors, various types of cancers such as primary tumors and tumor metastasis, restenosis (e.g. coronary, carotid, and cerebral lesions), hematological disorders, abnormal stimulation of endothelial cells (atherosclerosis), insults to body tissue due to surgery, abnormal wound healing, abnormal angiogenesis, diseases that produce fibrosis of tissue, macular degeneration, liver fibrosis, kidney fibrosis, lung fibrosis, scleroderma, atherosclerosis, and Alzheimer's disease, repetitive motion disorders, disorders of tissues that are not highly vascularized, and proliferative responses associated with organ transplants.

Generally, cells in a benign tumor retain their differentiated features and do not divide in a completely uncontrolled manner. A benign tumor is usually localized and nonmetastatic. Specific types of benign tumors that can be treated using the present disclosure include, but are not limited to, hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In a malignant tumor cells become undifferentiated, do not respond to the body's growth control signals, and multiply in an uncontrolled manner. The malignant tumor is invasive and capable of spreading to distant sites (metastasizing). Malignant tumors are generally divided into two categories: primary and secondary. Primary tumors arise directly from the tissue in which they are found. A secondary tumor, or metastasis, is a tumor which originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.)

Primary and metastatic tumors that may be treated by the methods disclosed herein may include, but not be limited to, lung cancer (including, but not limited to, lung adenocarcinoma, squamous cell carcinoma, large cell carcinoma, bronchioloalveolar carcinoma, non-small-cell carcinoma, small cell carcinoma, mesothelioma); breast cancer (including, but not limited to, ductal carcinoma, lobular carcinoma, inflammatory breast cancer, clear cell carcinoma, mucinous carcinoma); colorectal cancer (including, but not limited to, colon cancer, rectal cancer); anal cancer; pancreatic cancer (including, but not limited to, pancreatic adenocarcinoma, islet cell carcinoma, neuroendocrine tumors); prostate cancer; ovarian carcinoma (including, but not limited to, ovarian epithelial carcinoma or surface epithelial-stromal tumour including serous tumour, endometrioid tumor and mucinous cystadenocarcinoma, sex-cord-stromal tumor); liver and bile duct carcinoma (including, but not limited to, hepatocelluar carcinoma, cholangiocarcinoma, hemangioma); esophageal carcinoma (including, but not limited to, esophageal adenocarcinoma and squamous cell carcinoma); non-Hodgkin's lymphoma; bladder carcinoma; carcinoma of the uterus (including, but not limited to, endometrial adenocarcinoma, uterine papillary serous carcinoma, uterine clear-cell carcinoma, uterine sarcomas and leiomyosarcomas, mixed mullerian tumors); glioma, glioblastoma, medullablastoma, and other tumors of the brain; kidney cancers (including, but not limited to, renal cell carcinoma, clear cell carcinoma, Wilm's tumor); cancer of the head and neck (including, but not limited to, squamous cell carcinomas); cancer of the stomach (including, but not limited to, stomach adenocarcinoma, gastrointestinal stromal tumor); multiple myeloma; testicular cancer; germ cell tumor; neuroendocrine tumor; cervical cancer; carcinoids of the gastrointestinal tract, breast, and other organs; and signet ring cell carcinoma.

Mesenchymal tumors may include, but not be limited to, sarcomas, fibrosarcomas, haemangioma, angiomatosis, haemangiopericytoma, pseudoangiomatous stromal hyperplasia, myofibroblastoma, fibromatosis, inflammatory myofibroblastic tumour, lipoma, angiolipoma, granular cell tumour, neurofibroma, schwannoma, angiosarcoma, liposarcoma, rhabdomyosarcoma, osteosarcoma, leiomyoma, and leiomysarcoma.

Specific types of cancers or malignant tumors, either primary or secondary, that can be treated using this disclosure also include, but are not limited to, skin cancer, bone cancer, brain cancer, cancer of the larynx, gall bladder, pancreas, parathyroid, thyroid, adrenal, neural tissue, head and neck, bronchi, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Hematologic disorders include abnormal growth of blood cells which can lead to dysplastic changes in blood cells and hematologic malignancies such as various leukemias. Examples of hematologic disorders include but are not limited to acute myeloid leukemia, acute promyelocytic leukemia, acute lymphoblastic leukemia, chronic myelogenous leukemia, the myelodysplastic syndromes, and sickle cell anemia.

Acute myeloid leukemia (AML) is the most common type of acute leukemia that occurs in adults. Several inherited genetic disorders and immunodeficiency states are associated with an increased risk of AML. These include disorders with defects in DNA stability, leading to random chromosomal breakage, such as Bloom's syndrome, Fanconi's anemia, Li-Fraumeni kindreds, ataxia-telangiectasia, and X-linked agammaglobulinemia.

Acute promyelocytic leukemia (APML) represents a distinct subgroup of AML. This subtype is characterized by promyelocytic blasts containing the 15;17 chromosomal translocation. This translocation leads to the generation of the fusion transcript comprised of the retinoic acid receptor and a sequence PML.

Acute lymphoblastic leukemia (ALL) is a heterogenerous disease with distinct clinical features displayed by various subtypes. Reoccurring cytogenetic abnormalities have been demonstrated in ALL. The most common cytogenetic abnormality is the 9;22 translocation. The resultant Philadelphia chromosome represents poor prognosis of the patient.

Chronic myelogenous leukemia (CML) is a clonal myeloproliferative disorder of a pluripotent stem cell. CML is characterized by a specific chromosomal abnormality involving the translocation of chromosomes 9 and 22, creating the Philadelphia chromosome. Ionizing radiation is associated with the development of CML.

The myelodysplastic syndromes (MDS) are heterogeneous clonal hematopoietic stem cell disorders grouped together because of the presence of dysplastic changes in one or more of the hematopoietic lineages including dysplastic changes in the myeloid, erythroid, and megakaryocytic series. These changes result in cytopenias in one or more of the three lineages. Patients afflicted with MDS typically develop complications related to anemia, neutropenia (infections), or thrombocytopenia (bleeding). Generally, from about 10% to about 70% of patients with MDS develop acute leukemia.

Treatment of abnormal cell proliferation due to insults to body tissue during surgery may be possible for a variety of surgical procedures, including joint surgery, bowel surgery, and keloid scarring. Diseases that produce fibrotic tissue include emphysema. Repetitive motion disorders that may be treated using the present disclosure include carpal tunnel syndrome. An example of cell proliferative disorders that may be treated using the disclosure is a bone tumor.

The proliferative responses associated with organ transplantation that may be treated using this disclosure include those proliferative responses contributing to potential organ rejections or associated complications. Specifically, these proliferative responses may occur during transplantation of the heart, lung, liver, kidney, and other body organs or organ systems.

The pharmaceutical formulations described herein may be used for the prevention or treatment of a wide variety of diseases which have collagen cross-linking or increased fibrosis as one part of their etiology. For example, the indication for the composition can also include fibrosis. Fibrosis is the abnormal accumulation of fibrous tissue that can occur as a part of the wound-healing process in damaged tissue. Such tissue damage may result from physical injury, inflammation, infection, exposure to toxins, and other causes. Examples of fibrosis include dermal scar formation, keloids, liver fibrosis, lung fibrosis (e.g., silicosis, asbestosis), kidney fibrosis (including diabetic nephropathy), and glomerulosclerosis. Other examples include, but are not limited to, emphysema and chronic obstructive pulmonary disease (COPD); multiple sclerosis; chronic asthma; atherosclerosis; rheumatoid arthritis; glaucoma; and age-related macular degeneration (wet AMD and dry AMD).

Cardiovascular Fibrosis

Compositions, methods, systems, medical devices and kits are provided herein for the treatment or prevention of cardiovascular or cardiac fibrosis, for example, associated with cardiovascular diseases such as congestive heart failure, cardiomyopathy, post-myocardial infarction defects in heart function, hypertensive heart disease (HHD), myocardial infarction (MI), atherosclerosis, restenosis (e.g. coronary, carotid, and cerebral lesions), and heart disease associated with cardiac ischemic events.

Expression of specific lysyl oxidases may be associated with different stages of the inflammatory response and wound healing after myocardial infarction. By specifically inhibiting the particular lysyl oxidase/s associated with the downstream fibrotic response, the detrimental consequences of cardiac remodeling and wound healing can be avoided, while allowing the immediate post-MI repair/healing process to occur.

The post MI-healing response can induce expression of LOX/LOXL but if this process continues unchecked, excessive cross-linking leads to extracellular matrix remodeling or fibrosis that results in cardiac dysfunction. The enzymes that break down matrices and cross-linked collagen or elastin appear to function more slowly or less efficiently and are outpaced by crosslinking events. As LOX/LOXL also plays a role in epithelial-mesenchymal transition (EMT), this contributes further to cardiomyocyte remodeling and cardiomyocyte hypertrophy, in addition to matrix remodeling.

Initial reparative fibrosis induced by the MI may be helpful (e.g., prevents aneurysm and related damage) and may be allowed to proceed unhindered. However, while not wishing to be bound to a particular theory or mechanism of action, the inventors believe that anti-LOX/LOXL treatment initiated following this reparative fibrosis phase could attenuate reactive (mal-adaptive) fibrosis that leads to cardiac dysfunction. For example, anti-LOX/LOXL treatment may be initiated 2, 4, 6, 8, 10, 12, 14, 16, 16, 20, 22, 24, 36, 48 or more hours after MI, inclusive of all integers and times in between. Additionally, anti-LOX/LOXL treatment may be initiated 2, 3, 4, 5, 6, 7, 8, 9, 10, 11, 12, 13, 14, or more days after MI. Similarly, increases in blood pressure (hypertension) result in increased collagen deposition and reduced protein degradation in cardiac tissue. (Berk et al., *J. Clin. Invest.*, 117(3): 568-575 (2007)). Anti-LOX/LOXL treatment initiated following diagnosis and/or establishment of hypertensive heart disease or hypertension can prevent, reduce, or ameliorate fibrosis associated with hypertension. Such anti-LOX/LOXL treatment is initiated 2, 3, 4, 5, 6, 7, 8, 9, 10, 11, 12, 13, 14 or more days after increases in hypertension or systemic blood pressure are diagnosed or detected.

In some embodiments, biomarkers may be used to determine when an inappropriate level of cross-linking might be occurring: LOX levels have been shown to correlate with C reactive protein (CRP), a commonly used biomarker, and treatment may begin when CRP levels are elevated above appropriate normal levels. More directly, methods and test kits exist to measure the release of cross-linked collagen telopeptides in urine or blood. Elevated levels of these collagen fragments may indicate a transition from reparative fibrosis to reactive (mal-adaptive) fibrosis. In addition, measures of cardiac function and output, including those associated with efficient contraction of the ventricle, may be made.

In some embodiments, a limited duration of treatment is envisioned. Treatment should typically be sustained only long enough to prevent or attenuate reactive fibrosis to prevent or reduce cardiac dysfunction. For example, short-lived Fab antibody fragments are used when shorter durations of treatment are desired. Alternatively, full-length antibodies that have a longer half-life in serum may be used, with limited dosing over 1, 2, 3, 4, 5, 6, 7, 8, 9, 10, 11, 12, or more weeks, inclusive of all days in between. Standard tests of cardiac function may be used to monitor progress and adjust dosing as necessary, along with assessment of relevant biomarkers discussed above. Limited duration of treatment adds to the safety of this approach.

The indications for the administration of the compositions described herein also include fibroses found outside of cardiovascular indications. Fibrosis is the abnormal accumulation of fibrous tissue that can occur as a part of the wound-healing process in damaged tissue. Such tissue damage may result from physical injury, inflammation, infection, exposure to toxins, as well as other causes. Examples of fibrosis include dermal scar formation, keloids, liver fibrosis, lung fibrosis (e.g., silicosis, asbestosis), and kidney fibrosis (including diabetic nephropathy and glomerulosclerosis). Additionally, fibrosis and deposition of collagen have been implicated in the formation of β-amyloid plaques, thus contributing to the development and progression of Alzheimer's disease. The compositions described herein are also contemplated for the treatment, prevention, and/or amelioration of the following fibrotic conditions.

Dermal Scar and Keloid Formation

Dermal scar and keloid formation are known to involve excessive collagen deposition and/or dysregulation of collagen deposition. This deviation from normal fibroblast remodeling of injured dermal tissue can result in thick and unsightly scarring. Keloids are known to be, in part, the result of dysregulated wound healing and subsequent elevated collagen deposition. Keloids, unlike the scars seen in normal wound healing, do not fade or regress over time. Though keloids are typically benign dermal tumors, they are unsightly and can accumulate into more problematic skin deformations and/or lesions. (Appleton, I., et al., *Apoptosis, Necrosis, and Proliferation: Possible Implications in the Etiology of Keloids*, Am. J. Pathol., 149(5): 1441-1447 (1996)). The accumulation of collagen in the skin is also implicated in scleroderma, a generalized term for numerous conditions of thickening or hardening of dermal tissue, where the common element is the overproduction or dysregulation of collagen in the dermal tissues by fibroblasts. (Akagi, A. et al., *Expression of Type XVI Collagen in Human Skin Fibroblasts: Enhanced Expression in Fibrotic Skin Disease*, J. Invest. Dermatol., 113: 246-250 (1999)). Given the central role of collagen deposition in fibrotic skin diseases such as scleroderma and keloid formation, the compositions described herein are useful in the prevention, treatment, and/or amelioration of fibrotic skin diseases, including but not limited to, scleroderma and keloid formation.

Liver Fibrosis

Fibrosis of the liver is implicated in the pathology of numerous hepatic diseases. As previously noted, fibrosis occurs as a complication of haemochromatosis, Wilson's disease, alcoholism, schistosomiasis, viral hepatitis, bile duct obstruction, exposure to toxins, and metabolic disorders. Left unchecked, hepatic fibrosis progresses to cirrhosis (defined by the presence of encapsulated nodules), liver failure, and death.

Liver fibrosis, including, but not limited to, cirrhosis, and associated conditions such as chronic viral hepatitis, non-alcoholic fatty liver disease (NAFLD), alcoholic steatohepatitis (ASH), non-alcoholic steatohepatitis (NASH), primary biliary cirrhosis (PBC), biliary cirrhosis, and autoimmune hepatitis, may be treated by the compositions and methods disclosed herein.

The chronic insults to the liver from such sources as parasites and viral infection (e.g. HBV, HCV, HIV, schistosomiasis) or the long term stress from alcohol consumption typically result in remodeling of the liver, presumably to encapsulate the damaged area and protect the remaining liver tissue from damage. (Li and Friedman, *Gastroenterol. Hepatol.* 14:618-633, 1999). Liver fibrosis results in extracellular matrix changes, including 3-10 fold increases in total collagen content and replacement of the low density basement membrane with high-density matrix, which impair the metabolic and synthesis function of hepatocytes, hepatic stellate cells and endothelial cells. (Girogescu, M., *Non-invasive Biochemical Markers of Liver Fibrosis*, J. Gastrointestin. Liver Dis., 15(2): 149-159 (2006)). The compositions described herein are thus useful for the prevention, treatment, and/or amelioration of fibrotic liver diseases, and such use is contemplated herein.

Kidney Fibrosis

Like liver fibrosis, kidney fibrosis can result from various diseases and insults to the kidneys. Examples of such diseases and insults include chronic kidney disease, metabolic syndrome, vesicoureteral reflux, tubulointerstitial renal fibrosis, diabetes (including diabetic nephropathy), and resultant glomerular nephritis (GN), including, but not limited to, focal segmental glomerulosclerosis and membranous glomerulo-nephritis, mesangiocapillary GN.

It has become recognized that metabolic syndrome is a cluster of abnormalities including diabetic hallmarks such as insulin resistance, as well as central or visceral obesity and hypertension. In nearly all cases, dysregulation of glucose results in the stimulation of cytokine release and upregulation of extracellular matrix deposition. Additional factors contributing to chronic kidney disease, diabetes, metabolic syndrome, and glomerular nephritis include hyperlipidemia, hypertension, and proteinuria, all of which result in further damage to the kidneys and further stimulate the extracellular matrix deposition. Thus, regardless of the primary cause, insults to the kidneys may result in kidney fibrosis and the concomitant loss of kidney function. (Schena, F. and Gesualdo, L., *Pathogenic Mechanisms of Diabetic Nephropathy, J. Am. Soc. Nephrol.*, 16: S30-33 (2005); Whaley-Connell, A., and Sower, J. R., *Chronic Kidney Disease and the Cardiometabolic Syndrome, J. Clin. Hypert.*, 8(8): 546-48 (2006)). The compositions described herein are thus useful for the prevention, treatment, and/or amelioration of fibrotic kidney diseases (chronic kidney disease, diabetic nephropathy, glomerular nephritis, metabolic syndrome), and such use is contemplated herein.

Lung Fibrosis

Fibrosis of the lung includes many syndromes and diseases. Exemplary diseases include idiopathic pulmonary fibrosis (IPF), idiopathic interstitial pneumonia, and acute respiratory distress syndrome (ARDS). Lung fibrosis may also include, but not be limited to, cryptogenic fibrosing alveolitis, chronic fibrosing interstitial pneumonia, interstitial lung disease (ILD), and diffuse parenchymal lung disease (DPLD).

The pathogenesis of most lung fibroses, including the aforementioned diseases are not well understood, however all are characterized by an influx of inflammatory cells and a subsequent increase in the synthesis and deposition of collagen-rich extracellular matrix. (Chua et al., $Am\ J.\ Respir.\ Cell.\ Mol.\ Biol.$, 33:9-13 (2005); Tzortzaki et al., $J.\ Histochem.\ \&\ Cytochem.$, 54(6): 693-700 (2006); Armstrong et al., $Am.\ J.\ Respir.\ Crit.\ Care\ Med.$, 160: 1910-1915 (1999)). Given the identified role of increased collagen and extracellular matrix deposition in lung fibroses, the compositions described herein are useful for the prevention, treatment, and/or amelioration of lung fibroses by the inhibition of LOX/LOXL.

Alzheimer's Disease

Alzheimer's disease is a progressive neurodegenerative disorder characterized by neuronal loss due to accumulation of amyloid-beta plaques, and lysyl oxidase activity is also known to be increased in Alzheimer's disease. (Gilad et al., Neurosci. Lett., 376(3): 210-13 (2005)). Amyloid-beta contains multiple lysine residues which represent targets for LOX/LOXL activity, thus inhibition of LOX/LOXL can treat, prevent, or ameliorate the accumulation of amyloid plaques in Alzheimer's disease. Amyloid-beta plaques are also known to consist of additional proteins. One such protein contributing to the formation and content of amyloid-beta plaques is a collagen protein termed CLAC-P. CLAC-P is similar to collagen Type XIII in structure but is distributed in neurons. CLAC-P binds with amyloid-beta and contributes to the formation of amyloid-beta plaques. (Soederberg et al., J. Biol. Chem., 280(2): 1007-1015 (2005)). The compositions described herein are thus useful for the prevention, treatment, and/or amelioration of Alzheimer's disease, including, but not limited to, the prevention of amyloid-beta plaque formation as well as the reduction in the persistence of amyloid-beta plaques.

Abnormal angiogenesis that may be treated or prevented by using the methods and compositions described herein include abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopaphy, and other ocular angiogenic diseases such as retinopathy of prematurity (retrolental fibroplastic), macular degeneration, corneal graft rejection, neuroscular glaucoma and Oster Webber syndrome.

Diseases associated with abnormal angiogenesis require or induce vascular growth. For example, corneal angiogenesis involves three phases: a pre-vascular latent period, active neovascularization, and vascular maturation and regression. The identity and mechanism of various angiogenic factors, including elements of the inflammatory response, such as leukocytes, platelets, cytokines, and eicosanoids, or unidentified plasma constituents have yet to be revealed.

In another embodiment, the pharmaceutical formulations of the present disclosure may be used for treating diseases associated with undesired or abnormal angiogenesis. The method comprises administering to a patient suffering from undesired or abnormal angiogenesis a LOX/LOXL inhibitor in combination with anti-neoplastic agent or anti-angiogenic agent that is not the LOX/LOXL inhibitor. The particular dosage of these agents required to inhibit angiogenesis and/or angiogenic diseases may depend on the severity of the condition, the route of administration, and related factors that can be decided by the attending physician. Generally, accepted and effective daily doses are the amount sufficient to effectively inhibit angiogenesis and/or angiogenic diseases.

According to this embodiment, the pharmaceutical formulations of the present disclosure may be used to treat a variety of diseases associated with undesirable angiogenesis such as retinal/choroidal neuvascularization and corneal neovascularization. Examples of retinal/choroidal neuvascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid abostructive diseases, chronic uveitis/vitritis, mycobacterial infections, Lyme's disease, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neuvascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

In yet another embodiment, the pharmaceutical formulations of the present disclosure may be used for treating chronic inflammatory diseases associated with abnormal angiogenesis. The method comprises administering to a patient suffering from a chronic inflammatory disease associated with abnormal angiogenesis a LOX/LOXL inhibitor in combination with anti-neoplastic agent or anti-angiogenic agent that is not the LOX/LOXL inhibitor. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis using the pharmaceutical formulations of the present disclosure may prevent the formation of the granuloamas, thereby alleviating the disease. Examples of chronic inflammatory disease include, but are not limited to, inflammatory bowel diseases such as Crohn's disease and ulcerative colitis, psoriasis, sarcoidois, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by the pharmaceutical formulations of the present disclosure should inhibit the formation of the sprouts and prevent the formation of granulomas. The inflammatory bowel diseases also exhibit extra intestinal manifestations, such as skin lesions. Such lesions are characterized by inflammation and angiogenesis and can occur at many sites other the gastrointestinal tract. Inhibition of angiogenesis by the pharmaceutical formulations of the present disclosure should reduce the influx of inflammatory cells and prevent the lesion formation.

Sarcoidois, another chronic inflammatory disease, is characterized as a multi-system granulomatous disorder. The granulomas of this disease can form anywhere in the body and, thus, the symptoms depend on the site of the granulomas and whether the disease is active. The granulomas are created by the angiogenic capillary sprouts providing a constant supply of inflammatory cells. By using the pharmaceutical formulations of the present disclosure to inhibit angionesis, such granulomas formation can be inhibited. Psoriasis, also a chronic and recurrent inflammatory disease, is characterized by papules and plaques of various sizes. Treatment using the pharmaceutical formulations of the present disclosure should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using the pharmaceutical formulations of the present disclosure alone or in conjunction with other anti-RA agents may prevent the formation of new blood vessels necessary to maintain the chronic inflammation and provide the RA patient relief from the symptoms.

8. Diagnosis of Diseases

The present disclosure also provides methods for diagnosing, monitoring, staging or detecting the diseases described above by using agents that recognize different forms of LOX or LOXL. For example, as described above, antibodies against different forms of LOX or LOXL, the preproprotein, secreted, mature form, can be used for these purposes.

As described above, mature LOX or LOXL is cleaved and can be detected by virtue of it changes in molecular weight (immunoblot) or by use of antibodies that detect the uncleaved vs. cleaved form of LOX/LOXL, along with cellular localization by using various detection methods such as immunohistochemistry (IHC).

It is believed that the extracellular matrix and conditioned medium (e.g., See Example 4) should contain proteolytically processed LOX or LOXL whereas uncleaved LOX/LOXL should be localized intracellularly. Some cleaved LOX/LOXL may also be detected inside the cell as a consequence of uptake from the extracellular space.

Samples from individuals can be collected and analyzed by determining inactive or active LOX levels or different forms of LOX/LOXL levels. This analysis may be performed prior to the initiation of treatment using lysyl oxidase-specific therapy to identify tumors having elevated active LOX/LOXL expression or activity. Such diagnosis analysis can be performed using any sample, including but not limited to cells, protein or membrane extracts of cells, biological fluids such as sputum, blood, serum, plasma, or urine, or biological samples such as tissue samples, formalin-fixed or frozen tissue sections.

Any suitable method for detection and analysis of inactive and/or active LOX/LOXL can be employed. As used herein, the term "sample" refers to a sample from a human, animal, or to a research sample, e.g., a cell, tissue, organ, fluid, gas, aerosol, slurry, colloid, or coagulated material. The sample may be tested in vivo, e.g., without removal from the human or animal, or it may be tested in vitro. The sample may be tested after processing, e.g., by histological methods. The term "sample" may also refer to a cell, tissue, organ, or fluid that is freshly taken from a human or animal, or to a cell, tissue, organ, or fluid that is processed or stored.

In one embodiment, methods are provided for diagnosing cancer metastasis in a subject, comprising assessing active LOX or LOXL levels or activity in the blood, whereby a change in active LOX or LOXL levels or activity in the blood in comparison with a reference sample, indicates the presence of metastatic tumor growth. In some instances, the active LOX or LOXL levels or activities in the blood may be lower than those when measured earlier, which may indicate that the subject is at a greater risk of cancer metastasis; that the cancer has metastasized; or that cancer metastasis has increased.

In another embodiment, methods are provided for diagnosing cancer metastasis in a subject having a tumor, comprising assessing active LOX or LOXL levels or activity in the tumor, whereby a change in active LOX or LOXL levels or activity in the tumor in comparison with a reference sample indicates the presence of metastatic tumor growth. In some instances, the active LOX or LOXL levels or activities in the tumor may be higher than those when measured earlier, which may indicate that the subject is at a greater risk of cancer metastasis; that the cancer has metastasized; or that cancer metastasis has increased.

The reference sample may derive from the same subject, taken from the same tumor at a different time point or from other site of the body, or from another individual.

Measurement of active LOX or LOXL levels may take the form of an immunological assay, which detects the presence of active LOX or LOXL protein with an antibody to the protein, for example, an antibody specifically binding to active or secreted LOX or LOXL.

Immunoassays also can be used in conjunction with laser induced fluorescence (see, for example, Schmalzing and Nashabeh, *Electrophoresis* 18:2184-93 (1997)); Bao, *J. Chromatogr. B. Biomed. Sci.* 699:463-80 (1997), each of which is incorporated herein by reference). Liposome immunoassays, such as flow-injection liposome immunoassays and liposome immunosensors (Rongen et al., *J. Immunol. Methods* 204:105-133 (1997), also can be used to determine active LOX or LOXL levels according to a method of the disclosure). Immunoassays, such as enzyme-linked immunosorbent assays (ELISAs), are useful in the methods provided herein. A radioimmunoassay also can be useful for determining whether a sample is positive for active LOX or LOXL or for determining the level of active LOX or LOXL. A radioimmunoassay using, for example, an iodine-125 labeled secondary antibody, may be used.

In addition, one may measure the activity of active LOX or LOXL, thus ignoring the amount of inactive enzyme. Enzymatic activity of active LOX or LOXL may be measured in a number of ways, using a soluble elastin or soluble collagen with labeled lysine as a substrate. Details of an activity assay are given in Royce et al., "*Copper metabolism in mottled mouse mutants. The effect of copper therapy on lysyl oxidase activity in brindled (Mobr) mice,*" Biochem J. 1982 Feb. 15; 202(2): 369-371. Chromogenic assays may be used. One is described in Palamakumbura, et al. "*A fluorometric assay for detection of lysyl oxidase enzyme activity in biological samples,*" Anal Biochem. 2002 Jan. 15; 300(2):245-51.

Also provided here is a method for monitoring a subject's response to a therapy including a modulator of LOX/LOXL such as the treatment of cancer, tumors, and fibrotic diseases. The method comprises: detecting a change in the level C-reactive protein, or other acute-phase reactants, in the subject after administration of a modulator of LOX or LOXL to the subject, wherein the change indicates that the LOX or LOXL modulator has a therapeutic effect on the subject. A C-reactive protein is an important pharmacodynamic marker for systemic inflammation. Furthermore, C-reactive protein is thought to enhance LOX expression (Li et al., *Circulation Research*; (2004) 95:877). Thus, without being bound by theory, a reduced level of C-reactive protein (e.g., in the blood sample of the subject) as compared to that prior to the administration of the LOX or LOXL inhibitor can be indicative of the subject's response to the therapy using an inhibitor of LOX or LOXL. Methods includes including monitoring an increase or decrease in levels of C-reactive protein, which would be indicative of the subject's response to the therapy.

In another embodiment, methods are provided for monitoring a subject's response to a therapy including a modulator of LOX/LOXL such as the treatment of cancer, tumors, and fibrotic diseases. The method comprises: detecting a change in the level of collagen telopeptides or hydroxyproline content in the subject after administration of a modulator of LOX or LOXL to the subject, wherein the change indicates that the LOX or LOXL modulator has a therapeutic effect on the subject. The change can be an increase or decrease. For example, a decrease in collagen telopeptides or hydroxyproline content can be indicative of a therapeutic effect.

Although exemplary embodiments of the present disclosure have been described and depicted, it will be apparent to the artisan of ordinary skill that a number of changes, modifications, or alterations to the disclosure as described herein may be made, none of which depart from the spirit of the present disclosure. All such changes, modifications, and alterations should therefore be seen as within the scope of the present disclosure. The following examples are offered to illustrate but not to limit the disclosure.

EXAMPLES

Example 1

EMT/MET Assay

Figure 4:
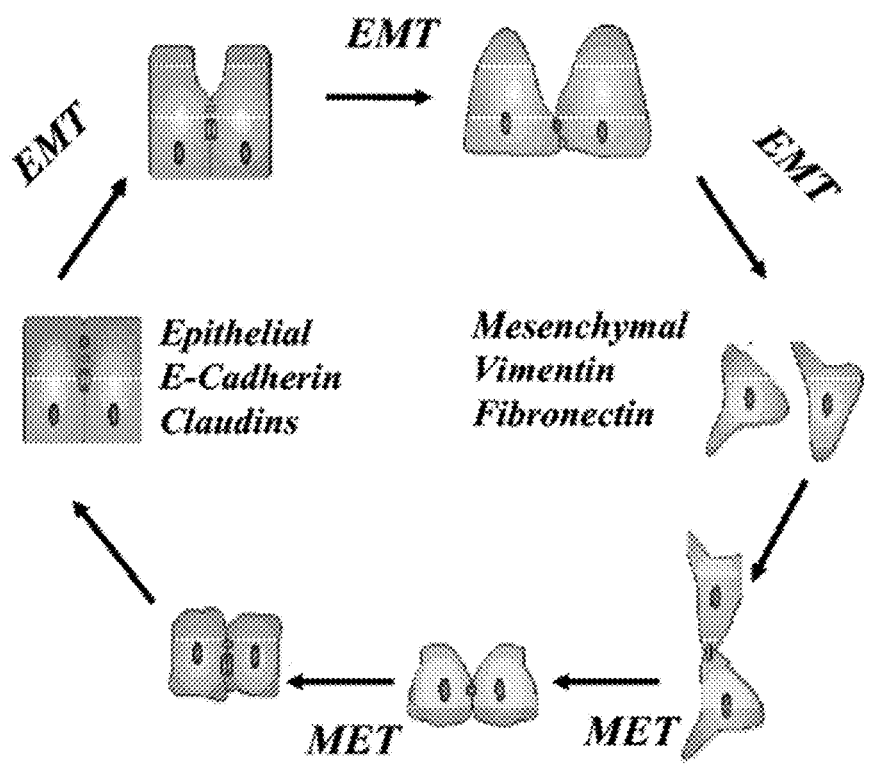
FIG. 4 is a schematic of the EMT and MET and markers for to assess EMT or MET phenotypes of cells.
Figure 5:
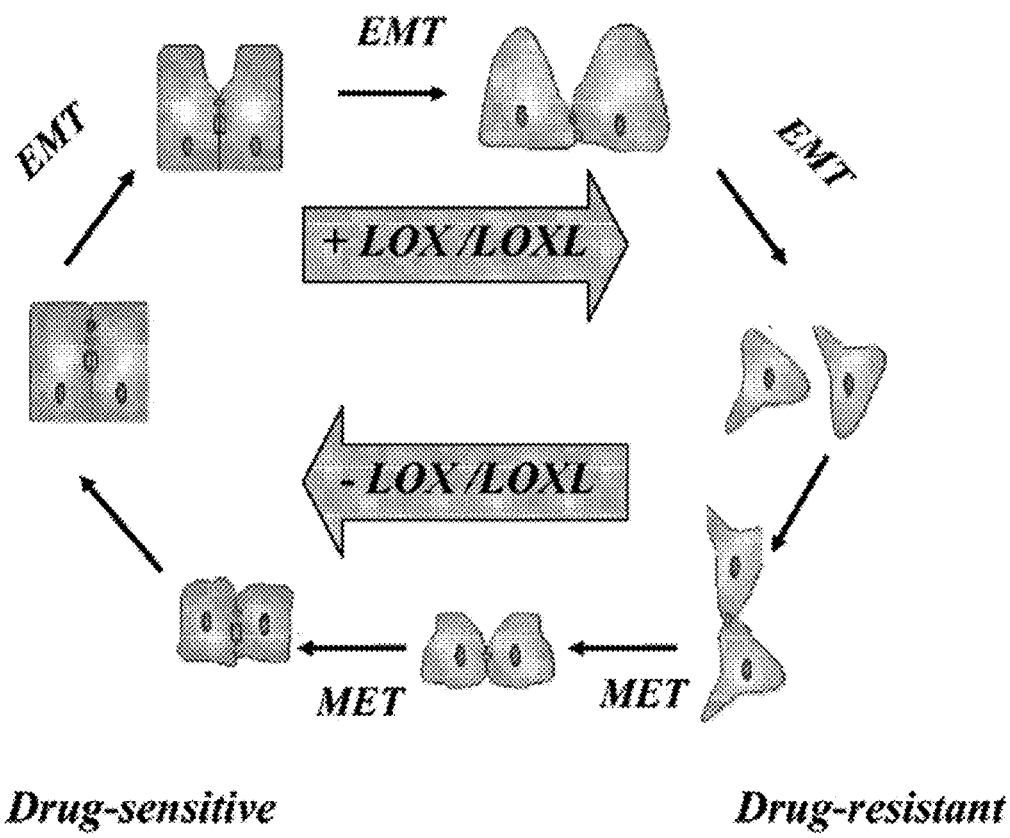
FIG. 5 is a schematic of the role of LOX/LOXL in EMT-MET promotion or reduction, and the drug-resistance or sensitivity of the EMT-MET cells.

To detect whether a cell is in an EMT or MET state, cells are stained with antibodies specific to cellular protein markers for epithelial or mesenchymal states such as E-cadherin, vimentin, fibronectin, and phalloidin to detect F-actin (FIG. 4).

Rhodamine Phalloidin Staining Protocol:

Cells were seeded 24 hours prior to day of staining; cells should be approximately 80% confluent 24 hours later in an 8-chambered slide. The next day, the media was aspirated and the chambers were rinsed with 1×PBS. Cells were then fixed with 4% Parafomaldehyde (PFA) for 20 minutes at room temperature and then rinsed once with 1×PBS. For permeabilization, the cells were treated with 0.5% Saponin (JT Baker, Phillipsburg, N.J.) in PBS for 5 minutes at room temperature. The chambers were carefully rinsed once with 1×PBS and a 1:100 dilution of rhodamine phalloidin (Invitrogen, Carlsbad, Calif.) in PBS was added to the cells and incubated for 15 minutes at room temperature. The chambers were rinsed two times with 1×PBS and the slides were mounted with Vectashield (Vector Laboratories, Burlingame, Calif.).

E-Cadherin Staining Protocol:

Cells were seeded 24 hours prior to day of staining; cells should be approximately 80% confluent the next day in an 8-chambered slide. The next day, the media was aspirated and the chambers were rinsed with 1×PBS. Cells were then fixed with ice cold methanol and then incubated for 2 minutes in $-20°$ C. The cells were rinsed once with 1×PBX and 1 µg/ml of E-cadherin Ab (Calbiochem, Gibbstown, N.J.) was added to the slide chambers. The slides were then incubated at 37° C. for 1 hour. After carefully rinsing the chambers one time with 1×PBS, the secondary Ab (anti-mouse IgG cy3 conjugated, Jackson Immuno Research, West Grove, Pa.) was added and incubated at room temperature for 30-45 minutes. The chambers were rinsed two times with 1×PBS and mounted with Vectashield (Vector Laboratories, Burlingame, Calif.).

Example 2

Assay for LOX/LOXL Inhibitors that Reduce EMT/Promote MET in Cells Endogenously Expressing Significant Levels of LOX/LOXL BT-549, Hs5788t, MDA-MB-231, or NCI-H226 cells express significant levels of LOX/LOXL and are in an EMT or EMT-like state. The cells are seeded onto 8-well chamber glass slides (Nalgene Nunc International. Rochester, N.Y.) at ~25-50% confluence. The cells are incubated for 18 h under hypoxic (2% oxygen), anoxic (0.02% oxygen), or normoxic (21% oxygen) conditions.

LOX/LOXL inhibitors (e.g. anti-LOX/LOXL antibody, LOX/LOXL siRNA, LOX/LOXL shRNA, small molecule inhibitors, such as βAPN or D-penacillamine) and controls (e.g. LOX/LOXL sense oligonucleotides, irrelevant control antibody, small molecule vehicle such as DMSO) are added to the cell culture media. LOX/LOXL levels are determined by RT-PCR and immunoblot analysis.

After 48-72 hours, cells are stained according to Example 1. Cells transfected with LOX/LOXL sense oligonucleotides should maintain EMT characteristics of positive vimentin or fibronectin staining with low levels of E-cadherin staining and an elongated and remodeled actin cytoskeleton as revealed by phalloidin staining of F-actin. Cells treated with candidate LOX/LOXL inhibitors that do not effectively target LOX/LOXL to effect MET induction of the EMT cells should also maintain these EMT characteristics.

Cells treated with LOX/LOXL inhibitors should reduce EMT characteristics and manifest MET characteristics of increased E-cadherin staining and reduced or negligible vimentin or fibronectin staining. The rhodamine-phalloidin staining of these cells should reveal a more compact and regular actin cytoskeleton.

Figure 33:
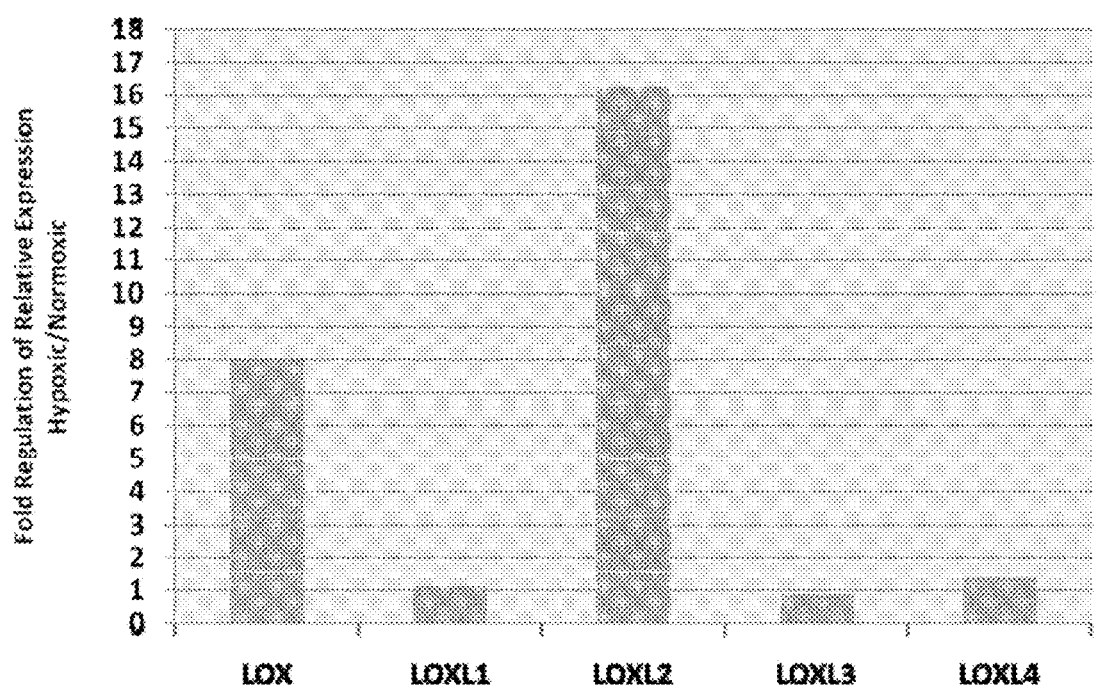
FIG. 33 shows the co-expression of LOX and LOXL2 in hypoxic MCF-7 cells. LOX and LOXL2 are both induced by hypoxia in MCF7 cells, which normally express very low levels of LOX and LOXL2 (fold upregulation vs cells grown under normoxic conditions is plotted on the left axis). Cells were grown in a tissue culture incubator adjusted to 2% O2, 5% CO2 for 3 days (vs. normoxia: ~20% $O_2$, 5% $CO_2$). MCF7: breast tumor cell line.
Figure 34:
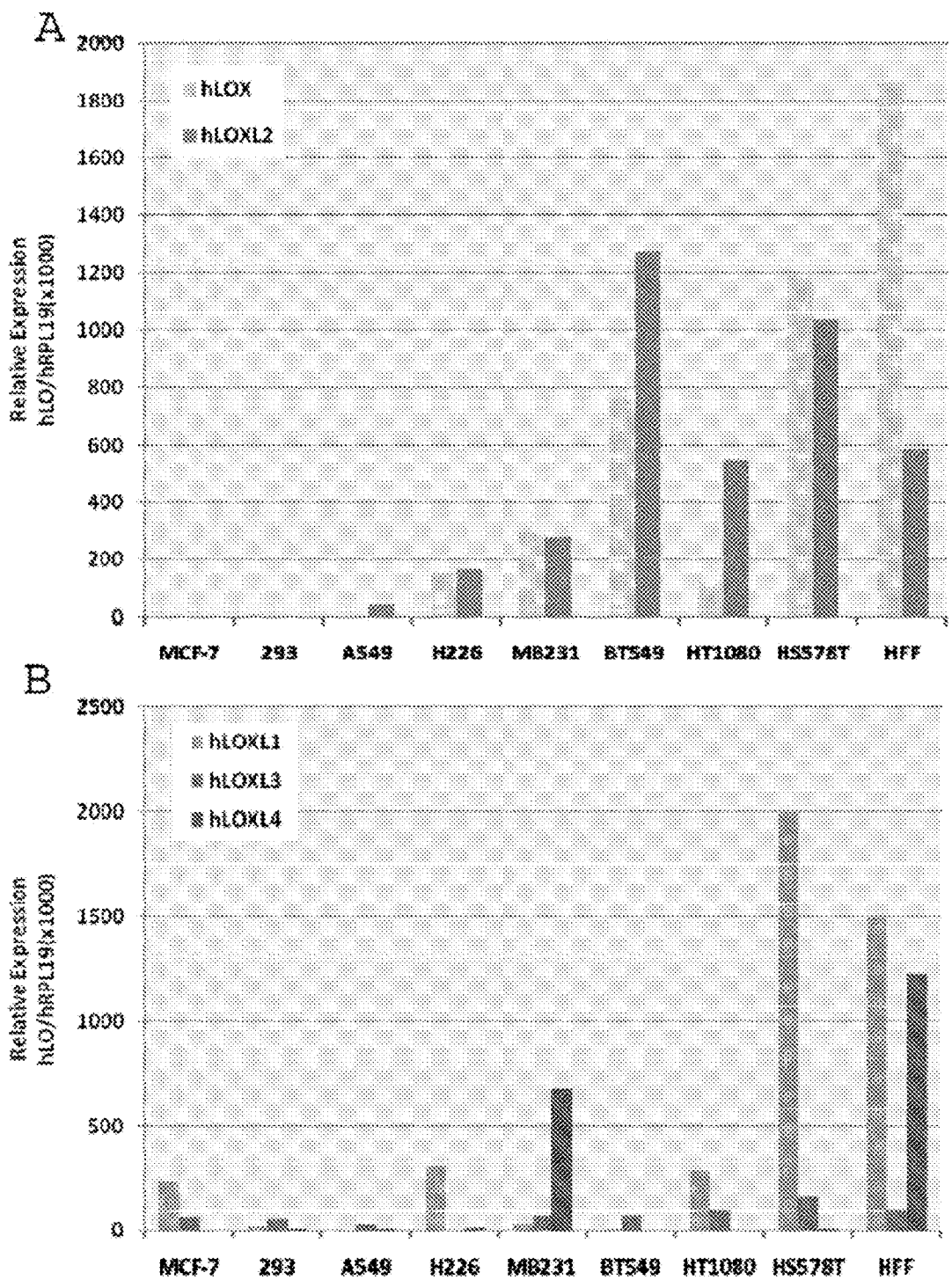
FIG. 34 A-B shows mRNA levels of lysyl oxidase family members in human cell lines. One-step qRT-PCR was performed on 100 ng/rxn RNA. MCF7, MB231, BT549, Hs578t: breast tumor cell lines; A549: lung tumor cell line; HT1080: fibrosarcoma cell line; HFF: fibroblast cell line.

Invasion/migration assays are also used to assess EMT and MET phenotypes of the cells, as increased invasiveness and migratory capacity are associated with EMT. (See e.g. Bedogni et al., *Cancer Res.* 64:2552-2560 (2004)) Cells are serum deprived for 24 h then $10^4$-$10^6$ cells are seeded in triplicate on coated and uncoated inserts (for example, Matrigel™ coated inserts from BD Biosciences), and incubated under normoxic or oxygen-deprived conditions for 24 h (for example, LOX/LOXL expression can differ under normoxic/hyposic conditions as shown in FIG. 33). Treatments with LOX/LOXL inhibitors and controls are continued throughout the experiment.

The cells maintaining an EMT state should be invasive and migratory, and able to invade through the Matrigel™-coated inserts, or migrate across other surface-modified inserts, more readily in comparison to MET cells. A similar analysis is conducted using a wound-healing or scratch assay, in which a scratch is made using a pipet tip in a confluent lawn of cells. The scratch is monitored over 24-96 h using a microscope. Cells in a state of EMT that are more invasive and migratory should fill the scratch more rapidly than less invasive or migratory cells.

Those LOX/LOXL inhibitors that reduce EMT and promotes MET are selected as candidates for further development.

Figure 26:
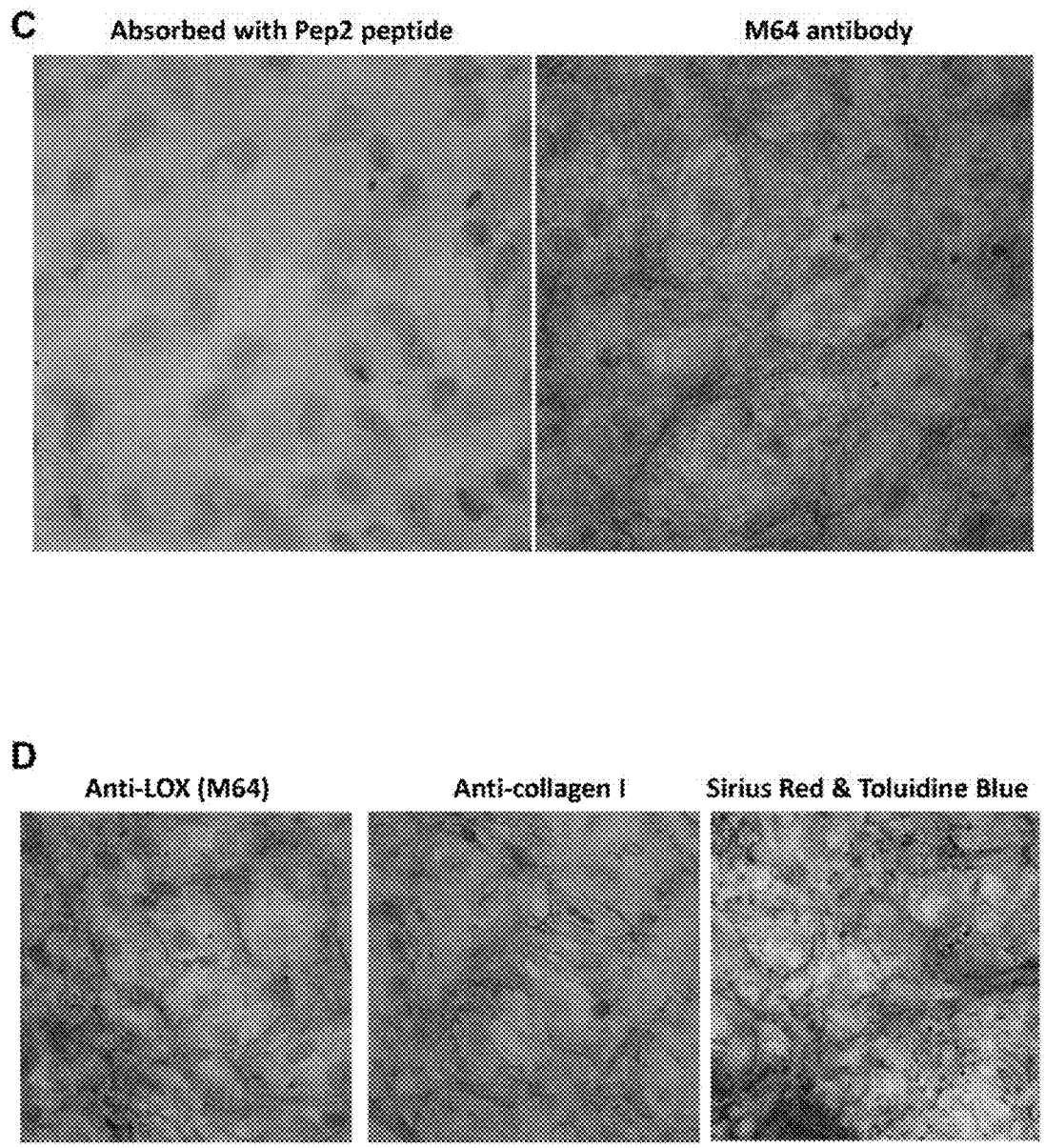
FIG. 26 shows the specificity of LOX Pep2 M64. mAbs were screened for their ability to inhibit cell invasion and migration through (A) Collagen I and/or (B) Collagen IV matrix. (C) Specificity of M64Mab on Hs578T cells was detected on chamber slides (post-confluent: Day 6). (D) LOX localization compared with collagen Hs578T cells on chamber slides (post-confluent: Day 6). Cells were not permeablized and images were at 63× magnification.

As depicted in FIGS. 26A and B a screen for mAbs that inhibit cell invasion and migration that was performed. Final Pep2 supernatants screened were purified and concentrated (MO63 to MO82, 50 ng and 200 ng for each). MDA MB 231 cells were serum deprived for 24 hours and were seeded at 20,000 cells/well in serum free media. Cells were treated with triplicate sets of 50 ng and 200 ng of antibody sera and were incubated for 48 hours. Invasive cells were dyed with calcein AM and the fluorescence was measured on a 96 well fluorescent reader (485 nm excitation, 520 emission).

Example 3

Figure 6:
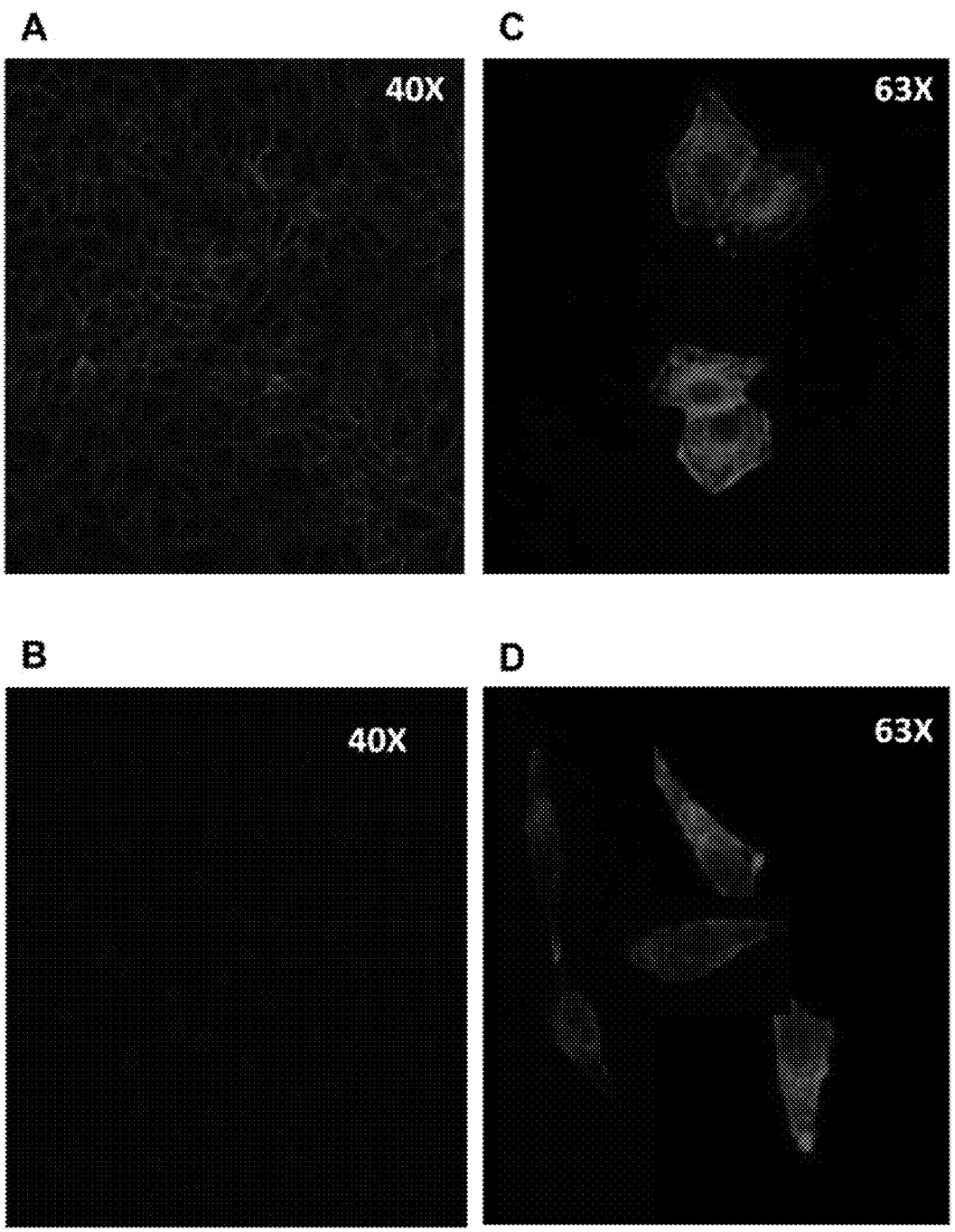
FIG. 6 shows induction of EMT by transfection of MCF-7 (low LOXL2) cells with LOXL2. (A) MCF-7 wild type (WT) cells and (B) MCF-7-Loxl2.clone 1 were stained for E-cadherin. Primary antibody: anti-E-cadherin (10 µg/ml); Secondary antibody: anti-mouse-cy3 (red); DAPI: nuclei (blue). (C) MCF-7 wild type cells and (D) MCF-7-Loxl2.clone 1 were stained with rhodamine phalloidin: actin cytoskeleton (red) and DAPI: nuclei (blue). Wild-type MCF7 shows epithelial phenotype, strongly E-cadherin positive (membraneous staining) (A) and rhodamine phalloidin staining of the actin cytoskeleton reveals a circular pattern (C). MCF7 transfected with LOXL2 changes to a mesenchymal phenotype, losing E-cadherin expression (B), with remodeling of the actin cytoskeleton (elongation, spindly shaped, long actin fibers) (D).

Assay for LOX/LOXL Inhibitors that Reduce EMT/Promote MET with Cells Transfected with LOX/LOXL MDCK, MCF-7, or SW620 cells do not express significant levels of LOX/LOXL and are not in an EMT state. The cells are transfected with plasmids that express LOX/LOXL to induce EMT in the cells (see for example FIG. 6). The transfected cells are incubated for 18 h under normoxic (21% oxygen), hypoxic (2% oxygen) or anoxic (0.02% oxygen) conditions. Expression of LOX/LOXL levels are determined by RT-PCR and immunoblot analysis.

The transfected cells are treated with LOX/LOXL inhibitors and controls, MET/EMT status determined as described in Example 2. Expression of LOX/LOXL levels of treated cells are determined by RT-PCR and immunoblot analysis.

Effective LOX/LOXL inhibitors should prevent the EMT state, or induce MET, of the transfected cells. (FIG. 7) Transfected cells treated with LOX/LOXL sense oligonucleotides should be in an EMT state as should transfected cells without any treatment, or treatment with controls such as an irrelevant control antibody. The EMT/MET state of the treated transfected cells are analyzed as described in Example 1. The cells can also be analyzed using invasion and/or migration assays as described in Example 2.

Those LOX/LOXL inhibitors that reduce EMT and promote MET are selected as candidates for further development.

Example 4

Assay for LOX/LOXL Inhibitors that Reduce EMT/Promote MET with Cells Treated with Conditioned Media (CM)

Making CM from CHO Cells:
CHO-Loxl2 cells were seeded into a T175 flask with a volume of 25 mls of media (MEM+10% FBS, complete). 48 hours later, the media was replaced with 20 mls of SFMII media (cells were 90-95% confluent at this point). The media was collected 72 hours later and filtered in a 0.22 uM polyethylene filter. The filtered media was concentrated 20-25 times using an amicon (15 kD cutoff) concentrator. Nine to ten flasks of 20 mls of media was prepared to make 8 mls of concentrated conditioned media for experiments.

Figure 8:
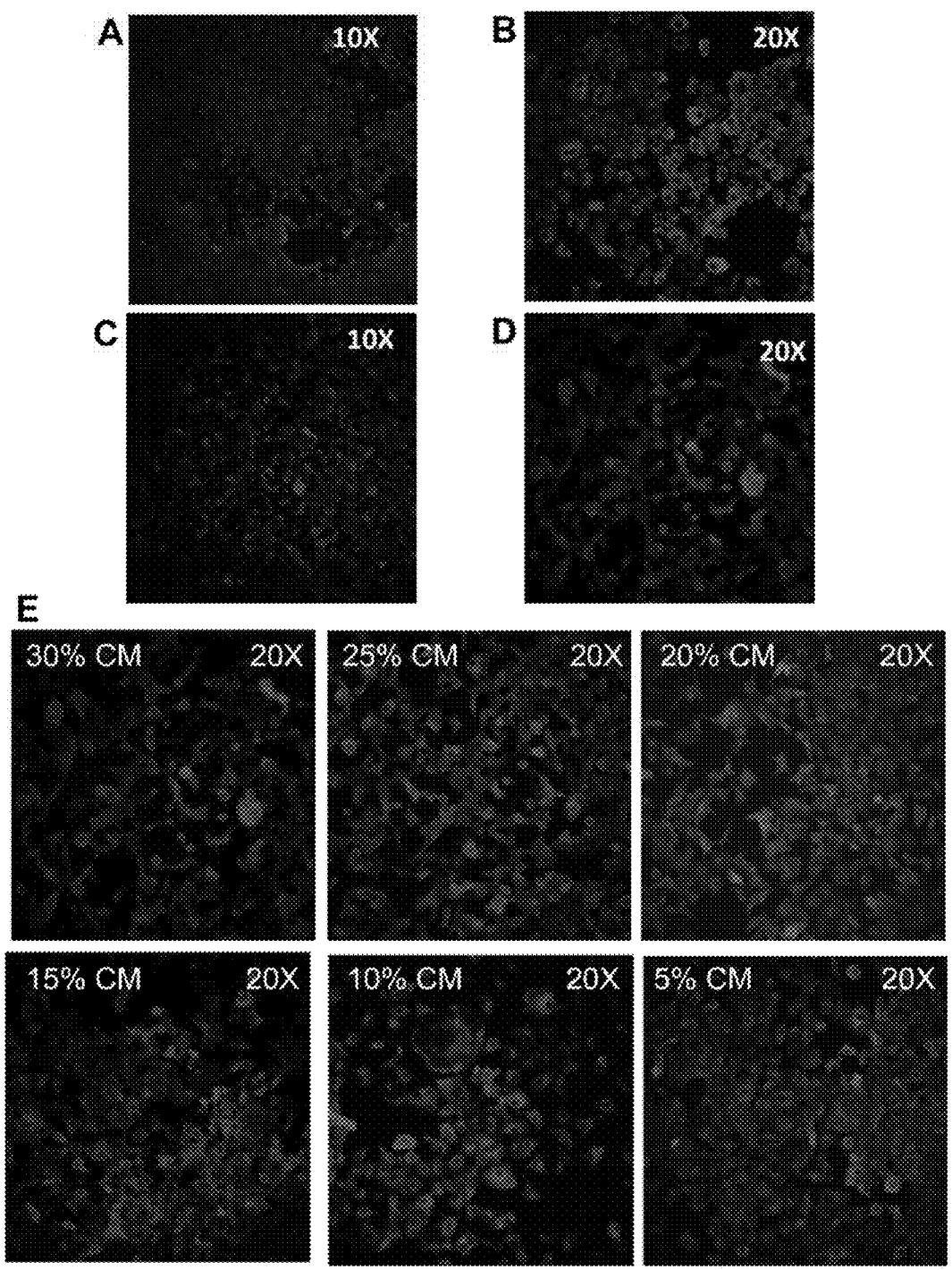
FIG. 8 shows the effects of Conditioned Media (CM) derived from stable CHO-Loxl2 cells on MCF-7 WT cells. (A-B) MCF-7 cells grown in 30% SFII media: 150 µl of SFII media (media used for CHO-Loxl2 cells) in 350 µl of regular MCF-7 complete media. (C-D) MCF-7 cells grown in 30% Conditioned Media (CM): 150 µl of CM from CHO-Loxl2 (concentrated 22× from 3 day serum free CM) in 350 µl of regular MCF-7 complete media. The MCF-7 cells treated with concentrated serum free CM from CHO-Loxl2 cells for 4 days. MCF-7 treated with conditioned media from LOXL2-expression cells (C-D) undergoes a phenotype change compared to cells treated with control conditioned media (CHO cells not expressing LOXL2) (A-B), as revealed by rhodamine-phalloidin staining of the actin cytoskeleton. Cells are elongated with long F-actin fibers, similar to cells undergoing EMT, unlike control-treated cells that show a more circular "actin rim" staining. These data support that the EMT-like change induced by LOXL2 is induced by secreted (extracellular) LOXL2. (E) illustrates effects of different concentrations of CM derived from stable CHO-Loxl2 cells on MCF-7 WT cells and their morphological changes. Treating cells with increasing concentrations of LOXL2-containing CM results in a concordant increase in EMT-like phenotype change.

Treating Cells with CM:
MCF-7 cells were seeded at 50,000 cells per well of an 8-chambered slide 1 day prior to treating with CM. Cells were seeded with complete media (MEM+10% FBS, 1× L-glutamine). 500 μls of fresh conditioned media from Cho-Loxl2 cells was added to the chambers containing MCF7 cells. The cells were incubated with the CM for 48 hours. Conditioned media from MCF7 wildtype cells was used as a negative control. After 48 hour incubation with CM, the cells were stained with rhodamine phalloidin (FIG. 8).

Example 5

Anti-LOXL2 mAb Blocking Assays with Cells Treated with Conditioned Media (CM)

MDA-MB-231 (FIGS. 9, 10, 12) or Hs578t cells (FIG. 11) were seeded in a T75 flask at 80% confluency and cultured in DMEM, 10% FBS, and 1× L-glutamine. These cells were grown for 72 hours to acquire the CM used for experiments. After 72 hours the CM was briefly centrifuged to eliminate dead cells and debris and was placed onto MCF-7 cells (FIGS. 10, 11) or SW620 cells (FIG. 12) that were previously seeded at 50,000 cells per well in an 8-chambered slide. EMT-like phenotype changes were typically seen after 48 hour incubation with the conditioned media. MCF-7 or SW620 CM was used as a negative control. Two separate experiments were performed to demonstrate the blocking ability of anti-loxl2 mAbs to inhibit the phenotypic changes that occur with epithelial-mesenchymal transition (EMT).

Figure 9:
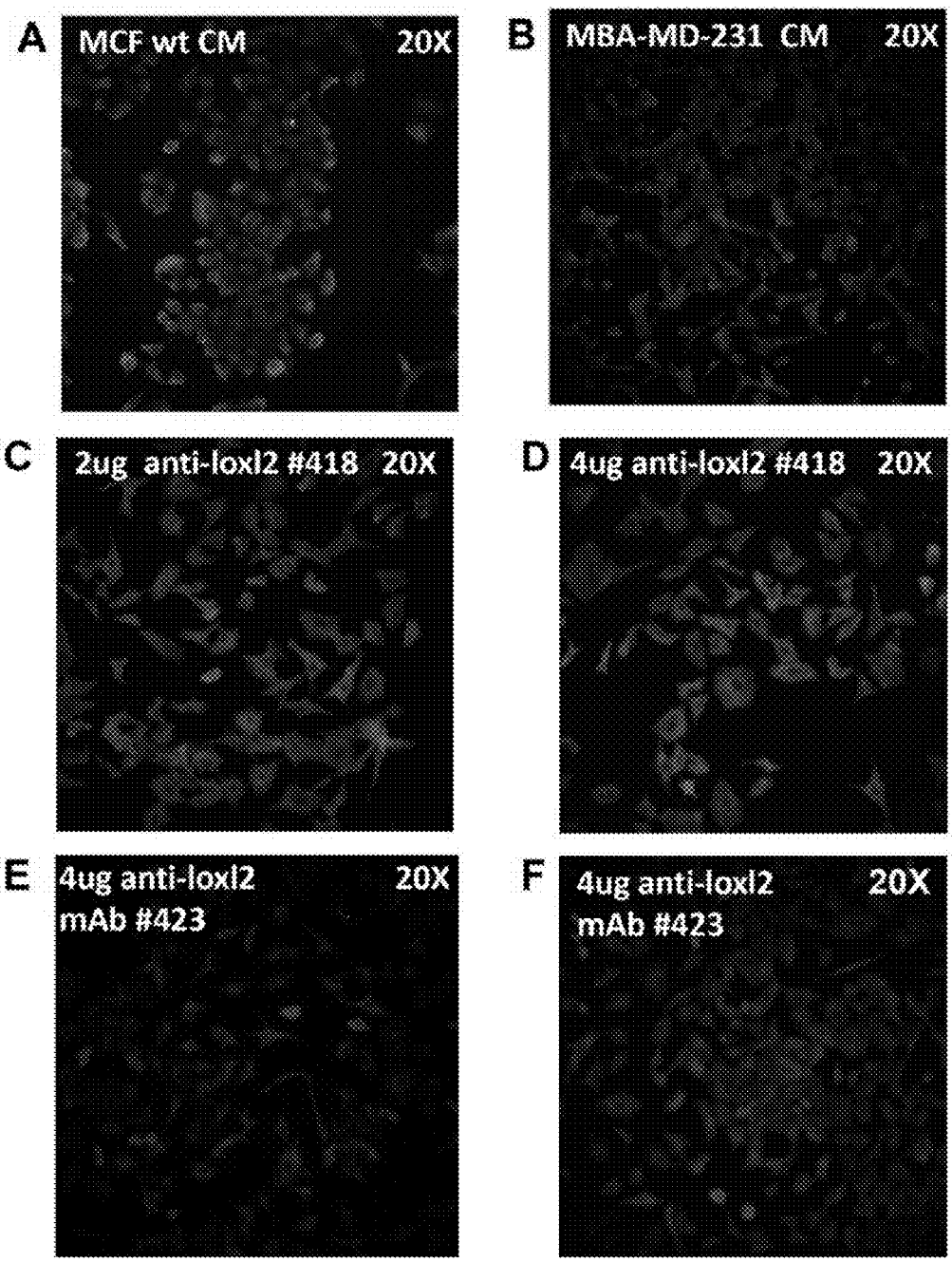
FIG. 9 shows anti-Loxl2 mAbs can block the EMT phenotype observed from incubating MBA-MD-MB-231 (expresses high levels of LOXL2) CM with MCF-7 WT cells. (A, C, E) MCF-7 WT cells with CM from MCF-7 cells and (B, D, F) MCF-7 WT cells with CM from MBA-MD-231 cells, with (C—F) showing cells with CM that was pre-incubated with anti-Loxl2 mAbs prior to addition to MCF-7 cells (C, D): mAb #418 and (E, F): mAb #423, respectively), with varying concentration of antibody (C, E): 2 µg; (D, F): 4 µg).
Figure 10:
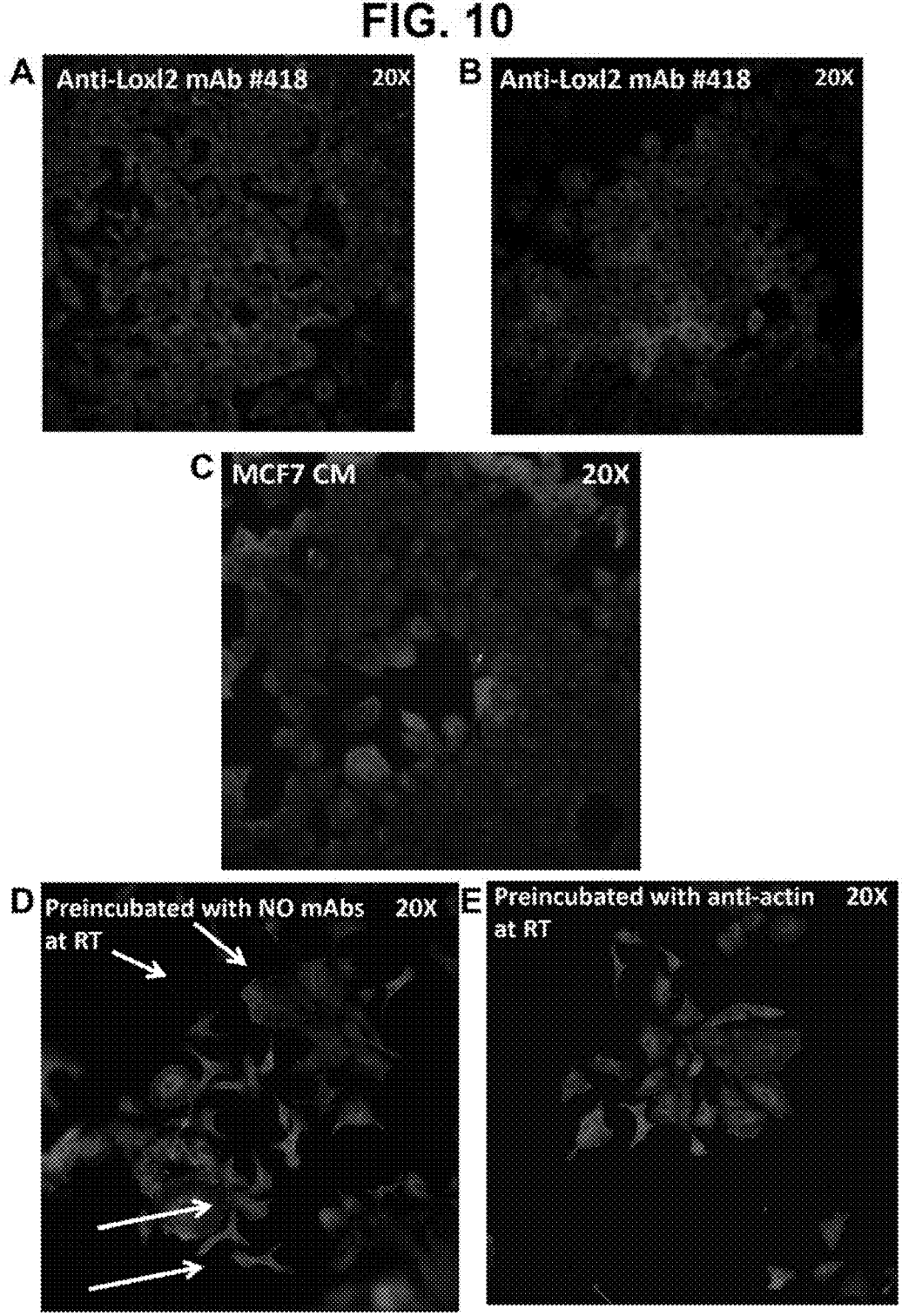
FIG. 10 demonstrates that the specific blocking effect of the EMT-like change from incubating MDA-MB-231 CM with MCF-7 cells. (A) "Pre-incubation": CM, collected and cleared, was pre-incubated with antiLoxl2 (1.5 hrs at room temperature (RT)) #418 or #422 mAb, then applied onto MCF-7 cells for 4 days. (B) "Not pre-incubated": CM with MDA-MB-231 cells was in the presence of anti-Loxl2 #418 or #422 mAb (3 days) and before being collected and cleared, then applied onto MCF-7 for 4 days. EMT-like morphology is blocked in both (A) and (B). As a non-EMT-like control, (C) MCF-7 cells treated with 3 day Conditioned Media (CM) from MCF-7 cells for 4 days and had a round and flattened morphology that is typical of WT MCF-7 cells. As EMT-like controls, (D) MCF-7 cells treated with 3 day CM from MDA231 cells that was not incubated with any loxl2 mAbs (4 day incubation) and (E) MCF-7 cells treated with 3 day CM from MDA231 cells that was pre-incubated with an anti-actin antibody (4 day incubation). Both (D) and (E), an EMT-like morphology of spindly shaped cells is seen.

Experiment 1: "Pre-Incubation":
One ml of CM (centrifuged to eliminate cellular debris) from MDA-MB-231 or Hs578t cells was pre-incubated with 2 μg or 4 μg (final concentration) of anti-loxl2 for 1 hour and 30 minutes prior to adding to MCF7 or SW620 cells. Anti-actin was used as a negative mAb control. (FIG. 10E) The conditioned media was then added to the MCF7 or SW620 cells and incubated in 37 C and 5% CO2 for 48 hours. The actin cyto skeleton of the MCF7 or SW620 cells were stained with rhodamine phalloidin to analyze the blocking of EMT phenotypic changes (FIG. 9).

Figure 11:
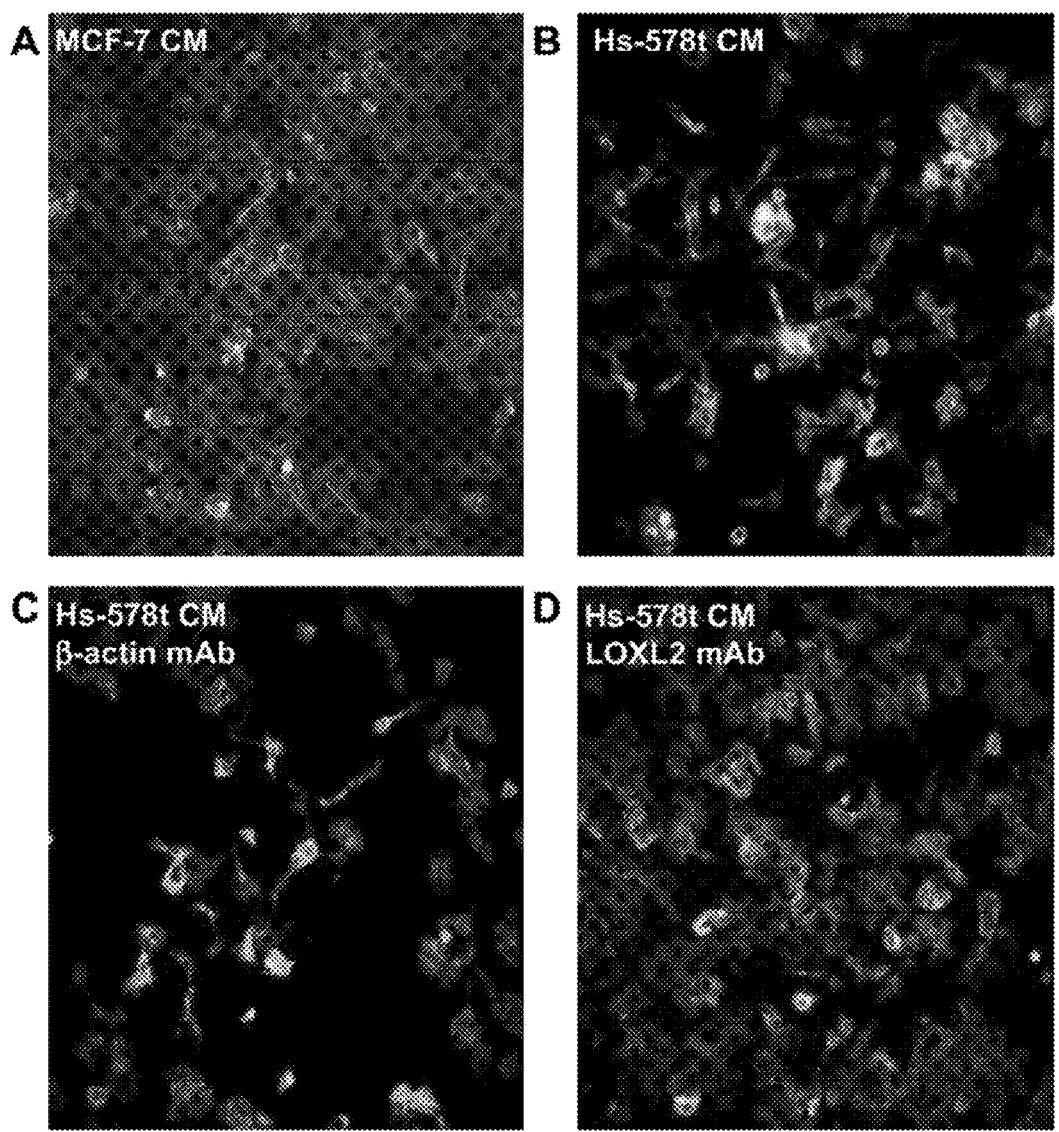
FIG. 11 shows the induction of an EMT-like phenotype change by treating MCF-7 (low LOXL2) with conditioned media from Hs578t tumor cells (expresses high levels of LOXL2) and anti-Loxl2 mAbs can block the EMT phenotype observed. (A) Conditioned media from 3 day Conditioned Media (CM) from MCF-7 cells was applied to MCF-7 cells for 4 days and had a round and flattened morphology that is typical of WT MCF-7 cells. (B, C, D) Conditioned media from Hs-578t cells (LOXL2 high) was applied to MCF-7 cells (LOXL2 low/negative). (A-D) Cells stained with rhodamine-phalloidin (F-actin, red) and DAPI (nuclei, blue). Confirming that these effects are specific to LOXL2 and not other proteins, conditioned media was mixed with 4 µg of either (C) anti β-actin antibody as a negative control or (D) anti LOXL2 antibody. EMT-like phenotype was blocked when the conditioned media from Hs578t cells was pre-incubated with an anti-LOXL2 antibody prior to addition to MCF7 cells (D). Treating the CM in the same manner with an anti β-actin antibody failed to block the phenotype change in the MCF7 cells (C), supporting that the blockade by the LOXL2 antibody was specific and not a non-specific effect due to addition of antibody to CM.

Experiment 2: "Not-Preincubated":
MDA-MB-231 or Hs578t cells were seeded into a T25 flask at 80% confluency and cultured in DMEM, 10% FBS, and 1× L-glutamine. Anti-Loxl2 mAbs (4 μg final concentration) were added to each flask respectively and the flasks were incubated with the media for 72 hours. Anti-actin was used as a negative mAb control (FIG. 10E). The conditioned media was centrifuged to eliminate any cellular debris and then added to the MCF7 or SW620 cells and incubated in 37 C and 5% CO2 for 48 hours. The actin cytoskeleton of the MCF7 or SW620 cells were stained with rhodamine phalloidin to analyze the blocking of EMT phenotypic changes (FIGS. 11, 12).

Example 6

Figure 13:
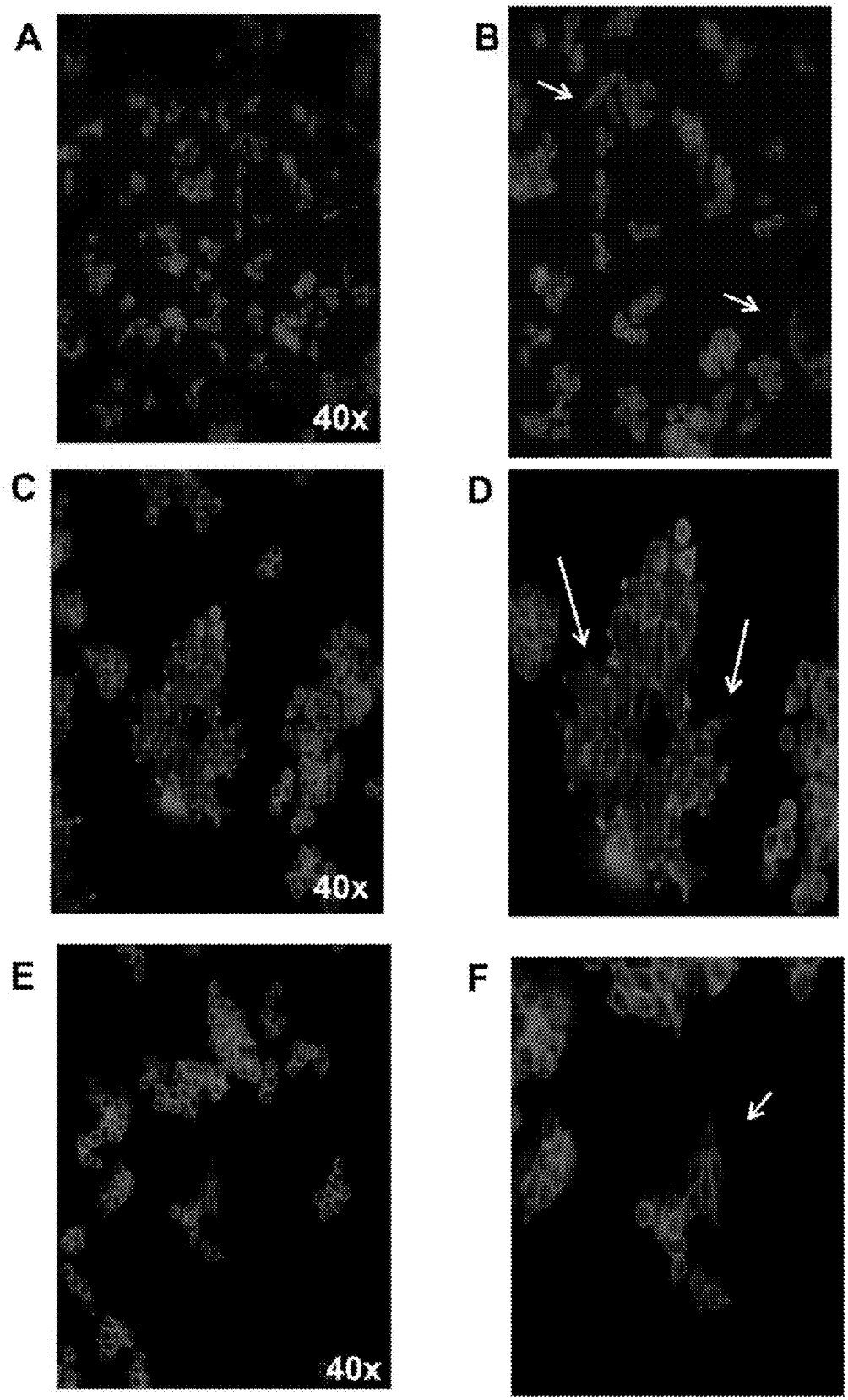
FIG. 13 shows SW620 cells incubated with CM from 293: Loxl2.MCD transfectants. (A, C, E) shows cells undergoing EMT phenotype (as indicated by rhodamine phalloidin staining) changes −72 hours later (50% CM: 50% compete media). (B, C, E) are magnifications of (A, C, E), respectively, with arrows indicating the morphology of SW620 cells undergoing EMT-like phenotype. The 293:Loxl2.MCD were 293 cells transfected with and expressing a fragment of LOXL2, referred to as the LOXL2-MCD, which includes the lysyl oxidase enzymatic domain. It appears that this portion of LOXL2 is alone sufficient to induce at least a partial EMT-like phenotype change. Not all cells are undergoing the phenotype change, but groups of cells that are, are clearly distinguished.
Figure 22:
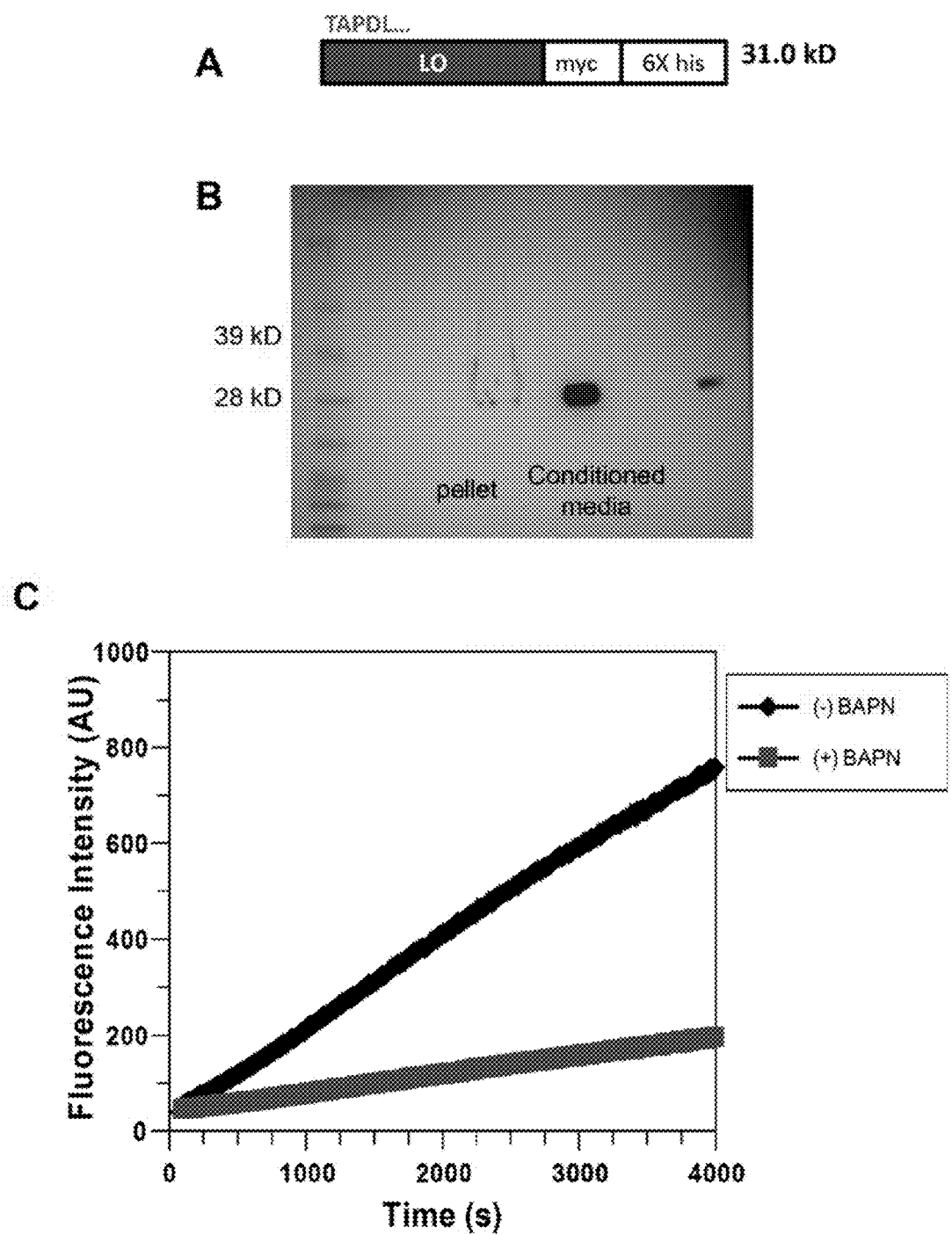
FIG. 22 shows a minimal catalytic domain region (MCD) of LOXL2 is enzymatically active. (A) is schematic of LOXL2 MCD construction (TAPDL and 6×His tag disclosed as SEQ ID NOS 58 and 59, respectively). (B) LOXL2 MCD is secreted efficiently. (C) LOXL2 MCD is enzymatically active.

Anti-LOXL2 mAb Blocking Assays with Cells Treated with CM from Transfected Cells Generation of hLOXL-2 MCD Stable Cell Line
pSecTag2hygro-hLOXL2 MCD (Minimal Catalytic domain, amino acids TAPDLVLNAE (SEQ ID NO:19) . . . to end of reading frame+Myc+His tags) was transfected into Hek293 cells and individual clones selected under Hygromycin B selection. Expression was gauged via Western blot with an anti-His antibody (see FIG. 22)
Generation of Conditioned Media for EMT Studies in SW620 Cells
hLOXL2 MCD Hek293 stable cell line #7 was plated into a T175 flask using 12E6 cells or 6E6 cells, both in 30 ml of cDMEM (DMEM+L-glutamine+10% FBS, no Penn/Strep). The cells were grown for 72 hours and then the conditioned media was harvested for use in the SW620/EMT experiment described below. As a control, Hek293 cells were plated out at the same densities and treated in the same respect.
Conditioned Media from Stable Loxl2-MCD and Induction of EMT:
SW620 cells were seeded at 50,000 cells per well in an 8-chambered well slide with DMEM, 10% FBS, and 1× L-glutamine. The conditioned media from cells expressing human Loxl2-MCD was harvested for use in the SW620/EMT assay as described above. In each chamber, 500 µls of conditioned media was added to the respective wells. Conditioned media from 293 cells was used as a negative control. EMT-like phenotype changes were typically seen after 72-96 hours later. (FIG. 13)
CM from stable clones expressing human Loxl2-SRCR domains 1-2 and 3-4 did not induce EMT-like phenotype changes after 72-96 hours.

Example 7

Assay for LOX/LOXL Inhibitors with Chemotherapeutic Agents

LOX/LOXL inhibitors identified in Examples 2, 3, or 4 that reduce EMT/promote MET are used to treat BT-549, Hs5788t, MBA-MD231, or NCI-H226 tumor cell lines, or alternatively, cell lines such as MCF-7 or SW620 that have been transfected to express LOX/LOXL or treated with CM from cells expressing LOX/LOXL.

Chemotherapeutic agents such as, alkylating agents (e.g. cisplatin, carboplatin), antimetabolites (e.g. methotrexate, gemcitibine), anthracyclines (e.g. doxorubicin); topoisomerase inhibitors (e.g. etoposide), mitotic inhibitors (e.g. paclitaxel), EGFR inhibitors (e.g. erlotinib or gefitinib), or other agents, such as, doclitaxel, anthracycline, 5-fluoruracil, are added to the cells concomitant with, or after, treatment with the LOX/LOXL inhibitor.

Cells treated with LOX/LOXL inhibitors and a chemotherapeutic agent are compared to cells treated with a chemotherapeutic agent alone using cell viability and apoptosis assays. Cell viability is measured using CellTiter-Glo™ (Promega) and apoptosis is measured using Apo-ONE™ (Promega), protocols as described in the manufacturer's manual.

A dose response curve for each set of experimental conditions (range of chemotherapeutic doses, LOX/LOXL inhibitor dose, number of doses, time of treatment) using triplicates, is plotted. Invasion and migration assays are also used for analysis, to determine if any synergy is observed between a LOX/LOXL inhibitor and chemotherapeutic drug in reducing cell invasion and migration.

LOX/LOXL inhibitors that act in synergy with a chemotherapeutic agent should have decrease in cell viability, increase in number of apoptotic cells, and/or decrease in invasion or migratory ability in comparison to cells treated with the chemotherapeutic agent alone.

Those LOX/LOXL inhibitors that act in synergy with a chemotherapeutic agent are selected as candidates for further development.

Example 8

Figure 36:
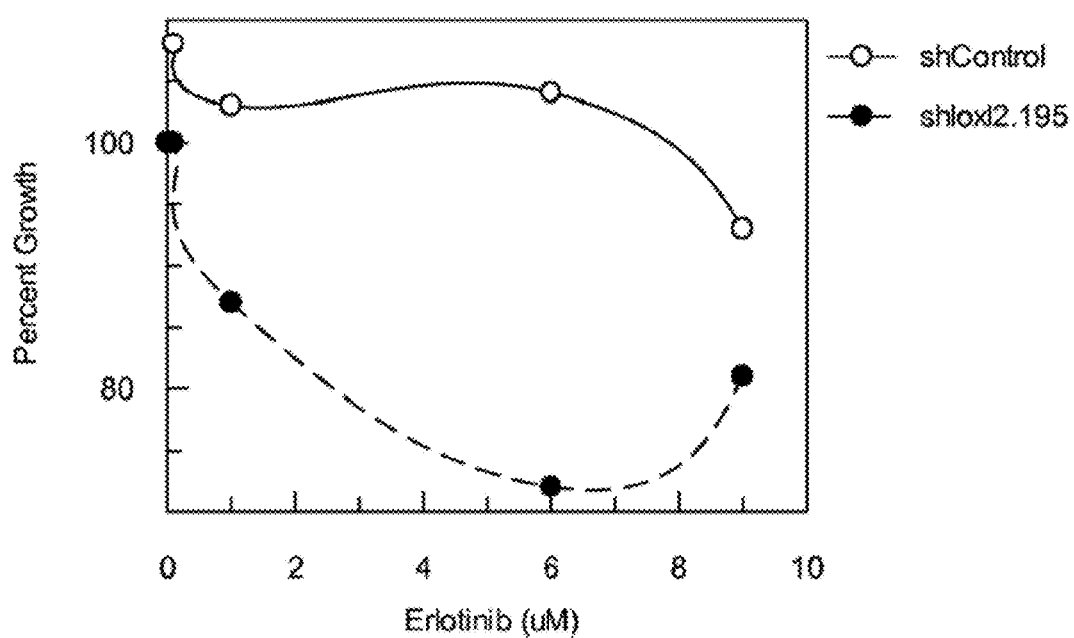
FIG. 36 is a graph showing erlotinib sensitivity of shLOXL2 cells. shLOXL2 knockdown cell line (shLOXL2.195) showed approximately 7 fold reduction in cell viability. The calculated IC50 was compared to the control line (sh control). The parental cell line is MDA-MB-231. Percent growth (viability) is plotted on the left axis. Erlotinib represents the drug class EGFR inhibitors, including gefitinib.
Figure 37:
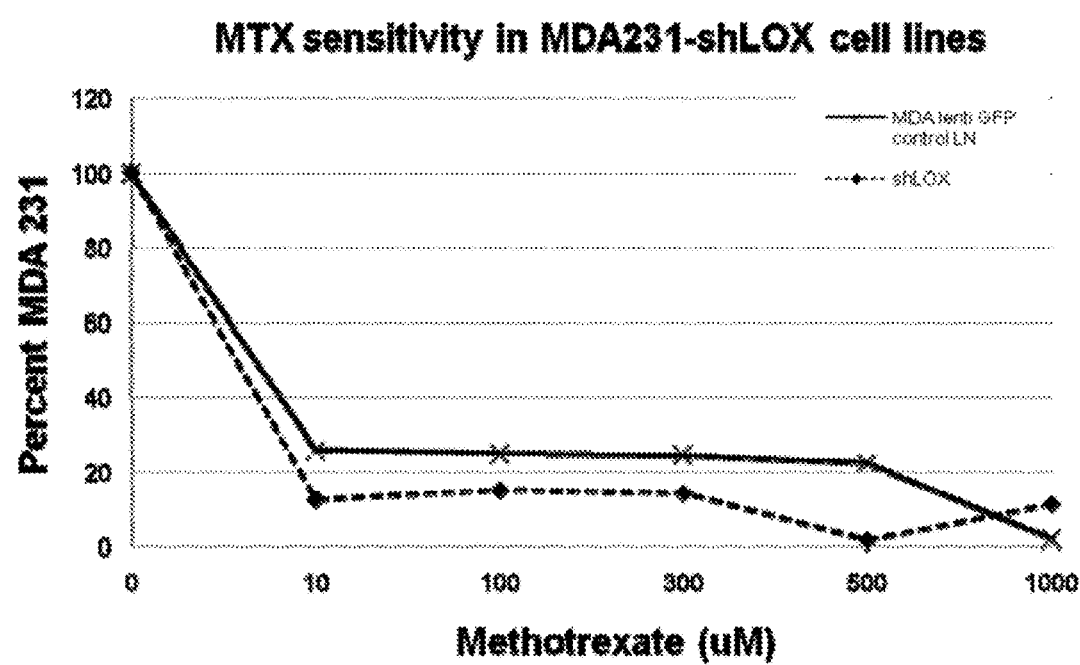
FIG. 37 is a graph showing methotrexate (MTX) sensitivity of MDA-MB-231 shLOX cell line. Percent growth (viability) is plotted on the left axis. The shLOX knockdown cell line showed approximately a 2 fold reduction in viability as compared to the control line (GFP control).
Figure 38:
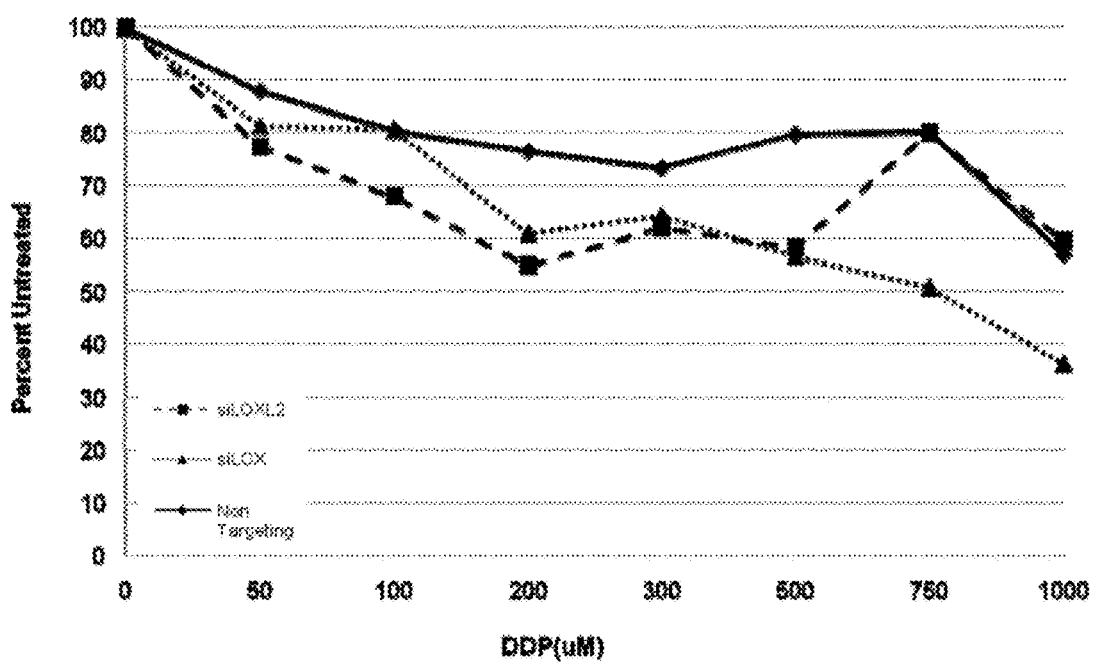
FIG. 38 is a graph showing cisplatin (DDP) sensitivity with siLOX/LOXL2 or LOX antibody. (A) MDA-MB-231 siLOX and siLOXL2 cell lines or (B) MiaCaPa 2 cell lines with anti-LOX and their sensitivity to DDP. Viability is plotted on the left axis. The siLOX and siLOXL2 knockdown cell lines had an approximately 25% reduction in viability as compared to the control line (non-targeting control). (C) The IC50 of DDP of MiaCaPa 2 and other cell lines treated with or without anti-LOX. (D) A graph of the growth inhibition of LOX (M64) or LOXL2 (M20) antibody alone as compared to untreated (Unt).
Figure 38:
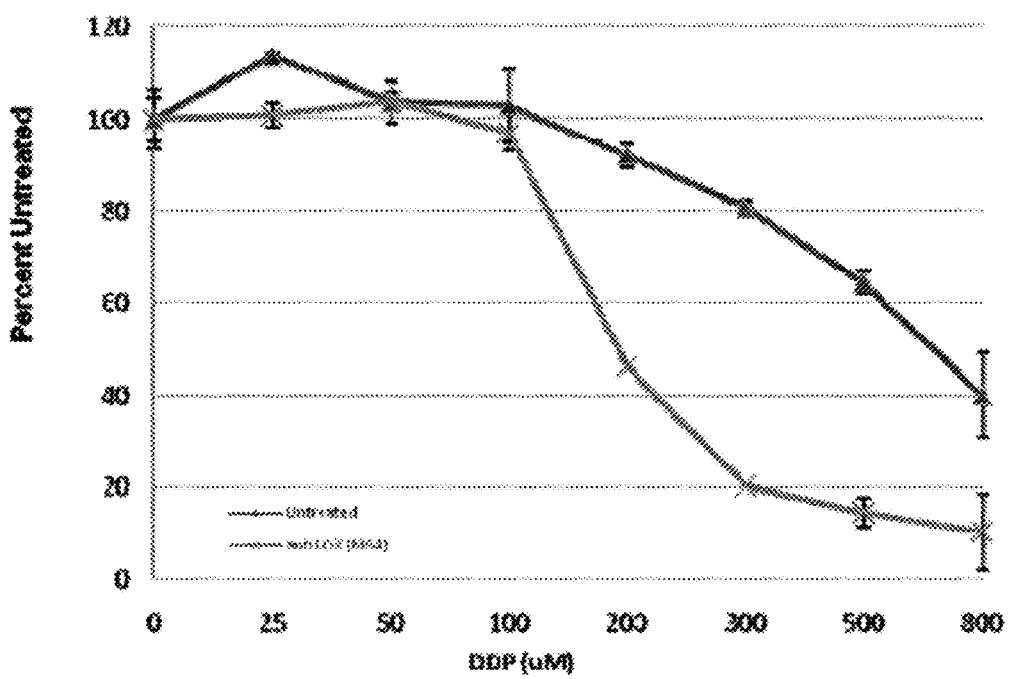
Figure 38:
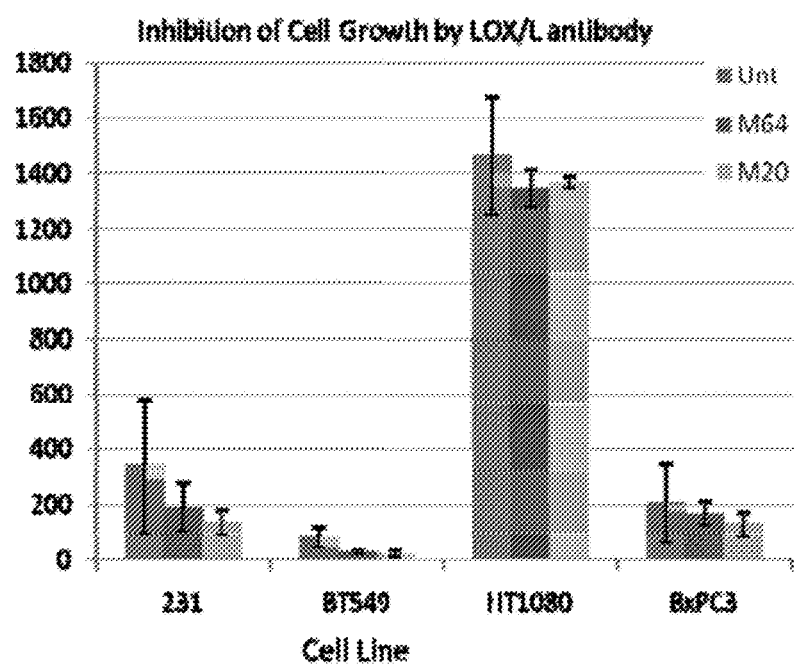
Figure 39:
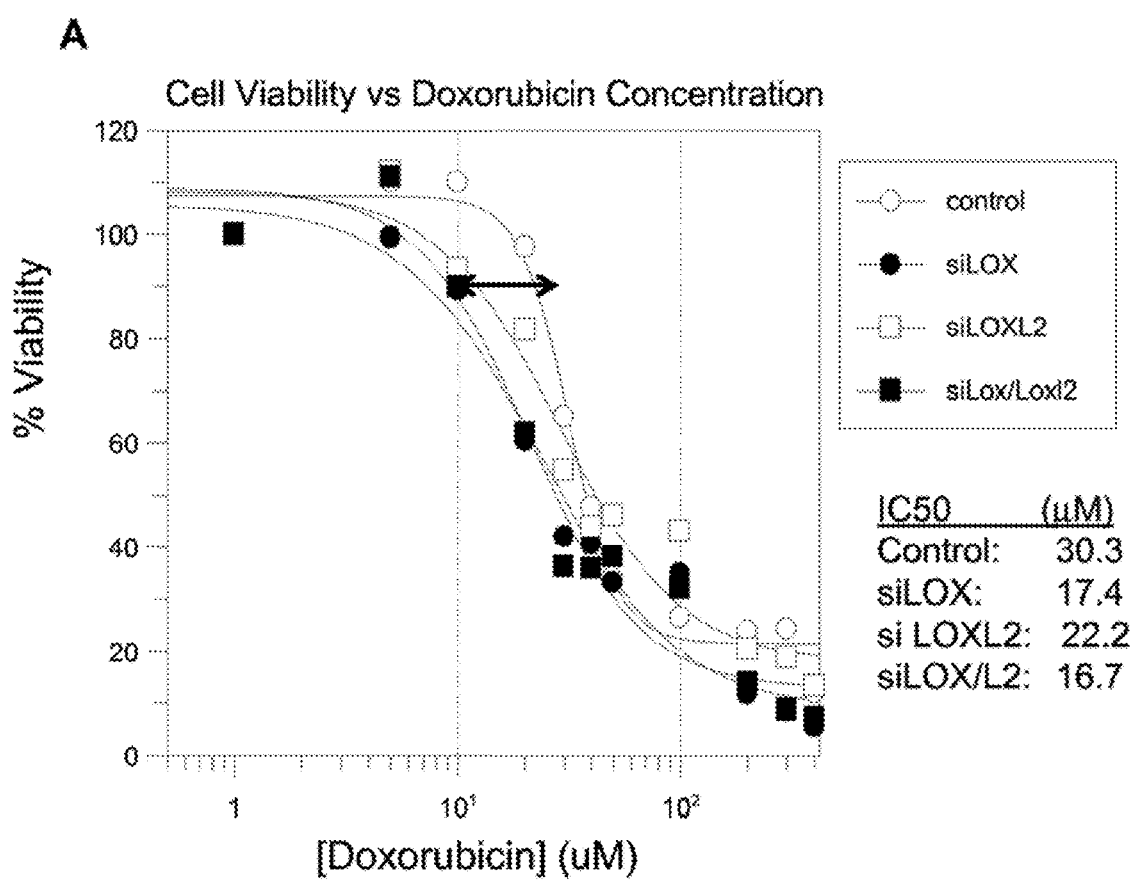
FIG. 39 shows doxorubicin sensitivity of MDA-MB-231 siRNA or shRNA cell lines. (A) siLOX, siLOXL2, and siLOX/LOXL2 cell lines. Viability is plotted on the left axis. The siLOX, siLOXL2 and siLOX/siLOXL2 double knockdown cell lines show increased sensitivity to doxorubicin, with calculated IC50 showing a 27%-55% decrease as compared to parent cell line (control). (B) A graph showing doxorubicin sensitivity of MDA-MB-231siLOX, siLOXL2, and siLOX/LOXL2 knockout compared to (C) doxorubicin sensitivity of MDA-MB-231 shLOX and shLOXL2 cell lines. Viability is plotted on the left axis.
Figure 39:
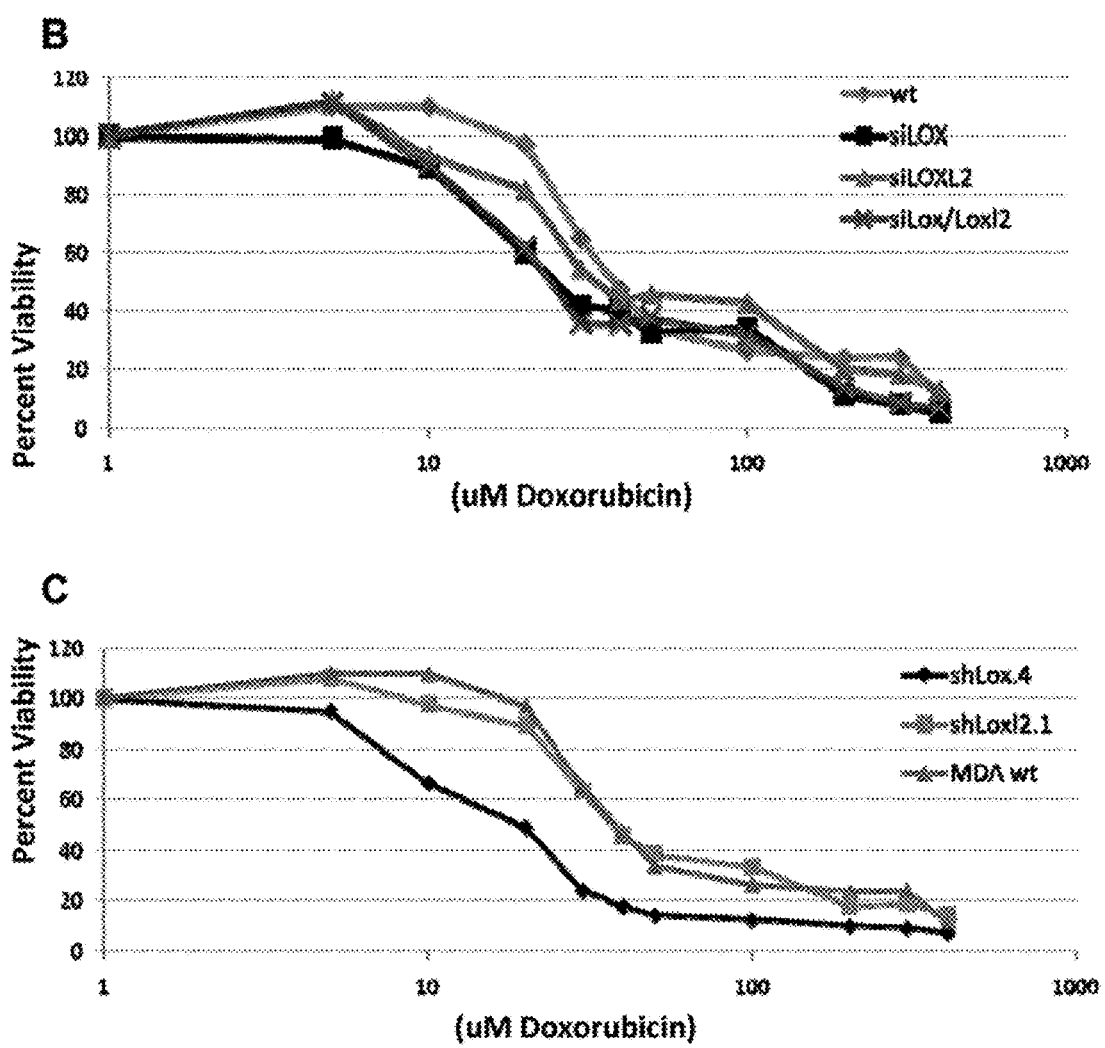
Figure 40:
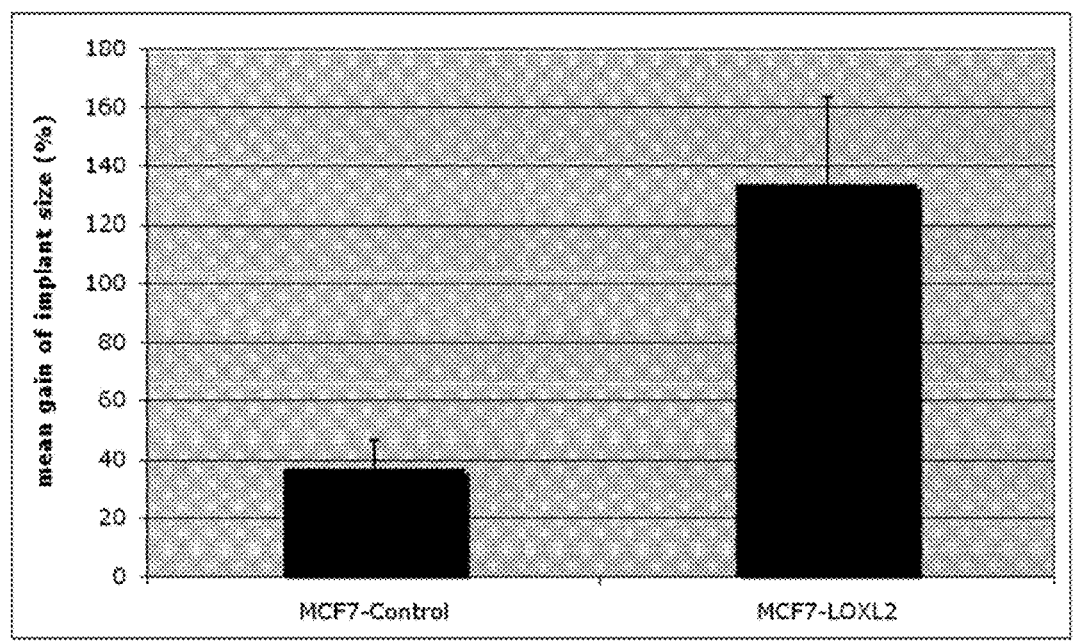
FIG. 40 is a graph showing mean gain of implant size from MCF7 tumor cells and MCF7 cells transfected with LOXL2 implanted into the subrenal capsule of nude mice. The implants were allowed to form tumors for 16 days. Stable transfection of LOXL2 into MCF7 (MCF7-LOXL2) resulted in much larger/more aggressive primary tumors than those observed for wild-type MCF7 cells.

Drug Sensitivity Assays with LOX/LOXL Inhibition 96 well plates were seeded with 7,500 cells per well and 24 hrs later the medium was replaced with medium containing various concentrations of Cisplatin (Calbiochem, Gibbstown, N.J.), Erlotinib (LC Laboratories, Woburn, Mass.), Paclitaxel (MP Biomedicals, Solon, Ohio), Methotrexate (Calbiochem, Gibbstown, N.J.), B-aminopropionitrile (Sigma-Aldrich, St. Louis, Mo.) or 250 ng/well antibody. After 5 days of continuous exposure, cultures were rinsed and live cell number was determined using CellTiter Glo™ (Promega, San Luis Obispo, Calif.) according to manufacturer instructions. Each drug concentration had 3 samples per cell line. (FIGS. 36, 37, 38)

Figure 35:
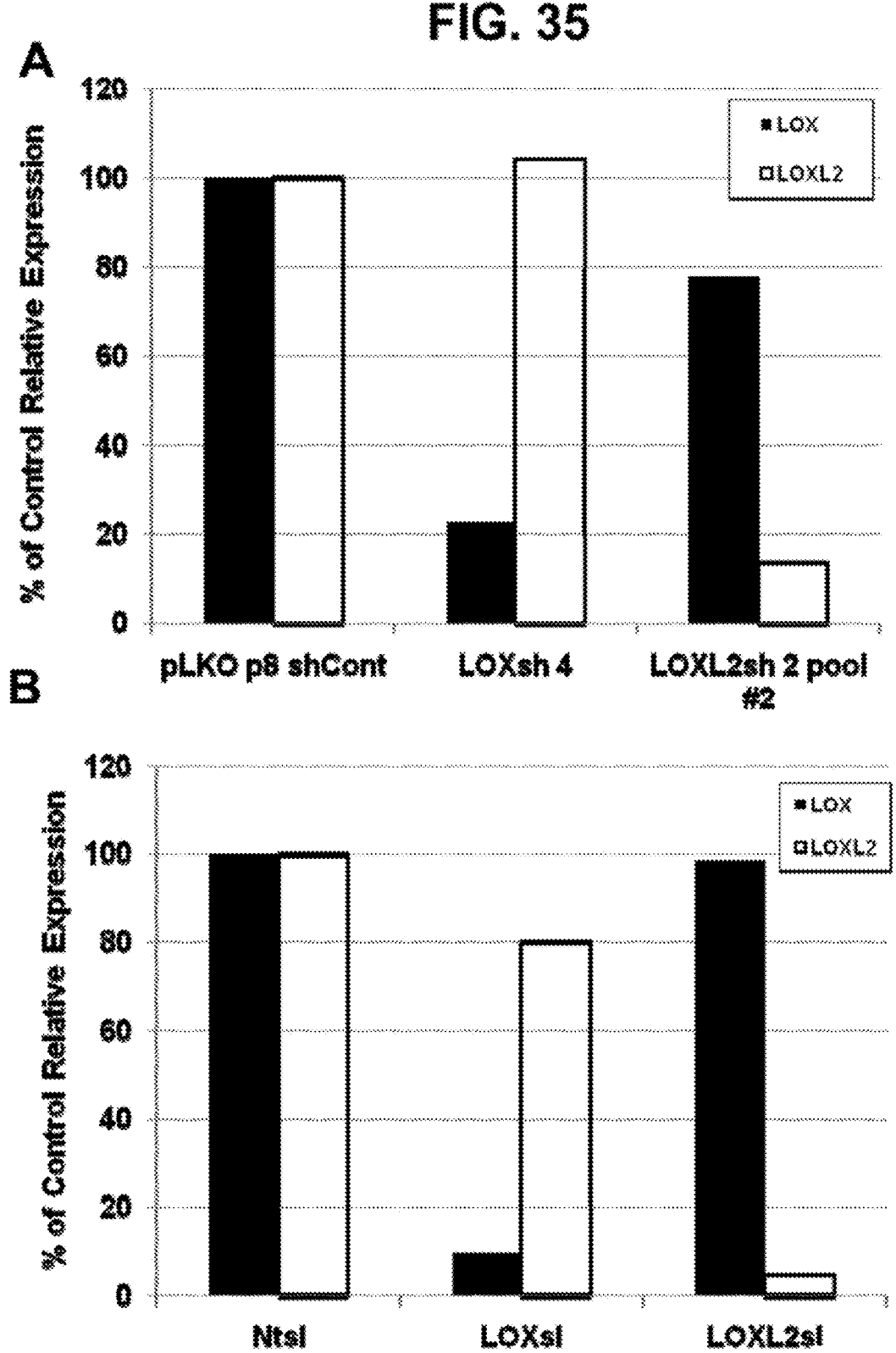
FIG. 35 is a graph of RT PCR validation of (A) shRNA and (B) siRNA knockdown of LOX/LOXL2 in FIGS. 36-39. (C) A migration assay using MDA-MB 231 cells transfected with Lox, Loxl2, Lox/Loxl2 siRNA was also performed. Lox siRNA knockdown inhibits MDA MB 231 cells invasive properties by 52% compared to non-targeting siRNA control. (D) Supporting Taqman data for siRNA knockdown in MDA MB 231 cells shown in (C).

For siRNA drug sensitivity studies, cells were transiently transfected with 20 uM LOX, LOXL2, or non-targeting Stealth Select™ RNAi validated oligos using the Dharmafect transfection reagent according to manufacturer instructions (Thermo Scientific, Lafayette, Colo.) 24 hrs prior to drug exposure. Knock down levels following drug exposure were verified with quantitative PCR. Stable shRNA cell lines were generated using the MISSION© shRNA Lentiviral System (Sigma-Aldrich, St. Louis, Mo.). Knock down of LOX or LOXL2 was verified with quantitative PCR (FIG. 35).

Example 9

Antibodies to LOX and LOXL2

Antibodies recognizing LOX and LOXL2 proteins are generated by immunizing mice with the peptides listed in Table 1. SEQ ID NOs:1 and 8 are used to generate antibodies. The antibodies generated are screened to determine whether the antibodies specifically recognize the uncleaved, non-active form of LOX, the mature, active form, or both the uncleaved and cleaved forms.

Peptides of SEQ ID NOs:2-6 are based on the mature LOX or LOXL2 enzyme. A peptide selected from Table 1 is used to immunize mice. BALB/c mice are injected with 160 mg of purified peptide. For the initial injection, the peptide is mixed with Freund's complete adjuvant (1:1) and injected subcutaneously. Subsequent injections are intraperitoneally in the absence of adjuvant.

Serum antibody to LOX or LOXL2 is determined by an enzyme linked immunosorbent assay (ELISA) in which the full-length or active LOX or LOXL2 protein is bound to polystyrene plates. After at least 2 immunizations over a period of at least 2 months, the spleen of one mouse with a high titer antibody directed against LOX or LOXL2 is removed and fused with cells of the $P_3 U_1$ mouse plasmacytoma cell line. The resulting clones are screened for their ability to bind LOX or LOXL2, or both, using the full-length as well as the active forms, in ELISA assays.

The specificity of the antibody to LOX or LOXL2, individually or cross-reactive, is determined by ELISA. A hybridoma-producing antibody reactive with LOX or LOXL2 is isolated and subcloned. This hybridoma is grown in tissue culture media as well as in ascites to serve as a source of LOX or LOXL2 antibody.

For generating human monoclonal antibody to LOX or LOXL2, as described in EP 0239400 (Winter et al.), the above-described mouse monoclonal is altered by substitution of its complementarity determining regions (CDRs) into a human monoclonal antibody or monoclonal antibody fragment. The CDRs from human heavy and light chain Ig variable region domains are substituted with alternative CDRs from murine variable region domains. These altered Ig variable regions may subsequently be combined with human Ig constant regions to create antibodies, which are totally human in composition except for the substituted murine CDRs. Such CDR-substituted antibodies would be predicted to be less likely to elicit an immune response in humans compared to chimeric antibodies because the CDR-substituted antibodies contain considerably less non-human components. The process for humanizing monoclonal antibodies via CDR "grafting" has been termed "reshaping." (Riechmann et al., *Nature* 332: 323-327 (1988); Verhoeyen et al., *Science* 239: 1534-1536 (1988)).

Transplantation of the murine LOX or LOXL2 antibody CDRs (such as CDRs from the murine monoclonal antibodies as described in Burbelo et al. *Coll. Relat. Res.* 6:153-162 (1986)) is achieved by genetic engineering whereby CDR DNA sequences are determined by cloning of murine heavy and light chain variable (V) region gene segments, and are then transferred to corresponding human V regions by site directed mutagenesis. In the final stage of the process, human constant region gene segments of the desired isotype (usually gamma I for CH and kappa for CL) are added and the humanized heavy and light chain genes are co-expressed in mammalian cells to produce soluble humanized antibody.

The transfer of these CDRs to a human antibody confers on this antibody the antigen binding properties of the original murine antibody. The six CDRs in the murine antibody are mounted structurally on a V region "framework" region. The reason that CDR-grafting is successful is that framework regions between mouse and human antibodies may have very similar 3-D structures with similar points of attachment for CDRS, such that CDRs can be interchanged. Such humanized antibody homologs may be prepared, as exemplified in Jones et al., *Nature* 321: 522-525 (1986); Riechmann et al., *Nature* 332:323-327 (1988); Queen et al., *Proc. Nat. Acad. Sci. USA* 86:10029 (1989); and Orlandi et al., *Proc. Natl. Acad. Sci. USA* 86:3833 (1989).

Nonetheless, certain amino acids within framework regions are thought to interact with CDRs and to influence overall antigen binding affinity. The direct transfer of CDRs from a murine antibody to produce a humanized antibody without any modifications of the human V region frameworks often results in a partial or complete loss of binding affinity. Thus it may be desired to alter residues in the framework regions of the acceptor antibody in order to obtain binding activity.

Queen et al., *Proc. Nat. Acad. Sci. USA* 86: 10029-10033 (1989) and WO 90/07861 (Protein Design Labs Inc.) have described the preparation of a humanized antibody that contains modified residues in the framework regions of the acceptor antibody by combining the CDRs of a murine mAb (anti-Tac) with human immunoglobulin framework and constant regions. They have demonstrated one solution to the problem of the loss of binding affinity that often results from direct CDR transfer without any modifications of the human V region framework residues; their solution involves two key steps. First, the human V framework regions are chosen by computer analysis for optimal protein sequence homology to the V region framework of the original murine antibody, in this case, the anti-Tac MAb. In the second step, the tertiary structure of the murine V region is modeled by computer in order to visualize framework amino acid residues, which are likely to interact with the murine CDRs and these murine amino acid residues are then superimposed on the homologous human framework. Their approach of employing homologous human frameworks with putative murine contact residues resulted in humanized antibodies with similar binding affinities to the original murine antibody with respect to antibodies specific for the interleukin 2 receptor (Queen et al., 1989 [supra]) and also for antibodies specific for herpes simplex virus (HSV) (Co. et al., *Proc. Nat. Acad. Sci. USA* 88: 2869-2873, (1991)).

Further details of this humanization procedure are given in U.S. Pat. No. 5,225,539 to Winter et al., U.S. Pat. No. 4,816, 397 to Boss et al and U.S. Pat. No. 4,816,567 and U.S. Pat. No. 6,331,415 to Cabilly et al., all of which are known to those in the art and are specifically incorporated by reference for purposes of describing the exemplified preparation.

Antibodies recognizing both LOX and LOXL2 are generated by immunizing mice as described above, with peptides having randomized amino acids of non-conserved amino acids between LOX and LOXL2, for example, between SEQ ID NOs:4 and 5, and between SEQ ID NOs:6 and 7. The antibodies generated should be cross-selective for LOX and LOXL2.

Those LOX/LOXL2 antibodies that are specific for LOX or LOXL2, or cross-reactive to both LOX and LOXL2, are selected as candidates for further development.

TABLE 1

LOX/LOXL2 immunogen peptides

| SEQ ID. | GENE | SEQUENCE | SELECTIVE |
|---|---|---|---|
| 1 | LOX | SRVDGMVGDDPYNPYK | Collagenase IV site |
| 2 | LOX | DTYERPRPGGRYRPG | Mature peptide |
| 3 | LOXL2 | RRLLRFSSQIHNNGQSDFRPKNGR | Enzyme domain |
| 4 | LOX | EDTSCDYGYHRRFA | Enzyme domain, cross-selective with SEQ ID NO: 5 |
| 5 | LOXL2 | EDTECEGDIQKNYE | Enzyme domain, cross-selective with SEQ ID NO: 4 |

TABLE 1-continued

LOX/LOXL2 immunogen peptides

| SEQ ID. | GENE | SEQUENCE | SELECTIVE |
|---|---|---|---|
| 6 | LOX | DPYYIQASTYVQKMSMYNLRC | Enzyme domain, cross-selective with SEQ ID NO: 7 |
| 7 | LOXL2 | NAEMVQQTTYLEDRPMFMLQC | Enzyme domain, cross-selective with SEQ ID NO: 6 |
| 8 | LOX | GSQYGPGRRRDPGA | Pro-peptide |

Example 10

Generation of Antibodies Cross-Reactive to LOX and LOXL Members

Antibodies cross-reactive to LOX and LOXL members are generated by immunizing mice with peptides derived from the highly conserved C-terminal region of the LOX/LOXL proteins, which also encompasses the catalytic domain. Antibodies generated against this region recognize the active form of LOX/LOXL.

Domains from which peptides to generate antibodies may be derived from are the catalytic domain, copper-binding domain, lysyl-tyrosylquinone co-factor domain, and cytokine receptor-like domain. Sequences of the copper-binding domain and catalytic domain are listed in Table 2 and are used to immunize mice as described in Example 9. Similarly, the specificity of the antibody generated is determined by ELISA against the full-length and processed forms of LOX, LOXL, LOXL2, LOXL3, and LOXL4.

Peptides with randomized amino acids of non-conserved amino acids between LOX, LOXL, LOXL2, LOXL3, and LOXL4 are also used to immunize mice to generate antibodies that are cross-reactive with the various forms of LOX/LOXL protein, for example LOX and LOXL, or for all 5 LOX family members. Immunization of mice and generation of mouse and human antibodies is described in Example 9.

The LOX/LOXL antibodies that are cross-reactive for LOX and various LOXL members are selected as candidates for further development.

TABLE 2

LOX/LOXL immunogen peptides

| SEQ ID. | GENE | SEQUENCE | DOMAIN |
|---|---|---|---|
| 9 | LOX | WEWHSCHQHYH | Cu Binding |
| 10 | LOXL | WEWHSCHQHYH | Cu Binding |
| 11 | LOXL2 | WIWHDCHRHYH | Cu Binding |
| 12 | LOXL3 | WVWHECHGHYH | Cu Binding |
| 13 | LOXL4 | WVWHQCHRHYH | Cu Binding |
| 14 | LOX | DIDCQWIDITDVKPGNY | Catalytic domain |
| 15 | LOXL | DIDCQWIDITDVQPGNY | Catalytic domain |
| 16 | LOXL2 | DIDCQWVDITDVPPGDY | Catalytic domain |
| 17 | LOXL3 | DIDCQWIDITDVKPGNY | Catalytic domain |
| 18 | LOXL4 | DIDCQWVDITDVGPGNY | Catalytic domain |

Example 11

Generation of Antibodies Recognizing Active LOX/LOXL that Reduce EMT/Promotes MET EMT cells secrete active LOX/LOXL. Antibodies generated from Examples 9 and 10 are used in treating EMT cells in Examples 2, 3 or 4. The EMT or MET characteristics of the cells are then determined as described in Example 1. Antibodies that recognize the active LOX/LOXL2 should reduce EMT and promote MET of the cells.

Those LOX/LOXL antibodies that reduce EMT and promote MET of the cells are selected as candidates for further development.

Example 12

Inhibition of LOX/LOXL Activity by Antibodies

Antibodies generated from Examples 9 or 10 are used in LOX/LOXL activity assays as described in Fogelgren et al., J. Biol. Chem. 280:24690-24697 (2005). Briefly, the LOX/LOXL activity assay reaction mixture consists of 50 mM sodium borate (pH 8.2), 1.2M urea, 40 uM Amplex Red, 0.1 units/ml horseradish peroxidase, and 10 mM 1,5-diamineopentane (cadaverine) substrate. Alternatively, the Amplex Red assay is performed in a physiological buffer such as phosphate buffer at pH 7.5. The protein, LOX/LOXL, is added to the reaction mixture in the presence or absence of 500 uM BAPN or antibodies from Examples 9 or 10, and incubated. The fluorescent product is excited at 560 nm, and emission is read at 590 nm (e.g. BMG Labtechnologies Inc. Polarstar Optima). LOX/LOXL in the presence of BAPN serves as a negative control, whereas absence of BAPN serves as a positive control. The measure of activity is based on the amount of fluorescence.

Those LOX/LOXL antibodies that inhibit LOX/LOXL activity are selected as candidates for further development.

Example 13

Inhibition of LOX/LOXL Binding to Other Cellular or Extracellular Matrix Components by LOX/LOXL Antibodies Antibodies generated from Examples 9 or 10 are used in ECM binding assays. Solid phase binding assays are performed as described in Fogelgren et al., J. Biol. Chem. 280: 24690-24697 (2005). Wells of high protein-binding EIA/RIA microplate (Corning) are coated with tropoelastin, Type I collagen, soluble plasma fibronectin (pFN), insoluble cellular fibronectin (cFN), laminin, or BSA overnight at 4° C. The wells are blocked, washed, and then incubated overnight with a tagged version of LOX/LOXL (e.g. GST-LOX/LOXL) with or without the LOX/LOXL antibodies. The wells are again washed and the amount of LOX/LOXL binding is detected by a primary antibody against the tag of the LOX/LOXL (e.g. anti-GST), followed by a peroxidase-labeled secondary antibody. The peroxidase activity is then quantitated with a fluorogenic peroxidase substrate kit (Pierce). The samples are performed in triplicate and dissociation constants calculated with statistical software (e.g. Prism3 from Graphpad, Inc.).

Binding assays are also performed in which LOX/LOXL is used to coat the microplate wells. Antibodies from Examples 9 or 10 are added to the wells, prior to, or concurrent with tropoelastin, Type I collagen, pFN, cFN, or BSA. Binding is measured as described above, where the ECM proteins are detected with their respective antibodies, or an antibody against the tag, if a tagged form of the ECM protein is used, to detect the amount of ECM bound.

Binding of LOX/LOXL with other proteins, such as cellular receptors (e.g. uptake receptor integrin beta1), BTK (burton agamgloublinemia tyrosine kinase), or other integrins is also performed using the aforementioned assay, wherein instead of ECM proteins are used, cellular receptors (e.g. uptake receptor integrin beta1), BTK (burton agamagloublinemia tyrosine kinase) or other integrins are used.

Those LOX/LOXL antibodies that inhibit LOX/LOXL binding to ECM proteins, cellular receptors, and integrins, are selected as candidates for further development.

Example 14

Inhibition of LOX Activity

Figure 15:
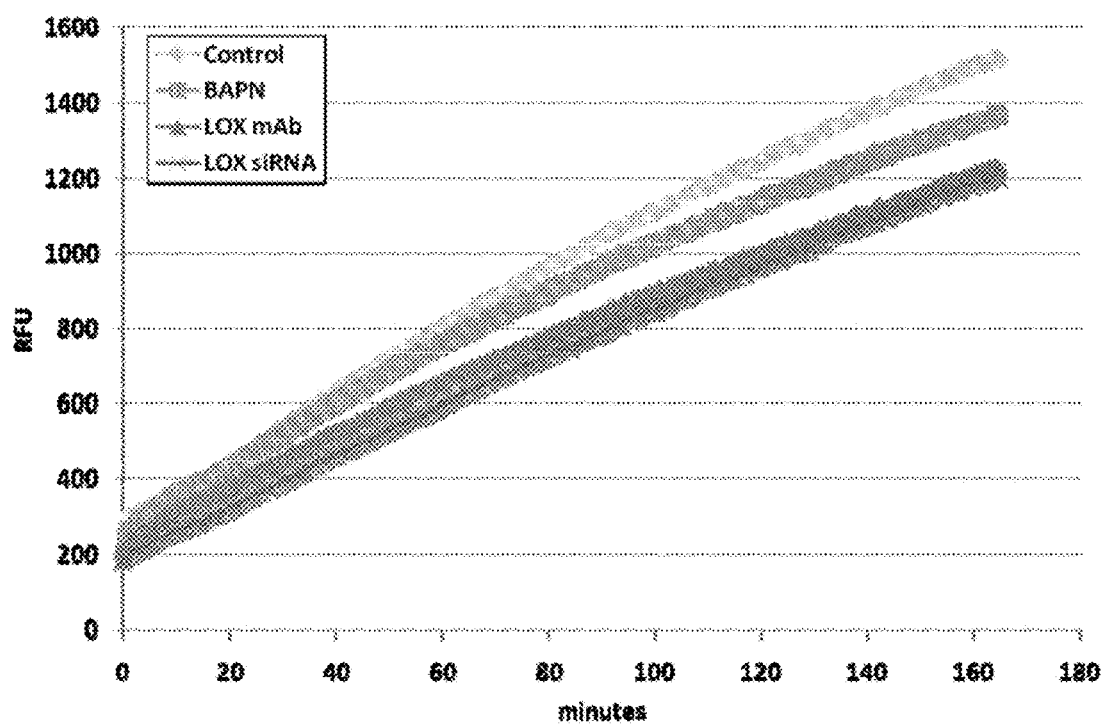
FIG. 15 is a graph showing surface-associated LOX activity in 3T3 cells is inhibited by BAPN, LOX mAb, and LOX siRNA. Specific LOX activity is evident on the cell surface of 3T3 cells quantitated with a horseradish peroxidase-coupled fluorescent assay method based on the oxidation of Amplex Ultra Red with a 1,5-diaminopentane substrate. LOX activity was inhibited with the irreversible small molecule inhibitor BAPN, with a monoclonal antibody raised against a LOX peptide, and with a siRNA oligonucleotide specifically targeting LOX mRNA.
Figure 17:
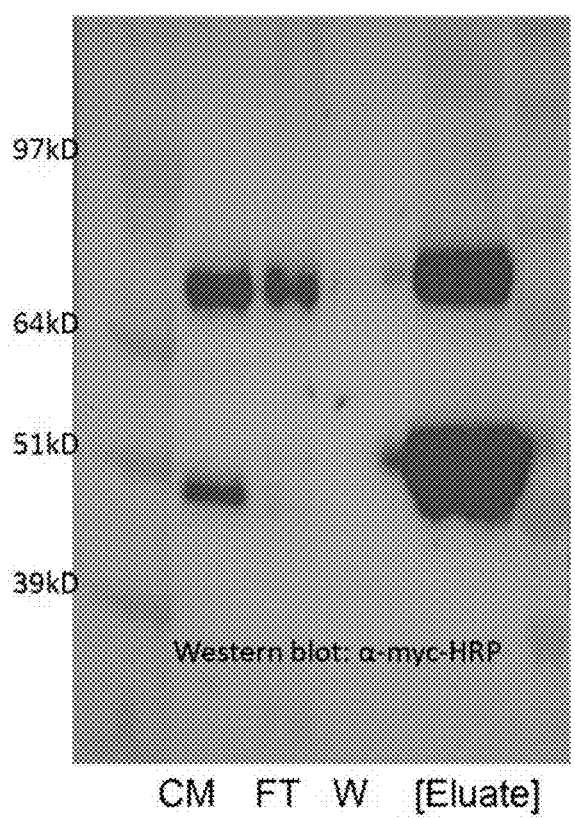
FIG. 17 shows LOXL2 protein expression purified from CHO cells. Myc-His tagged (C-terminal) LOXL2 was expressed in CHO cells. 2 forms predominate (as in FIG. 16): propeptide LOXL2 and LOXL2 cleaved between SRCR2 and SRCR3. LOXL2 is also secreted in CHO cells.

Specific LOX activity was evident on the cell surface of NIH3T3 cells. Activity was quantitated with a horseradish peroxidase-coupled fluorescent assay method based on the oxidation of Amplex Ultra Red with a 1,5-diaminopentane substrate. LOX activity was inhibited with the irreversible small molecule inhibitor, BAPN, with a monoclonal antibody raised against a LOX peptide, and with a siRNA oligonucleotide specifically targeting LOX mRNA. (FIG. 15)

NIH 3T3 cells were transfected with 100 nM of LOX siRNA (Invitrogen Stealth, HSS106117, AUAACAGCCAG-GACUCAAUCCCUGU (SEQ ID NO:20)) or non-targeting control. 25 ul of Dharmafect® #3 (Dharmacon) was mixed with 1 ml of OPTIMEM I® (Invitrogen) and sat for 5 minutes at room temperature. 50 ul of 20 uM siRNA was then added, mixed and the transfection mix was incubated at room temperature for 15 minutes. 1 ml of transfection mix was then added to a trypsinized cell suspension in growth media containing $1 \times 10^6$ cells and the resulting mixture was plated into a 10 cm$^2$ culture dish. Six days after transfection, cells were trypsinized and re-plated into 96 well plate format at 50,000 cells/well. Day seven after transfection, cells were washed 2× with PBS and incubated with 100 ul of the following reaction mix: 100 uM Amplex Ultra Red® (Invitrogen), 20 mM diaminopentane (Fluka), and 4 u/ml horseradish peroxidase (Sigma) in PBS. BAPN and LOX mAb were added to 1 mM and 15 ug/ml final concentrations, respectively, immediately before diaminopentane and HRP addition. The plate was read in a Molecular Devices M5 plate reader at 37° C. The plate reader was configured to read fluorescence (ex=544 nm, em=590 nm) in kinetics mode for approximately 2.5 hours.

Example 15

Inhibition of LOXL2 Activity

All plates were obtained from Corning. Secondary antibody and Pico substrate were from Pierce. Amplex red reagent was from Invitrogen. Horse radish peroxidase (HRP), 1,5-diaminopentane, antifoam were from Sigma. All ProteOn reagents were from Bio-Rad. LOXL2 was from R&D systems. Antibodies used in this study were produced at Antibody Solution or via ascites from Aragen Biosciences. All other reagents were of the highest quality possible.

Binding Via ELISA

Binding of antibody to LOXL2 was determined using a luminescence based ELISA. White Corning plates were coated with 0.1 µg/mL of LOXL2 or antigen of interest in 50 mM borate buffer (pH 8.0) overnight at 4° C. Plates were washed using BioTek plate washer and blocked with 5% skim milk in PBST (0.05% tween-20) for 1 hour at room temperature. Plates were washed with PBST (0.05% tween-20) and then used immediately or stored at 4° C. in dessicator for future use. The antibody to be tested was serially diluted in PBST (0.01% tween-20) and 100 µL of each dilution was added per well. Plates were incubated with test article for 1 hour at room temperature and then washed with PBST (0.05% tween-20). Detection antibody (anti-mouse HRP conjugate) was diluted 16000 fold in 5% skim milk in PBST (0.05% tween-20) and 100 µL was applied per well. Plates were incubated for 1 hour with detection antibody and then washed with PBST (0.05% PBST). Signal was detected using the SuperSignal ELISA pico chemiluminescent substrate from Pierce following the manufacturer's instructions. Luminescence was measured using a Molecular Devices M5 plate reader with an integration time of 500 ms capturing all wavelengths. Data was background corrected and the dependence of luminescence signal to antibody concentration was fit using the Langmuir isotherm equation using the GraFit program. In instances where the antigen concentration was similar to the dissociation constant the quadratic equation of tight binding was used. Reported dissociation values were obtained from the fits to these equations.

Langmuir Isotherm Equation $$[PL] = \frac{B_{max} * [L]}{K_D * [L]}$$

Tight Binding Equation $$[PL] = B_{max} * \frac{([E]_T + [S]_T + K_D) - \sqrt{([E]_T + [S]_T + K_D)^2 - 4[E]_T [S]_T}}{2[E]_T}$$

Binding Via SPR (Surface Plasmon Resonance)

Binding affinities were measured using a Bio-Rad ProteOn instrument thermostated to 25° C. The binding affinities were determined using two methods, using amine coupling; one in which the antibody was immobilized and the antigen (LOXL2) was added, and another in which the antigen (LOXL2) was immobilized and antibody was added. Antibody or antigen was immobilized on a GLC chip using at 1:1 ratio of NHS to EDC provided with the ProteOn immobilization kit. Chip was first activated with NHS/EDC a mixture and then antigen or antibody at 1 µg/mL in acetate buffer pH 4.5 was flowed over activated surface to couple. This typically yielded a coupling of about 500 RU's. The activated chip surface was then capped with the addition of 1M ethanolamine. Coupled chips were stored at 4° C. and regenerated with 50 mM sodium hydroxide.

Dissociation constants were determined by probing the coupled chip with a dilution series of antibody or antigen in PBST (0.05% tween-20). Data was acquired on all six channels available on the ProteOn using a non-coupled channel as a reference. Collected data was analyzed using ProteOn manager software from Bio-Rad.

Screening Assays

Antibody candidates were initially chosen based on ELISA point tests. ELISA on multiple antigens was performed by Antibody Solutions and antibodies showing strong ELISA signal in the antigen of interest were selected for further characterization in enzymatic assays. LOXL2 produces hydrogen peroxide when the substrate 1,5-diaminopentane is deaminated and the enzyme regenerated.

Antibodies were assessed for their ability to inhibit enzymatic activity using a biochemical assay that couples the production of peroxide (liberated by LOXL2) to HRP and measuring the conversion of amplex red to a fluorescent product. Antibody hybridoma supernatant (10 µL) was added to 40 µL enzyme mixture (50 mM sodium borate pH 8.0, 5 units/mL HRP, 125 nM LOXL2, 10 ppm antifoam) and incubated at room temperature for 1 hour in a 96 well full area black plate. Enzymatic reaction was started with the addition of 50 µL of substrate solution (62.5 mM sodium borate, 100 uM amplex red reagent, 20 mM 1,5-diaminopentane, 10 ppm antifoam) and read in a Molecular Devices M5 plate reader at 37° C. The plate reader was configured to read fluorescence (ex=544 nm, em=590 nm) in kinetics mode for 1 hour. Data was recorded as the slope of the fluorescence response to time. These slopes were compared to a control in which hydridoma media was added to the enzyme mixture. Slopes less than that of control were considered inhibitors.

IC50 Determinations

Figure 20:
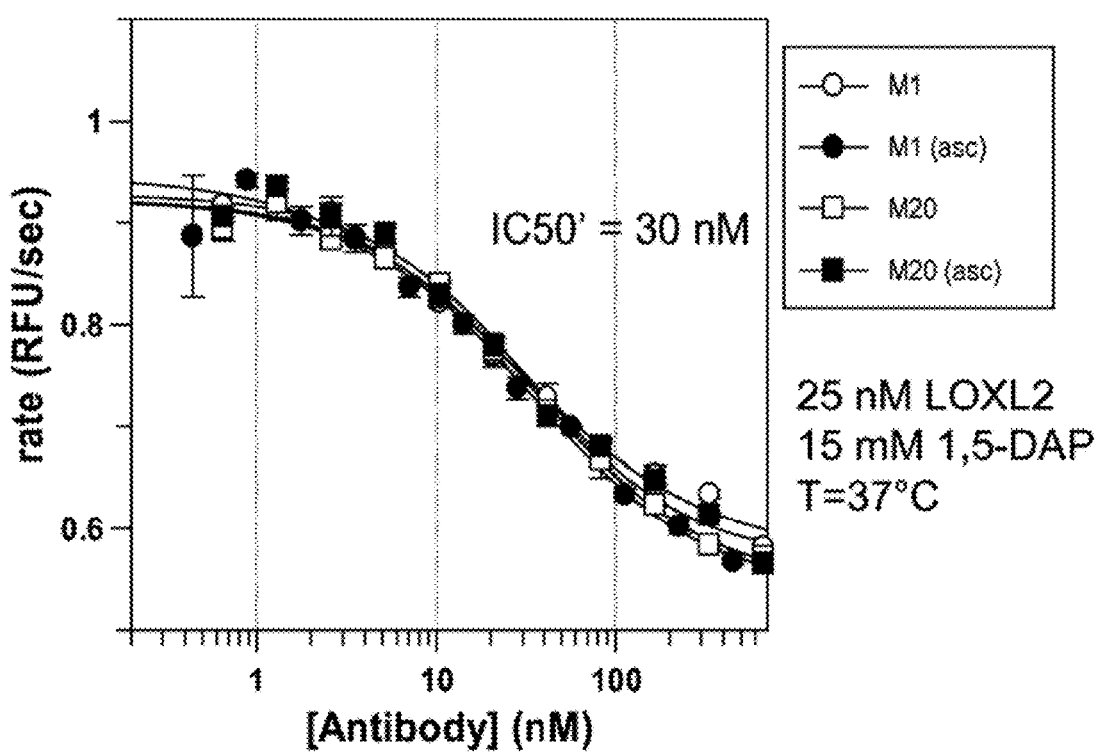
FIG. 20 is an IC50 graph for LOXL2. Inhibition of LOXL2 was performed in an in vitro enzymatic assay using active LOXL2 and a LOXL2 antibody, AB0023. M1 and M20 are both AB0023. Asc=ascites generated, unlabeled=bioreactor generated, same results. Dose response showing decreased activity with increasing concentration of antibody. LOXL2 preparation includes both processed forms (propeptide and mature).

Dose responses on selected antibodies were carried out against LOXL2 using the coupled enzymatic assay described above. A dilution series of antibody was created in PBST (0.01% tween-20) and 10 µL of this was added to 40 µL of enzyme mixture (50 mM sodium borate pH 8.0, 5 units/mL HRP, 125 nM LOXL2, 10 ppm antifoam) and incubated at room temperature for 1 hour in a 96 well full area black plate. Enzymatic reaction was started with the addition of 50 µL of substrate solution (62.5 mM sodium borate, 100 uM amplex red reagent, 20 mM 1,5-diaminopentane, 10 ppm antifoam) and read in an M5 plate reader using conditions described above. The slopes of the fluorescence response as a function of time were plotted against antibody concentration and the data was fit to a four parameter fit using GraFit. The midpoint of this plot is the apparent IC50 and is the concentration at which fifty percent of the total response is inhibited (for example, FIG. 20).

Mode of Inhibition

Mode of inhibition of antibodies against LOXL2 was conducted using the model described below. In these experiments, the dependence of the steady state rate on the concentration of 1,5-diaminopentane was monitored under increasing concentrations of antibody. The purpose was to assess whether the $K_m$ for substrate, $k_{cat}$ or both change in the presence of antibody. Collected data was analyzed globally with Grafit using the model shown in FIGURE below. Parameter α describes the effect of the compound on substrate affinity. An α value equal to one describes a situation in which the compound binds equally well the free enzyme and the enzyme-substrate complex (non-competitive inhibition like). Values less than one describe an interaction in which the compound binds the enzyme-substrate complex (uncompetitive inhibition like). Values greater than one correspond to the compound binding the free enzyme better than the enzyme-substrate complex (competitive inhibition like). The β value describes the effect of the modulator on the rate of the enzyme. Inhibitors have values less than one (for a complete inhibitor β=0) and activators have values greater than one. $K_A$ is the dissociation constant of the compound, $K_s$ is the Michaelis constant for the substrate and k is the catalytic rate of the enzyme. The steady state rates were determined from the slope of the fluorescence response as a function of time as described above. Data was plotted as the dependence of steady state rate on the concentration of substrate (1,5-diaminopentane) at several fixed concentrations of antibody and analyzed with GraFit. (for example, FIG. 21A, and using a direct competitor, as shown in FIG. 21B).

Example 16

Detection of LOX/LOXL by Immunoblot and Immunohistochemistry (IHC) Analysis

Immunoblot (western blot) analysis was performed by lysing cells in lysis buffer (for example, 100 mM $NaH_2PO_4$, 10 mM Tris-HCL, 8M Urea, 0.05% tween-20, pH 8.0; or EDTA, NP40, Tris, NaCl, PMSF and "Complete mini, protease inhibitor cocktail" (Roche, #11836153001); or "Laemmli's SDS sample buffer, 4×" (Boston BioProducts, #BP-110R). The lysate (typically 15-25 µg total protein) was loaded onto 4-12% Tris-Glycine gels (Invitrogen Carlsbad, Calif.) or NuPAGE Novex 4-12% Bis Tris gels (Invitrogen). Size fractionated proteins were transferred onto PVDF membrane (Invitrogen Carlsbad, Calif.) or Nictrocellulose membranes (Invitrogen).

Immunoblots were blocked overnight at 4° C. in 2% BSA, 5% dry milk in PBS. Following incubation with anti-LOX/LOXL primary antibody (monoclonal or polyclonal), blots were incubated with secondary antibodies to enable detection, such as anti-rabbit IgG-HRP" (GE Healthcare or Jackson Immunoresearch Lab), anti-mouse IgG-HRP" (GE Healthcare), anti-goat IgG-HRP" (Jackson Immunoresearch Lab), or IRDye680-conjugated goat anti-mouse IgG, IRDye680-conjugated donkey anti-rabbit IgG (Rockland Inc.), following the manufacturers recommended conditions. Chemiluminescent signals were developed and detected using SuperSignal West Femto Max or Pico Max Sensitivity Substrate (Pierece) or alternatively by using ECL anti-mouse IgG HRP (Amersham) with detection using Chemiglow West (Alpha Innotech). Fluorescently-labeled secondary antibodies were directly detected.

In addition to immunoblots prepared from tissues, commercially-available pre-loaded immunoblots containing size-fractionated proteins isolated from a range of normal tissues and tumor tissues (eg. from ProSci Incorporated, CA) were used for analysis of molecular weight distribution of LOX/LOXL in normal tissues and tumor tissues.

LOX/LOXL protein expression and cellular localization was detected in normal tissues and tumor tissues using tissue sections and sections of tissues arranged in tissue microarrays (eg. available from Cybrdi, Pro Sci, and other sources). Tissue samples were blocked for non-specific binding using BACKGROUND sniper (Biocare Medical) following the manufacturer's instructions. Antigen retrieval was performed in a variety of buffers, pH conditions, and temperatures to ensure robust detection in tissue sections. Antibodies (monoclonal or polyclonal, generated using mice or rabbits) against LOX/LOXL are evaluated for IHC using tumor cell lines. Suitable antibodies were incubated with tissue sections (typically, at a concentration of 1-10 µg/ml, diluted in dilution buffer (Biocare Medical (Concord, Calif.) or DAKO (Carpinteria, Calif.) according to manufacturer's instructions.

Detection was performed using Rabbit-Probe HRP polymer kit (MACH2 or MACH3 by Biocare Medical or EnVision by DAKO) or Mouse-Probe HRP polymer kit (MACH2 or MACH3 by Biocare Medical or EnVision by DAKO) according to manufacturer's directions. Alternatively, detection was performed using horse radish peroxidase conjugated to anti-mouse, rabbit, or goat IgG (GE Healthcare or Jackson Immunoresearch Lab), or Vectastain Elite ABC kit (anti-mouse, rabbit, or goat, Vector laboratories) or an EnVision kit (anti mouse and rabbit, DAKO), following the manufacturers' instructions.

Example 17

Detection of 2 Forms of LOXL2

Figure 18:
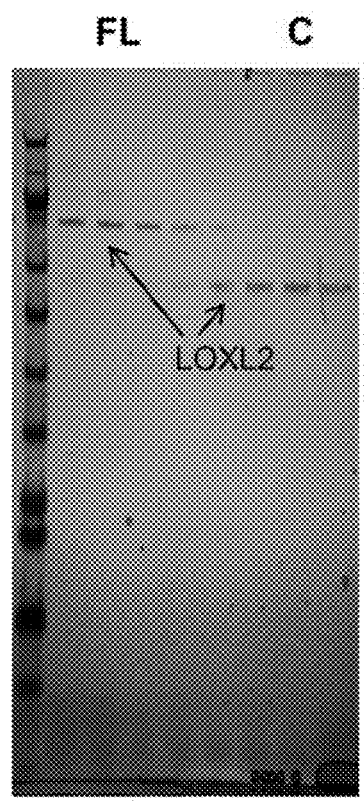
FIG. 18 shows a Western blot analysis confirming separation of LOXL2 species by chromatography. "FL" indicates full-length LOXL2 protein. "C" indicates a cleaved form of LOXL2 protein.
Figure 19:
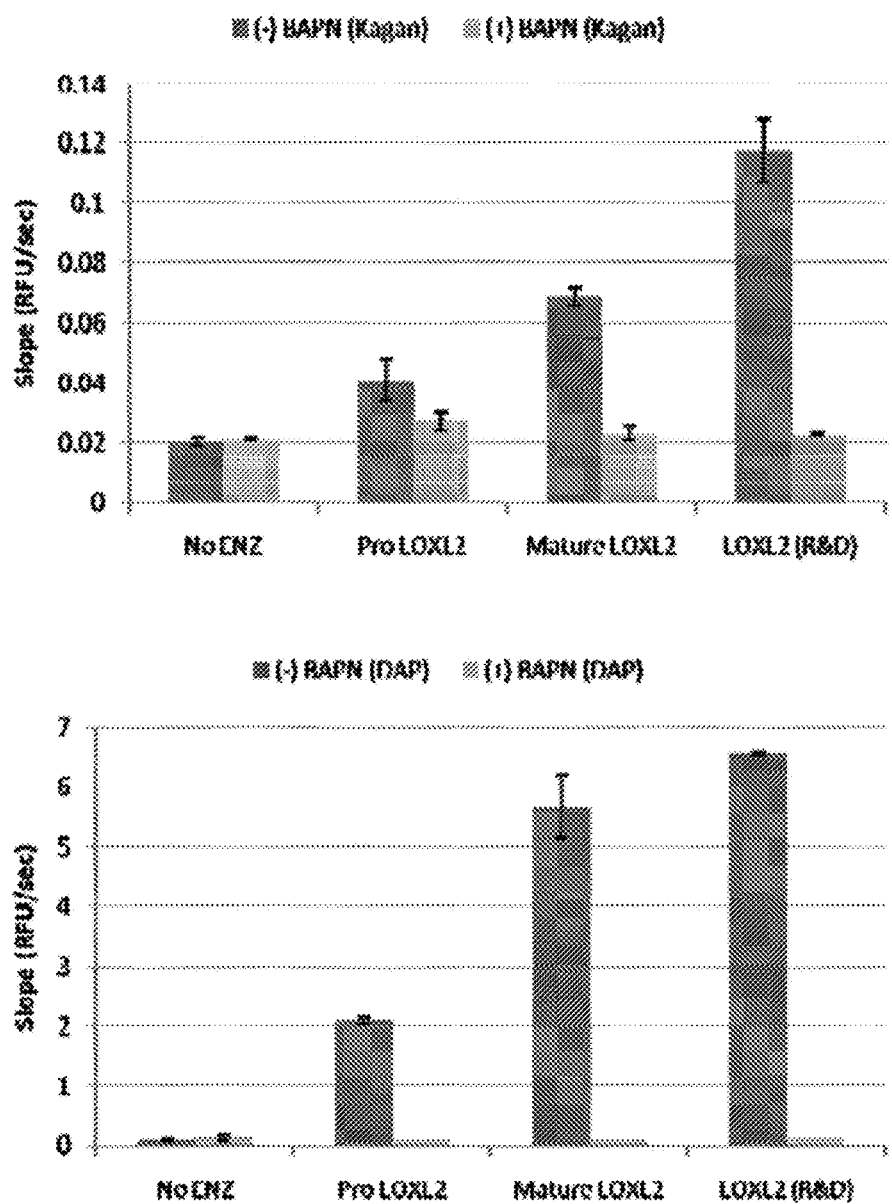
FIG. 19 shows an in vitro enzymatic assay that indicates that both forms of LOXL2 are active (GGGGEKGGGGG disclosed as SEQ ID NO: 57).

LOXL2 is cleaved and was detected by virtue of its change in molecular weight by Western blot (FIG. 16, 17). The two forms were separated by chromatography (FIG. 18), and the activity of both forms tested (FIG. 19).

Example 18

Internalization and Uptake of LOX/LOXL2

Hs578t cells were cultured in DMEM containing 10% FBS and 1× glutamine. The cells were seeded in an 8 chamber glass slide (BD Falcon, Franklin Lakes, N.J.) and allowed to adhere overnight. For low confluency, cells were seeded at 30-40,000 cells per slide. Low confluency was used for detection of Lox in the cytosol 24 hours later. For high confluency, cells were seeded at 100,000 cells per slide. High confluency was used for detection of Lox associated with the matrix and collagen approximately 48-72 hours later.

The following day, 1 µg/ml (final concentration in regular growth medium) of anti-Lox M64 or anti-Loxl2 M20 monoclonal Ab (mAb) was added to the chambers. For continuous uptake, the mAbs were incubated with cells at different timepoints: for example, 3 hour, 8 hour, 24 hour (overnight). After an appropriate amount of continuous uptake, the media was removed and the chambers were rinsed with 1×PBS. The cells were fixed in 4% PFA (paraformaldehyde) at room temperature for 20 minutes. After fixation, the cells were washed with 1×PBS at room temperature for 5 minutes and then quenched in 50 mM ammonium chloride at room temperature for 10 minutes. The cells were washed again with 1×PBS at room temperature for 5 minutes.

The cells were permeabilized by adding saponin buffer (0.5% Saponin/1% BSA in PBS) at room temperature for 20 minutes. The secondary detection Ab (Alexa Fluor 488 donkey anti-mouse IgG, Invitrogen, Carlsbad, Calif.) was added at room temperature in saponin buffer and the cells were incubated for 30-45 minutes. The cells were then washed 3× in saponin buffer. The slides were mounted with vectashield (Vector Laboratories, Burlingame, Calif.).

To detect collagen detection, anti-collagen antibody (1:50, Calbiochem anti-collagen type I Rabbit polyclonal, Gibbstown, N.J.) was incubated one hour prior to fixing the cells with 4% PFA. Secondary Ab for collagen was donkey anti-rabbit Cy3 (ImmunoJacksonLabs, West Grove, Pa.).

siRNA Knockdown of Lox and Loxl2 in Hs578t Cells:

Hs578t cells were cultured in DMEM containing 10% FBS and 1× glutamine in 10 cm tissue culture plates. The cells were grown until they were approximately 75% confluent. The transfection reaction/mixture was set up the day the cells reached 75% confluency. Two mixtures were made: In one 15 ml conical tube, 60 µls of 20 uM of siRNA was mixed with 1 ml of optimum (final siRNA concentration was 100 nM). In another 15 ml conical tube, 30 µls of Dharmafect™ 3 (Thermo Scientific, Chicago, Ill.) transfection reagent was mixed with 1 ml of OptiMEM™. The two tubes were incubated at room temperature for 5 minutes. After 5 minutes, the contents of both tubes were mixed into one. The mix was carefully pipetted up and down and incubated for 20 minutes at room temperature.

Figure 23:
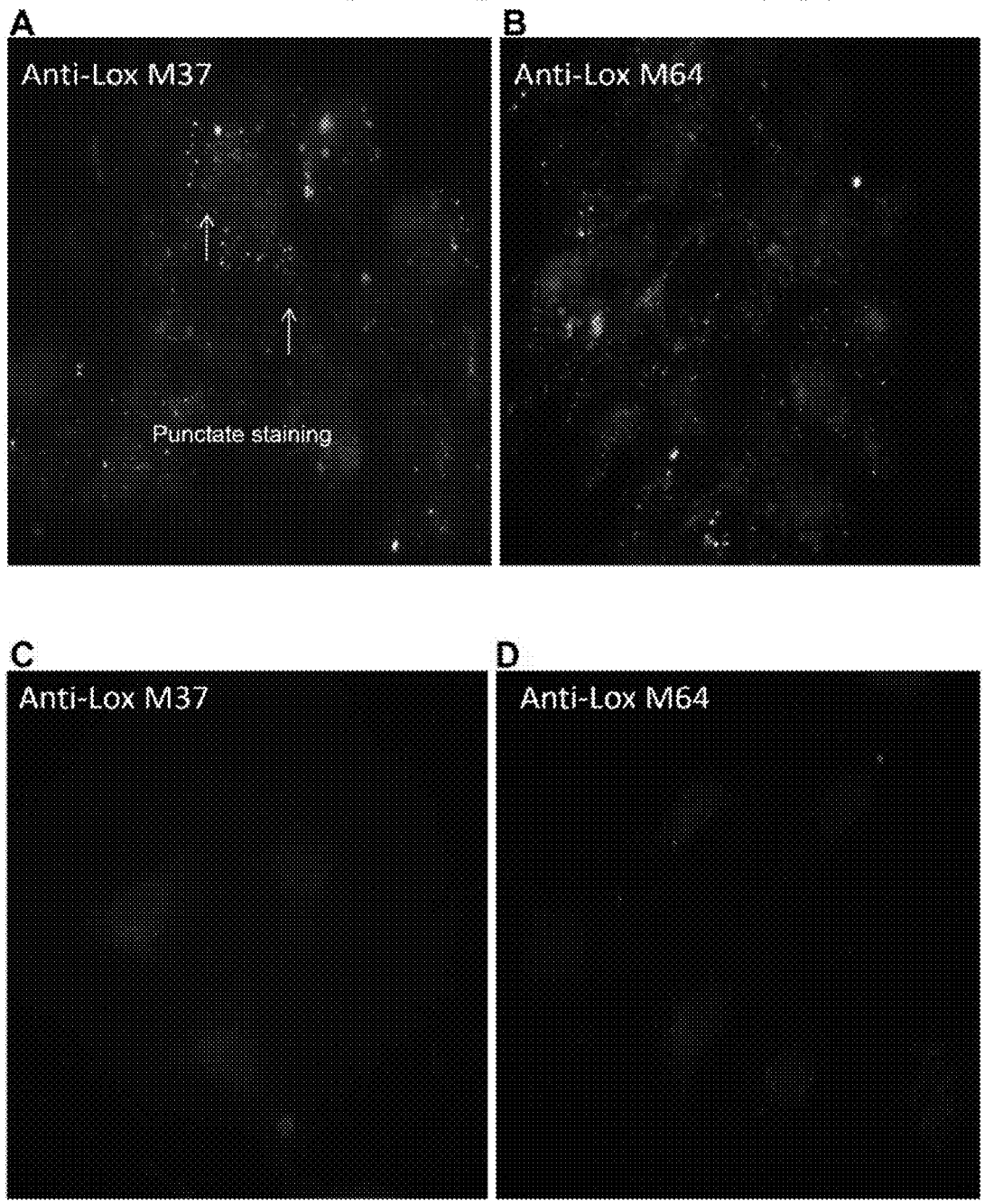
FIG. 23 illustrates internalization and uptake for anti-LOX antibody. Immunofluorescence analysis of LOX in live tumor cells was performed using antibodies. (A-B) Hs578t cells were transfected with siNT (non-targeting knockdown control) and incubated for 3 hours with mAbs. Lox was localized in the cytosol. (C-D) Hs578t cells were incubated for 3 hours with mAbs transfected with siLOX. LOX protein levels were diminished, supporting depletion by siLOX. LOX protein was also periplasmic in the cell. LOX was detected with M37 (A, C) or M64 antibody (B, D). Similar results of internalization and uptake of LOXl2 mAbs was obtained. Thus, the results support conclusions that staining is specific for LOX or LOXL2.

Hs578t cells were trypsinized and resuspended in 10 mls of complete media and were added to a 10 cm tissue culture plate. For each siRNA condition, 2 mls of the combined transfection mixture was added to the 10 cm plate. The plates were gently swirled and were placed in the incubator with 37 C and 5% CO2 overnight. The media did not need to be changed and was left on the cells for many days. For immunofluorescent studies (FIGS. 23, 24, 35), the transfection proceeded for at least 5 days to ensure sufficient knockdown and lowered protein levels.

Summary

Figure 25:
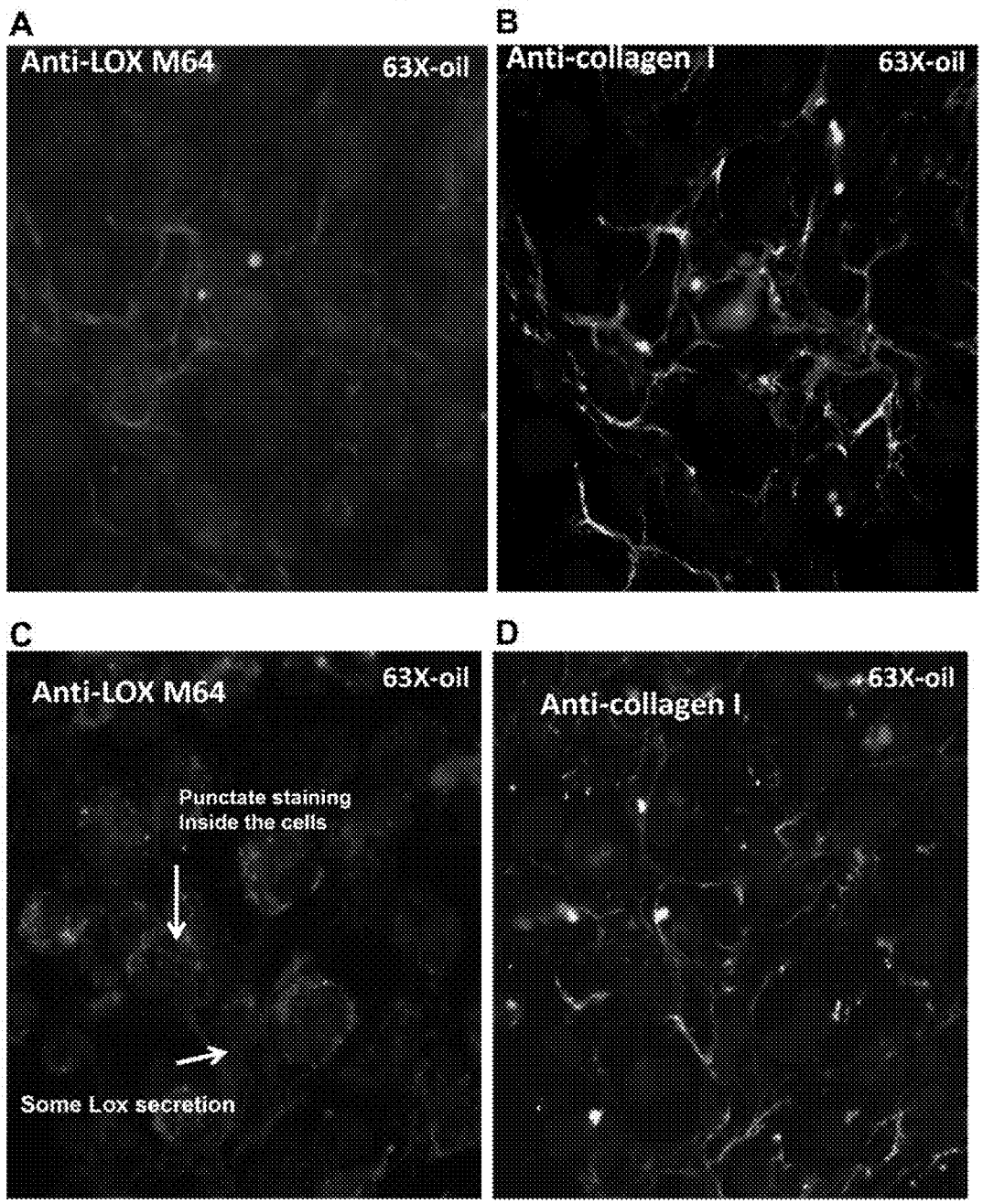
FIG. 25 illustrates internalization and uptake for anti-LOX antibody in Hs578t transfected with siRNA and. Hs578t cells were transfected with (A, B) siNT or (C, D) siLOX and incubated with LOX antibody for 5 hours. Images of cells, detected with anti-Lox M64 (A, C) or anti-collagen I (B, D), were taken 7 days post-transfection. Similar results of internalization and uptake of Loxl2 mAbs was obtained.

The results demonstrate that at low cell confluency, LOX and LOXL2 do not remain secreted in the extracellular matrix but instead can be re-uptaken by tumor cells (as the antibody is internalized). The specificity of these staining patterns (FIGS. 23, 24, 25) was supported by matched siRNA knockdown controls. At high cell confluency, LOX and LOXL2 are now detected readily outside the cell in the extracellular matrix, with apparently little re-uptake. Staining patterns were supported by matched siRNA knockdown controls. Similar results of internalization and uptake of anti-Lox and anti-Loxl2 mAbs and their colocalization with collagen was obtained for Loxl2 mAbs treatment of cells in place of siRNA knockdown.

Example 19

Time Course of LOX/LOXL2 Internalization and Uptake

The time course was initiated on cells that were already confluent (day 0). The cell line used was breast tumor cell line Hs578t, which expresses both LOX and LOXL2.

IHC protocol (cells on chamber slides; based on DAKO's EnVision+System-HRP):

All the steps were done at RT (room temperature), the primary antibody concentration was 5 µg/ml for anti-LOX and 15 ug/ml for anti-LOXL2. The cells were washed with PBS (×3). Then a peroxidase block (5 min) was performed before washing again with PBS (×3). The cells were then incubated with primary antibody diluted in 0.05 M Tris-HCl, pH 7.6 w/1% BSA (30 min). M64 and M20, LOX and LOXL2 monoclonal antibodies, respectively, (see for example FIG. 26) were used. The cells were then washed with PBS (×3) before being fixed with 4% PFA (10 min). The cells were then washed again with PBS (×3) before adding Peroxidase Labelled Polymer (30 min). The cells were then washed with PBS (×3). The Substrate-Chromogen (20 µL DAB per 1 mL Substrate Buffer) was then added for 5-10 min. The cells were then washed with distilled water before counterstaining with hematoxylin (optional at times), dehydrated and permanently mounted with Entellan.

Picro-Sirius Red (Sirius Red F3B) Staining Protocol:

Siruis Red staining was used for collagen histochemistry. The cells were fixed with 4% PFA (10 min), however, the fixation is not critical. The cells were then stained in Picro-Sirius Red (Sirius Red 0.1% in saturated picric acid (Electron Microscopy sciences, cat#26357-02) for 1 hour at RT. The cells were then washed in 2 changes of acidified water (5 mL acetic acid in 1 L of distilled water) before being dehydrated in graded series of ethanol and mounted.

Results

Figure 27:
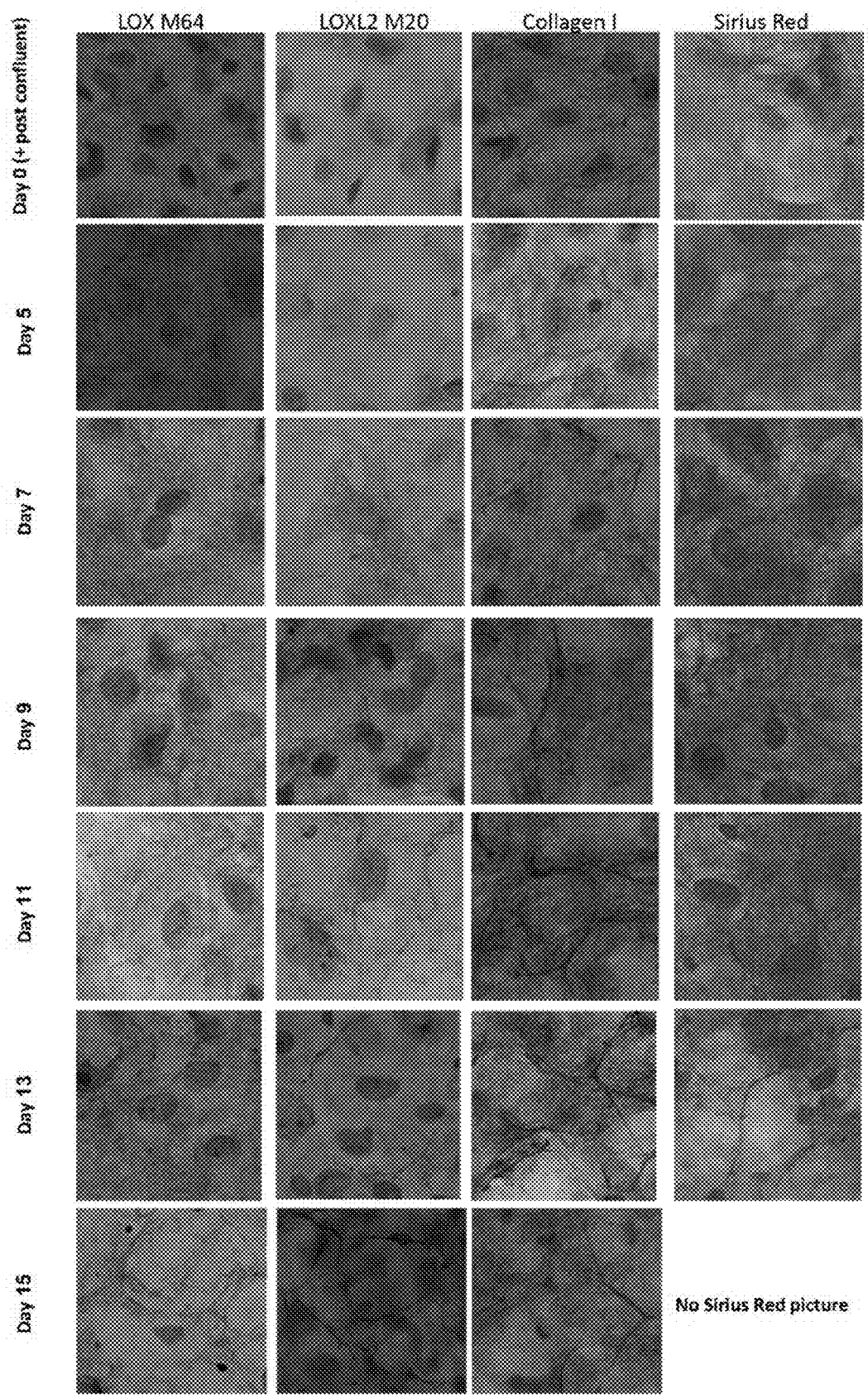
FIG. 27 shows a time-course study of Hs578T cells from Day 0 to Day 15 post-confluent.

As shown in FIG. 27, at Day 0, LOX and collagen I were already secreted and associated with the matrix, but LOXL2 was localized in the cytosol and was not secreted nor associated with the matrix yet. At Day 5, more LOX and collagen I was secreted, and LOXL2 was secreted/associated with the matrix. At Day 9, LOX, LOXL2, collagen I and Sirius red all showed similar staining patterns, indicating LOX, LOXL2 and collagen I co-localize in the same regions. At Day 11, a change in LOX staining pattern was detected, indicating less LOX was being secreted and/or associated with the matrix. LOXL2, collagen I and Sirius Red staining, however, were still similar to each other and no real change in staining patterns was detected. Staining patterns of all the proteins at Day 13 and Day 15 were similar to those of Day 11. Based on these results, there were some differences in the timing of the secretion of LOX and LOXL2, respectively. The secretion of LOX and LOXL2 appears to be regulated and related to cell confluency. The timing of secretion may regulate the availability of active, extracellular LOX and LOXL2, which in turn, may initiate collagen cross-linking.

This example, combined with other Examples disclosed herein, demonstrate that the secretion of LOX and LOXL2 is highly regulated. At low cell density, the data disclosed herein indicates secreted LOX and LOXL2 are rapidly re-uptaken by cells (as the specific LOX and LOXL2 antibodies are detected inside the cell, suggesting that they are efficiently internalized). At high cell density, LOX and LOXL2 are no longer re-uptaken but are found associated with the collagen matrix (extracellular), as determined by localization of specific LOX and LOXL2 antibodies. IHC analysis of tumor cells and liver fibrosis cells indicate that a similar regulation of LOX and LOXL2 can occur, with differential distributions of intracellular and extracellular LOX/LOXL in areas of disease.

Example 20

LOX and LOXL2 Tissue Expression

The decloaking chamber and solutions used are from BioCareMedical (Concord, Calif.) unless otherwise stated. All procedures were performed at room temperature unless otherwise stated.

The decloaking chamber was filled with 500 ml of distilled water (diH20). One slide container was filled with 200 mls of Universal Decloaker antigen retrieval solution and another slide container was filled with 200 mls of Hot Rinse; the tissue microarray (TMA) slides (Cybrdi, Frederick, Md.) were placed into the container with the decloaking solution and were then placed into the decloaking chamber. The temperature settings were set at 80° C. for 30 minutes for breast TMAs. Once the temperature reached 90° C., the slides were removed from the decloaking antigen retrieval solution and placed into the container with hot rinse. The temperature in the hot rinse container was brought down slowly by exchanging ⅓ of the hot rinse with ⅓ of diH20 every two minutes until the temperature within the container was at room temperature. The slides were then rinsed once with diH20 and then once in PBS with 0.1% Tween-20.

Figure 28:
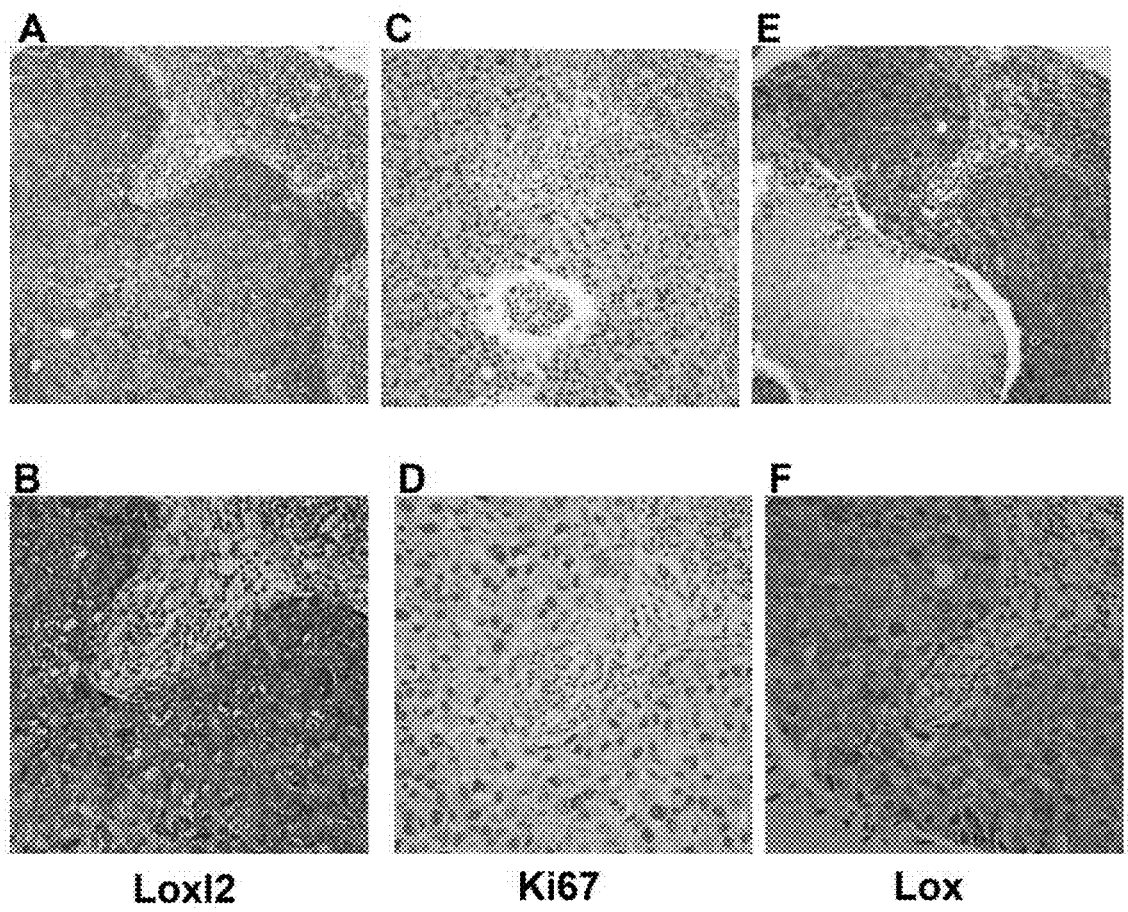
FIG. 28 depicts immunohistochemistry (IHC) using LOXL2 and LOX antibodies on metastatic breast tumor tissue (lymph node) sample. IHC was performed using Breast TMA: CC08-21-002 (Cybrdi), a metastatic nonspecific infiltrating ductal carcinoma sample, with (A, B) LOXL2, (C, D) Ki67, a marker of cell proliferation, and (E, F) and LOX. LOXL2 and LOX are both expressed by the tumor cells and there is evidence of expression of both LOXL2 and LOX by stromal cells. (brown staining). (A, C, E) 20× magnification; (B, E, F) 40× magnification.
Figure 29:
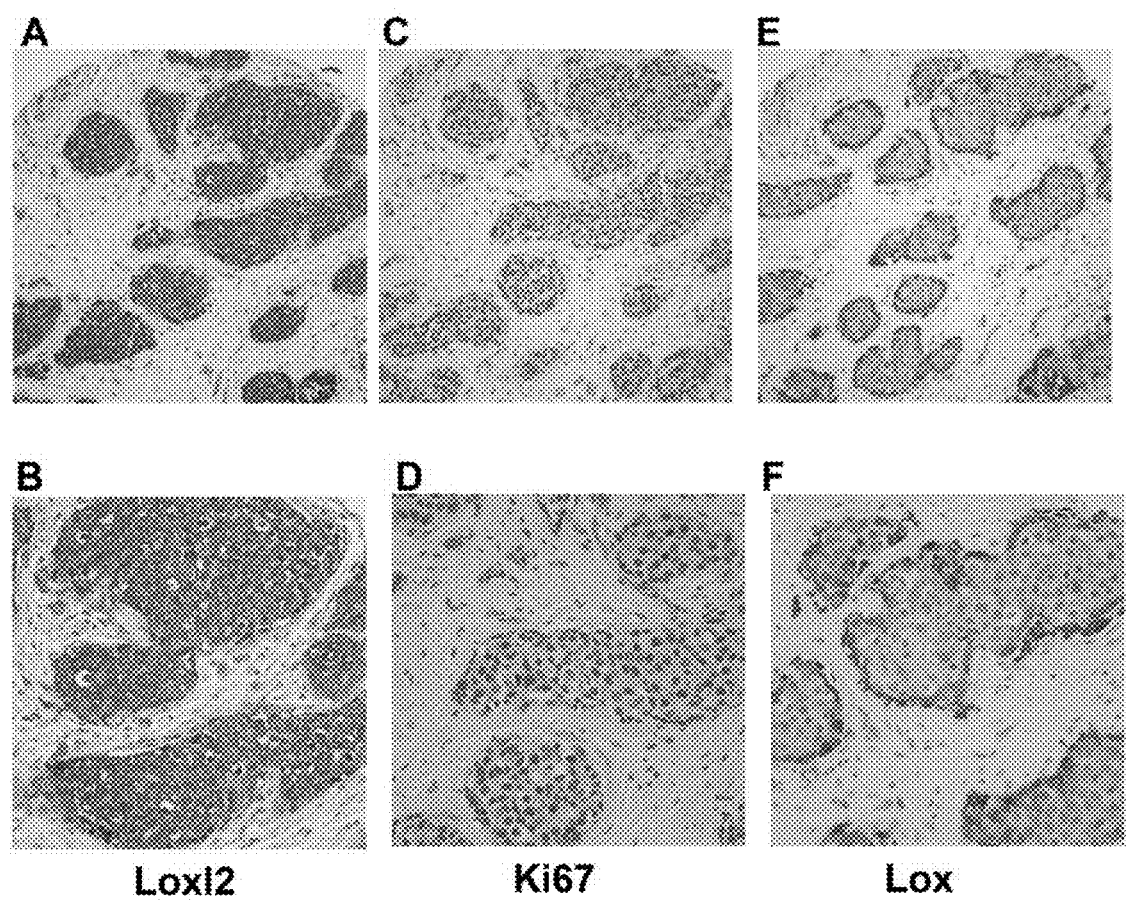
FIG. 29 depicts immunohistochemistry (IHC) using LOXL2 and LOX antibodies on primary breast tumor samples. IHC was performed using Breast TMA: CC08-21-002 (Cybrdi), a non specific infiltrating ductal carcinoma-grade II sample, with (A, B) LOXL2, (C, D) Ki67, a marker of cell proliferation, and (E, F) and LOX. There is co-expression of LOXL2 and LOX in the primary breast tumor, and LOXL2 protein is strongly detected in tumor cells and LOX protein is primarily detected in stromal cells immediately surrounding the tumor cells (stromal fibroblasts and/or stromal myofibroblasts). (A, C, E) 20× magnification; (B, E, F) 40× magnification.
Figure 30:
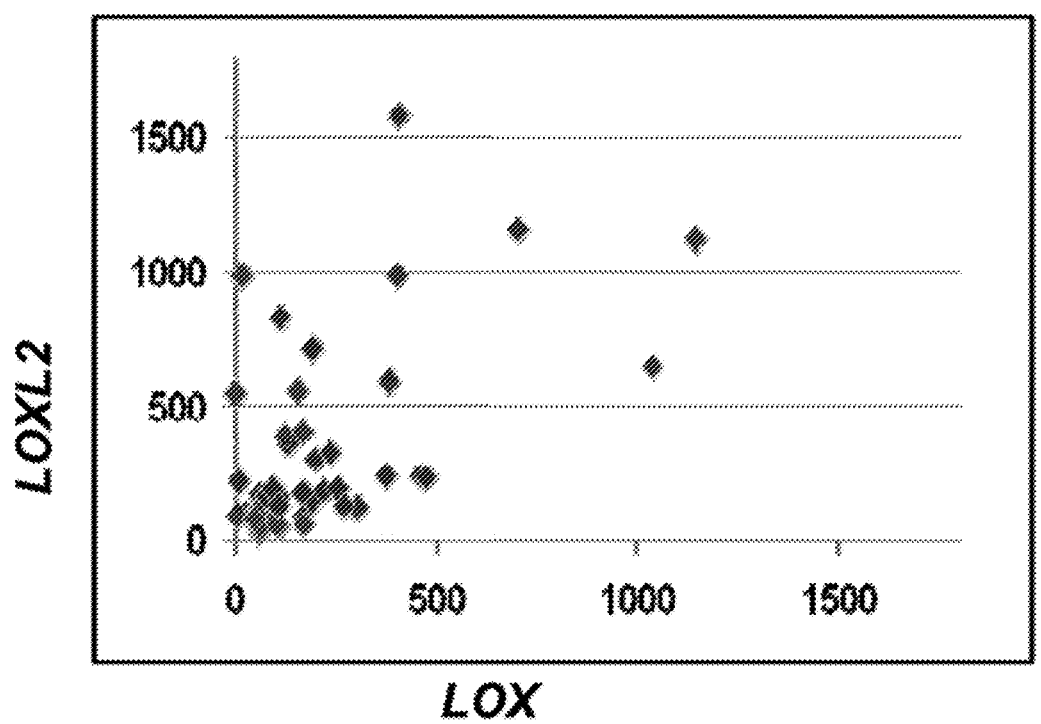
FIG. 30 is a graph showing mRNA levels of LOX and LOXL2 overexpressed in tumors and fibrotic disease tissues compared to normal tissues as measured by using DNA chips provided by Affymetrix, Inc.

The slides were treated with Peroxidazed-1 for 5 minutes and then rinsed one time in PBS for 2 minutes. Then, the slides were background blocked with SNIPER for 5 to 10 minutes and then rinsed one time in PBS for 2 minutes. Primary antibody (Ab) was diluted in Da Vinci Green Universal Diluent. 5 µg/ml of rabbit polyclonal anti-Loxl2 antibody and 3 µg/ml of monoclonal anti-Lox M64 was used. The slides were incubated with the primary antibodies for 2 hours and were then rinsed 3 times in PBS-Tween-20, 2 minutes each rinse. The Mach3 polymer kit was used for antigen detection by adding mouse or rabbit probe for 20 minutes. The slides were then rinsed once with PBS-Tween-20 and followed by the addition of mouse or rabbit polymer for 20 minutes. The slides were then rinsed 5 times in PBS-Tween-20, 2 minutes for each wash. DAB chromagen was added to the slides for 7 minutes and rinsed once in diH20. DAB sparkle was added to the slides for 1 minute and rinsed once in diH20. The slides were then counter stained with hematoxylin for 30 seconds to 1 minute and were then rinsed with water for 5 minutes and followed by dehydration with graded alcohol. The slides were mounted with entellan mounting media (Electron Microscopy Sciences, Hatfield, Pa.). Tissue expression is as shown in FIGS. 28 and 29.

Example 21

LOX and LOXL2 Expression in Lung Adenocarcinoma

Figure 32:
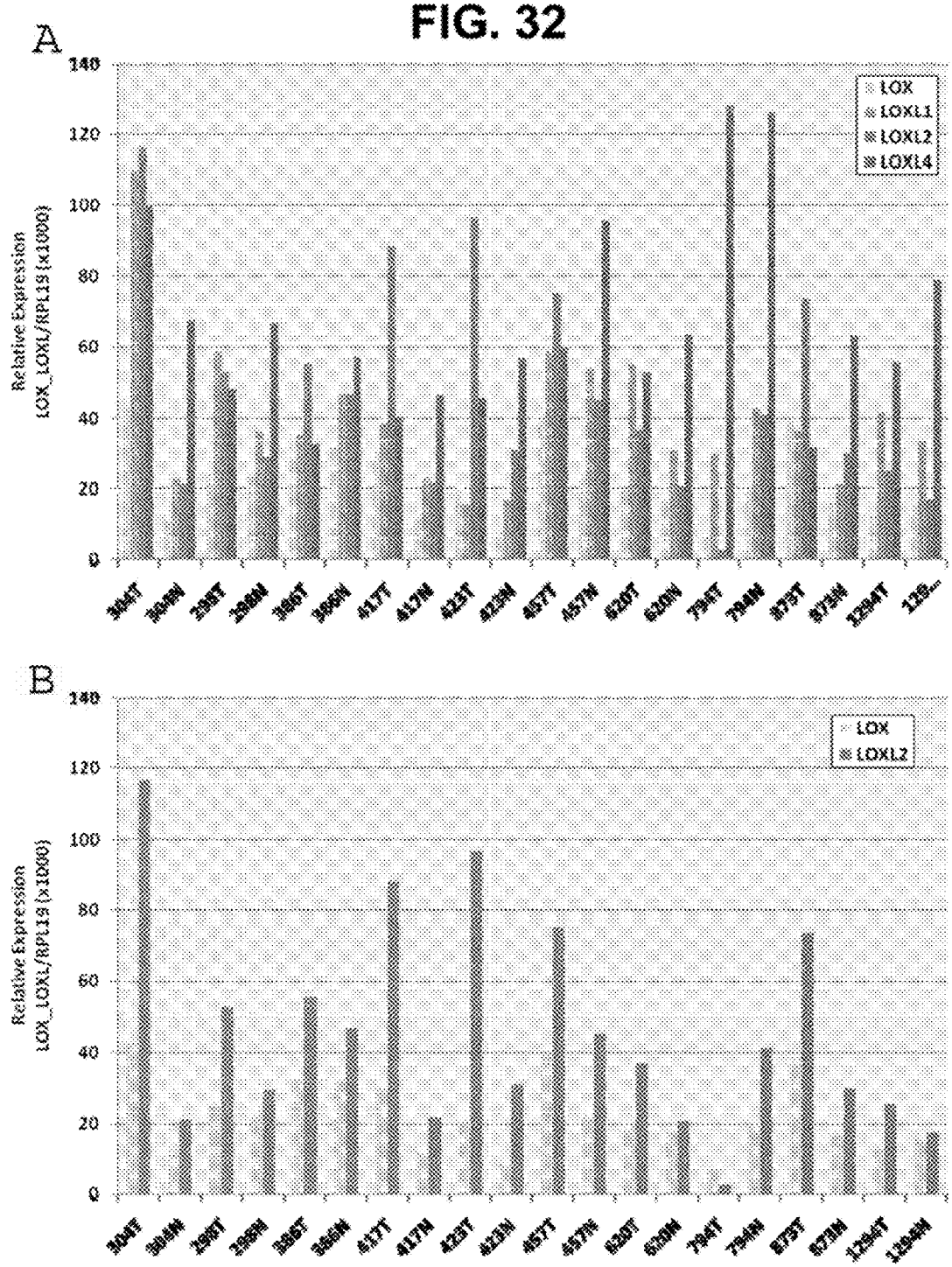
FIG. 32 depicts the expression of LOX/LOXL in lung adenocarcinoma samples normalized to a housekeeping gene RPL19. The tumor and adjacent normal samples are plotted separately, (A) LOX, LOXL1, LOXL2, LOXL4 and (B) only LOX and LOXL2 plotted, based on the same data as (A). T: tumor; N: normal.

RT-PCR analysis of LOX and LOXL2 was performed on lung adenocarcinoma. Analysis was performed on primary tumors, but some were associated with metastasis or recurrence. The data are a ratio of tumor to a matched adjacent "normal" piece of tissue that is not necessarily completely normal, the individual transcript data for tumor and normal are plotted in FIGS. 31 and 32. LOXL2 was overexpressed in about 4-5 out of 10 tumors and tended to be associated with tumors known to be associated with lymph node metastasis or other recurrence/metastasis (TABLE 3). Primers and probes used are listed in TABLE 4.

TABLE 3

Lung Adenocarcinoma Pathology

| Sample | male/female | | | | | | |
|---|---|---|---|---|---|---|---|
| 304T | M | poorly differentiated, lung tumor nodule "metastasis" | pT1, NO, M1 | III | 21 | * | High LOXL2, LOXL1, LOX |
| 304N | M | | | | 22 | | |
| 298T | F | moderately differentiated | pT1, NO, MX | | 23 | | |
| 298N | F | | | | 24 | | |
| 386T | M | poorly differentiated | pT2, 1B, NO, MO | III | 25 | | |
| 386N | M | | | | 26 | | |
| 417T | M | poorly; non-invasive, primary | pT2, 1B, NO, MX | III | 27 | * | high LOXL2, LOX |
| 417N | M | | | | 28 | | |
| 423T | M | poorly differentiated | tumor recurred | 3 | 29 | * | high LOXL2, LOX |
| 423N | M | | | | 30 | | |

TABLE 3-continued

Lung Adenocarcinoma Pathology

| Sample | male/female | | | | | | |
|---|---|---|---|---|---|---|---|
| 457T | M | mod. to poorly differentiated | pT4, IIIB, N1, MX | 2 | 31 | | high LOXL2, high "adjacent normal" |
| 457N | M | | | | 32 | | |
| 620T | M | well differentiated | pT2, NO, MX | I | 33 | | |
| 620N | M | | | | 34 | | |
| 794T | M | moderately differentiated | pT1, II, NO, MX | II | 35 | | |
| 794N | M | | | | 36 | | |
| 873T | M | poorly differentiated | pT2, IIB, N1, MX | III | 37 | * | high LOXL2, LOX |
| 873N | M | | | | 38 | | |
| 1294T | F | moderately differentiated | NO, MX | II | 39 | | |
| 1294N | F | | | | 40 | | |

TABLE 4 qRT-PCR Sequences
(SEQ ID NOs: 21-56, respectively, in order of appearance)

| Short Name | Ref Seq | Sequence | Probe | Quencher |
|---|---|---|---|---|
| LOX | NM_002317 | CTTGACTGGGGAAGGGTCTG | | |
| LOX | NM_002317 | AAAACGGGGCTCAAATCACG | | |
| LOX | NM_002317 | ATCCCACCCTTGGCATTGCTTGGT | FAM | BHQ-1 |
| LOXL1 | NM_005576 | AGCAGACTTCCTCCCCAACC | | |
| LOXL1 | NM_005576 | CAGTAGGTCGTAGTGGCTGAAC | | |
| LOXL1 | NM_005576 | CACGGCACACCTGGGAGTGGCAC | FAM | BHQ-1 |
| LOXL2 | NM_002318 | GGGGTTTGTCCACAGAGCTG | | |
| LOXL2 | NM_002318 | ACGTGTCACTGGAGAAGAGC | | |
| LOXL2 | NM_002318 | TGGAGCAGCACCAAGAGCCAGTCT | FAM | BHQ-1 |
| LOXL3 | NM_032603 | GTGTGCGACAAAGGCTGGAG | | |
| LOXL3 | NM_032603 | CCGCGTTGACCCTCTTTTCG | | |
| LOXL3 | NM_032603 | AAGCCCAGCATCCCGCAGACCAC | FAM | BHQ-1 |
| LOXL4 | NM_032211 | CTTACCACACACATGGGTGTTTC | | |
| LOXL4 | NM_032211 | TCAAGCACTCCGTAACTGTTGG | | |
| LOXL4 | NM_032211 | CCTTGGAAGCACAGACCTCGGGCA | FAM | BHQ-1 |
| RPL19 | NM_000981 | CCGGCTGCTCAGAAGATAC | | |
| RPL19 | NM_000981 | TTCAGGTACAGGCTGTGATACAT | | |
| RPL19 | NM_000981 | TGGCGATCGATCTTCTTAGATTCACG | FAM | BHQ-1 |
| LOX | NM_010728 | CAAGAGGGAAGCAGAGCCTTC | | |
| LOX | NM_010728 | GCACCTTCTGAATGTAAGAGTCTC | | |
| LOX | NM_010728 | ACCAAGGAGCACGCACCACAACGA | FAM | BHQ-1 |
| LOXL1 | NM_010729 | GGCCTTCGCCACCACCTATC | | |
| LOXL1 | NM_010729 | GTAGTACACGTAGCCCTGTTCG | | |
| LOXL1 | NM_010729 | CCAGCCATCCTCCTACCCGCAGCA | FAM | BHQ-1 |
| LOXL2 | NM_033325 | GCTATGTAGAGGCCAAGTCCTG | | |
| LOXL2 | NM_033325 | CAGTGACACCCCAGCCATTG | | |

TABLE 4-continued qRT-PCR Sequences
(SEQ ID NOs: 21-56, respectively, in order of appearance)

| Short Name | Ref Seq | Sequence | Probe | Quencher |
|---|---|---|---|---|
| LOXL2 | NM_033325 | TCCTCCTACGGTCCAGGCGAAGGC | FAM | BHQ-1 |
| LOXL3 | NM_013586 | GCAAGGAGAGAATAGACAGAGAAG | | |
| LOXL3 | NM_013586 | AGCATGGTGTCCTCATTCATAAAG | | |
| LOXL3 | NM_013586 | ACATCCACCCATCCCATCCCACCC | FAM | BHQ-1 |
| LOXL4 | NM_053083 | CAAGACAGGTCCAGTAGAGTTAGG | | |
| LOXL4 | NM_053083 | AGGTCTTATACCACCTGAGCAAG | | |
| LOXL4 | NM_053083 | ACAGAGCACAGCCGCCTCACTGGA | FAM | BHQ-1 |
| RPL19 | NM_009078 | AGAAGGTGACCTGGATGAGAA | | |
| RPL19 | NM_009078 | TGATACATATGGCGGTCAATCT | | |
| RPL19 | NM_009078 | CTTCTCAGGAGATACCGGGAATCCAAG | FAM | BHQ-1 |

Example 22

Animal Model for Diabetic Nephropathy/Kidney Fibrosis

Transgenic mice which overexpress inducible cAMP early repressor display severe diabetes and exhibit glomerular hypertrophy, glomerular basement membrane thickening and sclerotic lesions. These mice may be used as a model for diabetic nephropathy. The compounds described herein can be administered to this model system and analyzed for their ability to prevent, treat, and/or ameliorate kidney fibrosis.

Transgenic mice are raised under established protocols and guidelines for animal experiments. Treatment group size, regimens, and controls are established based on previously identified doses and administration time-points for LOX/LOXL inhibitors. Mice are monitored and/or sacrificed at pre-determined time-points throughout the experimental time-frame for histological and biochemical analyses.

Histological analyses include microscopic and immunohistochemical analyses of kidney sections. Glomerular surface area and glomerular number are identified via established biochemical staining and microscopic analyses. Glomerular basement membrane thickening is determined via established methods for electron microscopy of kidney sections.

Serum and urinary variables are also monitored for determination of kidney activity/failure. Blood glucose and insulin levels are determined via established methodologies including ELISA and HPLC. Serum proteins such as creatinine and albumin are also monitored via established assays. Urine samples are assayed for protein levels including albumin and creatinine. Established assays are used for the detection of proteins in urine, including ELISA and HPLC.

Utilizing an animal model system such as the diabetic nephropathy mouse model described above, the compounds disclosed herein may be tested for prevention, treatment, and/or amelioration of kidney fibroses.

Example 23

Animal Model for Myocardial Ischemia/Infarction Fibrosis and ECM Remodeling

Male Wistar rats are housed and handled per current animal handling guidelines and protocols. Treatment group size, regimens, and controls are established based on previously identified doses and administration time-points for LOX/LOXL inhibitors. Rats are subject to ischemia/reperfusion injury are monitored and/or sacrificed at pre-determined time-points followed by x-ray, microCT imaging, microscopic tissue examination, and immunohistochemical analyses.

Ischemia/Reperfusion Injury Protocol

Rats are anesthetized and placed on ventilation. Hearts are surgically exposed and a mini-pneumatic coronary occluder (catheter-based occlusion system) is placed around the desired coronary artery. The chest is then closed and the occluder-catheter and venous tubing are exteriorized between the scapulae. After surgery, the animals are allowed to recover for five days prior to starting the ischemia/reperfusion protocol.

Ischemia

Ischemia is implemented via the occluder-catheter on a schedule that include at least one pre-conditioning occlusion for 20 seconds followed by 5 minutes of recovery, and at least one occlusion for 2 minutes, followed by 5 minutes of recovery. Thereafter, occlusion time can vary up to 30 minutes. Ischemic protocol lengths can vary, with a typical protocol length of 4 weeks. Ischemia is implemented once per week, and cardiac function is monitored via echocardiography throughout the protocol. Rats are euthanized at the end of the protocol, and hearts are excised and examined for microvasculature, chamber size and function, and extent of fibrosis. LOX/LOXL inhibitors are administered at predetermined time points and dosages throughout the ischemia protocol. Ascending dosages and increasing frequencies of administration are administered in groupings sufficient to establish dose-limiting toxicities and efficacies. Control animals and protocols are maintained throughout all protocols.

Analyses

Ventricle size is determined via recordation of ventricle short-axis views by echocardiography during the protocol. Diastolic and systolic areas, defined as the minimum and maximum ventricle cavity areas during cardiac phase are analyzed. Coronary flow and microvasculature of the excised hearts is determined via a variety of imaging and staining techniques including microCT and x-ray. Fibrosis of the chambers is determined via sectioning of the cardiac tissue and trichrome staining or other established staining for cardiac tissue. Cross-sectional microscopy and histological analysis is also performed for evaluation of ventricle volume, size, and ventricle wall thinning.

Utilizing an animal model system such as the cardiac ECM remodeling system described above, the compounds described herein can be tested for prevention, treatment, and/or amelioration of cardiac fibrosis and cardiac ECM remodeling.

Example 24

Animal Model for Lung Fibrosis and ECM Remodeling

Bleomycin induced pulmonary fibrosis is a standard model for assessment of lung fibrogenesis including IPF, Interstitial Pneumonia, and ARDS. Male Wistar rats are housed and handled as per animal handling guidelines and protocols. Treatment group size, regimens, and controls are established based on previously identified doses and administration timepoints for LOX/LOXL inhibitors. Rats are intra-tracheally injected with bleomycin at established dosages (typically 5 mg/kg). Control animals are maintained throughout the treatment period.

Following administration of bleomycin, test groups are then administered the predetermined LOX/LOXL inhibitor and monitored and/or sacrificed at pre-determined timepoints for assessment of lung fibroses. Test periods can vary, with an exemplary test period being 4 weeks. Following sacrifice, rat lungs are examined for fibrosis and collagen content. Rat lung sections are stained and examined via established staining procedures and microscopy for the presence and extent of fibrosis. Additionally, collagen content of the rat lungs is determined via established assays such as a hydroxyproline assay.

Utilizing an animal model system such as the bleomycin-induced lung fibrosis animal model described above, the compounds described herein can be tested for prevention, treatment, and/or amelioration of lung fibroses.

What is claimed is:

1. A method of treating fibrosis, comprising:
administering to a human in need thereof a monoclonal anti-lysyl oxidase-like 2 (LOXL2) antibody or antigen-binding fragment thereof, wherein the monoclonal antibody or fragment thereof specifically binds to SEQ ID NO.: 3 or 7.

2. The method of claim 1, wherein the fibrosis is or is associated with cardiac fibrosis, dermal scar formation, keloids, liver fibrosis, lung fibrosis, silicosis, asbestosis, kidney fibrosis, diabetic nephropathy, scleroderma, or glomerulosclerosis.

3. The method of claim 2, wherein the fibrosis is cardiac fibrosis associated with hypertension, hypertensive heart disease, myocardial infarction, atherosclerosis, or restenosis.

4. The method of claim 1, wherein the fibrosis occurs as a complication of haemochromatosis, Wilson's disease, alcoholism, schistosomiasis, viral hepatitis, bile duct obstruction, exposure to toxins or a metabolic disorder.

5. The method of claim 2, wherein the fibrosis is lung fibrosis.

6. The method of claim 5, wherein the lung fibrosis is or is associated with idiopathic pulmonary fibrosis (IPF), idiopathic interstitial pneumonia, acute respiratory distress syndrome, cryptogenic fibrosing alveolitis, chronic fibrosing interstitial pneumonia, interstitial lung disease, or diffuse parenchymal lung disease.

7. The method of claim 6, wherein the lung fibrosis is IPF.

8. The method of claim 2, wherein the fibrosis is liver fibrosis.

9. The method of claim 1, wherein the antibody or fragment thereof is humanized or human.

10. The method of claim 1, further comprising administering to the human an anti-neoplastic agent, a chemotherapeutic agent, an anti-angiogenic agent, or an anti-fibrotic agent.

11. The method of claim 1, wherein the antibody or fragment is an inhibitor of LOXL2.

12. The method of claim 1, wherein the antibody or fragment thereof specifically binds to SEQ ID NO.: 3.

13. The method of claim 1, wherein the antibody or fragment thereof specifically binds to SEQ ID NO.: 7.

14. A method of treating fibrosis, comprising:
administering to a human in need thereof a monoclonal anti-LOXL2 antibody or antigen-binding fragment thereof, wherein the monoclonal antibody or fragment thereof specifically binds to SEQ ID NO.: 5.

15. The method of claim 4, wherein the antibody or fragment is an inhibitor of LOXL2.

16. The method of claim 14, wherein the antibody or fragment thereof is humanized or human.

17. The method of claim 14, further comprising administering to the human an anti-neoplastic agent, a chemotherapeutic agent, an anti-angiogenic agent, or an anti-fibrotic agent.

18. The method of claim 14, wherein the fibrosis is lung fibrosis.

19. The method of claim 18, wherein the lung fibrosis is or is associated with idiopathic pulmonary fibrosis (IPF), idiopathic interstitial pneumonia, acute respiratory distress syndrome, cryptogenic fibrosing alveolitis, chronic fibrosing interstitial pneumonia, interstitial lung disease, or diffuse parenchymal lung disease.

20. The method of claim 19, wherein the lung fibrosis is IPF.

21. A method of treating lung fibrosis, comprising:
administering to a human in need thereof a monoclonal anti-LOXL2 antibody or antigen-binding fragment thereof, wherein the antibody or fragment thereof specifically binds to SEQ ID NO.: 3 or 7.

22. The method of claim 21, wherein the antibody or fragment thereof is humanized or human.

23. The method of claim 21, further comprising administering to the human a chemotherapeutic agent, an anti-angiogenic agent, an anti-neoplastic agent, or an anti-fibrotic agent.

24. The method of claim 21, wherein the antibody or fragment is an inhibitor of LOXL2.

25. The method of claim 21, wherein the antibody or fragment thereof specifically binds to SEQ ID NO.: 3.

26. The method of claim 21, wherein the antibody or fragment thereof specifically binds to SEQ ID NO.: 7.

27. A method of treating fibrosis, comprising:
administering to a human in need thereof a monoclonal anti-lysyl oxidase-like 2 (LOXL2) antibody or antigen-binding fragment thereof, wherein the monoclonal antibody or fragment thereof specifically binds to a peptide consisting of SEQ ID NO.: 3 or 7.

28. The method of claim 27, wherein the fibrosis is or is associated with cardiac fibrosis, dermal scar formation, keloids, liver fibrosis, lung fibrosis, silicosis, asbestosis, kidney fibrosis, diabetic nephropathy, scleroderma, or glomerulosclerosis.

29. The method of claim 27, wherein the fibrosis is lung fibrosis.

30. The method of claim 29, wherein the lung fibrosis is idiopathic pulmonary fibrosis (IPF).

* * * * *